United States Patent [19]
Godel et al.

[11] Patent Number: 5,665,718
[45] Date of Patent: Sep. 9, 1997

[54] IMIDAZODIAZEPINES

[75] Inventors: Thierry Godel, Basel; Walter Hunkeler, Magden; Heinz Stadler; Ulrich Widmer, both of Rheinfelden, all of Switzerland

[73] Assignee: Hoffmann-La Roche Inc., Nutley, N.J.

[21] Appl. No.: 586,439

[22] Filed: Jan. 16, 1996

Related U.S. Application Data

[63] Continuation-in-part of Ser. No. 545,471, Nov. 20, 1995, which is a continuation of Ser. No. 400,917, Mar. 8, 1995, abandoned.

[30]    Foreign Application Priority Data

Mar. 16, 1994 [CH] Switzerland .................. 783/94
Jan. 3, 1995 [CH] Switzerland .................. 10/95

[51] Int. Cl.$^6$ .................. A61K 31/555; C07D 521/000
[52] U.S. Cl. .................. 514/220; 540/499; 540/498
[58] Field of Search .................. 540/494, 498; 514/220

[56]                References Cited

U.S. PATENT DOCUMENTS

| | | | |
|---|---|---|---|
| 4,507,313 | 3/1985 | Braestrup et al. | 540/498 |
| 4,622,321 | 11/1986 | Watjen et al. | 540/498 |
| 4,670,433 | 6/1987 | Watjen et al. | 540/498 |
| 4,772,599 | 9/1988 | Watjen et al. | 540/498 |
| 4,775,671 | 10/1988 | Hunkeler et al. | 540/498 |
| 4,886,797 | 12/1989 | Watjen et al. | 540/498 |
| 4,904,654 | 2/1990 | Lin et al. | 514/220 |
| 4,939,139 | 7/1990 | Lin et al. | 514/220 |

FOREIGN PATENT DOCUMENTS

| | | | |
|---|---|---|---|
| 0109921 | 11/1983 | European Pat. Off. | 514/220 |
| 0197282 | 2/1986 | European Pat. Off. | 514/220 |

OTHER PUBLICATIONS

Israel abridgment of 74070 pp. 2216–2217 (Jan. 16, 1985).
Israel abridgment of 82117 p. 330 (Apr. 6, 1987).
Nature 294, pp. 763–765 (1981).
J. Neurochemistry 37, pp. 714–722 (1981).
Journal of Medicinal Chemistry vol.32, No. 10, pp. 2282–2291 (Oct. 1989).
Research Communications In Chemical Pathology & Pharmacology, vol. 80, No. 3, pp. 357–362 (Jun. 1993).
Journal of Medicinal Chemistry vol. 36, No. 4, pp. 479–490 (Feb. 19, 1993).
Advances In Biochemical Psychopharmacology vol. 45, pp. 209–217 (1988).

*Primary Examiner*—Robert T. Bond
*Attorney, Agent, or Firm*—George W. Johnston; Ellen Ciambrone Coletti; Robert A. Silverman

[57]    ABSTRACT

The invention relates to compounds of the formula

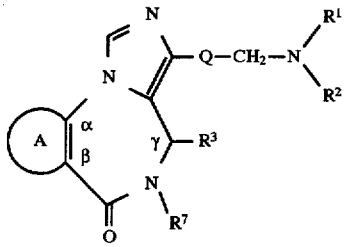

wherein

A together with the two carbon atoms denoted by α and β is one of the residues

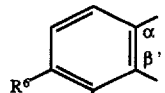 (A$^1$)

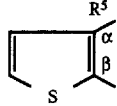

(A$^2$)

and

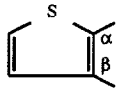 (A$^3$)

Q is one of the residues

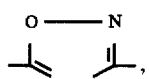 (Q$^1$)

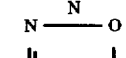

(Q$^2$)

and

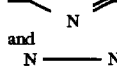 (Q$^3$)

R$^1$ and R$^2$ each independently are hydrogen, lower alkyl, lower alkenyl, lower alkynyl, lower hydroxyalkyl, lower alkoxy-lower alkyl, (C$_3$–C$_6$)-cycloalkyl, (C$_3$–C$_6$)-cycloalkyl-lower alkyl, amino-lower alkyl, lower alkylamino-lower alkyl, di-lower alkylamino-lower alkyl or aryl-lower alkyl or together with the nitrogen atom are a 5- to 8-membered membered heterocycle optionally containing a further hetero atom or a fused benzene ring, R$^3$ is hydrogen and R$^4$ is lower alkyl or R$^3$ and R$^4$ together are dimethylene or trimethylene and R$^5$ and R$^6$ each independently are hydrogen, halogen, trifluoromethyl, lower alkoxy or nitro, the compounds of formula I having the (S) configuration with reference to the carbon atom denoted by γ when R$^3$ and R$^4$ together are dimethylene or trimethylene, and pharmaceutically acceptable acid addition salts thereof. These compounds and salts have pronounced anxiolytic, anticonvulsant, muscle relaxant and sedative-hypnotic properties.

26 Claims, No Drawings

IMIDAZODIAZEPINES

This application claims the priority of CIP application Ser. No. 08/545,471, filed 20 Nov. 1995, which is a continuation application of Ser. No. 08/400,197, filed 8 Mar. 1995, now abandoned.

DESCRIPTION OF THE INVENTION

The present invention is concerned with imidazodiazepines of the formula

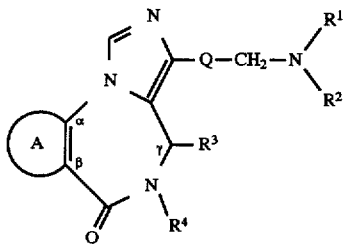

wherein

A together with the two carbon atoms denoted by α and β is one of the residues

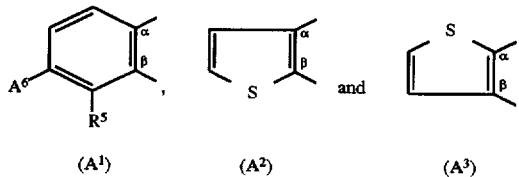

Q is one of the residues

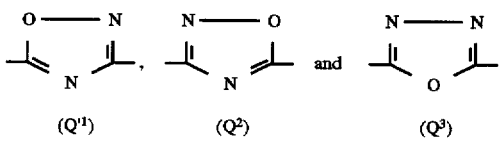

$R^1$ and $R^2$ each independently are hydrogen, lower alkyl, lower alkenyl, lower alkynyl, lower hydroxyalkyl, lower alkoxy-lower alkyl, $(C_3-C_6)$-cycloalkyl, $(C_3-C_6)$-cycloalkyl-lower alkyl, amino-lower alkyl, lower alkylamino-lower alkyl, di-lower alkylamino-lower alkyl or aryl-lower alkyl or together with the nitrogen atom are a 5- to 8-membered heterocycle optionally containing a further hetero atom or a fused benzene ring, $R^3$ is hydrogen and $R^4$ is lower alkyl or $R^3$ and $R^4$ together are dimethylene or trimethylene and $R^5$ and $R^6$ each independently are hydrogen, halogen, trifluoromethyl, lower alkoxy or nitro, the compounds of formula I having the (S) configuration with reference to the carbon atom denoted by γ when $R^3$ and $R^4$ together are dimethylene or trimethylene, and pharmaceutically acceptable acid addition salts thereof.

These compounds and salts have valuable pharmacodynamic properties and exhibit only a low toxicity. They are suitable for therapeutic purposes, especially for anxiolytic and/or anticonvulsant and/or muscle relaxant and/or sedative-hypnotic purposes.

Objects of the present invention are compounds of formula I and pharmaceutically acceptable acid addition salts thereof per se and as therapeutically active substances, the manufacture of these compounds and the use of the substances in accordance with the invention for therapeutic purposes or for the production of corresponding medicaments as well as medicaments containing a compound of formula I or a pharmaceutically acceptable acid addition salt thereof and the production of such medicaments.

The term "lower" denotes residues or compounds with a maximum of 7, preferably a maximum of 4, carbon atoms. The term "alkyl" denotes straight-chain or branched saturated hydrocarbon residues such as methyl, ethyl, n-propyl, iso-propyl, n-butyl, sec.-butyl, iso-butyl, tert.-butyl and the like. The term "alkoxy" denotes alkyl groups bonded via an oxygen atom, such as methoxy, ethoxy and the like. The term "cycloalkyl" denotes saturated cyclic hydrocarbon residues such as cyclopropyl and the like. The terms "alkenyl" and "alkynyl" denote straight-chain or branched hydrocarbon residues which contain a C—C double or, respectively, triple bond, such as allyl, but-2-enyl, 3-methyl-but-2-enyl, propargyl and the like. The term "aryl" denotes a phenyl residue optionally substituted by halogen, trifluoromethyl, lower alkyl or lower alkoxy. The term "halogen" embraces fluorine, chlorine, bromine and iodine. When $R^1$ and $R^2$ together with the nitrogen atom signify a 5- to 8-membered heterocycle optionally containing a further hetero atom or a benzene ring, then this is a residue such as 1-pyrrolidinyl, 1-pyrrolinyl, piperidino, 2,6-dimethylpiperidino, 3,3-dimethylpiperidino, hexamethyleneimin-1-yl, heptamethyleneimin-1-yl, morpholino, 4-methyl-1-piperazinyl, isoindolin-2-yl and the like.

Preferably, Q in formula I is a residue of formula $Q^2$ or of formula $Q^3$. $R^1$ and $R^2$ each preferably are independently lower alkyl, lower hydroxyalkyl alkyl or $(C_3-C_6)$-cycloalkyl-lower alkyl or together with the nitrogen atom are piperidino or isoindolin-2-yl. A together with the two carbon atoms denoted by α and β preferably is a residue of formula $A^1$ in which $R^5$ is hydrogen, chlorine, fluorine, trifluoromethyl or lower alkoxy and $R^6$ is hydrogen or fluorine or is a residue of formula $A^2$. Finally, it is preferred that $R^3$ is hydrogen and $R^4$ is methyl or $R^3$ and $R^4$ together are dimethylene.

Especially preferred compounds of formula I are:

3-(5-Dipropylaminomethyl-1,2,4-oxadiazol-3-yl)-8-fluoro-5-methyl-5,6-dihydro-4H-imidazo[1,5-a][1,4]benzodiazepin-6-one;

(S)-8-chloro-1-(5-dipropylaminomethyl-1,2,4-oxadiazol-3-yl)-12,12a-dihydro-9H,11H-azeto[2,1-c]imidazo[1,5-a][1,4]-benzodiazepin-9-one;

(S)-1-(5-dipropylaminomethyl-1,2,4-oxadiazol-3-yl)-11,11a-dihydro-8H,10H-azeto[1,2-a]imidazo[5,1-c]thieno[3,2-e][1,4]diazepin-8-one;

8-fluoro-5-methyl-3-[5-(piperidin-1-ylmethyl)-1,2,4-oxadiazol-3-yl]-5,6-dihydro-4H-imidazo[1,5-a][1,4]benzodiazepin-6-one;

(S)-1-(5-diallylaminomethyl-1,2,4-oxadiazol-3-yl)-8-chloro-7-fluoro-12,12a-dihydro-9H,11H-azeto[2,1-c]imidazo[1,5-a][1,4]-benzodiazepin-9-one;

3-(5-dipropylaminomethyl-1,2,4-oxadiazol-3-yl)-5-methyl-5,6-dihydro-4H-imidazo[1,5-a][1,4]benzodiazepin-6-one;

3-(5-dipropylaminomethyl-1,3,4-oxadiazol-2-yl)-8-fluoro-5-methyl-5,6-dihydro-4H-imidazo[1,5-c][1,4]benzodiazepin-6-one;

3-(5-diethylaminomethyl-1,2,4-oxadiazol-3-yl)-8-fluoro-5-methyl-5,6-dihydro-4H-imidazo[1,5-a][1,4]benzodiazepin-6-one;

(S)-8-chloro-1-[5-(piperidin-1-yl)methyl-1,2,4-oxadiazol-3-yl]-12,12a-dihydro-9H,11H-azeto[2,1-c]imidazo[1,5-a][1,4]benzodiazepin-9-one;

7-fluoro-5-methyl-3-(5-dipropylaminomethyl-1,2,4-oxadiazol-3-yl)-5,6-dihydro-4H-imidazo[1,5-a][1,4]benzodiazepin-6-one;

7-chloro-3-(5-diethylaminomethyl-1,2,4-oxadiazol-3yl)-5-methyl-5,6-dihydro-4H-imidazo[1,5-a][1,4]benzodiazepin-6-one;

7-chloro-3-(5-dipropylaminomethyl-1,3,4-oxadiazol-2-yl)-5-methyl-5,6-dihydro-4H-imidazo[1,5-a][1,4]benzodiazepin-6-one;

(S)-1-(5-diethylaminomethyl-1,2,4-oxadiazol-3-yl)-11,11a-dihydro-8H,10H-azeto[1,2-a]imidazo[5,1-c]thieno[3,2-e][1,4]diazepin-8-one;

(S)-1-(5-dibutylaminomethyl-1,3,4-oxadiazol-2-yl)-11,11a-dihydro-8H,10H-azeto[1,2-a]imidazo[5,1-c]thieno[3,2-e][1,4]diazepin-8-one;

3-(5-diisopropylaminomethyl-1,2,4-oxadiazol-3-yl)-5-methyl-5,6-dihydro-4H-imidazo[1,5-a][1,4]benzodiazepin-6-one; and 3-(5-diisopropylaminomethyl-1,2,4-oxadiazol-3-yl)-8-fluoro-5-methyl-5,6-dihydro-4H-imidazo[1,5-a][1,4]benzodiazepin-6-one.

Further compounds of formula I which are preferred are:

(S)-1-(5-diallylaminomethyl-1,2,4-oxadiazol-3-yl)-8-chloro-12,12a-dihydro-9H,11H-azeto[2,1-c]imidazo[1,5-a][1,4]benzodiazepin-9-one;

(S)-1-(5-diallylaminomethyl-1,2,4-oxadiazol-3-yl)-8-trifluoromethyl-12,12a-dihydro-9H,11H-azeto[2,1-c]imidazo[1,5-a]-[1,4]benzodiazepin-9-one;

3-(5-diallylaminomethyl-1,2,4-oxadiazol-3-yl)-8-fluoro-5-methyl-5,6-dihydro-4H-imidazo[1,5-a][1,4]benzodiazepin-6-one;

8-fluoro-3-(5-isoindolin-2-ylmethyl-1,2,4-oxadiazol-3-yl)-5-methyl-5,6-dihydro-4H-imidazo[1,5-a][1,4]benzodiazepin-6-one;

(S)-1-(5-diallylaminomethyl-1,2,4-oxadiazol-3-yl)-11,11a-dihydro-8H,10H-azeto[1,2-a]imidazo[5,1-c]thieno[3,2-e][1,4]diazepin-8-one;

3-(5-dipropylaminomethyl-1,2,4-oxadiazol-3-yl)-5-methyl-5,6-dihydro-4H-imidazo[1,5-a]thieno[2,3-f][1,4]diazepin-6-one;

3-(5-dipropylaminomethyl-1,2,4-oxadiazol-3-yl)-5-methyl-7-trifluoromethyl-5,6-dihydro-4H-imidazo[1,5-a][1,4]benzodiazepin-6-one; and (S)-8-chloro-1-(5-dipropylaminomethyl-1,3,4-oxadiazol-2-yl)-12,12a-dihydro-9H, 11H-azeto[2,1-c]imidazo[1,5-a][1,4]benzodiazepin-9-one.

The compounds of formula I above and their pharmaceutically acceptable acid addition salts can be manufactured in accordance with the invention by a) reacting a reactive functional derivative of a carboxylic acid of the general formula

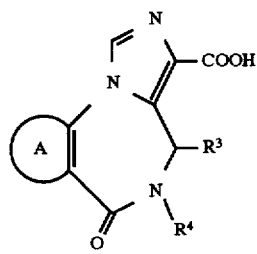

II or

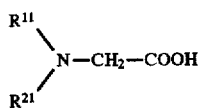

III with an amidoxime of the general formula

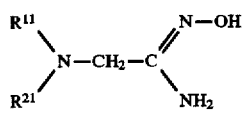

IV or, respectively,

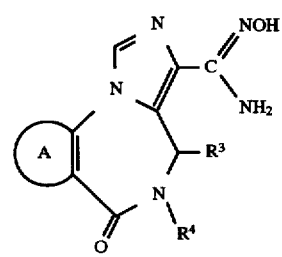

V or with a hydrazide of the general formula

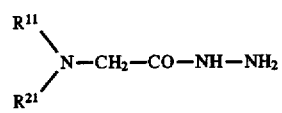

VI or, respectively,

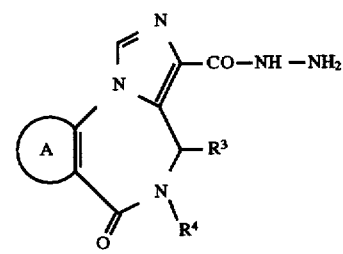

VII wherein A, $R^3$ and $R^4$ have the above significance and $R^{11}$ and $R^{21}$ each signify lower alkyl, lower alkenyl, lower alkynyl, lower alkoxy-lower alkyl, ($C_3$–$C_6$)-cycloalkyl, ($C_3$–$C_6$)-cycloalkyl-lower alkyl, di-lower alkylamino-lower alkyl or aryl-lower alkyl or together with the nitrogen atom signify a 5- to 8-membered heterocycle optionally containing a further hetero atom or a fused benzene ring.

b) reacting a compound of the general formula

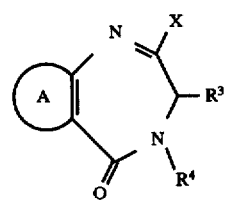

VIII wherein A, $R^3$ and $R^4$ have the above significance and X signifies a leaving group, in the presence of a base with an isonitrile of the general formula

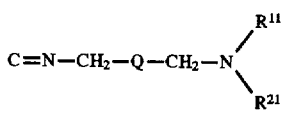

wherein Q, $R^{11}$ and $R^{21}$ have the above significance, or c) reacting a compound of the general formula

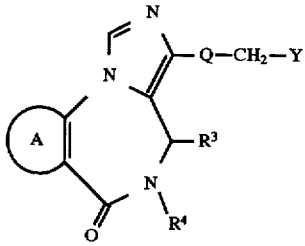

wherein A, Q, $R^3$ and $R^4$ have the above significance and Y signifies a leaving group, with an amine of the general formula

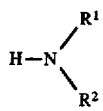

wherein $R^1$ and $R^2$ have the above significance, or d) cleaving off the protecting group(s) from a compound of the general formula

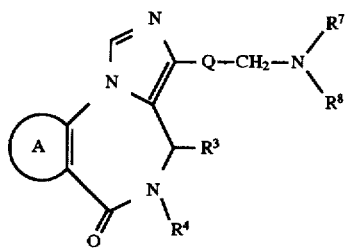

wherein A, Q, $R^3$ and $R^4$ have the above significance and $R^7$ signifies a protecting group, protected lower hydroxyalkyl, protected amino-lower alkyl or protected lower alkylamino-lower alkyl and $R^8$ signifies hydrogen, lower alkyl, lower alkenyl, lower alkynyl, protected lower hydroxyalkyl, lower alkoxy-lower alkyl, ($C_3$–$C_6$)-cycloalkyl, ($C_3$–$C_6$)-cycloalkyl-lower alkyl, protected amino-lower alkyl, protected lower alkylamino-lower alkyl, di-lower alkylamino-lower alkyl or aryl-lower alkyl or $R^7$ and $R^8$ together signify a protecting group, or e) appropriately N-alkylating a compound of the general formula

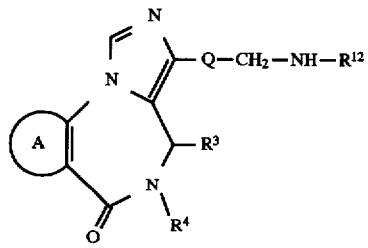

wherein A, Q, $R^3$ and $R^4$ have the above significance and $R^{12}$ signifies hydrogen, lower alkyl, lower alkenyl, lower alkynyl, lower hydroxyalkyl, lower alkoxy-lower alkyl, ($C_3$–$C_6$)-cycloalkyl, ($C_3$–$C_6$)-cycloalkyl-lower alkyl, amino-lower alkyl, lower alkylamino-lower alkyl, di-lower alkyl-amino-lower alkyl or aryl-lower alkyl, or f) reducing a compound of the general formula

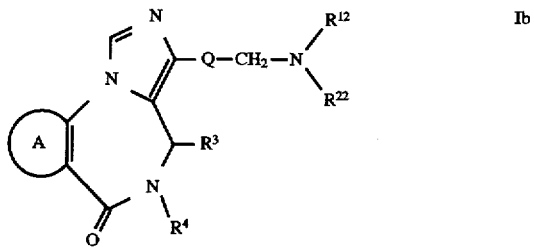

wherein A, Q, $R^3$ and $R^4$ and $R^{12}$ have the above significance and $R^{22}$ signifies lower alkenyl or lower alkynyl, and, if desired, g) converting a compound of general formula I into a pharmaceutically usable acid addition salt.

Compounds of formula I in which $R^1$ and $R^2$ each signify lower alkyl, lower alkenyl, lower alkynyl, lower alkoxy-lower alkyl, ($C_3$–$C_6$)-cycloalkyl, ($C_3$–$C_6$)-cycloalkyl-lower alkyl, di-lower alkylamino-lower alkyl or aryl-lower alkyl or together with the nitrogen atom signify a 5- to 8-membered heterocycle optionally containing a further hetero atom or a fused benzene ring are manufactured in accordance with process variant a) by synthesizing the oxadiazole residue Q from compounds of formulae II and IV, from compounds of formulae III and V or from compounds of formula II and VI or III and VII.

The reactive functional derivatives of the carboxylic acids of formulae II and III which are used are conveniently the corresponding imidazolides which can be prepared according to known methods from the respective free carboxylic acids, for example by reaction with 1,1'-carbonyl-diimidazole in an inert organic solvent such as N,N-dimethylformamide.

Carboxylic acid chlorides, which can be prepared from the corresponding free carboxylic acids by means of thionyl chloride, can, however, also be used, for example, as reactive functional derivatives.

The reaction of a reactive functional derivative of a carboxylic acid of formula II or III with an amidoxime of formula IV or, respectively, V is conveniently effected by heating for several hours to about 70° to 130° C. in an inert solvent such as N,N-dimethylformamide. The non-cyclized condensation product which results as an intermediate is conveniently not isolated, but is cyclized spontaneously under the prevailing reaction conditions.

The reaction of a reactive functional derivative of a carboxylic acid of formula II or III with a hydrazide of formula VI or, respectively VII is conveniently effected at room temperature in an inert organic solvent such as N,N-dimethylformamide. The non-cyclized condensation product which thereby results can be isolated and thereupon cyclized, conveniently by heating to about 100° C. with polyphosphoric acid for 1 to several hours.

Compounds of formula I in which $R^1$ and $R^2$ each signify lower alkyl, lower alkenyl, lower alkynyl, lower alkoxy-lower alkyl, ($C_3$–$C_6$)-cycloalkyl, ($C_3$–$C_6$)-cycloalkyl-lower alkyl, di-lower alkylamino-lower alkyl or aryl-lower alkyl or together with the nitrogen atom signify a 5- to 8-membered heterocycle optionally containing a further hetero atom or a fused benzene ring are also obtained according to process variant b). The leaving group denoted by X in formula VIII is, for example, a readily cleavable residue of a phosphoric acid derivative, for example, a group of the formula

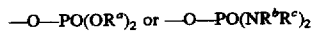

wherein $R^a$ signifies lower alkyl or aryl and $R^b$ and $R^c$ each signify lower alkyl, lower alkenyl (such as allyl) or aryl or together with the nitrogen atom signify a 5- to 8-membered heterocycle optionally containing a further hetero atom (such as morpholine), a halogen atom, an alkylthio group, an aralkylthio group, a N-nitrosoalkylamino group, an alkoxy group, a mercapto group and the like. The reaction of a compound of formula VIII with an isonitrile of formula IX is effected in an inert solvent such as dimethylformamide, hexamethylphosphoric acid triamide, dimethyl sulphoxide, tetrahydrofuran or in any other suitable organic solvent and in the presence of a base which is sufficiently strongly basic to form the anion of the isonitrile. Suitable bases are alkali metal alkoxides such as sodium methoxide or potassium t-butoxide, alkali metal hydrides such as sodium hydride, alkali metal amides such as lithium amide or lithium diisopropylamide, butyllithium, tertiary amines such as 1,8-diazabicyclo[5.4.0]undec-7-ene (1,5-5), and the like. The reaction temperature conveniently lies between about −70° C. and about room temperature.

Compounds of formula I in which $R^1$ and $R^2$ have the above significance are obtained in accordance with process variant c). The leaving group denoted by Y in formula X is conveniently a halogen atom, preferably a chlorine or bromine atom, or a readily cleavable sulphonyloxy group such as methanesulphonyloxy, benzenesulphonyloxy, p-toluenesulphonyloxy or the like. The reaction of a compound of formula X with an amine of formula XI is effected in the presence of an inert solvent such as N,N-dimethylformamide formamide and in the presence of a base, conveniently an organic base, for example, a tertiary amine such as N-ethyldiisopropyl-amine or the like, whereby an excess of the amine of formula XI can also serve as the organic base.

Compounds of formula I in which $R^1$ signifies hydrogen lower hydroxyalkyl, amino-lower alkyl or lower alkylamino-lower alkyl and $R^2$ signifies hydrogen, lower alkyl, lower alkenyl, lower alkynyl, lower hydroxyalkyl, lower alkoxy-lower alkyl, $(C_3-C_6)$-cycloalkyl, $(C_3-C_6)$-cycloalkyl-lower alkyl, amino-lower alkyl, lower alkylamino-lower alkyl, di-lower alkylamino-lower alkyl or aryl-lower alkyl are obtained in accordance with process variant d). Suitable protecting groups and methods for their cleavage will be familiar to any person skilled in the art, although of course there can be used only those protecting groups which can be cleaved off by methods under the conditions of which other structural elements in the compounds of formula XII are not affected.

The tert.-butoxycarbonyl group (BOC), which can be cleaved off by means of trifluoroacetic acid, is, for example, a suitable N-protecting group.

The tert.-butyl group (tBu), which can also be cleaved off by means of trifluoroacetic acid, is, for example, a suitable O-protecting group.

When $R^7$ and $R^8$ together signify a protecting group, then the residue $NR^7R^8$ signifies, for example, a phthalimido group, which can be cleaved to the $NH_2$ group by means of methylamine.

Compounds of formula I in which at least one of $R^1$ and $R^2$ is different from hydrogen are obtained in accordance with process variant e). Suitable alkylating agents and alkylating methods will be familiar to any person skilled in the art. Particularly suitable alkylating agents are corresponding halides such as propyl bromide, Propyl iodide, butyl iodide, allyl bromide, crotyl bromide, 4-bromo-1-butene, 3,3-dimethylallyl bromide, propargyl bromide, cyclopropylmethyl bromide, benzyl bromide or α,α'-dibromo-o-xylene (whereby by means of the latter a $NH_2$ group can be converted into an isoindolin-2-yl group). The alkylation is effected in the presence of a base, conveniently an organic base such as N-ethyldiisopropylamine, 1,8-diazabicyclo[5.4.0]undec-7-ene(1,5-5) or the like. Furthermore, the alkylation is conveniently effected in an inert solvent such as N,N-dimethylformamide.

Compounds of formula I in which at least one of $R^1$ and $R^2$ signifies lower alkyl are obtained in accordance with process variant f) from corresponding compounds of formula I in which at least one of $R^1$ and $R^2$ signifies lower alkenyl or lower alkynyl, that is from compounds of formula Ib, by reduction of the C—C double or triple bond. This reduction is conveniently effected by catalytic hydrogenation, for example in the presence of a palladium catalyst such as Pd/C. Furthermore, this reduction is effected in an inert solvent such as ethyl acetate.

The compounds of formula I can be converted into pharmaceutically acceptable acid addition salts in accordance with process variant g). Not only salts with inorganic acids, but also salts with organic acids come into consideration. Examples of such salts are the hydrochlorides, hydrobromides sulfates, nitrates, citrates, acetates, maleates, succinates, methanesulphonates, p-toluenesulphonates and the like. These salts can be manufactured according to known methods and which will be familiar to any person skilled in the art.

The starting materials of formulae III, IV, VI and XI above belong to generally known classes of compound and will therefore be readily accessible to any person skilled in the art. The starting materials of formulae II, V, VII and VIII also belong to known classes of compound (see e.g. EP 0 150 040 A2 and EP 0 027 214 A1). The starting materials of formula XII can be prepared, for example, in analogy to process variants a) and b) described previously. The preparation of starting materials of formulae IX and X is illustrated hereinafter on the basis of Reaction Schemes 1 to 3 and, respectively, 4. Moreover, many of the Examples described hereinafter contain detailed information with respect to the preparation of specific starting materials.

Reaction Scheme 1
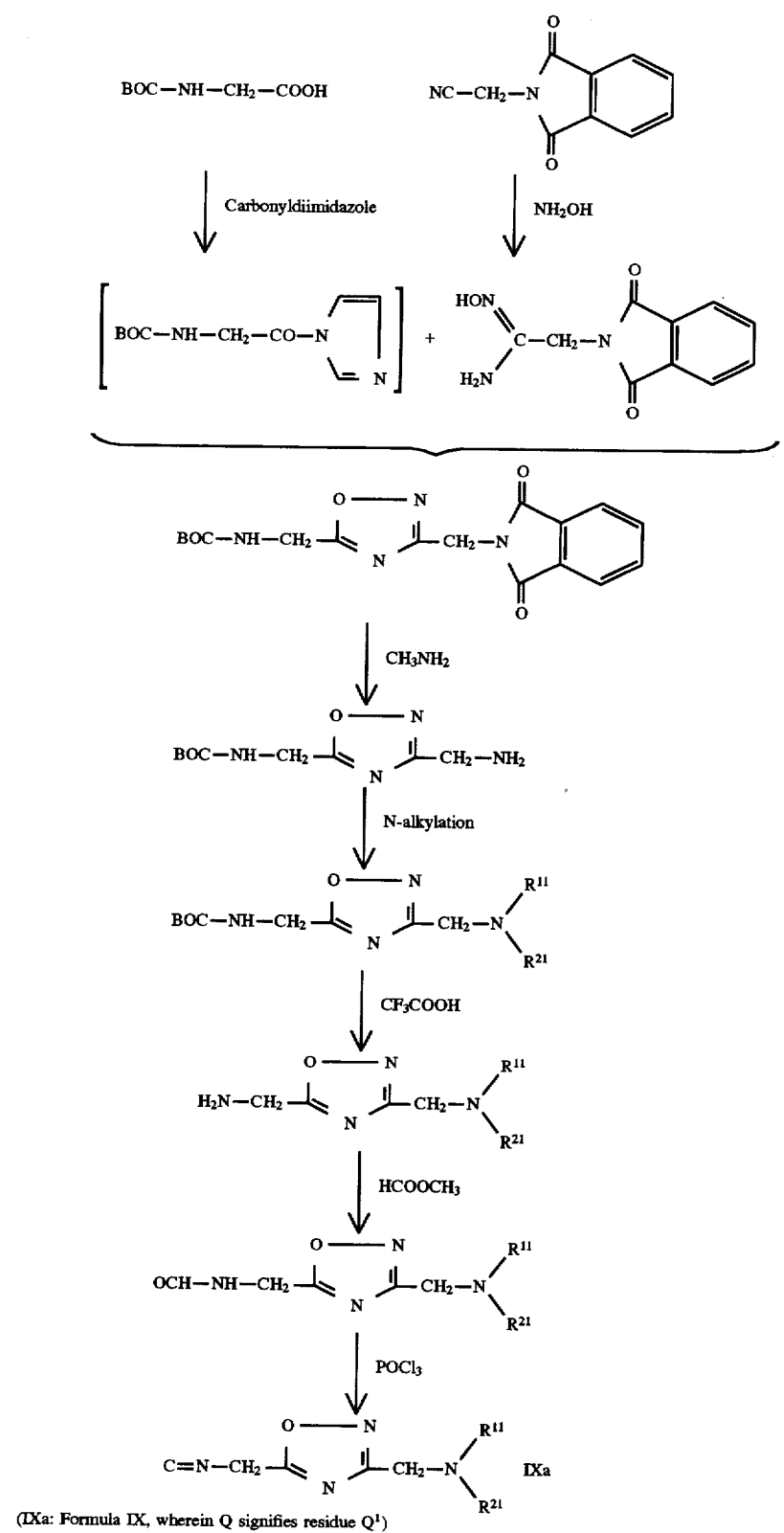
(IXa: Formula IX, wherein Q signifies residue Q¹)

Reaction Scheme 2
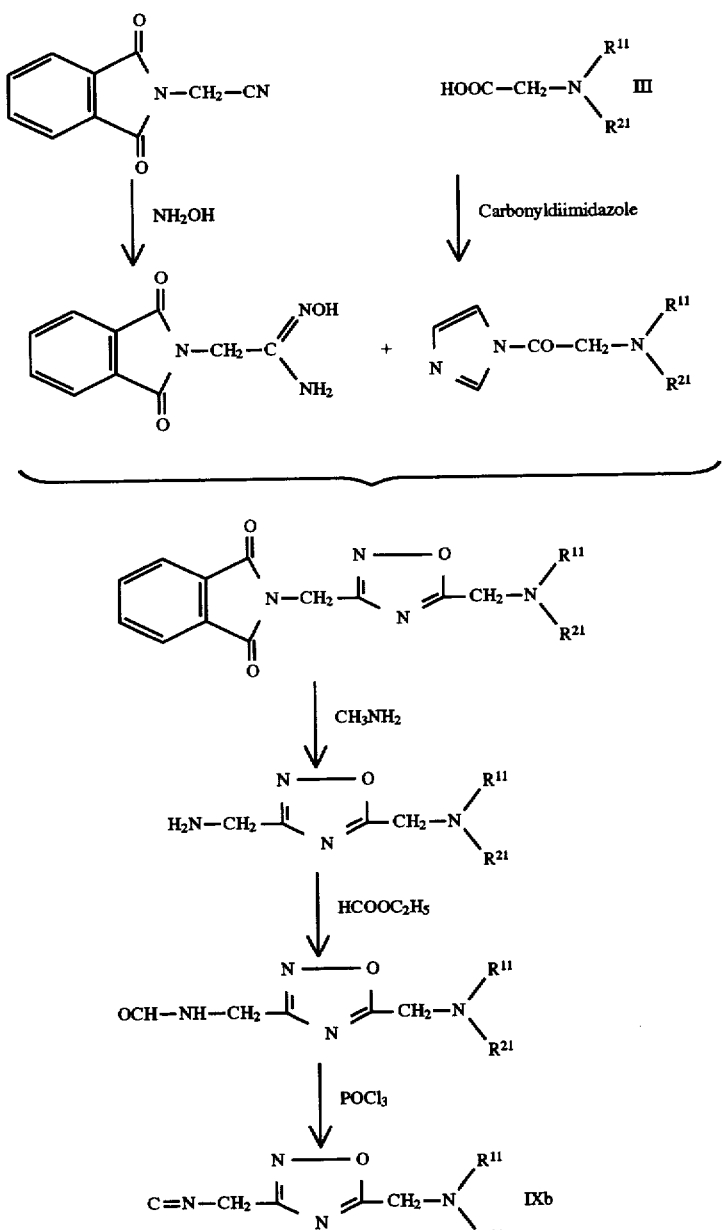
(IXb: Formula IX, wherein Q signifies residue $Q^2$)
Reaction Scheme 3
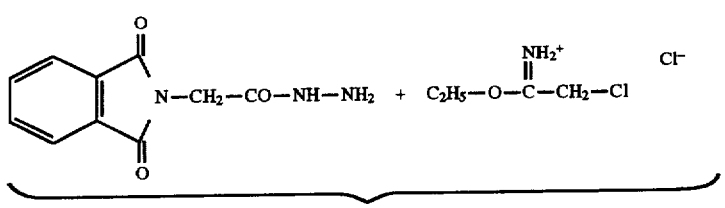

-continued
Reaction Scheme 3
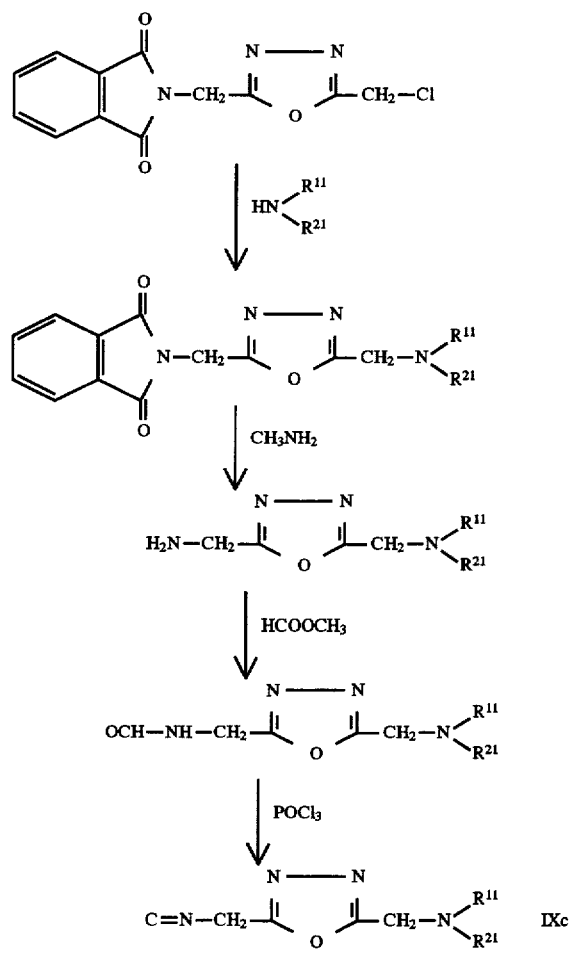
(IXc: Formula IX, wherein Q signifies residue $Q^3$)
Reaction Scheme 4
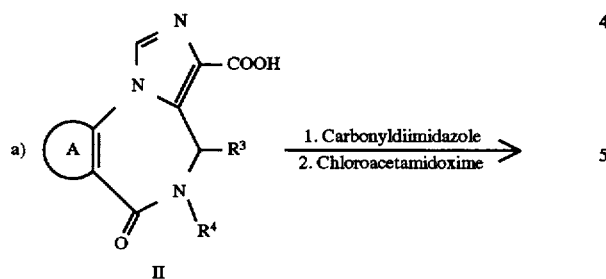
-continued
Reaction Scheme 4
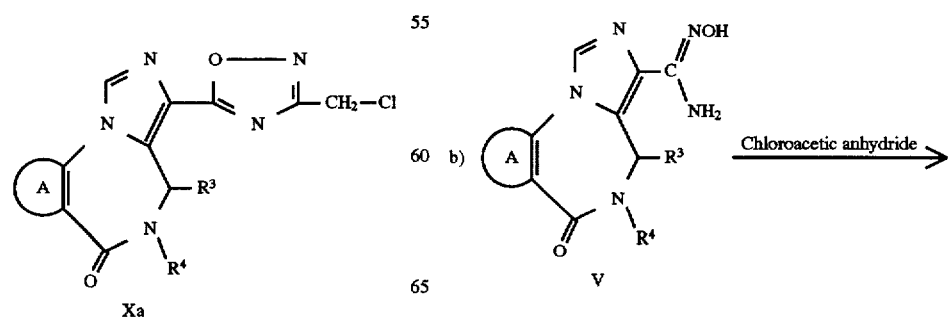

-continued
Reaction Scheme 4

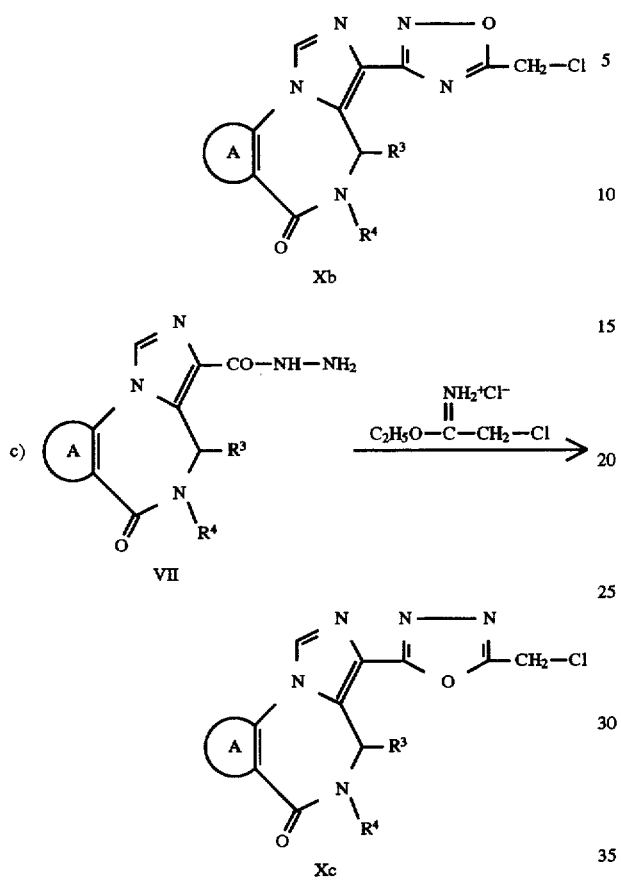

(Xa, Xb and Xc: Formula X, wherein Y signifies chlorine and Q signifies the residue $Q^1$ or $Q^2$ or $Q^3$)

As mentioned earlier, the compounds of formula I have valuable pharmacodynamic properties and exhibit only a low toxicity. They have as a common feature a pronounced affinity to the central benzodiazepine receptors and, because of their agonistic activity at these receptors, they have pronounced anxiolytic, anticonvulsant, muscle relaxant and sedative-hypnotic hypnotic properties. They form acid addition salts which have very good water solubility and are therefore particularly suitable for the production of aqueous injection solutions.

The affinity of compounds of general formula I to the central benzodiazepine receptors was established in vitro according to the methods described in Nature 294, 763–765 (1981) and J. Neurochemistry 37, 714–722 (1981). According to these methods, the inhibition of the binding of tritiated flumazenil to the specific benzodiazepine receptors in the cortex of rats by the respective test substances is determined. The $IC_{50}$ ("50% inhibiting concentration") denotes that concentration of the respective test substance which brings about a 50 per cent inhibition of the specific binding of tritiated flumazenil to the specific benzodiazepine receptors in the cortex of rats.

The sedative/muscle relaxant properties of the compounds of formula I in accordance with the invention can be determined, for example, in the rotating rod test. Mice weighing 19–21 g are used for this test. They have free access to feed and drinking water up to 1 hour before the beginning of the test. They are brought into the test laboratory at least 30 minutes before the test. In the rotating rod test the animals are placed on a horizontally arranged, smooth metal rod having a diameter of 3 cm, which is rotated at 2 revolutions per minute. Initially, the animals are given the opportunity of familiarizing themselves with the test situation for 30 seconds. Subsequently, those animals which succeed in remaining on the rod for at least 1 minute are selected. These animals are then given the test preparations intravenously in different dosages. At various points in time it is then determined whether the animals are able to remain on the rod for a minimum period (minimum period: 10 seconds; from 5 minutes after administration: 1 minute.). That dosages at which 50% of the animals are capable of remaining on the rod (ED 50) is determined.

The results which have been obtained with representative members of the class of compound defined by general formula I in the tests described previously are compiled in the following Table.

TABLE

| Compound | Affinity to benzodiazepine receptors IC50 nmol/l | Rotating rod test, ED50 in mg/kg, i.v., determined at the following points in time after administration | | | | | | | |
|---|---|---|---|---|---|---|---|---|---|
| | | 15 sec | 30 sec | 60 sec | 2 min | 5 min | 15 min | 30 min | 60 min |
| A | 13 | 0.3 | 0.3 | 0.7 | 0.8 | 1.4 | 2.1 | 7.3 | >10 |
| B | 4.3 | 0.1 | 0.1 | 0.2 | 0.4 | 0.7 | 3.5 | >10 | >10 |
| C | 50 | 0.8 | 0.8 | 1.2 | 1.6 | 3.2 | ≧10 | >10 | >10 |
| D | 3.3 | 0.2 | 0.2 | 0.3 | 0.3 | 0.8 | 2.6 | >10 | >10 |
| E | 10 | 0.2 | 0.3 | 0.3 | 0.4 | 0.8 | 3.9 | ≧10 | >10 |
| F | 6.9 | 0.2 | 0.4 | 0.5 | 0.9 | ≧10 | >10 | >10 | >10 |
| G | 18.3 | 0.3 | 0.3 | 0.7 | 1.1 | 3.6 | ≧10 | >10 | >10 |
| H | 25 | 0.1 | 0.2 | 0.4 | 0.7 | 1.2 | 4.3 | 5.1 | >10 |
| I | 4.4 | 0.1 | 0.7 | 0.7 | 1.0 | 1.1 | 3.1 | ≧10 | >10 |
| J | 2.3 | 0.1 | 0.2 | 0.3 | 0.4 | 1.1 | >10 | >10 | >10 |
| K | 1.4 | 0.1 | 0.3 | 0.3 | 0.6 | 2.0 | ≧10 | ≧10 | ≧10 |
| L | 4.5 | 0.3 | 0.4 | 0.6 | 1.5 | 5.0 | >10 | >10 | >10 |
| M | 6.5 | 0.2 | 0.3 | 0.3 | 1.1 | 2.1 | >10 | >10 | >10 |
| N | 4.8 | 0.3 | 0.3 | 0.3 | 0.6 | 2.4 | >10 | >10 | >10 |
| O | 6.4 | 0.3 | 0.5 | 0.7 | 1.0 | 3.0 | >10 | >10 | >10 |
| P | 4.1 | 0.1 | 0.2 | 0.3 | 0.7 | 1.0 | 4.3 | ≧10 | >10 |

TABLE-continued

| | Affinity to benzodiazepine receptors | Rotating rod test, ED50 in mg/kg, i.v., determined at the following points in time after administration | | | | | | |
|---|---|---|---|---|---|---|---|---|
| Compound | IC50 nmol/l | 15 sec | 30 sec | 60 sec | 2 min | 5 min | 15 min | 30 min | 60 min |

A: (S)-8-Chloro-1-(5-dipropylaminomethyl-1,2,4-oxadiazol-3-yl)-12,12a-dihydro-9H,11H-azeto[2,1-c]imidazo[1,5-a][1,4]benzodiazepin-9-one.
B: (S)-1-(5-Dipropylaminomethyl-1,2,4-oxadiazol-3-yl)-11,11a-dihydro-8H,10H-azeto[1,2-a]imidazo[5,1-c]thieno[3,2-e][1,4]diazepin-8-one.
C: 8-Fluoro-5-methyl-3-[5-(piperidin-1-ylmethyl)-1,2,4-oxadiazol-3-yl)-5,6-dihydro-4H-imidazo[1,5-a][1,4]benzodiazepin-6-one.
D: 3-(5-Dipropylaminomethyl-1,2,4-oxadiazol-3-yl)-8-fluoro-5-methyl-5,6-dihydro-4H-imidazo[1,5-a][1,4]-benzodiazepin-6-one.
E: (S)-1-(5-Diallylaminomethyl-1,2,4-oxadiazol-3-yl)-8-chloro-7-fluoro-12,12a-dihydro-9H,11H-azeto[2,1-c]imidazo[1,5-a]-[1,4]benzodiazepin-9-one.
F: 3-(5-Dipropylaminomethyl-1,2,4-oxadiazol-3-yl)-5-methyl-5,6-dihydro-4H-imidazo[1,5-a][1,4]benzodiazepin-6-one.
G: 3-(5-Dipropylaminomethyl-1,3,4-oxadiazol-2-yl)-8-fluoro-5-methyl-5,6-dihydro-4H-imidazo[1,5-c][1,4]benzodiazepin-6-one.
H: 3-(5-Diethylaminomethyl-1,2,4-oxadiazol-3-yl)-8-fluoro-5-methyl-5,6-dihydro-4H-imidazo[1,5-a][1,4]benzodiazepin-6-one.
I: (S)-8-Chloro-1-[5-(piperidin-1-yl)methyl-1,2,4-oxadiazol-3-yl]-12,12a-dihydro-9H,11H-azeto[2,1-c]imidazo[1,5-a][1,4]benzodiazepin-9-one.
J: 7-Fluoro-5-methyl-3-(5-dipropylaminomethyl-1,2,4-oxadiazol-3-yl)-5,6-dihydro-4H-imidazo[1,5-a][1,4]benzodiazepin-6-one.
K: 7-Chloro-3-(5-diethylaminomethyl-1,2,4-oxadiazol-3-yl)-5-methyl-5,6-dihydro-4H-imidazo[1,5-a][1,4]benzodiazepin-6-one.
L: 7-Chloro-3-(5-dipropylaminomethyl-1,3,4-oxadiazo-2-yl)-5-methyl-5,6-dihydro-4H-imidazo[1,5-a][1,4]benzodiazepin-6-one.
M: (S)-1-(5-Diethylaminomethyl-1,2,4-oxadiazol-3-yl)-11,11a-dihydro-8H,10H-azeto[1,2-a]imidazo[5,1-c]thieno[3,2-e][1,4]diazepin-8-one.
N: (S)-1-(5-Dibutylaminomethyl-1,3,4-oxadiazol-2-yl)-11,11a-dihydro-8H,10H-azeto[1,2-a]imidazo[5,1-c]thieno[3,2-e][1,4]diazepin-8-one.
O: 3-(5-Diisopropylaminomethyl-1,2,4-oxadiazol-3-yl)-5-methyl-5,6-dihydro-4H-imidazo[1,5-a][1,4]benzodiazepin-6-one.
P: 3-(5-Diisopropylaminomethyl-1,2,4-oxadiazol-3-yl)-8-fluoro-5-methyl-5,6-dihydro-4H-imidazo[1,5-a][1,4]benzodiazepin-6-one.

From the above Table it will be evident that compounds A to P display a sedative activity which sets in very rapidly and lasts only a relatively short time.

Having regard to their agonistic activity on the benzodiazepine receptors, the compounds of formula I can be used as sedatives/hypnotics, anticonvulsants, muscle relaxants and anxiolytics. They are suitable, for example, as rapid, but short acting hypnotics for peroral administration, but especially—in the form of aqueous solutions of their acid addition salts—as injectable short-term hypnotics for pre-medication, sedation as well as narcosis induction and narcosis maintenance; preferred possible applications are thus premedication prior to narcosis induction, basal sedation prior to diagnostic or surgical intervention with or without local anaesthesia, long-term sedation in intensive care nursing wards, use as an induction agent in inhalation narcosis or as a sleep-inducing component in combination narcosis (including total intravenous anaesthesia) etc.

A series of compounds of formula I, including the above compounds A, B, D and E, were administered to mice and rats in doses of 32 and 100 mg/kg i.v. without fatalities occurring.

The compounds of formula I and pharmaceutically acceptable acid addition salts thereof can be used as medicaments, for example, in the form of pharmaceutical preparations. The pharmaceutical preparations can be administered orally, for example, in the form of tablets, coated tablets, dragées, hard and soft gelatine capsules, solutions, emulsions or suspensions. The administration can, however, also be effected rectally, for example, in the form of suppositories, or parenterally, for example, in the form of injection solutions.

The compounds of formula I and pharmaceutically acceptable acid addition salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, saccharose, invert sugar, glucose and the like. Adjuvants such as alcohols, polyols, glycerol, vegetable oils and the like can be used for aqueous injection solutions of water-soluble acid addition salts of compounds of formula I, but as a rule are not necessary. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, coating agents or antioxidants. They can also contain other therapeutically valuable substances.

As mentioned earlier, medicaments containing a compound of formula I or a pharmaceutically acceptable acid addition salt thereof and a therapeutically inert excipient are also an object of the present invention, furthermore also a process for the production of such medicaments which comprises bringing one or more compounds of formula I or pharmaceutically acceptable acid addition salts thereof and, if desired, one or more other therapeutically valuable substances into a galenical administration form together with one or more therapeutically inert carriers.

As mentioned earlier, the compounds of formula I and pharmaceutically acceptable acid addition salts thereof can be used in accordance with the invention for therapeutic purposes, especially for anxiolytic and/or anticonvulsant and/or muscle relaxant and/or sedative-hypnotic purposes. The dosage can vary within wide limits and will, of course, be fitted to the individual requirements in each particular case. In general, in the case of intravenous administration a daily dosage of about 1 mg to 1000 mg should be appropriate.

Finally, as mentioned earlier, the use of compounds of formula I and of pharmaceutically usable acid addition salts thereof for the production of medicaments, especially of anxiolytic and/or anticonvulsant and/or muscle relaxant and/or sedative-hypnotic medicaments, is also an object of the invention.

The following Examples are intended to illustrate the present invention in more detail, but are not intended to limit its scope in any manner. All temperatures are given in degrees Celsius.

EXAMPLE 1 a) 1.89 g (10 mmol) of BOC-sarcosine were dissolved in 10 ml of N,N-dimethylformamide, treated portionwise with 1.63 g (10 mmol) of 1,1'-carbonyldiimidazole and stirred at 50° C. for 20'. After adding 3.05 g (10 mmol) of 7-chloro-5,6-dihydro-5-methyl-6-oxo-4H-imidazo[1,5-a][1,4]benzodiazepine-3-carboxamidoxime the mixture was stirred at 90° for a further 7 hours. The reaction mixture was cooled and poured into 300 ml of water. The suspension obtained was filtered and the crystals were rinsed with water and dried. There were obtained 3.16 g (69%) of 7-chloro-5,6-dihydro-5-methyl-3-(5-N-BOC-N-methylaminomethyl-1,2,4-oxadiazol- 3-yl)-4H-imidazo[1,5-a][1,4]benzodiazepin-6-one of m.p. 114°–117°.

b) 3.09 g (6.73 mmol) of 7-chloro-5,6-dihydro-5-methyl-3-(5-N-BOC-N-methylaminomethyl-1,2,4-oxadiazol-3-yl)-4H-imidazo[1,5-a][1,4]benzodiazepin-6-one were stirred for 2.5 hours in 20 ml of trifluoroacetic acid at room temperature. The solution was concentrated, whereupon the residue was taken up in water and washed twice with methylene chloride. The aqueous phase was made alkaline with 25% ammonia and extracted four times with methylene chloride. After drying and evaporating the combined organic phases and recrystallizing the residue from methanol there were obtained 1.3 g (54%) of 7-chloro-5,6-dihydro-5-methyl-3-(5-methylaminomethyl-1,2,4-oxadiazol-3-yl)-4H-imidazo[1,5-a][1,4]benzodiazepin-6-one of m.p. 192°–193°.

EXAMPLE 2 a) 4.60 g (16.95 mmol) 5,6-dihydro-5-methyl-6-oxo-4H-imidazo[1,5-a][1,4]benzodiazepine-3-carboxamidoxime were stirred with 3.19 g (18.65 mmol) of chloroacetic anhydride in 25 ml of N,N-dimethylformamide at room temperature for 30 minutes and at 105° for 2 hours. The reaction mixture was evaporated, the residue was dissolved in methylene chloride and the solution was washed with saturated sodium bicarbonate solution. After drying over magnesium sulfate the solution was concentrated and the crystalline residue was chromatographed on silica gel while eluting with ethyl acetate. There were obtained 3.94 g (70%) of 3-(5-chloromethyl-1,2,4-oxadiazol-3-yl)-5,6-dihydro-5-methyl-4H-imidazo[1,5-a][1,4]benzodiazepin-6-one of m.p. 208°–209°.

b) 3.3 g (10 mmol) of 3-(5-chloromethyl-1,2,4-oxadiazol-3-yl)-5,6-dihydro-5-methyl-4H-imidazo[1,5-a][1,4]benzodiazepin-6-one were stirred with 5.06 g (50 mmol) of dipropylamine in 20 ml of N,N-dimethylformamide at room temperature for 4 hours. The reaction mixture was evaporated and the residue was chromatographed on silica gel while eluting with ethyl acetate. There were obtained 3.65 g (92%) of 3-(5-dipropylaminomethyl-1,2,4-oxadiazol-3-yl)-5-methyl-5,6-dihydro-4H-imidazo[1,5-a][1,4]benzodiazepin-6-one of melting point 130°–132°, which was converted into the hydrochloride of m.p. 213°–215°.

EXAMPLE 3

1.4 g (13.5 mmol) of N,N-dimethylglycine were suspended in 20 ml of N,N-dimethylformamide, treated with 2.6 g (15.9 mmol) of 1,1'-carbonyldiimidizole and stirred at room temperature for 1 hour and at 75° for 1 hour. 3.9 g (12.3 mmol) of (S)-8-chloro-12,12a-dihydro-9-oxo-9H,11H-azeto[2,1-c]imidazo[1,5-a][1,4]-benzodiazepine-1-carboxamidoxime were added and the mixture was stirred at 90° overnight. By concentration of the reaction mixture and chromatography of the residue on silica gel while eluting with methylene chloride and methanol 19/1 there were obtained, after recrystallization from ethyl acetate, 2.53 g (54%) of (S)-8-chloro-12,12a-dihydro-1-(5-dimethylaminomethyl-1,2,4-oxadiazol-3-yl)-9H,11H-azeto[2,1-c]imidazo[1,5-a][1,4]benzodiazepin-9-one of melting point 127°–129°, which was converted into the hydrochloride of m.p. 178°.

EXAMPLE 4

2.55 g (13.5 mmol) of 1-pyrrolidine-acetic acid were dissolved in 20 ml of N,N-dimethylformamide and treated portionwise with 2.6 g (15.9 mmol) of 1,1'-carbonyldiimidazole. After stirring for 45 minutes 3.9 g (12.3 mmol) of (S)-8-chloro-12,12a-dihydro-9-oxo-9H,11H- azeto[2,1-c]imidazo[1,5-a][1,4]benzodiazepine-1-carboxamidoxime were added and the mixture was stirred at 90° overnight. 0.2 g of p-toluenesulphonic acid was added and the mixture was stirred at 90° for a further 4 hours. The reaction mixture was concentrated. By chromatography of the residue on silica gel while eluting with methylene chloride/methanol 19/1 and recrystallization from ethyl acetate and hexane there were obtained 1.6 g (32%) of (S)-8-chloro-12,12a-dihydro-1-[5-(pyrrolidin-1-ylmethyl)-1,2,4-oxadiazol-3-yl]-9H,11H-azeto[2,1-c]imidazo[1,5-a][1,4]benzodiazepin-9-one of m.p. 117°–120°, which was converted into the hydrochloride.

EXAMPLE 5

1.4 g (13.5 mmol) of N,N-dimethylglycine were dissolved in 20 ml of N,N-dimethylformamide and treated portionwise with 2.6 g (15 mmol) of 1,1'-carbonyldiimidazole. After completion of the $CO_2$ elimination the solution was stirred at 70° for 30'. Then, 4.02 g (15 mmol) of (S)-8-chloro-11,12,13,13a-tetrahydro-9-oxo-9H-imidazo[1,5-a]pyrrolo[2,1-c][1,4]benzodiazepine-1-carboxamidoxime were added and the mixture was stirred at 90° overnight. By evaporation of the solution and chromatography of the residue on 340 g of silica gel while eluting with methylene chloride/methanol 19/1 there were obtained 1.99 g (40%) of (S)-8-chloro-1-(5-dimethylaminomethyl-1,2,4-oxadiazol-3-yl)-11,12,13,13a-tetrahydro-9H-imidazo[1,5-a]pyrrolo[2,1-c][1,4]-benzodiazepin-9-one, which was converted into the hydrochloride of m.p. 261°.

EXAMPLE 6 a) 3.5 g (20 mmol) of BOC-glycine were dissolved in 20 ml of N,N-dimethylformamide and treated portionwise with 3.35 g (20 mmol) of 1,1'-carbonyldiimidazole. After stirring at 45° for 10 minutes 6.35 g (20 mmol) of (S)-8-chloro-12, 12a-dihydro-9-oxo-9H,11H-azeto[2,1-c]imidazo[1,5-a][1, 4]benzodiazepine-1-carboxamidoxime were added and the mixture was stirred at 90° overnight. The reaction mixture was concentrated; the residue was dissolved in methylene chloride and the solution was washed three times with water, dried over magnesium sulfate and evaporated. By chromatography of the residue on silica gel while eluting with ethyl acetate there were obtained 7.5 g (82%) of (S)-1-(5-BOC-aminomethyl-1,2,4-oxadiazol-3-yl)-8-chloro-12,12a-dihydro-9H,11H-azeto[2,1-c]imidazo[1,5-a][1,4] benzodiazepine-9-one, which was used in the next step without further purification.

b) 7.29 g (16 mmol) of crude (S)-1-(5-BOC-aminomethyl-1,2,4-oxadiazol-3-yl)-8-chloro-12,12a-dihydro-9H,11 H-azeto-[2,1-c]imidazo[1,5-a][1,4] benzodiazepin-9-one were stirred for 2 hours in 25 ml of trifluoroacetic acid. The solution was concentrated, the residue was taken up in water and the aqueous solution was washed twice with methylene chloride. The aqueous phase was made alkaline with 25% ammonia and extracted seven times with methylene chloride. By drying and evaporating the combined organic phases there were obtained 5.12 g (90%) of (S)-1-(5-aminomethyl-1,2,4-oxadiazol-3-yl)-8-chloro-12,12a-dihydro-9H,11H-azeto[2,1-c]imidazo[1,5-a] [1,4]benzodiazepin-9-one of m.p. 212°–214°, which was converted into the hydrochloride of m.p. 252°–255°.

EXAMPLE 7 a) 3.8 g (20 mmol) of BOC-sarcosine were dissolved in 20 ml of N,N-dimethylformamide and treated portionwise with 3.5 g (21.6 mmol) of 1,1'-carbonyldiimidazole. After stirring at 45° for 10 minutes 6.35 g (20 mmol) of (S)-8-chloro-12, 12a-dihydro-9-oxo-9H,11H-azeto[2,1-c]imidazo[1,5-a][1, 4]benzodiazepine-1-carboxamidoxime were added and the mixture was stirred at 90° overnight. By concentration of the reaction solution and chromatography of the residue on silica gel while eluting with ethyl acetate there were obtained 7.58 g (80%) of (S)-8-chloro-12,12a-dihydro-1-[5-(N-BOC-N-methyl)-aminomethyl-1,2,4-oxadiazol-3-yl]-9H,11H-azeto[2,1-c]imidazo[1,5-a][1,4]benzodiazepin-9-one, which was used in the next step without further purification.

d) 8 g (17 mmol) of crude (S)-8-chloro-12,12a-dihydro-1-[5-(N-BOC-N-methyl)-aminomethyl-1,2,4-oxadiazol-3-yl]-9H,11H-azeto[2,1-c]imidazo[1,5-a][1,4]benzodiazepin-9-one were stirred at room temperature for 2 hours in 25 ml of trifluoroacetic acid. The solution was concentrated, the residue was taken up in water and the aqueous solution was washed twice with methylene chloride. The aqueous phase was made alkaline with 25% ammonia and extracted seven times with methylene chloride. By drying and evaporating the combined organic phases there were obtained 4.35 g (69%) of (S)-8-chloro-12,12a-dihydro-1-(5-methylaminomethyl-1,2,4-oxadiazol-3-yl)-9H,11H-azeto[2, 1-c]imidazo[1,5-a][1,4]benzodiazepin-9-one, which was converted into the hydrochloride of m.p. 250°.

EXAMPLE 8

1.96 g (13.5 mmol) of 4-morpholino-acetic acid were dissolved in 20 ml of N,N-dimethylformamide and treated portionwise with 2.6 g (15.9 mmol) of 1,1'-carbonyldiamidazole. After stirring at 80° for 15 minutes 3.9 g (1.23 mmol) of (S)-8-chloro-12,12a-dihydro-9-oxo-9H, 11H-azeto[2,1-c]imidazo[1,5-a][1,4]-benzodiazepine-1-carboxamidoxime were added and the mixture was stirred at 90° overnight. The reaction mixture was concentrated. By chromatography of the residue on silica gel while eluting with methylene chloride/methanol 19/1 and recrystallization from ethyl acetate there were obtained 1.85 g (35%) of (S)-8-chloro-12,12a-dihydro-1-[5-(pyrrolidin-1-ylmethyl)-1,2,4-oxadiazol-3-yl]-9H,11H-azeto[2,1-c]imidazo[1,5-a] [1,4]benzodiazepine, which was converted into the hydrochloride.

EXAMPLE 9

1.75 g (17 mmol) of N,N-dimethylglycine were dissolved in 20 ml of N,N-dimethylformamide and treated portionwise with 3.08 g (15 mmol) of 1,1'-carbonyldiimidazole. After completion of the $CO_2$ evolution the solution was stirred at 70° for 30'. Then, 4.02 g (15 mmol) of (S)-7-fluoro-12,12a-dihydro-9-oxo-9H,11H-azeto[2,1-c]imidazo[1,5-a][1,4] benzodiazepine-1-carboxamidoxime were added and the mixture was stirred at 90° C. overnight. By evaporation of the solution, chromatography of the residue on 240 g of silica gel while eluting with methylene chloride/methanol 19/1 and crystallization from ethyl acetate there were obtained 1.35 g (24%) of (S)-7-fluoro-12,12a-dihydro-1-[5-(dimethylaminomethyl)-1,2,4-oxadiazol-3-yl]-9H,11H-azeto-[2,1-c]imidazo[1,5-a][1,4]benzodiazepin-9-one of m.p. 187°–190°, which was converted into the hydrochloride of m.p. 150°–155°.

EXAMPLE 10 a) 6.81 g (36 mmol) of BOC-sarcosine were dissolved in 30 ml of N,N-dimethylformamide and treated portionwise with 6.5 g (40 mmol) of 1,1'-carbonyldiimidazole. After completion of the $CO_2$ evolution the solution was stirred at 40° for 30'. Then, 9.04 g (15 mmol) of (S)-7-fluoro-12,12a-dihydro-9-oxo-9H,11H-azeto[2,1-c]imidazo[1,5-a][1,4] benzodiazepine-1-carboxamidoxime were added and the mixture was stirred at 90° overnight. By evaporation of the solution and chromatography of the residue on 450 g of silica gel while eluting with methylene chloride/methanol 19/1 there were obtained 8.81 g (65%) of (S)-7-fluoro-12, 12a-dihydro-1-[5-(N-BOC-N-methylaminomethyl)-1,2,4-oxadiazol-3-yl]-9H,11H-azeto[2,1-c]imidazo[1,5-a][1,4] benzodiazepin-9-one, which was used in the next step without further purification.

b) 7.74 g (17 mmol) of crude (S)-7-fluoro-12,12a-dihydro-1-[5-(N-BOC-N-methylaminomethyl)-1,2,4-oxadiazol-3-yl]-9H,11H-azeto[2,1-c]imidazo[1,5-a][1,4] benzodiazepin-9-one were stirred for 2 hours in 25 ml of trifluoroacetic acid. The solution was concentrated, the residue was taken up in water and the solution was washed twice with methylene chloride. The aqueous phase was made alkaline with 25% ammonia and extracted seven times with methylene chloride. There were obtained 5.12 g (85%) of (S)-7-fluoro-12,12a-dihydro-1-(5-methylaminomethyl-1, 2,4-oxadiazol-3-yl)-9H,11H-azeto[2,1-c]imidazo-[1,5-a][1, 4]benzodiazepin-9-one of m.p. 187°–190°, which was converted into the hydrochloride of m.p. 155°–160°.

EXAMPLE 11

4.13 g (11.13 mmol) of (S)-8-chloro-12,12a-dihydro-1-(5-methylaminomethyl-1,2,4-oxadiazol-3-yl]-9H,11H-azeto [2,1-c]imidazo[1,5-a][1,4]benzodiazepin-9-one, 20 ml of N,N-dimethylformamide, 2 g (13 mmol) of 1,8-diazabicyclo [5.4.0]undec-7-ene(1,5-5) and 1.58 g (13 mmol) of allyl bromide were stirred at room temperature for 60 hours. The reaction mixture was purified by chromatography on silica gel while eluting with methylene chloride/methanol 19/1. There were obtained 2.86 g (62%) of (S)-1-[5-(N-allyl-N-methyl)-aminomethyl-1,2,4-oxadiazol-3-yl ]-8-chloro-12, 12a-dihydro-9H,11H-azeto[2,1-c]imidazo [1,5-a][1,4]-benzodiazepin-9-one, which was converted into the hydrochloride of m.p. 187°–192°.

EXAMPLE 12 a) 8.41 g (48 mmol) of BOC-glycine were dissolved in 30 ml of N,N-dimethylformamide and treated portionwise with 7.8 g (48 mmol) of 1,1'-carbonyldiimidazole. After completion of the $CO^2$ evolution the solution was stirred at 45° for 10'. Then, 12.05 g (40 mmol) of (S)-7-fluoro-12,12a-dihydro-9-oxo-9H,11H-azeto-[2,1-c]imidazo[1,5-a][1,4] benzodiazepine-1-carboxamidoxime were added and the mixture was stirred at 90° overnight. By evaporation of the solution, chromatography of the residue on 550 g of silica gel while eluting with methylene chloride/methanol 19/1 and recrystallization from ethyl acetate there were obtained 10.78 g (61%) of (S)-1-[5-(BOC-aminomethyl)-1,2,4-oxadiazol-3-yl]-7-fluoro-12,12a-dihydro-9H,11H-azeto[2, 1-c]imidazo[1,5-a][1,4]benzodiazepin-9-one of m.p. 147°–150°.

b) 4.40 g (10 mmol) of (S)-1-[5-(BOC-aminomethyl)-1, 2,4-oxadiazol-3-yl]-7-fluoro-12,12a-dihydro-9H,11H-azeto [2,1-c]imidazo[1,5-a][1,4]benzodiazepin-9-one were stirred for 2 hours in 20 ml of trifluoroacetic acid. The solution was concentrated, the residue was taken up in water and the aqueous solution was washed twice with methylene chloride. The aqueous phase was made alkaline with 25% ammonia and extracted seven times with methylene chloride. After drying and evaporating the combined organic phases there were obtained 2.77 g (81%) of (S)-1-(5-aminomethyl-1,2,4-oxadiazol-3-yl)-7-fluoro-12,12a-dihydro-9H,11H-azeto[2,1-c]imidazo[1,5-a][1,4] benzodiazepin-9-one of m.p. 195°–198°, which was converted into the hydrochloride of m.p. 275°.

EXAMPLE 13

1.24 g (12 mmol) of N,N-dimethylglycine were dissolved in 20 ml of N,N-dimethylformamide and treated portionwise with 2.43 g (15 mmol) of 1,1'-carbonyldiimidazole. After completion of the $CO_2$ evolution the solution was stirred at 70° for 30'. Then, 3.35 g (10 mmol) of (S)-8-chloro-7-fluoro-12,12a-dihydro-9-oxo-9H,11H-azeto[2,1-c]imidazo [1,5-a][1,4]benzodiazepine-1-carboxamidoxime were added and the mixture was stirred at 90° for 3.5 hours. By evaporation of the solution, chromatography of the residue on 300 g of silica gel while eluting with ethyl acetate/methanol 9/1 and crystallization from ethyl acetate and hexane there was obtained 0.98 g (24%) of (S)-8-chloro-7-fluoro-12,12a-dihydro-1-[5-(dimethylaminomethyl)-1,2,4-oxadiazol-3-yl]-9H,11H- azeto[2,1-c]imidazo[1,5-a][1,4] benzodiazepin-9-one of m.p. 166°–169°, which was converted into the hydrochloride of m.p. 223°–227°.

EXAMPLE 14

470 mg (1.32 mmol) of (S)-7-fluoro-12,12a-dihydro-1-(5-methylaminomethyl-1,2,4-oxadiazol-3-yl)-9H,11H-azeto [2,1-c]imidazo[1,5-a][1,4]benzodiazepin-9-one and 750 mg (1.92 mmol) of (S)-7-fluoro-12,-12a-dihydro-1-(5-methylaminomethyl-1,2,4-oxadiazol-3-yl)-9H,11H-azeto[2, 1-c]imidazo[1,5-a][1,4]benzodiazepin-9-one hydrochloride, 837 mg (5.5 mmol) of 1,8-diazabicyclo[5.4.0]undec-7-ene (1,5-5) and 450 mg (3.5 mmol) allyl bromide were stirred in 15 ml of N,N-dimethylformamide at room temperature overnight and at 55° for 2.5 hours. The reaction mixture was purified by chromatography on silica gel while eluting with methylene chloride/methanol 19/1. There were obtained 1.15 g (88%) of (S)-1-[5-(N-allyl-N-methyl)-aminomethyl-1,2,4-oxadiazol-3-yl]-7-fluoro-12,12a-dihydro-9H,11H-azeto[2, 1-c]imidazo[1,5-a][1,4]benzodiazepin-9-one, which was converted into the hydrochloride of m.p. 224°–226°.

EXAMPLE 15 a) 3.02 g (16 mmol) of BOC-sarcosine were dissolved in 15 ml of N,N-dimethylformamide and treated portionwise with 2.75 g (17 mmol) of 1,1'-carbonyldiimidazole. After stirring at 50° for 15 minutes 5.04 g (15 mmol) of (S)-8-chloro-7-fluoro-12,12a-dihydro-9-oxo-9H,11H-azeto[2,1-c] imidazo[1,5-a][1,4]benzodiazepine-1-carboxamidoxime were added and the mixture was stirred at 90° overnight. By concentration of the reaction solution and chromatography of the residue on silica gel while eluting with ethyl acetate there were obtained 5.0 g (68%) of (S)-8-chloro-7-fluoro-12,12a-dihydro-1-[5-(N-BOC-N-methyl)-aminomethyl-1,2,4-oxadiazol-3-yl]-9H,11H-azeto[2,1-c]imidazo-[1,5-a] [1,4]benzodiazepin-9-one, which was used in the next step without further purification.

b) 4.42 g (9 mmol) of (S)-8-chloro-7-fluoro-12,12a-dihydro-1-[5-(N-BOC-N-methyl)-aminomethyl-1,2,4-oxadiazol-3-yl]-9H,11H-azeto[2,1-c]imidazo-[1,5-a][1,4] benzodiazepin-9-one were left to stand overnight in 20 ml of trifluoroacetic acid. The solution was evaporated, the residue was dissolved in water and the solution was washed three times with methylene chloride. The aqueous phase was made alkaline with conc. ammonia and extracted eight times with methylene chloride (a total of about 1 l). By evaporation of the organic phases, combined and dried over magnesium sulfate, there were obtained 2.97 g (84%) of (S)-8-chloro-7-fluoro-12,12a-dihydro-1-(5-methylaminomethyl-1,2,4-oxadiazol-3-yl)-9H,11H-azeto[2,1-c]imidazo[1,5-a] [1,4]benzodiazepin-9-one, which was used without further purification as the starting material for the Example described hereinafter.

EXAMPLE 16

2.95 g (7.6 mmol) of crude (S)-8-chloro-7-fluoro-12,12a-dihydro-1-(5-methylaminomethyl-1,2,4-oxadiazol-3-yl)-9H,11H-azeto[2, 1-c]imidazo[1,5-a][1,4]benzodiazepin-9-one, 15 ml of N,N-dimethylformamide, 1.4 g (9.4 mmol) of 1,8-diazabicyclo[5.4.0]undec-7-ene (1,5-5) and 1.1 g (9 mmol) of allyl bromide were stirred at room temperature overnight and at 55° for 6 hours. The reaction mixture was purified by chromatography on silica gel while eluting with methylene chloride/methanol 19/1. There were obtained 1.39 g (42%) of (S)-1-[5-(N-allyl-N-methyl)-aminomethyl-1,2,4-oxadiazol-3-yl]-8-chloro-7-fluoro-12,12a-dihydro-9H,11H-azeto[2,1-c]imidazo[1,5a][1,4]benzodiazepin-9-one, which was converted into the hydrochloride of m.p. 199°–203°.

EXAMPLE 17 a) 3.02 g (16 mmol) of BOC-sarcosine were dissolved in 25 ml of N,N-dimethylformamide and treated portionwise with 2.75 g (17 mmol) of 1,1'-carbonyldiimidazole. After completion of the $CO_2$ evolution the solution was stirred at 60° for 30'. Then, 4.02 g (15 mmol) of (S)-8-chloro-11,12, 13,13a-tetrahydro-9-oxo-9H-imidazo[1,5-a]pyrrolo[2,1-c] [1,4]benzodiazepine-1-carboxamidoxime were added and the mixture was stirred at 95° overnight. By evaporation of the solution and chromatography of the residue on 300 g of silica gel while eluting with ethyl acetate there were obtained 3.6 g (49%) of (S)-8-chloro-11,12, 13,13a-tetrahydro-1-(5-N-BOC-N-methylaminomethyl-1,2,4-oxadiazol-3-yl)-9H-imidazo[1,5-a]pyrrolo[2,1-c][1,4]-benzodiazepin-9-one, which was used in the next step without further purification.

b) 3.6 g (7.4 mmol) of crude (S)-8-chloro-11,12,13,13a-tetrahydro-1-(5-N-BOC-N-methylaminomethyl-1,2,4-oxadiazol-3-yl)-9H-imidazo[1,5-a]pyrrolo[2,1-c][1,4]-benzodiazepin-9-one were stirred at room temperature for 1 hour in 25 ml of trifluoroacetic acid. The solution was concentrated, the residue was taken up in water and the aqueous solution was washed twice with methylene chloride. The aqueous phase was made alkaline with 25% ammonia and extracted five times with methylene chloride. By drying and evaporating the combined organic phases there were obtained 2.47 g (87%) of (S)-8-chloro-11,12,13,13a-tetrahydro-1-(5-N-BOC-N-methylaminomethyl-1,2,4-oxadiazol-3-yl)-9H-imidazo[1,5-a]pyrrolo[2,1-c][1,4]-benzodiazepin-9-one of m.p. 161°–163°.

EXAMPLE 18

2.19 g (5.7 mmol) of (S)-8-chloro-11,12,13,13a-tetrahydro-1-(5-methylamino-methyl-1,2,4-oxadiazol-3-yl)-9H-imidazo [1,5-a]pyrrolo[2,1-c][1,4]-benzodiazepin-9-one, 20 ml of N,N-dimethylformamide, 1.07 g (7 mmol) of 1,8-diazabicyclo[5.4.0]undec-7-ene (1.5-5) and 850 mg (7 mmol) of allyl bromide were stirred at 60° for 4.5 hours. The reaction mixture was concentrated and the residue was purified by chromatography on silica gel while eluting with methylene chloride/methanol 19/1. There were obtained 1.32 g (54%) of (S)-1-(5-N-allyl-N-methylaminomethyl-1, 2,4-oxadiazol-3-yl)-8-chloro-11,12,13,13a-tetrahydro-9H-imidazo[1,5-a]pyrrolo[2,1-c][1,4]benzodiazepin-9-one, which was converted into the hydrochloride.

EXAMPLE 19 a) 7.47 g (16.35 mmol) of (S)-1-(5-BOC-aminomethyl-1, 2,4-oxadiazol-3-yl)-8-chloro-12,12a-dihydro-9H,11H-azeto [2,1-c]imidazo [1,5-a][1,4]benzodiazepin-9-one, 20 ml of N,N-dimethylformamide, 800 mg of sodium hydride and 4.34 g (36 mmol) of allyl bromide were stirred at 65° overnight. After evaporating the solvent the residue was taken up in methylene chloride, whereupon the solution was washed twice with water, dried and evaporated. By chromatography of the residue on silica gel while eluting with methylene chloride/methanol 19/1 there were obtained 2.08 g (25%) of (S)-1-(5-N-allyl-N-BOC-aminomethyl-1,2,4-oxadiazol-3-yl)-8-chloro-12,12a-dihydro-9H,11H-azeto[2, 1-c]imidazo [1,5-a][1,4]benzo-diazepin-9-one, which was used in the next step without further purification.

b) 2.08 g (4.2 mmol) of crude (S)-1-(5-N-allyl-N-BOC-aminomethyl-1,2,4-oxadiazol-3-yl)-8-chloro-12,12a-dihydro-9H,11H-azeto[2,1-c]imidazo[1,5-a][1,4] benzodiazepin-9-one were stirred for ¾ hour in 10 ml of trifluoroacetic acid. After evaporating the reaction mixture the residue was dissolved in methylene chloride, whereupon the solution was washed with saturated sodium bicarbonate solution and with water, dried over magnesium sulfate and concentrated. The residue was purified by chromatography on silica gel while eluting with methylene chloride/methanol 19/1. There was obtained 0.75 g (48%) of (S)-1-(5-allylaminomethyl-1,2,4-oxadiazol-3-yl)-8-chloro-12,12a-dihydro-9H,11H-azeto[2,1-c]imidazo[1,5-a][1,4] benzodiazepin-9-one, which was converted into the hydrochloride of m.p. 227°–228°.

EXAMPLE 20

36.5 g (235 mmol) of diallylglycine were dissolved in 165 ml of N,N-dimethylformamide and treated portionwise with 40.5 g (250 mmol) of 1,1'-carbonyldiimidazole. After stirring for 10 minutes 40 g (126 mmol) of (S)-8-chloro-12, 12a-dihydro-9-oxo-9H,11H-azeto[2,1-c]imidazo[1,5-a][1, 4]benzodiazepine-1-carboxamidoxime were added and the mixture was stirred at room temperature for 1 hour and at 110° for 3.5 hours. The reaction mixture was concentrated and the residue was purified by chromatography on silica gel while eluting with methylene chloride/ethyl acetate 1/1. There were obtained 27.1 g (45%) of (S)-1-(5-diallylaminomethyl-1,2,4-oxadiazol-3-yl)-8-chloro-12,12a-dihydro-9H,11H-azeto[2,1-c]imidazo[1,5-a][1,4] benzodiazepin-9-one, which was converted into the hydrochloride of m.p. 181°–182.5°.

EXAMPLE 21

2.70 g (7.2 mmol) of (S)-1-(5-aminomethyl-1,2,4-oxadiazol-3-yl)-8-chloro-7-fluoro-12,12a-dihydro-9H,11H-azeto[2,1-c]-imidazo[1,5-a][1,4]benzodiazepin-9-one, 35 ml N,N-dimethyl-formamide, 3.39 g (22.2 mmol) of 1,8-diazabicyclo[5.4.0]undec-7-ene (1.5°–5) and 2.61 g (21.6 mmol) of allyl bromide were stirred at room temperature for 20 hours. After evaporating the reaction mixture the residue was taken up in methylene chloride, the solution was washed three times with water, dried over magnesium sulfate and evaporated. The residue was chromatographed on 300 g of silica gel while eluting with methylene chloride/methanol 19/1. The uniform fractions with R=0.19 were concentrated. There were obtained 1.21 g (37%) of (S)-1-(5-allylaminomethyl-1,2,4-oxadiazol-3-yl)-8-chloro-7-fluoro-12,12a-dihydro-9H,11H-azeto[2,1-c]imidazo[1,5-a][1,4] benzo-diazepin-9-one, which was converted into the hydrochloride of decomposition point 190°.

EXAMPLE 22 a) 25.4 g (100 mmol) of (S)-5-chloro-6-fluoro-1,10a-dihydro- 2H-azeto[2,1-c][1,4]benzodiazepine-4,10(9H)-dione were dissolved in 125 ml of N,N-dimethylformamide, treated at −30° with 4.8 g (110 mmol) of sodium hydride dispersion (55–65% in oil, washed with n-hexane) and deprotonated for 40 min. at −30° to −18°. A solution of 26.86 g (100 mmol) of phosphoric acid diphenyl ester chloride in 5 ml of N,N-dimethylformamide was added at −60° and the mixture was stirred at max. −45° for 35 min. In the meanwhile and separately, 12.3 g (110 mmol) of potassium tert.-butylate were dissolved in 30 ml of N,N-dimethylformamide and treated at −60° C. with 12.2 g (107 mmol) of ethyl isocyanoacetate. The deprotonated ethyl isocyanoacetate was cooled to −70° and the reaction mixture was added dropwise using a dropping funnel cooled with dry ice at max. −65° within 5/4 hours. The mixture was stirred in an acetone/dry ice bath for 1 hour, neutralized with 12 ml of acetic acid and poured into 500 ml of ice-water. The mixture was extracted five times with methylene chloride (a total of 1.2 l), dried over magnesium sulfate and evaporated to dryness. By chromatography of the residue on 1.5 kg of silica gel while eluting with ethyl acetate there were obtained 14.4 g (41%) of ethyl (S)-8-chloro-7-fluoro-12, 12a-dihydro-9-oxo-9H,11H-azeto[2,1-c]imidazo[1,5-a][1, 4]-benzodiazepine-1-carboxylate of m.p. 161°–163°.

b) 57.3 g (164 mmol) of ethyl (S)-8-chloro-7-fluoro-12, 12a-dihydro-9-oxo-9H,11H-azeto[2,1-c]imidazo[1,5-a][1, 4]-benzodiazepine-1-carboxylate, 40 ml of ethanol, 60 ml of water and 51.5 ml (206 mmol) of 4N sodium hydroxide solution were heated to reflux on a steam bath for 30 min. The alcohol was evaporated on a rotary evaporator. The aqueous phase remaining behind was washed twice with methylene chloride and acidified to pH 3-4 with 51.5 ml (206 mmol) of 4N hydrochloric acid. The suspension obtained was cooled and filtered, and the filter residue was washed with a small amount of ice-water and dried. There were obtained 47.92 g (91%) of (S)-8-chloro-7-fluoro-12, 12a-dihydro-9-oxo-9H,11H-azeto[2,1-c]imidazo[1,5-a][1, 4]benzodiazepine-1-carboxylic acid of m.p. 225°–226°.

c) 40 g (124 mmol) of (S)-8-chloro-7-fluoro-12,12a-dihydro-9-oxo-9H,11H-azeto[2,1-c]imidazo[1,5-a][1,4] benzodiazepine-1-carboxylic acid were suspended in 190 ml of N,N-dimethylformamide and treated portionwise at room temperature with 21 g (129.5 mmol) of 1,1'-carbonyldiimidazole. After completion of the $CO_2$ evolution the clear brown solution was stirred at 50° for 30 min., cooled and treated dropwise with 30 ml of conc. ammonia at a temperature below 25° within about 10 min. After stirring for 30 minutes the suspension obtained was poured into 700 ml of ice-water, stirred at room temperature for 30 min. and filtered, whereupon the crystals were rinsed with a small amount of water. After drying there were obtained 31.36 g (78%) of (S)-8-chloro-7-fluoro-12,12a-dihydro-9-oxo-9H,11H-azeto[2,1-c]imidazo[1,5-a][1,4] benzodiazepine-1-carboxamide of m.p. 296°–298°.

d) 33.67 g (105 mmol) of (S)-8-chloro-7-fluoro-12,12a-dihydro-9-oxo-9H,11H-azeto[2,1-c]imidazo[1,5-a][1,4] benzodiazepine-1-carboxamide were suspended in 140 ml of dioxan and 18 ml of pyridine and treated dropwise with 22.6 g (107.6 mmol) of trifluoroacetic anhydride at a temperature of <8° within 30 min. The mixture was stirred at 50° for 2.5 hours and poured into 700 ml of water. The suspension was filtered and, after drying the residue, there were obtained 28.62 g (90%) of (S)-8-chloro-7-fluoro-12,12a-dihydro-9-oxo-9H,11H-azeto[2,1-c]imidazo[1,5-a][1,4] benzodiazepine-1-carbonitrile of m.p. 225°–228°.

e) 3.1 g (134.8 mmol) of sodium were dissolved in 140 ml of methanol. 10 g (145 mmol) of hydroxylamine hydrochloride and 28.6 g (94.5 mmol) of (S)-8-chloro-7-fluoro-12, 12a-dihydro-9-oxo-9H,11H-azeto[2,1-c]imidazo[1,5-a][1, 4]benzodiazepine-1-carbonitrile were added in succession at room temperature. The suspension was stirred at room temperature overnight, cooled to 0° during 30 min., the crystals were filtered off, suspended in 50 ml of water and filtered off. The methanol solution was concentrated, whereupon the residue was suspended in 30 ml of water and the crystals were filtered off. By drying the combined crystallizate there were obtained 30.94 g (97%) of (S)-8-chloro-7-fluoro-12,12a-dihydro-9-oxo-9H,11H-azeto[2,1-c]imidazo [1,5-a][1,4]benzodiazepine-1-carboxamidoxime of m.p. 236°–238°.

f) 17.08 g (97 mmol) of BOC-glycine were dissolved in 165 ml of N,N-dimethylformamide and treated portionwise with 16.9 g (104 mmol) of 1,1'-carbonyldiimidazole. After completion of the $CO_2$ evolution the solution was stirred at 50° for 30 min. Then, 30.8 g (91mmol) of (S)-8-chloro-7-fluoro-12,12a-dihydro-9-oxo-9H,11H-azeto[2,1-c]imidazo [1,5-a][1,4]benzodiazepine-1-carboxamidoxime were added and the mixture was stirred at 90° overnight. By evaporation of the solution and chromatography of the residue on 1.5 kg of silica gel while eluting with methylene chloride/methanol 19/1 there were obtained 36.8 g (84%) of (S)-1-[5-(BOC-aminomethyl)-1,2,4-oxadiazol-3-yl]-8-chloro-7-fluoro-12, 12a-dihydro-9H,11H-azeto[2,1-c]imidazo[1,5-a][1,4] benzodiazepin-9-one, which was used in the next step without further purification.

g) 36.8 g (77.5 mmol) of crude (S)-1-[5-(BOC-aminomethyl)-1,2,4-oxadiazol-3-yl]-8-chloro-7-fluoro-12, 12a-dihydro-9H,11H-azeto[2,1-c]imidazo[1,5-a][1,4] benzodiazepin-9-one and 90 ml of trifluoroacetic acid were stirred at room temperature for 2 hours. The solution was evaporated, the residue was dissolved in water and the aqueous solution was washed three times with methylene chloride. The aqueous phase was made alkaline with conc. ammonia and extracted eight times with methylene chloride (a total of about 1 l). By evaporating the organic phases, combined and dried over magnesium sulfate, there were obtained 23.8 g (82%) of (S)-1-(5-aminomethyl-1,2,4-oxadiazol-3-yl)-8-chloro-7-fluoro-12,12a-dihydro-9H,11H-azeto[2,1-c]imidazo[1,5-a][1,4]benzodiazepin-9-one, which was used without further purification as the starting material for the Example described hereinafter.

EXAMPLE 23

26.6 g (71 mmol) of crude (S)-1-(5-aminomethyl-1,2,4-oxadiazol-3-yl)-8-chloro-7-fluoro-12,12a-dihydro-9H,11H-azeto[2,1-c]imidazo[1,5-a][1,4]benzodiazepin-9-one, 400 ml of methylene chloride, 85 ml (496 mmol) of N-ethyldiisopropylamine and 34.5 g (285 mmol) of allyl bromide were stirred at room temperature for 20 hours. The reaction solution was washed three times with water, dried over magnesium sulfate and evaporated. The residue was chromatographed on 2 kg of silica gel while eluting with ethyl acetate. The uniform fractions were evaporated and recrystallized from toluene and n-hexane. There were obtained 22.34 g (69%) of (S)-1-(5-diallylaminomethyl-1, 2,4-oxadiazol-3-yl)-8-chloro-7-fluoro-12,12a-dihydro-9H, 11H-azeto[2,1-c]imidazo[1,5-a][1,4]benzodiazepin-9-one of m.p. 103°–104°.

EXAMPLE 24 a) 4.16 g (23.6 mmol) of BOC-glycine were dissolved in 30 ml of N,N-dimethylformamide and treated portionwise with 4.08 g (25.2 mmol) of 1,1'-carbonyldiimidazole. After completion of the $CO_2$ evolution the solution was stirred at 50° for 20 min. Then, 7.36 g (22.2 mmol) of (S)-8-chloro-11,12,13,13a-tetrahydro-9-oxo-9H-imidazo[1,5-a]pyrrolo [2,1-c][1,4]benzodiazepine-1-carboxamidoxime were added and the mixture was stirred at 90° overnight. The reaction mixture was evaporated, the residue was dissolved in methylene chloride and the solution was washed once with water and once with saturated sodium bicarbonate solution. After drying and concentrating there were obtained 7.75 g (74%) of (S)-1-(5-BOC-aminomethyl-1,2,4-oxadiazol-3-yl)-8-chloro-11,12,13,13a-tetrahydro-9H-imidazo[1,5-a]pyrrolo [2,1-c][1,4]benzodiazepin-9-one, which was used in the next step without further purification.

b) 7.75 g (16.5 mmol) of crude (S)-1-(5-BOC-aminomethyl-1,2,4-oxadiazol-3-yl)-8-chloro-11,12,13,13a-tetrahydro-9H-imidazo[1,5-a]pyrrolo[2,1-c][1,4] benzodiazepin-9-one were stirred at room temperature for 1.5 hours in 25 ml of trifluoroacetic acid. The solution was concentrated, the residue was taken up in saturated sodium bicarbonate solution and the solution was extracted ten times with methylene chloride. By drying and evaporating the combined organic phases there were obtained 5.53 g (90%) of (S)-1-(5-aminomethyl-1,2,4-oxadiazol-3-yl)-8-chloro-11, 12,13,13a-tetrahydro-9H-imidazo[1,5-a]pyrrolo[2,1-c][1,4] -benzodiazepin-9-one, which was used without further purification as the starting product for the Example described hereinafter.

EXAMPLE 25

2.47 g (6.7 mmol) of crude (S)-1-(5-aminomethyl-1,2,4-oxadiazol-3-yl)-8-chloro-11,12,13,13a-tetrahydro-9H- imidazo[1,5-a]pyrrolo[2,1-c][1,4]benzodiazepin-9-one, 20 ml of N,N-dimethylformamide, 9 ml (60 mmol) of 1,8-diazabicyclo[5.4.0]undec-7-ene (1,5-5) and 10.26 g (54 mmol) of benzyl bromide were stirred at room temperature overnight and at 50° for 6 hours. The reaction mixture was concentrated and the residue was purified by chromatography on silica gel while eluting with methylene chloride/methanol 19/1. After recrystallization from ethyl acetate and hexane there were obtained 2.16 g (58%) of (S)-1-(5-dibenzylaminomethyl-1,2,4-oxadiazol-3-yl)-8-chloro-11, 12,13,13a-tetrahydro-9H-imidazo[1,5-a]pyrrolo[2,1-c][1,4]benzodiazepin-9-one of m.p. 107°–109°.

EXAMPLE 26

3.0 g (8.1 mmol) of (S)-1-(5-aminomethyl-1,2,4-oxadiazol-3-yl)-8-chloro-11,12,13,13a-tetrahydro-9H-imidazo[1,5-a]pyrrolo[2,1-c][1,4]benzodiazepin-9-one, 20 ml of N,N-dimethylformamide, 3 ml (20 mmol) of 1,8-diazabicyclo[5.4.0]undec-7-ene (1,5-5) and 6.54 g (54 mmol) of allyl bromide were stirred at 40° overnight. The reaction mixture was concentrated, the residue was dissolved in methylene chloride and the solution was washed with water. After drying the product was purified by chromatography on silica gel while eluting with melthylene chloride/methanol 19/1. There were obtained 1.8 g (49%) of (S)-1-(5-diallylaminomethyl-1,2,4-oxadiazol-3-yl)-8-chloro-11,12,13,13a-tetrahydro-9H-imidazo[1,5-a]pyrrolo[2,1-c][1,4]-benzodiazepin-9-one, which was converted into the hydrochloride.

EXAMPLE 27 a) 6.68 g (22 mmol) of (S)-8-chloro-12,12a-dihydro-9-oxo-9H,11H-azeto[2,1-c]imidazo[1,5-a][1,4]benzodiazepine-1-carboxylic acid were dissolved in 70 ml of N,N-dimethylformamide, treated portionwise with 3.84 g (24 mmol) of 1,1'-carbonyldiimidazole at 40° and stirred at this temperature for 30 min. After adding 5.78 g (26 mmol) of phthaloylglycine amidoxime the reaction mixture was stirred at 60° for 2.5 hours and at 110° for 18 hours and concentrated. By chromatography of the residue on silica gel while eluting with ethyl acetate there were obtained 6.01 g (56%) of (S)-8-chloro-12,12a-dihydro-1-(3-phthalimidomethyl-1,2,4-oxadiazol-5-yl)-9H,11H-azeto[2,1-c]imidazo[1,5-a][1,4]benzodiazepin-9-one of m.p. 189°–192°.

b) 6.01 g (12.3 mmol) of (S)-8-chloro-12,12a-dihydro-1-(3-phthalimidomethyl-1,2,4-oxadiazol-5-yl)-9H,11H-azeto[2,1-c]imidazo[1,5-a][1,4]benzodiazepin-9-one were placed in 60 ml of ethanol and treated dropwise with 120 ml of methylamine (33% in ethanol) at 60° within 30 min. The solution was stirred at 70° for 2 hours and subsequently concentrated. By chromatography of the residue on silica gel while eluting with ethyl acetate/methanol 8/2 there were obtained 4.0 g (91%) of (S)-1-(3-aminomethyl-1,2,4-oxadiazol-5-yl)-8-chloro-12,12a-dihydro-9H,11H-azeto[2,1-c]imidazo[1,5-a][1,4]benzodiazepin-9-one of m.p. 206°–208°.

EXAMPLE 28

5.02 g (14 mmol) of (S)-1-(3-aminomethyl-1,2,4-oxadiazol-5-yl)-8-chloro-12,12a-dihydro-9H,11H-azeto[2,1-c]imidazo[1,5-a][1,4]benzodiazepin-9-one, 75 ml of N,N-dimethylformamide, 21 g (173.8 mmol) of allyl bromide and 29.4 g (193 mmol) of 1,8-diazabicyclo[5.4.0]undec-7-ene (1,5-5) were stirred at 75° for 60 hours. The solution was concentrated and the residue was purified by chromatography on 350 g of silica gel while eluting with ethyl acetate. There were obtained 1.97 g (35%) of (S)-1-(3-diallylaminomethyl-1,2,4-oxadiazol-5-yl)-8-chloro-12,12a-dihydro-9H,11H-azeto[2,1-c]imidazo[1,5-a][1,4]benzodiazepin-9-one, which was converted into the hydrochloride of m.p. 190°–192°.

EXAMPLE 29 a) 0.60 g (26 mmol) of sodium was dissolved in 32 ml of methanol. 1.95 g (28.1 mmol) of hydroxylamine hydrochloride and, after 1 hour, 5.77 g (346 mmol) of (S)-7-fluoro-12,12a-dihydro-9-oxo-9H,11H-azeto[2,1-c]imidazo[1,5-a][1,4]benzodiazepine-1-carbonitrile were added at room temperature. The suspension was stirred at 70° for 3.5 hours, cooled to 0° during 30 min. and the crystals were filtered off. By drying the crystallizate there were obtained 6.5 g (100%) of (S)-7-fluoro-12,12a-dihydro-9-oxo-9H,11H-azeto[2,1-c]imidazo[1,5-a][1,4]benzodiazepine-1-carboxamidoxime of m.p. 248°–250°.

b) 2.32 g (15 mmol) of diallylglycine were dissolved in 15 ml of N,N-dimethylformamide and treated with 2.75 g (17 mmol) of 1,1'-carbonyldiimidazole. After stirring at 50° C. for 20 minutes 3.01 (10 mmol) of (S)-7-fluoro-12,12a-dihydro-9-oxo-9H,11H-azeto[2,1-c]imidazo[1,5-a][1,4]benzodiazepine-1-carboxamidoxime were added and the mixture was stirred at 90° for 16 hours and at 120° for 2 hours. The solution was concentrated and the residue was purified by chromatography on 320 g of silica gel while eluting with ethyl acetate. There were obtained 1.54 g (37%) of (S)-1-(5-diallylaminomethyl-1,2,4-oxadiazol-3-yl)-7-fluoro-12,12a-dihydro-9H,11H-azeto[2,1-c]-imidazo[1,5-a][1,4]benzodiazepin-9-one, which was converted into the hydrochloride of m.p. 100°–105°.

EXAMPLE 30 a) 8 g (23.7 mmol) of (S)-8-trifluoromethyl-12,12a-dihydro-9-oxo-9H,11H-azeto[2,1-c]imidazo[1,5-a][1,4]benzodiazepine-1-carboxylic acid were dissolved in 50 ml of N,N-dimethylformamide, treated portionwise with 4.06 g (25 mmol) of 1,1'-carbonyldiimidazole and stirred at 55° for 30 min. After adding 5.26 g (24 mmol) of phthaloylglycine amidoxime the mixture was stirred at 105° for 20 hours. The reaction mixture was evaporated and the residue was chromatographed on silica gel while eluting with ethyl acetate. There were obtained 5.34 g (43%) of (S)-8-trifluoromethyl-12,12a-dihydro-1-(3-phthalimidomethyl-1,2,4-oxadiazol-5-yl)-9H,11H-azeto[2,1-c]imidazo[1,5-a][1,4]benzodiazepin-9-one of m.p. 243°–245°.

b) 5.3 g (10.2 mmol) of (S)-8-trifluoromethyl-12,12a-dihydro-1-(3-phthalimidomethyl-1,2,4-oxadiazol-5-yl)-9H,11H-azeto[2,1-c]imidazo[1,5-a][1,4]benzodiazepin-9-one in 70 ml of ethanol were treated dropwise with 150 ml of methylamine (33% in ethanol) at 60° within 45 min. The solution was stirred at 70° for 2 hours and subsequently concentrated. The residue was taken up in methylene chloride and 30 ml of 4N hydrochloric acid and the solution was washed three times with methylene chloride. The aqueous phase was made alkaline with 30 ml of 4N sodium hydroxide solution and extracted five times with methylene chloride. After drying the combined organic solutions and evaporating the solvent there were obtained 3.98 g (100%) of (S)-1-(3-aminomethyl-1,2,4-oxadiazol-5-yl)-8-trifluoromethyl-12,12a-dihydro-9H,11H-azeto[2,1-c]imidazo[1,5-a][1,4]benzodiazepin-9-one, which was used without further purification as the starting material for the Example described hereinafter.

EXAMPLE 31

2 g (5.1mmol) of crude (S)-1-(3-aminomethyl-1,2,4-oxadiazol-5-yl)-8-trifluoromethyl-12,12a-dihydro-9H,11H-azeto[2,1-c]imidazo[1,5-a][1,4]benzodiazepin-9-one, 30 ml of methylene chloride, 6.2 ml (36 mmol) of N-ethyldiisopropylamine and 2.57 g (1.8 mmol) of allyl bromide were stirred at room temperature for 18 hours. The reaction solution was washed three times with water, dried over magnesium sulfate and evaporated. The residue was chromatographed on 300 g of silica gel while eluting with ethyl acetate. There were obtained 1.62 g (67%) of (S)-1-(3-diallylaminomethyl-1,2,4-oxadiazol-5-yl)-8-trifluoromethyl-12,12a-dihydro-9H,11H-azeto[2,1-c]imidazo[1,5-a][1,4]benzodiazepin-9-one, which was converted into the hydrochloride of m.p. 147°–150°.

EXAMPLE 32

3.56 g (10 mmol) of (S)-1-(5-aminomethyl-1,2,4-oxadiazol-3-yl)-8-chloro-12,12a-dihydro-9H,11H-azeto[2,1-c]imidazo[1,5-a][1,4]benzodiazepin-9-one, 15 ml of methylene chloride, 8.6 ml (50 mmol) of N-ethyldiisopropylamine and 2.64 g (10 mmol) of α,α'-dibromo-o-xylene were stirred at room temperature for 20 hours. The reaction solution was washed three times with water, dried over magnesium sulfate and evaporated. The residue was chromatographed on 500 g of silica gel while eluting with methylene chloride/methanol 19/1. There were obtained 1.55 g (33%) of (S)-8-chloro-12,12a-dihydro-1-(5-isoindolin-2-ylmethyl-1,2,4-oxadiazol-3-yl)-9H,11H-azeto[2,1-c]imidazo[1,5-a][1,4]benzodiazepin-9-one, which was converted into the hydrochloride of m.p. 218°–222°.

EXAMPLE 33

473 mg (1.1 mmol) of (S)-1-(5-diallylaminomethyl-1,2,4-oxadiazol-3-yl)-8-chloro-12,12a-dihydro-9H,11H-azeto[2,1-c]imidazo[1,5-a][1,4]benzodiazepin-9-one were hydrogenated in 10 ml of ethyl acetate in the presence of 20 mg of 5% palladium-on-charcoal at room temperature and normal pressure. After separating the catalyst the solution was concentrated. There was obtained 0.42 g (80%) of (S)-8-chloro-1-(5-dipropylaminomethyl-1,2,4-oxadiazol-3-yl)-12,12a-dihydro-9H,11H-azeto[2,1-c]imidazo[1,5-a][1,4]benzodiazepin-9-one, which was converted into the hydrochloride of m.p. 147°–153°.

EXAMPLE 34

2.27 g (5 mmol) of (S)-1-(5-diallylaminomethyl-1,2,4-oxadiazol-3-yl)-8-chloro-7-fluoro-12,12a-dihydro-9H,11H-azeto[2,1-c]imidazo[1,5-a][1,4]benzodiazepin-9-one were hydrogenated in 80 ml of ethyl acetate in the presence of 35 mg of 5% palladium-on-charcoal at room temperature and normal pressure. After separating the catalyst the reaction mixture was purified by chromatography on silica gel while eluting with ethyl acetate. There were obtained 1.83 g (80%) of (S)-8-chloro-7-fluoro-12,12a-dihydro-1-(5-dipropylaminomethyl-1,2,4-oxadiazol-3-yl)-9H,11H-azeto[2,1-c]imidazo[1,5-a][1,4]benzodiazepin-9-one, which was converted into the hydrochloride.

EXAMPLE 35 a) 400 ml (600 mmol) of tert.butyllithium (1.5M in pentane) were added dropwise within 1 hour to a solution, cooled to −70°, of 57.2 g (250 mmol) of N-(tert.butoxycarbonyl)-3,4-difluoroaniline in 500 ml of tetrahydrofuran. Subsequently, 160 g of dry ice were added in small portions to the yellow suspension, the mixture was left to warm to 0° and 400 ml of water were added dropwise. The tetrahydrofuran and the pentane were distilled off and the aqueous phase was washed twice with ether and subsequently adjusted to pH=1 with conc. hydrochloric acid. The acidic aqueous phase was extracted three times with methylene chloride; the organic phase was dried over sodium sulfate, filtered and evaporated. The beige solid obtained was recrystallized from ethylene chloride and there were obtained 52 g (76%) of 2-(tert.-butoxycarbonyl)amino-5,6-difluorobenzoic acid as colourless needles of m.p. 159.5°–160.5°.

b) A solution of 108 ml of thionyl chloride in 300 ml of tetrahydrofuran was added dropwise while cooling with ice to a solution of 100 g (366 mmol) of 2-(tert.-butoxycarbonyl)amino-5,6-difluorobenzoic acid in 1.5 l of dry tetrahydrofuran, whereupon the mixture was stirred at room temperature for 16 hours. The brown solution was evaporated and the brown solid obtained was triturated with methylene chloride. The beige powder obtained was filtered off and dried in a high vacuum. There were obtained 56.5 g (77%) of 5,6-difluoro-2,4-dihydro-1H-3,1-benzoxazine-2,4-dione as a beige powder of m.p. >240°.

c) A solution of 19.6 g (98.4 mmol) of 5,6-difluoro-2,4-dihydro-1H-3,1-benzoxazine-2,4-dione and 9.95 g (98.4 mmol) of L-azetidine-2-carboxylic acid in 125 ml of dimethylformamide and 25 ml of acetic acid was stirred at 120° for 16 hours. The brown solution was evaporated and the brown residue obtained was crystallized from ethanol. There were obtained 16 g (68%) of (S)-5,6-difluoro-1,2,4,9,10,10a-hexahydro-azeto[2,1-c][1,4]benzodiazepine-4,10-dione as colourless needles of m.p. >250°.

d) A solution of 13.5 g (56.7 mmol) of (S)-5,6-difluoro-1,2,4,9,10,10a-hexahydro-azeto[2,1-c][1,4]benzodiazepine-4,10-dione in 65 ml of dimethylformamide was added dropwise to a suspension of 2.7 g (62.3 mmol) of NaH (55%, washed with hexane) in 5 ml of dimethylformamide −30° and the mixture was stirred at −30° for 40 minutes. After cooling to −60° a solution of 12.1 ml (56.7 mmol) of phosphoric acid diphenyl ester chloride in 3 ml of dimethylformamide was added dropwise in such a manner that the temperature did not rise above −45°. Subsequently, the mixture was stirred for a further 30 minutes.

In the meanwhile, 7.0 g (62.3 mmol) of potassium tert.butylate were dissolved in 20 ml of dimethylformamide and treated at −60° with 7 ml (60.6 mmol) of ethyl isocyanoacetate (95%). The reaction mixture obtained above was added dropwise to the thus-obtained solution at −70° via a dropping funnel cooled to −40°. The thus-obtained dark brown viscous solution was stirred at −60° for 1 hour and, after neutralization with 7 ml of acetic acid at −40°, poured into 300 ml of ice-water, whereupon the mixture was extracted five times with methylene chloride. The combined organic phases were dried over sodium sulfate, filtered and evaporated. The pale brown residue obtained was recrystallized from ethanol. There were obtained 8.9 g (47%) of ethyl (S)-7,8-difluoro-9-oxo-12,12a-dihydro-9H,11H-azeto[2,1-c]imidazo[1,5-a][1,4]benzodiazepine-1-carboxylate as colourless needles of m.p. 233.5°–235.5°.

e) 8.6 ml (34.3 mmol) of 4N sodium hydroxide solution were added dropwise to a suspension of 8.8 g (26.4 mmol) of ethyl (S)-7,8-difluoro-9-oxo-12,12a-dihydro-9H,11H-azeto[2,1-c]imidazo[1,5-a][1,4]benzodiazepine-1-carboxylate in 20 ml of ethanol and 30 ml of water and the mixture was heated at reflux for 30 minutes. Subsequently, the ethanol was distilled off. The aqueous phase was washed twice with methylene chloride and adjusted to pH=3 with 4N hydrochloric acid. Extraction with methylene chloride (five times), drying over sodium sulfate, filtration and evaporation yielded 7.2 g (89%) of (S)-7,8-difluoro-9-oxo-12,12a-dihydro-9H,11H-azeto[2,1-c]imidazo[1,5-a][1,4] benzodiazepine-1-carboxylic acid as colourless needles of m.p. 218.0°–219.5° (dec.).

f) 4.2 g (26 mmol) of 1,1'-carbonyldiimidazole were added portionwise to a suspension of 7.2 g (23.6 mmol) of (S)-7,8-difluoro-9-oxo-12,12a-dihydro-9H,11H-azeto[2,1-c]imidazo[1,5-a][1,4]benzodiazepine-1-carboxylic acid in 50 ml of dimethylformamide. The resulting pale brown solution was heated to 50° for 45 minutes. Subsequently, the solution was cooled to room temperature and 6 ml of aqueous ammonia solution were added. After stirring for a further 30 minutes the reaction mixture was poured into 100 ml of ice-water and extracted seven times with methylene chloride. Drying of the organic phase over sodium sulfate, filtration, evaporation and subsequent chromatography (silica gel, methylene chloride/methanol 19:1) yielded 7.0 g (97%) of (S)-7,8-difluoro-9-oxo-12,12a-dihydro-9H,11H-azeto[2,1-c]imidazo[1,5-a][1,4]benzo-diazepine-1-carboxamide as a colourless powder of m.p. 200.5°–204.0°.

g) 3 ml (21.7 mmol) of trifluoroacetic anhydride were added dropwise at 5°–8° to a suspension of 6.3 g (20.7 mmol) of (S)-7,8-difluoro-9-oxo-12,12a-dihydro-9H,11H-azeto[2,1-c]imidazo[1,5-a][1,4]benzodiazepine-1-carboxamide in 30 ml of dioxan and 5 ml of pyridine. The beige solution obtained was stirred at 50° for 2.5 hours and subsequently poured into 50 ml of ice-water. Extraction with methylene chloride (four times), drying over sodium sulfate, filtration and evaporation yielded 4.8 g (81%) of (S)-7,8-difluoro-9-oxo-12,12a-dihydro-9H,11H-azeto[2,1-c]imidazo[1,5-a]benzodiazepine-1-carbonitrile as a colourless powder of m.p. >250°.

h) 4.7 g (16.4 mmol) of (S)-7,8-difluoro-9-oxo-12,12a-dihydro-9H,11H-azeto[2,1-c]imidazo[1,5-a]benzodiazepine-1-carbonitrile and 2.7 g (36.1mmol) of hydroxylamine hydrochloride were added to a freshly prepared solution of sodium methylate in methanol (from 750 mg (32.8 mmol) of sodium in 25 ml of methanol) and the mixture was stirred at room temperature for 16 hours. Subsequently, the suspension was evaporated and the residue was partitioned between methylene chloride and water. The insoluble constituent was filtered off and dried in a high vacuum. The organic phase was dried over sodium sulfate, filtered and evaporated. The foam obtained and the insoluble constituent were chromatographed together (silica gel, methylene chloride/methanol 9:1) and there were obtained 4.4 g (84%) of (E)- and/or (Z)-(S)-7-fluoro-8- methoxy-12,12a-dihydro-9-oxo-9H,11H-azeto[2,1-c]imidazo[1,5-a][1,4]benzodiazepine-1-carboxamidoxime as a colourless foam. Rf=0.33 (silica gel, methylene chloride/methanol 9:1).

i) 2.5 g (15.4 mmol) of 1,1'-carbonyldiimidazole were added to a solution of 2.5 g (14.4 mmol) of BOC-glycine in 25 ml of dimethylformamide and the mixture was stirred at 50° for 30 minutes. Subsequently, 4.3 g (13.5 mmol) of (E)- and/or (Z)-(S)-7-fluoro-8-methoxy-12,12a-dihydro-9-oxo-9H,11H-azeto[2,1-c]imidazo[1,5-a[[1,4]benzodiazepine-1-carboxamidoxime were added and the mixture was stirred at 90° for 16 hours. The thus-obtained brown solution was evaporated in a high vacuum and the brown residue obtained was chromatographed (silica gel, methylene chloride/methanol 19:1). There were obtained 4.1 g (65%) of (S)-1-(5-BOC-aminomethyl-1,2,4-oxadiazol-3-yl)-7-fluoro-8-methoxy-12,12a-dihydro-9H,11H-azeto[2,1-c]imidazo[1,5-a][1,4]benzodiazepin-9-one as a colourless foam, Rf=0.18 (silica gel, methylene chloride/methanol 19:1).

k) A solution of 4.0 g (8.5 mmol) of (S)-1-(5-BOC-aminomethyl-1,2,4-oxadiazol-3-yl)-7-fluoro-8-methoxy-12,12a-dihydro-9H,11H-azeto[2,1-c]imidazo[1,5-a][1,4] benzodiazepin-9-one in 10 ml of trifluoroacetic acid was stirred at room temperature for 2 hours. The yellow solution was evaporated, the residue was dissolved in water and the aqueous phase was washed three times with methylene chloride. Subsequently, the aqueous phase was made basic with 5 ml of aqueous ammonia solution and extracted six times with methylene chloride. The organic phasses were dried over sodium sulfate, filtered and evaporated. The residue obtained was chromatographed (silica gel, methylene chloride/methanol/aqueous ammonia 110:10:1). There were obtained 2.3 g (73%) of (S)-1-(5-aminomethyl-1,2,4-oxadiazol-3-yl)-7-fluoro-8-methoxy-12,12a-dihydro-9H, 11H-azeto[2,1-c]imidazo[1,5-a][1,4]benzodiazepin-9-one as colourless crystals of m.p. 196°–198°.

EXAMPLE 36

5.1ml (29.8 mmol) of N-ethyldiisopropylamine and 1.46 ml (17.34 mmol) of allyl bromide were added to a solution of 800 mg (2.16 mmol) of (S)-1-(5-aminomethyl-1,2,4-oxadiazol-3-yl)-7-fluoro-8-methoxy-12,12a-dihydro-9H, 11H-azeto[2,1-c]imidazo[1,5-a][1,4]benzodiazepin-9-one in 12 ml of methylene chloride. The reaction solution was stirred at room temperature for 20 hours, subsequently diluted with methylene chloride and washed three times with water. The organic phases were dried over magnesium sulfate, filtered and evaporated. The residue obtained was chromatographed (silica gel, methylene chloride/methanol 19:1). There were obtained 770 mg (79%) of (S)-1-(5-diallylaminomethyl-1,2,4-oxadiazol-3-yl)-7-fluoro-8-methoxy-12,12a-dihydro-9H,11H-azeto[2,1-c]imidazo[1,5-a][1,4]benzodiazepin-9-one as a colourless foam, Rf=0.37 (silica gel, methylene chloride/methanol 19:1).

EXAMPLE 37

2.55 ml (14.9 mmol) of N-ethyldiisopropylamine and 0.73 ml (8.67 mmol) of allyl bromide were added to a solution of 800 mg (2.16 mmol) of (S)-2-(5-aminomethyl-1,2,4-oxadiazol-3-yl)-7-fluoro-8-methoxy-12,12a-dihydro-9H,11H-azeto[2,1-c]imidazo[1,5-a][1,4]benzodiazepin-9-one in 12 ml of methylene chloride. The reaction solution was stirred at room temperature for 20 hours, subsequently diluted with methylene chloride and washed three times with water. The organic phases were dried over magnesium sulfate, filtered and evaporated. The residue obtained was chromatographed (silica gel, methylene chloride/methanol 19:1). There were obtained 340 mg (35%) of (S)-1-(5-diallylaminomethyl-1,2,4-oxadiazol-3-yl)-7-fluoro-8-methoxy-12,12a-dihydro-9H,11H-azeto[2,1-c]imidazo[1,5-a][1,4]benzodiazepin-9-one as a colourless foam, Rf=0.37 (silica gel, methylene chloride/methanol 19:1), 30 mg of mixed fraction and 120 mg (13%) of (S)-1-(5-allylaminomethyl-1,2,4-oxadiazol-3-yl)-7-fluoro-8-methoxy-12,12a-dihydro-9H,11H-azeto[2,1-c]imidazo[1,5-a][1,4]benzodiazepin-9-one as a colourless foam, Rf=0.21 (silica gel, methylene chloride/methanol 19:1).

EXAMPLE 38

6.2 g (89.2 mmol) of hydroxylamine hydrochloride and 16.3 g (63.6 mmol) of 8-fluoro-5,6-dihydro-5-methyl-6-oxo-4H-imidazo[1,5-a][1,4]benzodiazepine-3-carbonitrile were added in succession at room temperature under argon to a sodium methylate solution which had been prepared in the usual manner from 2.0 g (86.9 mmol) of sodium and 85 ml of methanol. The reaction mixture was stirred at room temperature for 24 hrs. and then cooled in an ice bath. The separated crystals were filtered off and triturated in 35 ml of water. The white crystals were filtered off and dried at 60° in a vacuum. There were obtained 12.4 g (67%) of 8-fluoro-5,6-dihydro-5-methyl-6-oxo-4H-imidazo[1,5-a][1,4]benzodiazepine-3-carboxamidoxime as white crystals of m.p. 249°–250° (dec.).

Additional product (2.8 g), still contaminated with starting product, was obtained by evaporating the filtrate and repeating the procedure described above. This product was chromatographed on 100 g of silica gel, firstly with methylene chloride/acetone 9:1, 2:1 and finally with methylene chloride/methanol 9:1, there being obtained a further 1.72 g of 8-fluoro-5,6-dihydro-5-methyl-6-oxo-4H-imidazo[1,5-a][1,4]benzodiazepine-3-carboxamidoxime. Total yield: 77%.

b) 0.38 ml (2.2 mmol) of N-ethyldiisopropylamine was added to a suspension of 0.4 g (2.2 mmol) of morpholin-4-yl-acetic acid hydrochloride in 4 ml of DMF. 390 mg (2.4 mmol) of 1,1'-carbonyldiimidazole were added portionwise at room temperature, whereupon the solution was stirred at 50° for 30 min. and then treated at room temperature with 0.58 g (2.0 mmol) of 8-fluoro-5,6-dihydro-5-methyl-6-oxo-4H-imidazo[1,5-a][1,4]benzodiazepine-3-carboxamidoxime. The reaction mixture was heated to 90° for 20 hrs. The solvent was removed in a vacuum, the residue was taken up in 15 ml of water and the solution was extracted several times with ethyl acetate. The combined extracts were dried over sodium sulfate, filtered and evaporated. The crude material was purified by chromatography on silica gel (methylene chloride/methanol 19:1). The solvent was removed in a vacuum, the residue was dissolved in 5 ml of acetonitrile and the solution was made acid by the addition of ethereal HCl solution. The white crystals were filtered off under suction and recrystallized from acetonitrile. There was obtained 0.5 g (54%) of 8-fluoro-5-methyl-3-(5-morpholin-4-ylmethyl-1,2,4-oxadiazol-3-yl)-5,6-dihydro-4H-imidazo[1,5-a][1,4]benzodiazepin-6-one hydrochloride (3:5) of m.p. 198°–205° (dec.).

EXAMPLE 39 a) 11.8 g (39.2 mmol) of (S)-7-fluoro-11,12,13,13a-tetrahydro-9-oxo-9H-imidazo[1,5-a]-pyrrolo[2,1-c][1,4]benzodiazepine-1-carboxylic acid were dissolved in 80 ml of N,N-dimethylformamide, treated portionwise with 6.71 g (41.4 mmol) of 1,1'-carbonyldiimidazole and stirred at 50° for 20 min. After adding 8.77 g (40 mmol) of phthaloylglycine amidoxime the mixture was stirred at 100° overnight and at 120° for 5 hours. After evaporating the solvent the residue was dissolved in methylene chloride, whereupon the solution was washed three times with water, dried over magnesium sulfate and concentrated. By chromatography on silica gel while eluting with ethyl acetate there were obtained 9.6 g (50%) of (S)-7-fluoro-11,12,13,13a-tetrahydro-9H-1-(3-phthalimidomethyl-1,2,4-oxadiazol-5-yl)-imidazo[1,5-a]pyrrolo[2,1-c][1,4]benzodiazepin-9-one of m.p. 258°–260°, which was used in the next step without further purification.

b) 9.6 g (19.8 mmol) of (S)-7-fluoro-11,12,13,13a-tetrahydro-9H-1-(3-phthalimidomethyl-1,2,4-oxadiazol-5-yl)-imidazo[1,5-a]pyrrolo[2,1-c][1,4]benzodiazepin-9-one were dissolved in 130 ml of ethanol and treated dropwise with 130 ml of methylamine (33% in ethanol) at 65° within 30 min. The solution was stirred at 70° for 2 hours and subsequently concentrated. The residue was taken up in methylene chloride and 20 ml of 4N hydrochloric acid and the solution was washed three times with methylene chloride. The aqueous phase was made alkaline with 20 ml of 4N sodium hydroxide solution and extracted three times with methylene chloride and five times with ethyl acetate. After drying the combined organic solutions and evaporating the solvent there were obtained 6.73 g (96%) of (S)-1-(3-aminomethyl-1,2,4-oxadiazol-5-yl)-7-fluoro-11,12, 13,13a-tetrahydro-9H-imidazo[1,5-a]pyrrolo[2,1-c]-[1,4]benzodiazepin-9-one which was used without further purification as the starting material for the Example described hereinafter.

EXAMPLE 40

4 g (11.3 mmol) of crude (S)-1-(3-aminomethyl-1,2,4-oxadiazol-5-yl)-7-fluoro-11,12,13,13a-tetrahydro-9H-imidazo[1,5-a]pyrrolo[2,1-c][1,4]-benzodiazepin-9-one, 60 ml of methylene chloride, 13.6 ml (79 mmol) of N-ethyldiisopropylamine and 5.63 g (46 mmol) of allyl bromide were stirred at room temperature for 60 hours. The reaction solution was washed three times with water, dried over magnesium sulfate and evaporated. The residue was chromatographed on 360 g of silica gel while eluting with ethyl acetate. The uniform fractions were evaporated. There were obtained 2.19 g (45%) of (S)-1-(5-diallylaminomethyl-1,2,4-oxadiazol-3-yl)-7-fluoro-11,12,13,13a-tetrahydro-9H-imidazo[1,5-a]pyrrolo 2,1-c][1,4]benzodiazepin-9-one (oil: $R_f$ 0.43; Kieselgel 60 $F_{254}$; eluent: ethyl acetate), which was converted into the hydrochloride.

EXAMPLE 41 a) 6.31 g (21 mmol) of (S)-7-fluoro-9-oxo-11,12,13,13a-tetrahydro-9H-imidazo[1,5-a]pyrrolo[2,1-c][1,4]benzodiazepine-1-carboxamide were suspended in 20 ml of dioxan and 3.6 ml of pyridine and treated dropwise at 5° to 10° with 3.3 ml of trifluoroacetic anhydride. The reaction mixture was stirred at room temperature overnight and poured into 150 ml of water. The suspension obtained was filtered and the crystals were dried. There were obtained 5.36 g (90%) of (S)-7-fluoro-9-oxo-11,12,13,13a-tetrahydro-9H-imidazo[1,5-a]pyrrolo[2,1-c][1,4]benzodiazepine-1-carbonitrile of m.p. 254°–256°.

b) 61 5 mg (26.8 mmol) of sodium were dissolved in 35 ml of methanol. 2 g (28.8 mmol) of hydroxylamine hydrochloride and 5.3 g (18.8 mmol) of (S)-7-fluoro-11,12,13,13a-tetrahydro-9-oxo-9H-imidazo[1,5-a]pyrrolo[2,1-c][1,4]benzodiazepine-1-carbonitrile were added in succession at room temperature. The suspension was stirred at room temperature overnight, cooled to 0° during 30 min. and the crystals were filtered off. After drying there were obtained 4.97 (84%) of (S)o7-fluoro-11,12,13,13a-tetrahydro-9-oxo-9H-imidazo[1,5-a]pyrrolo[2,1-c][1,4]benzodiazepine-1-carboxamidoxime of m.p. 267°–268°.

c) 2.93 g (15.7 mmol) of BOC-glycine were dissolved in 30 ml of N,N-dimethylformamide and treated portionwise with 2.76 g (17 mmol) of 1,1'-carbonyldiimidazole. After completion of the $CO_2$ evolution the solution was stirred at 55° for 20 min. Then, 4.95 g (22.2 mmol) of (S)-7-fluoro-11,12,13,13a-tetrahydro-9-oxo-9H-imidazo[1,5-a]pyrrolo [2,1-c][1,4]benzodiazepine-1-carboxamidoxime were added and the mixture was stirred at 90° overnight. The reaction mixture was evaporated and the residue was chromatographed on silica gel while eluting with methylene chloride/methanol 19/1. There were obtained 4.45 g (61%) of (S)-1-(5-BOC-aminomethyl-1,2,4-oxadiazol-3-yl)-7-fluoro-11, 12,13,1:3a-tetrahydro-9H-imidazo[1,5-a]pyrrolo[2,1-c][1, 4]-benzodiazepin-9-one, which was used in the next step without further purification.

d) 4.4 g (9.7 mmol) of (S)-1-(5-BOC-aminomethyl-1,2, 4-oxadiazol-3-yl)-7-fluoro-11,12,13,13a-tetrahydro-9H-imidazo[1,5-a]pyrrolo[2,1-c][1,4]-benzodiazepin-9-one were stirred at room temperature for 1.5 hours in 15 ml of trifluoroacetic acid. The solution was concentrated. The residue was taken up in saturated sodium bicarbonate solution and extracted ten times with methylene chloride. By drying and evaporating the combined organic phases there were obtained 2.76 g (80%) of (S)-1-(5-aminomethyl-1,2, 4-oxadiazol-3-yl)-7-fluoro-11,12,13,13a-tetrahydro-9H-imidazo[1,5-a]pyrrolo[2,1-c][1,4]benzodiazepin-9-one, which was used without further purification as the starting material for the Example described hereinafter.

EXAMPLE 42

2.75 g (7.6 mmol) of crude (S)-1-(5-aminomethyl-1,2,4-oxadiazol-3-yl)-7-fluoro-11,12,13,13a-tetrahydro-9H-imidazo[1,5-a]pyrrolo[2,1-c][1,4]benzodiazepin-9-one, 50 ml of methylene chloride, 9 ml (53.3 mmol) of N-ethyldiisopropylamine and 3.75 g (31mmol) of allyl bromide were stirred at room temperature for 96 hours. The reaction solution was washed three times with water, dried over magnesium sulfate and evaporated. The residue was chromatographed on 360 g of silica gel while eluting with ethyl acetate. The uniform fractions were evaporated. There were obtained 2.46 g (74%) of (S)-1-(5-diallylaminomethyl-1,2,4-oxadiazol-3-yl)-7-fluoro-11,12,13,13a-tetrahydro-9H-imidazo[1,5-a]pyrrolo 2,1-c][1,4]benzodiazepin-9-one, which was converted into the hydrochloride.

EXAMPLE 43 a) 10 g (29.7 mmol) of (S)-8-trifluoromethyl-12,12a-dihydro-9-oxo-9H,11H-azeto[2,1-c]imidazo[1,5-a][1,4] benzodiazepine-1-carboxylic acid were suspended in 50 ml of N,N-dimethylformamide and treated portionwise at room temperature with 5.1 g (31.2 mmol) of 1,1'-carbonyldiimidazole. After completion of the $CO_2$ evolution the clear brown solution was stirred at 50° for 20 min., cooled and treated dropwise with 8 ml of conc. ammonia at a temperature below 150 within about 15'. After stirring for 40 minutes the suspension obtained was poured into 300 ml of ice-water, whereupon the mixture was stirred at room temperature for 20', filtered and rinsed with a small amount of water. After drying there were obtained 7.51 g (75%) of (S)-8-trifluoromethyl-12,12a-dihydro-9-oxo-9H,11H-azeto [2,1-c]imidazo[1,5-a][1,4]benzodiazepine-1-carboxamide of m.p. >300°.

b) 7.5 g (22.3 mmol) of (S)-8-trifluoromethyl-12,12a-dihydro-9-oxo-9H,11H-azeto[2,1-c]imidazo[1,5-a][1,4] benzodiazepine-1-carboxamide were suspended in 40 ml of dioxan and 4 ml of pyridine and treated dropwise with 3.6 ml of trifluoroacetic anhydride at 7 to 10° within 10 min. The mixture was stirred at room temperature for 3/4 hour and poured into 300 ml of water. The suspension obtained was filtered and, after drying the residue, there were obtained 3.75 g (52%) of (S)-8-trifluoromethyl-12,12a-dihydro-9-oxo-9H,11H-azeto[2,1-c]imidazo[1,5-a][1,4] benzodiazepine-1-carbonitrile of m.p. 115°–119°.

c) 730 mg (31.8 mmol) of sodium were dissolved in 40 ml of methanol. 2.37 g (34.1 mmol) of hydroxylamine hydrochloride and 7.1 g (22.3 mmol) of (S)-8-trifluoromethyl-12, 12a-dihydro-9-oxo-9H,11H-azeto[2,1-c]imidazo[1,5-a][1, 4]benzodiazepine-1-carbonitrile were added in succession at room temperature and the mixture was stirred at room temperature overnight. By evaporating the solvent there were obtained 7.8 g (100%) of (S)-8-trifluoromethyl-12, 12a-dihydro-9-oxo-9H,11H-azeto[2,1-c]imidazo[1,5-a][1, 4]benzodiazepine-1-carboxamidoxime, which was used in the next step without further purification.

d) 4.2 g (24 mmol) of BOC-glycine were dissolved in 40 ml of N,N-dimethylformamide and treated portionwise with 4.05 g (25 mmol) of 1,1'-carbonyldiimidazole. After completion of the $CO_2$ evolution the solution was stirred at 50° for 20 min. Then, 7.7 g (22 mmol) of (S)-8-trifluoromethyl-12,12a-dihydro-9-oxo-9H,11H-azeto[2,1-c] imidazo[1,5-a][1,4]benzodiazepine were added and the mixture was stirred at 90° overnight. The reaction mixture was concentrated and the residue was dissolved in methylene chloride. By washing, drying and evaporating the organic phase there were obtained 7.82 g (72%) of (S)-1-[5-(N-BOC-aminomethyl)-1,2,4-oxadiazol-3-yl]-8-trifluoromethyl-12,12a-dihydro-9H,11H-azeto[2,1-c] imidazo[1,5-a][1,4]benzodiazepin-9-one, which was used in the next step without further purification.

e) 7.8 g (15.9 mmol) of crude (S)-1-[5-(N-BOC-aminomethyl)-1,2,4-oxadiazol-3-yl]-8-trifluoromethyl-12, 12a-dihydro-9H,11H-azeto[2,1-c]imidazo[1,5-a][1,4] benzodiazepin-9-one and 30 ml of trifluoroacetic acid were stirred at room temperature for 1hour. The solution was evaporated. The residue was dissolved in water and washed three times with methylene chloride. The aqueous phase was made alkaline with conc. ammonia and extracted nine times with ethyl acetate (a total of about 1 l). By evaporating the organic phases, combined and dried over magnesium sulfate, there were obtained 4.57 g (73%) of (S)-1-(5-aminomethyl-1,2,4-oxadiazol-3-yl)-8-trifluoromethyl-12, 12a-dihydro-9H,11H-azeto[2,1-c]imidazo[1,5-a][1,4] benzodiazepin-9-one, which was used without further purification as the starting material for the Example described hereinafter.

EXAMPLE 44

3 g (7.7 mmol) of crude (S)-1-(5-aminomethyl-1,2,4-oxadiazol-3-yl)-8-trifluoromethyl-12,12a-dihydro-9H,11H-azeto[2,1-c]imidazo[1,5-a][1,4]benzodiazepin-9-one, 50 ml of methylene chloride, 14.2 ml (72 mmol) of N-ethyldiisopropylamine and 5.14 g (3.6 mmol) of allyl bromide were stirred at room temperature overnight and at 40° for 4 hours. The reaction solution was washed three times with water, dried over magnesium sulfate and evaporated. The residue was chromatographed on 390 g of silica gel while eluting with ethyl acetate. There were obtained 1.50 g (41%) of (S)-1-(5-diallylaminomethyl-1,2,4-oxadiazol-3-yl)-8-trifluoromethyl-12,12a-dihydro-9H,11H-azeto[2,1-c]imidazo[1,5-a][1,4]benzodiazepin-9-one, which was converted into the dihydrochloride with methanolic hydrochloric acid.

EXAMPLE 45

1.51 g (7.7 mmol) of (S)-1-(5-aminomethyl-1,Z,4-oxadiazol-3-yl)-8-trifluoromethyl-12,12a-dihydro-9H,11H-azeto[2,1-c]imidazo[1,5-a][1,4]benzodiazepin-9-one, 15 ml of methylene chloride, 4 ml (23.4 mmol) of N-ethyldiisopropylamine and 1.06 g (4 mmol) of α,α'-dibromo-o-xylene were stirred at room temperature overnight. The reaction solution was washed twice with water, dried over magnesium sulfate and evaporated. The residue was chromatographed on 240 g of silica gel while eluting with ethyl acetate/hexane/triethylamine 17/2/1. There was obtained 0.5 g (26%) of (S)-8-trifluoromethyl-12,12a-dihydro-1-(5-isoindolin-2-ylmethyl-1,2,4-oxadiazol-3-yl)-9H,11H-azeto[2,1-c]imidazo[1,5-a][1,4]benzodiazepin-9-one, which was converted into the hydrochloride of m.p. 185°–188°.

EXAMPLE 46 a) 40.58 g (128.7 mmol) of ethyl (S)-7-fluoro-12,12a-dihydro-9-oxo-9H,11H-azeto-[2,1-c]imidazo[1,5-a][1,4]benzodiazepine-1-carboxylate, 300 ml of ethanol and 32.5 ml (130 mmol) of 4N sodium hydroxide solution were heated to reflux on a steam bath for 1.5 hours. The alcohol was evaporated on a rotary evaporator. The aqueous phase was washed twice with methylene chloride and acidified to pH 3–4 with 32.5 ml (130 mmol) of 4N hydrochloric acid. The suspension obtained was cooled and filtered. The filter residue was washed with a small amount of ice water and dried. There were obtained 36.67 g (99%) of (S)-7-fluoro-12,12a-dihydro-9-oxo-9H,11H-azeto[2,1-c]imidazo[1,5-a][1,4]benzodiazepine-1-carboxylic acid of m.p. 159°–160°.

b) 20 g (69.6 mmol) of (S)-7-fluoro-12,12a-dihydro-9-oxo-9H,11H-azeto[2,1-c]imidazo[1,5-a][1,4]-benzodiazepine-1-carboxylic acid were dissolved in 40 ml of N,N-dimethylformamide, treated portionwise with 13 g (80.2 mmol) of 1,1'-carbonyldiimidazole and stirred at 60° for 10 min. After adding 16.78 g (76.6 mmol) of phthaloylglycine amidoxime a mixture was stirred at 90° for 1 hour. 14 ml of trifluoroacetic acid were added and the mixture was stirred at 85° for a further 18 hours. The suspension obtained was cooled, the crystals were filtered off and rinsed with methanol. There were obtained 16.74 g (51%) of (S)-7-fluoro-12,12a-dihydro-1-(3-phthalimidomethyl-1,2,4-oxadiazol-5-yl)-9H,11H-azeto[2,1-c]imidazo[1,5-a][1,4]benzodiazepin-9-one of m.p. 287°–288°, which was used in the next step without further crystallization.

c) 10.8 g (23 mmol) of crude (S)-7-fluoro-12,12a-dihydro-1-(3-phthalimidomethyl-1,2,4-oxadiazol-5-yl)-9H,11H-azeto[2,1-c]imidazo[1,5-a][1,4]benzodiazepin-9-one in 150 ml of ethanol were treated dropwise with 150 ml of methylamine (33% in ethanol) at 60° C. within 30 min. The solution was stirred at 70° for 2 hours and subsequently concentrated. The residue was taken up in methylene chloride and 30 ml of 4N hydrochloric acid and the solution was washed three times with methylene chloride. The aqueous phase was made alkaline with 30 ml of 4N sodium hydroxide solution and extracted five times with methylene chloride. After drying the combined organic solutions and evaporating the solvent there were obtained 7.5 g (96%) of (S)-1-(3-aminomethyl-1,2,4-oxadiazol-5-yl)-7-fluoro-12,12a-dihydro-9H,11H-azeto[2,1-c]imidazo[1,5-a][1,4]benzodiazepin-9-one, which was used without further crystallization as the starting material for the Example described hereinafter.

EXAMPLE 47

10.35 g (30.4 mmol) of crude (S)-1-(3-aminomethyl-1,2,4-oxadiazol-5-yl)-7-fluoro-12,12a-dihydro-9H,11H-azeto[2,1-c]imidazo[1,5-a][1,4]benzodiazepin-9-one, 100 ml of N,N-dimethylformamide, 13 ml (76 mmol) of ethyldiisopropylamine and 7.72 g (63.8 mmol) of allyl bromide were stirred at room temperature for 3 hours. After evaporating the reaction mixture the residue was purified by chromatography on silica gel while eluting with ethyl acetate. By recrystallization from ethyl acetate and hexane there were obtained 8.11 g (63%) of (S)-1-(3-diallyl-aminomethyl-1,2,4-oxadiazol-5-yl)-7-fluoro-12,12a-dihydro-9H,11H-azeto[2,1-c]imidazo[1,5-a][1,4]benzodiazepin-9-one, which was converted into the hydrochloride of m.p. 188°–190°.

EXAMPLE 48 a) 0.92 g (5.3 mmol) of BOC-glycine was dissolved in 7 ml of N,N-dimethylformamide under argon and treated portionwise at room temperature with 0.9 g (5.6 mmol) of 1,1'-carbonyldiimidazole. After completion of the $CO_2$ evolution the mixture was stirred at room temperature for a further 30 min. and thereupon treated with 1.44 g (5.0 mmol) of 8-fluoro-5,6-dihydro-5-methyl-6-oxo-4H-imidazo[1,5-a][1,4]benzodiazepine-3-carboxamidoxime. The mixture was heated to 90° for 18 hrs., left to cool to room temperature and diluted with 50 ml of water, whereby the product crystallized out. The product was filtered off under suction and dissolved in methylene chloride, and the solution was dried with sodium sulfate. 1.25 g of a white foam were obtained by evaporation in a vacuum.

The aqueous filtrate was extracted several times with methylene chloride and the extracts were dried with sodium sulfate, filtered and evaporated to give a further 0.95 g of a solid. This was taken up in 10 ml of water and triturated, whereby further product separated. The precipitated material was filtered off, dissolved in methylene chloride, dried with sodium sulfate, filtered and evaporated. A further 0.47 g of crude product was obtained.

The combined crude products (1.72 g) were crystallized from 7 ml of ethyl acetate. There were obtained 1.23 g (58%) of 3-(5-BOC-amino-methyl-1,2,4-oxadiazol-3-yl)-8-fluoro-5-methyl-5,6-dihydro-4H-imidazo[1,5-a][1,4]benzodiazepin-6-one of m.p. 170°–172°.

b) 0.64 g (1.5 mmol) of 3-(5-BOC-aminomethyl-1,2,4-oxadiazol-3-yl)-8-fluoro-5-methyl-5,6-dihydro-4H-imidazo[1,5-a][1,4]benzodiazepin-6-one was taken up in 1.5 ml of trifluoroacetic acid under argon and stirred at room temperature for 1 hr. The solvent was evaporated in a vacuum and the residue was dissolved in 10 ml of water. The solution was extracted with methylene chloride and the aqueous phase was made basic with conc. ammonia solution and extracted several times with methylene chloride. The combined organic extracts were dried with sodium sulfate, filtered and evaporated. The slightly pink coloured crystals obtained were heated in 10 ml of methanol, whereupon the mixture was filtered over Celite and the filtrate was evaporated. The residue was recrystallized from 9 ml of acetonitrile/methanolic hydrochloric acid 2:1. There was obtained 0.30 g (50%) of 3-(5-aminomethyl-1,2,4-oxadiazol-3-yl)-8-fluoro-5-methyl-5,6-dihydro-4H-imidazo[1,5-a][1,4]benzodiazepin-6-one hydrochloride (1:1.9) of m.p. 264°–266° (dec.).

EXAMPLE 49

A suspension of 0.49 g (1.5 mmol) of 3-(5-aminomethyl-1,2,4-oxadiazol-3-yl)-8-fluoro-5-methyl-5,6-dihydro-4H-imidazo[1,5-a][1,4]benzodiazepin-6-one hydrochloride (1:1.9) in 8 ml of methylene chloride was treated under argon with 1.8 ml (10.5 mmol) of N-ethyldiisopropylamene and 0.51ml (6.0 mmol) of allyl bromide and stirred at room temperature under argon for 42 hrs. The solution was washed three times with 10 ml of water, dried with sodium sulfate, filtered and evaporated. The crude product was purified by chromatography on 50 g of silica gel (ethyl acetate), whereupon the eluate was evaporated and the residue was taken up in 5 ml of methanol. The solution was acidified with ethereal hydrochloric acid and the solvent was removed in a vacuum. The residue was dissolved in 4 ml of methanol, whereupon the solution was filtered through Celite, cooled to about 0° and diluted with 8 ml of ether. Thereby, white crystals separated slowly and were filtered off. There were obtained 345 mg (50%) of 3-[5-(diallylaminomethyl)-1,2,4-oxadiazol-3-yl]-8-fluoro-5-methyl-5,6-dihydro-4H-imidazo[1,5-a ][1,4]benzodiazepin-6-one hydrochloride (2:3) of m.p. 133°–140° (dec.).

EXAMPLE 50

A suspension of 0.49 g (1.5 mmol) of 3-(5-aminomethyl-1,2,4-oxadiazol-3-yl)-8-fluoro-5-methyl-5,6-dihydro-4H-imidazo[1,5-a][1,4]benzodiazepin-6-one in 8 ml of methylene chloride was treated under argon with 0.77 ml (4.5 mmol) of N-ethyldiisopropylamine and 0.475 g (1.8 mmol) of α,α'-dibromo-o-xylene and stirred at room temperature under argon for 7 hrs. The solution was washed once with 10 ml of water, dried with sodium sulfate, filtered and evaporated. The crude product was purified by chromatography on 40 g of silica gel (methylene chloride/acetone 4:1, then 22:1), whereupon the eluate was evaporated and the residue was taken up in 3 ml of methanol. The solution was acidified with ethereal hydrochloric acid and the solvent was removed in a vacuum. The residue was dissolved in 3 ml of methanol, whereupon the solution was cooled to about 0° and diluted dropwise with 3 ml of ether. Thereby, white crystals separated slowly and were filtered off. There were obtained 190 mg (26%) of 8-fluoro-3-(5-isoindolin-2-ylmethyl-1,2,4-oxadiazol-3-yl)-5-methyl-5,6-dihydro-4H-imidazo[1,5-a][1,4]benzodiazepin-6-one hydrochloride (22:3) of m.p. 177°–184° (dec.).

EXAMPLE 51

1.85 g (5 mmol) of (S)-1-(3-aminomethyl-1,2,4-oxadiazol-5-yl)-8-chloro-11,12,13,13a-tetrahydro-9H-imidazo[1,5-a]pyrrolo[2,1-c][1,4]benzodiazepin-9-one, 20 ml of N,N-dimethylformamide, 3.4 ml (20 mmol) of N-ethyldiisopropylamine and 1.45 g (5.5 mmol) of α,α'-dibromo-o-xylene were stirred at room temperature overnight. After evaporating the reaction solution the residue was chromatographed on 430 g of silica gel while eluting with ethyl acetate/methanol 9/1. There was obtained 0.74 g (31%) of (S) 8-chloro-11,12,13,13a-tetrahydro-1-(3-isoindolin-2-ylmethyl- 1,2,4-oxadiazol-5-yl)-9H-imidazo[1,5-a]pyrrolo[2,1-c][1,4]benzodiazepin-9-one, which was converted into the hydrochloride of m.p. 165°–170°.

EXAMPLE 52

5 g (14 mmol) of (S)-1-(3-aminomethyl-1,2,4-oxadiazol-5-yl)-8-chloro-12,12a-dihydro-9H,11H-azeto[2,1-c]imidazo[1,5-a][1,4]benzodiazepin-9-one, 50 ml of methylene chloride, 12 ml (70 mmol) of N-ethyldiisopropylamine and 3.7 g (14 mmol) of α,α'-dibromo-o-xylene were stirred at room temperature for 72 hours. The reaction solution was washed three times with water, dried over magnesium sulfate and evaporated. The residue was chromatographed on 70 g of silica gel while eluting with methylene chloride/ethyl acetate 7/3. There were obtained 4.0 g (62%) of (S)-8-chloro-12,12a-dihydro-1-(3-isoindolin-2-ylmethyl-1,2,4-oxadiazol-5-yl)-9H,11H-azeto[2,1-c]imidazo[1,5-a][1,4]benzodiazepin-9-one, which was converted into the hydrochloride of m.p. 170°–175°.

EXAMPLE 53 a) 2.75 g (10.0 mmol) of 8-fluoro-5,6-dihydro-5-methyl-6-oxo-4H-imidazo[1,5-a][1,4]benzodiazepine-3-carboxylic acid were suspended in 20 ml of N,N-dimethylformamide under argon and 1.95 g (12.0 mmol) of 1,1'-carbonyldiimidazole were added portionwise at room temperature. After completion of the gas evolution, the reaction mixture was stirred at 50° for a further 30 min., then cooled to room temperature and treated with 2.41 g (11.0 mmol) of phthaloylglycine amidoxime. The mixture was heated to 90° for 18 hrs., cooled in an ice bath and diluted with 40 ml of ether, whereupon the precipitated crystals were filtered off and dried in a vacuum. There were obtained 2.88 g (63%) of 8-fluoro-5,6-dihydro-5-methyl-3-(3-phthalimidomethyl-1,2,4-oxadiazol-5-yl)-4H-imidazo [1,5-a][1,4]benzodiazepin-6-one of m.p. 273°–276°.

b) 10.1 g (22 mmol) of 8-fluoro-5,6-dihydro-5-methyl-3-(3-phthalimidomethyl-1,2,4-oxadiazol-5-yl)-4H-imidazo[1,5-a][1,4]benzodiazepin- 6-one were heated to 65° in 220 ml of ethanol, whereupon 150 ml of 33% ethanolic methylamine solution were added dropwise within 100 min. After completion of the addition the solution was heated for a further 17 hrs. and then cooled in an ice bath, whereby white crystals separated. These were filtered off and dried in a vacuum. After recrystallization from ethanol there were obtained 3.05 g of 3-(3-aminomethyl)-1,2,4-oxadiazol-5-yl)-8-fluoro-5,6-dihydro-5-methyl-4H-imidazo[1,5-a][1,4]benzodiazepin-6-one of m.p. 208°–217°. A further 2.5 g of product were obtained by chromatography on silica gel with methylene chloride/methanol 19:1, then 9:1. Total yield: 5.55 g (77%).

EXAMPLE 54

492 mg (1.5 mmol) of 3-(3-aminomethyl)-1,2,4-oxadiazol-5-yl)-8-fluoro-5,6-dihydro-5-methyl-4H-imidazo[1,5-a][1,4]benzodiazepin-6-one in 8 ml of methanol were treated under argon with 1.8 ml (10.5 mmol) of N-ethyldiisopropylamine and 0.51 ml (6.0 mmol) of allyl bromide and stirred at room temperature under argon for 24 hrs. The solution was washed once with 10 ml of water, dried with sodium sulfate, filtered and evaporated. The crude product was purified by chromatography on 40 g of silica gel (ethyl acetate), the eluate was evaporated and the residue was taken up in 5 ml of methanol. The solution was acidified with ethereal hydrochloric acid and the solvent was removed in a vacuum. The residue was dissolved in 5 ml. of methanol and the solution was cooled to about 0° and diluted with 18 ml of ether. White crystals separated slowly and were filtered off. There were obtained 270 mg (40%) of 3-(3-(diallylaminomethyl)-1,2,4-oxadiazol-5-yl)-8-fluoro-5-methyl-5,6-dihydro-4H-imidazo[1,5-a][1,4]benzodiazepin-6-one hydrochloride (1:1) of m.p. 181°–185° (dec.).

EXAMPLE 55

492 mg (1.5 mmol) of 3-(3-aminomethyl)-1,2,4-oxadiazol-5-yl)-8-fluoro-5,6-dihydro-5-methyl-4H-imidazo[1,5-a][1,4]benzodiazepin-6-one in 8 ml of methylene chloride were treated under argon with 1.3 ml (7.5 mmol) of N-ethyldiisopropylamine and 0.42 ml (3.6 mmol) of 3,3-dimethylallyl bromide and stirred at room temperature under argon for 2 hrs. The solution was evaporated and the crude product was purified by chromatography on 40 g of silica gel (ethyl acetate). The eluate was evaporated and the residue was taken up in 3 ml of methanol. The solution was acified with ethereal hydrochloric acid and evaporated, whereupon the residue was taken up in 10 ml of ethyl acetate. The solution was cooled to about 0° and the white crystals were filtered off. There were obtained 220 mg (29%) of 3-[3-[bis-(3-methyl-but-2-enyl)-aminomethyl]-1,2,4-oxadiazol-5-yl ]-8-fluoro-5-methyl-5,6-dihydro-4H-imidazo [1,5-a][1,4] benzodiazepin-6-one hydrochloride (1:1) of m.p. 181°–184° (dec.).

EXAMPLE 56

492 mg (1.5 mmol) of 3-(5-aminomethyl)-1,2,4-oxadiazol-3-yl)-8-fluoro-5,6-dihydro-5-methyl-4H-imidazo[1,5-a][1,4]benzodiazepin-6-one in 8 ml of methylene chloride were treated under argon with 1.3 ml (7.5 mmol) of N-ethyldiisopropylamine and 0.42 ml (3.6 mmol) of 3,3-dimethylallyl bromide and stirred at room temperature under argon for 2 hrs. The solution was evaporated and the crude product was purified by chromatography on 40 g of silica gel (ethyl acetate). The eluate was evaporated and the residue was taken up in 3 ml of methanol. The solution was acidified with ethereal hydrochloric acid and evaporated, whereupon the residue was taken up in 10 ml of ethyl acetate. The solution was heated to reflux for 30 min. and cooled to about 0°, whereupon the white crystals were filtered off. There were obtained 315 mg (40%) of 3-[5-[bis-(3-methyl-but-2-enyl)-aminomethyl]-1,2,4-oxadiazol-3-yl]-8-fluoro-5-methyl-5,6-dihydro-4H-imidazo[1,5-a][1,4]benzodiazepin-6-one hydrochloride (2:3) of m.p. 144°–148° (dec.).

EXAMPLE 57 a) A solution of 26.9 g (171mmol) of 2H-thieno[3,2-d][1,3]oxazine-2,4(1H)-dione (EP 27214) and 16.1 g (171 mmol) of L-azetidine-2-carboxylic acid in 200 ml of dimethylformamide and 40 ml of acetic acid was stirred at 120° for 3 hours. The brown solution was evaporated and the brown residue obtained was crystallized from ethanol. There were obtained 15.2 g (43%) of (S)-6,7-dihydroazeto[1,2-a]thieno[3,2-e][1,4]diazepine-5,9(4H,5aH)-dione as a colourless crystallizate of m.p. 274°.

b) A solution of 8.32 g (40 mmol) of (S)-6,7-dihydroazeto[1,2-a]thieno[3,2-e][1,4]diazepine-5,9(4H,5aH)-dione in 45 ml of dimethylformamide was added dropwise at –30° to a suspension of 1.92 g (44 mmol) of NaH (55%, washed with hexane) in 5 ml of dimethylformamide and the mixture was stirred at –30° for 40 minutes. After cooling to –60° a solution of 8.26 ml (40 mmol) of phosphoric acid diphenyl ester chloride in 3 ml of dimethylformamide was added dropwise in such a manner that the temperature did not rise above –45°. Subsequently, the mixture was stirred for a further 30 minutes.

In the meanwhile, 4.92 g (44 mmol) of potassium tert-.butylate were dissolved in 20 ml of dimethylformamide and treated at –60° with 4.7 ml (42.8 mmol) of ethyl isocyanoacetate (95%). The reaction mixture obtained above was added dropwise to the thus-obtained solution at –70° via a dropping funnel cooled to –40°. The dark brown viscous solution obtained was stirred at –60° for 1 hour and, after neutralization with 4.8 ml of acetic acid at –40°, poured into 300 ml of ice-water, whereupon the mixture was extracted five times with methylene chloride. The combined organic phases were dried over sodium sulfate, filtered and evaporated. The pale brown residue obtained was recyrstallized from ethanol. There were obtained 8.12 g (67%) of ethyl (S)-8-oxo-11,11a-dihydro-8H,10H-azeto[1,2-a]imidazo[5,1-c]thieno[3,2-e[]1,4]diazepine-1-carboxylate as colourless crystals of m.p. 188°–191°.

c) 13.9 ml (55.6 mmol) of 4N sodium hydroxide solution were added dropwise to a suspension of 13.5 g (44.5 mmol) of ethyl (S)-8-oxo-11,11a-dihydro-8H,10H-azeto[1,2-a]imidazo[5,1-c]thieno[3,2-e][1,4]diazepine-1-carboxylate in 10 ml of ethanol and 16 ml of water. The mixture was heated at reflux for 30 minutes and the ethanol was subsequently distilled off. The aqueous phase was washed twice with methylene chloride and adjusted to pH=3 with 4N hydrochloric acid. The resulting precipitate was filtered off and washed with water, ethanol and subsequently with diethyl ether. There were obtained 10.8 g (88%) of (S)-8-oxo-11,11a-dihydro-8H,10H-azeto[1,2-a]imidazo[5,1-c]thieno[3,2-e][1,4]diazepine-1-carboxylic acid as a colourless powder of m.p. 260° (dec.).

d) 7.65 g (47 mmol) of 1,1'-carbonyldiimidazole were added portionwise to a suspension of 12.43 g (45 mmol) of (S)-8-oxo-11,11a-dihydro-8H,10H-azeto[1,2-a]imidazo[5,1-c]thieno[3,2-e][1,4]diazepine-1-carboxylic acid in 70 ml of dimethylformamide. The resulting pale brown solution was heated to 50° for 45 minutes. Subsequently, the solution was cooled to room temperature and 10.9 ml of aqueous ammonia solution were added dropwise. After stirring for a further 30 minutes the reaction mixture was poured into 100 ml of ice-water and the resulting precipitate was filtered off and rinsed with water, ethanol and subsequently with ether. After drying at 70°/10 Torr there were obtained 11.0 g (89%) of (S)-8-oxo-11,11a-dihydro-8H,10H-azeto[1,2-a]imidazo[5,1-c]thieno[3,2-e][1,4]diazepine-1-carboxamide as colourless crystals of m.p. >250°.

e) 5.75 ml (41.3 mmol) of trifluoroacetic anhydride were added dropwise at 5°–8° to a suspension of 11.05 g (40.:2 mmol) of (S)-8-oxo-11,11a-dihydro-8H,10H-azeto[1,2-a]imidazo[5,1-c]thieno[3,2-e][1,4]diazepine-1-carboxamide in 55 ml of dioxan and 7 ml of pyridine. The beige solution obtained was stirred at 50° for 2.5 hours and subsequently poured into 50 ml of ice-water. Extraction with methylene chloride (four times), drying over sodium sulfate, filtration and evaporation yielded a pale brown residue which was chromatographed (silica gel, methylene chloride/methanol 10:1). There were obtained 8.5 g (82%) of (S)-8-oxo-11, 11a-dihydro-8H,10H-azeto[1,2-a]imidazo[5,1-c]thieno[3,2-e][1,4]diazepine-1-carbonitrile as a white powder of m.p. 211°–213°.

f) 8.44 g (32.9 mmol) of (S)-8-oxo-11,11a-dihydro-8H, 10H-azeto[1,2-a]imidazo[5,1-c]thieno[3,2-e][1,4]diazepine-1-carbonitrile and 3.48 g (50.5 mmol) of hydroxylamine hydrochloride were added to a freshly prepared solution of sodium methylate in methanol (from 1.08 g (47 mmol) of sodium in 50 ml of methanol), whereupon the mixture was stirred at room temperature for 48 hours. Subsequently, the suspension was evaporated and treated with 100 ml of water. The precipitate obtained was filtered off and dried in a high vacuum. There were obtained 7.8 g (82%) of (E)- and/or (S)-1-(amino-hydroxyimino-methyl)-11,11a-dihydro-8H,10H-azeto[1,2-a]imidazo[5,1-c]thieno[3,2-e][1,4]diazepin-8-one as a colourless powder of m.p. 195°–198°.

g) 5.12 g (31.5 mmol) of 1,1'-carbonyldiimidazole were added to a solution of 5.17 g (29.4 mmol) of BOC-glycine in 55 ml of dimethylformamide and the mixture was stirred at 50° for 30 minutes. Subsequently, 7.95 g (27.5 mmol) of (E)- and/or (S)-1-(aminohydroxyimino-methyl)-11,11a-dihydro-8H,10H-azeto[1,2-a]imidazo[5,1-c]thieno[3,2e][1, 4]diazepin-8-one were added and the mixture was stirred at 90° for 15 hours. The brown solution obtained was evaporated in a high vacuum and the brown residue obtained was chromatographed (silica gel, methylene chloride/methanol 10:1). There were obtained 11.6 g (98%) of (S)-1-(5-BOC-aminomethyl-1,2,4-oxadiazol-3-yl)-11,11a-dihydro-8H, 10H-azeto[1,2-a]imidazo[5,1-c]thieno[3,2-e][1,4]diazepin-8-one as a colourless foam, Rf=0.48 (silica gel, methylene chloride/methanol 10:1).

h) A solution of 11.6 g (27 mmol) of (S)-1-(5-BOC-aminomethyl-1,2,4-oxadiazol-3-yl)-11,11a-dihydro-8H, 10H-azeto[1,2-a]imidazo[5,1-c]thieno [3,2-e][1,4]diazepin-8-one in 20 ml of trifluoroacetic acid was stirred at room temperature for 2 hours. The yellow solution was evaporated, the residue was dissolved in water and the aqueous phase was washed three times with methylene chloride. Subsequently, the aqueous phase was made basic with 10 ml of aqueous ammonia solution and extracted six times with methylene chloride. The organic phases were dried over sodium sulfate, filtered and evaporated. The residue obtained was chromatographed (silica gel, methylene chloride/methanol 9:1). There were obtained 5.0 g (56%) of (S)-1-(5-aminomethyl-1,2,4-oxadiazol-3-yl)-11,11a-dihydro-8H,10H-azeto[1,2-a]imidazo[5,1-c]thieno[3,2-e]-[1,4]diazepin-8-one as colourless crystals of m.p. 235°–238°.

EXAMPLE 58

4.4 ml (25.2 mmol)of N-ethyldiisopropylamine and 1.77 ml (14.65 mmol) of allyl bromide were added to a solution of 1.2 g (3.65 mmol) of (S)-1-(5-aminomethyl-1,2,4-oxadiazol-3-yl)-11,11a-dihydro-8H,10H-azeto[1,2-a]imidazo[5,1-c]thieno[3,2-e][1,4]diazepin-8-one in 20 ml of methylene chloride and the mixture was stirred at room temperature for 48 hours. The reaction solution was subsequently diluted with methylene chloride and washed three times with water. The organic phases were dried over magnesium sulfate, filtered and evaporated. The residue obtained was chromatographed (silica gel, methylene chloride/methanol 19:1). There were thus obtained 980 mg (65%) of (S)-1-(5-diallylaminomethyl-1,2,4-oxadiazol-3-yl)-11,11a-dihydro-8H,10H-azeto[1,2-a]imidazo[5,1-c]thieno[3,2-e][1,4]diazepin-8-one as a colourless foam, Rf=0.52 (silica gel, methylene chloride/methanol 10:1).

EXAMPLE 59

1.6 g (2.3 mmol) of (S)-1-(3-diallylaminomethyl-1,2,4-oxadiazol-5-yl)-8-chloro-12,12a-dihydro-9H,11H-azeto[2,1-c]imidazo[1,5-a][1,4]benzodiazepin-9-one in 80 ml of ethyl acetate were hydrogenated at room temperature and normal pressure in the presence of 50 mg of 5% palladium-on-charcoal. After separating the catalyst the residue was purified by chromatography on silica gel while eluting with methylene chloride/ethyl acetate 1/1 and crystallization from ethyl acetate and hexane. There was obtained 0.71 g (44%) of (S)-8-chloro-12,12a-dihydro-1-(3-di-n-propylaminomethyl-1,2,4-oxadiazol-5-yl)-9H,11H-azeto[2,1-c]imidazo[1,5-a][1,4]benzodiazepin-9-one, which was converted into the hydrochloride of m.p. 179°–181°.

EXAMPLE 60 a) 13.46 g (50 mmol) of (S)-12,12a-dihydro-9-oxo-9H,11H-azeto[2,1-c]imidazo[1,5-a][1,4]-benzodiazepine-1-carboxylic acid were dissolved in 40 ml of N,N-dimethylformamide, treated portionwise with 10 g (61.7 mmol) of 1,1'-carbonyldiimidazole and stirred at 55° for 30 min. After adding 12.06 g (55 mmol) of phthaloylglycine amidoxime the mixture was stirred at 85 °for 2 hours. 10 ml of trifluoroacetic acid were added and the mixture was stirred at 85 °overnight. The reaction mixture was cooled to 10 °and the crystals were filtered off. After recrystallization from methanol there were obtained 9.16 g (40%) of (S)-12,12a-dihydro-1-(3-phthalimidomethyl-1,2,4-oxadiazol-5-yl)-9H,11H-azeto[2,1-c]imidazo[1,5-a][1,4]-benzodiazepin-9-one of m.p. 290°–292°.

b) 9 g (19.9 mmol) of (S)-12,12a-dihydro-1-(3-phthalimidomethyl-1,2,4-oxadiazol-5-yl)-9H,11H-azeto[2,1-c]imidazo[1,5-a][1,4]benzodiazepin-9-one in 20 ml of ethanol and 65 ml of methylamine (33%) in ethanol were stirred at 70° for 2 hours. The solution was concentrated and the residue was triturated with 70 ml of methylene chloride. The suspension obtained was filtered. After drying the filter residue there was obtained (S)-1-(3-aminomethyl-1,2,4-oxadiazol-5-yl)-12,12a-dihydro-9H,11H-azeto[2,1-c]imidazo[1,5-a][1,4]benzodiazepin-9-one, which was used without further crystallization as the starting material for the Example described hereinafter.

EXAMPLE 61

4.72 g (14.6 mmol) of crude (S)-1-(3-aminomethyl-1,2,4-oxadiazol-5-yl)-12,12a-dihydro-9H,11H-azeto[2,1-c]imidazo[1,5-a][1,4]benzodiazepin-9-one, 70 ml of methylene chloride, 6 ml (35 mmol) of N-ethyldiisopropylamine and 3.53 g (29.2 mmol) of allyl bromide were stirred at room temperature for 60 hours. The reaction mixture was evaporated and the residue was chromatographed on 180 g of silica gel while eluting with ethyl acetate. By concentrating the uniform fractions there was obtained (S)-1-(3-diallylaminomethyl-1,2,4-oxadiazol-5-yl)-12,12a-dihydro-9H,11H-azeto[2,1-c]imidazo[1,5-a][1,4]benzodiazepin-9-one, which was converted into the hydrochloride of m.p. 147°–150°.

EXAMPLE 62

1.78 g (5 mmol) of (S)-1-(5-aminomethyl-1,2,4-oxadiazol-3-yl)-8-chloro-12,12a-dihydro-9H,11H-azeto[2,1-c]imidazo[1,5-a][1,4]benzodiazepin- 9-one, 40 ml of ethylene chloride, 8.6 ml (50 mmol) of N-ethyldiisopropylamine and 9.10 g (60 mmol) of bromomethylcyclopropane were stirred at 75° overnight. The reaction solution was evaporated. The residue was chromatographed on 200 g of silica gel while eluting with ethyl acetate. There was obtained 0.7 g (30%) of (S)-1-[5-(bis-cyclopropylmethyl)-aminomethyl-1,2,4-oxadiazol-3-yl]-8-chloro-12,12a-dihydro-9H,11H-azeto[2,1-c]imidazo[1,5-a][1,4]benzodiazepin-9-one of m.p. 96°–99°, which was converted into the hydrochloride.

EXAMPLE 63 a) 2.6 g (37.7 mmol) of hydroxylamine hydrochloride were added at room temperature to a suspension of 4.9 g (35.2 mmol) of potassium carbonate in 40 ml of dimethylformamide. Subsequently, a solution of 7.2 g (25.2 mmol) of (S)-7,8-difluoro-9-oxo-12,12a-dihydro-9H,11H-azeto[2,1-c]imidazo[1,5-a][1,4]benzodiazepine-1-carbonitrile in 100 ml of dimethylformamide was added dropwise and the mixture was stirred at room temperature for 60 hours. The yellow suspension obtained was evaporated, the residue was partitioned between methylene chloride and water and the aqueous phase was extracted four times with methylene chloride. The organic phases were dried over sodium sulfate, filtered and evaporated. Subsequent chromatography (silica gel, methylene chloride/methanol 9:1) yielded 3 g (37%) of (E)- and/or (Z)-(S)-1-(aminohydroxylimino-methyl)-7,8-difluoro-12,12a-dihydro-9H,11H-azeto[2,1-c]imidazo[1,5-a][1,4]benzodiazepin-9-one as a colourless powder of m.p.>250°.

b) 2.7 g (16.9 mmol) of 1,1'-carbonyldiimidazole were added to a solution of 4.5 g (14.1 mmol) of BOC-glycine in 30 ml of dimethylformamide and the mixture was stirred at 50° for 30 minutes. Subsequently, 4.5 g (14.1 mmol) of (E)- and/or (Z)-(S)-1-(aminohydroxylimino-methyl)-7,8-difluoro-12,12a-dihydro-9H,11H-azeto[2,1-c]imidazo[1,5-a][1,4]benzodiazepin-9-one were added and the mixture was stirred at 90° for 16 hours. The brown solution obtained was evaporated in a high vacuum and the brown residue obtained was chromatographed (silica gel, methylene chloride/methanol 19:1). There were obtained 4.9 g (76%) of (S)-1-(5-BOC-aminomethyl-1,2,4-oxadiazol-3-yl)-7,8-difluoro-12,12a-dihydro-9H,11H-azeto[2,1-c]imidazo[1,5-a][1,4]

benzodiazepin-9-one as a colourless foam, Rf=0.21 (silica gel, methylene chloride/methanol 19:1).

c) A solution of 330 mg (0.72 mmol) of (S)-1-(5-BOC-aminomethyl-1,2,4-oxadiazol-3-yl)-7,8-difluoro-12,12a-dihydro-9H,11H-azeto[2,1-c]imidazo[1,5-a][1,4] benzodiazepin-9-one in 2 ml of trifluoroacetic acid was stirred at room temperature for 2 hours. The yellow solution was evaporated, the residue was dissolved in water and the aqueous phase was washed three times with methylene chloride. Subsequently, the aqueous phase was made basic with 2 ml of aqueous ammonia solution and extracted six times with methylene chloride. The organic phases were dried over sodium sulfate, filtered and evaporated. The residue obtained was crystallized from methylene chloride/ether. There were obtained 190 mg (73%) of (S)-1-(5-aminomethyl-1,2,4-oxadiazol-3-yl)-7,8-difluoro-12,12a-dihydro-9H,11H-azeto[2,1-c]imidazo[1,5-a][1,4]-benzodiazepin-9-one as a beige powder of m.p. 240° (dec.).

EXAMPLE 64

1.9 ml (11.2 mmol) of N-ethyldiisopropylamine and 710 mg (2.7 mmol) of α,α'-dibromo-orthoxylene were added to a solution of 800 mg (2.23 mmol) of (S)-2-(5-aminomethyl-1,2,4-oxadiazol-3-yl)-7,8-difluoro-12,12a-dihydro-9H,11H-azeto[2,1-c]imidazo[1,5-a][1,4]benzodiazepin-9-one in 60 ml of methylene chloride and the mixture was stirred at room temperature for 20 hours. The reaction solution was subsequently diluted with methylene chloride and washed three times with water. The organic phases were dried over magnesium sulfate, filtered and evaporated. The residue obtained was chromatographed (silica gel, methylene chloride/methanol 19:1). There were obtained 130 mg (12%) of (S)-1-(5-(isoindolin-2-ylmethyl-1,2,4-oxadiazol-3-yl)-7,8-difluoro-12,12a-dihydro-9H,11H-azeto[2,1-c]imidazo[1,5-a][1,4]benzodiazepin-9-one as a colourless foam, Rf=0.15 (silica gel, methylene chloride/methanol 19:1).

EXAMPLE 65

2.6 ml (15.4 mmol) of N-ethyldiisopropylamine and 1 ml (8.93 mmol) of 3,3-dimethylallyl bromide were added to a solution of 800 mg (2.23 mmol) of (S)-1-(5-aminomethl-1,2,4-oxadiazol-3-yl)-7,8-difluoro-12,12a-dihydro-9H,11H-azeto[2,1-c]imidazo[1,5-a][1,4]benzodiazepin-9-one in 60 ml of methylene chloride and the mixture was stirred at room temperature for 20 hours. The reaction solution was diluted with methylene chloride and washed three times with water. The organic phases were dried over magnesium sulfate, filtered and evaporated. The residue obtained was chromatographed (silica gel, methylene chloride/methanol 19:1). There were obtained 300 mg (27%) of (S)-1-[5-[bis-(3-methyl-but-2-enyl)-aminomethyl]-1,2,4-oxadiazol-3-yl]-7,8-difluoro-12,12a-dihydro-9H,11H-azeto[2,1-c]imidazo [1,5-a][1,4]benzodiazepin-9-one as a colourless foam, Rf=0.19 (silica gel, methylene chloride/methanol 19:1).

EXAMPLE 66

2.3 ml (13.5 mmol) of N-ethyldiisopropylamine and 0.66 ml (7.8 mmol) of allyl bromide were added to a solution of 700 mg (1.95 mmol) of (S)-1-(5-aminomethyl-1,2,4-oxadiazol-3-yl)-7,8-difluoro-12,12a-dihydro-9H,11H-azeto [2,1-c]imidazo[1,5-a][1,4]benzodiazepin-9-one in 40 ml of methylene chloride and the mixture was stirred at room temperature for 20 hours. The reaction solution was diluted with methylene chloride and washed three times with water. The organic phases were dried over magnesium sulfate, filtered and evaporated. The residue obtained was chromatographed (silica gel, methylene chloride/methanol 19:1). There were obtained 400 mg (46%) of S)-1-[5-(diallylaminomethyl)-1,2,4-oxadiazol-3-yl]-7,8-difluoro-12,12a-dihydro-9H,11H-azeto[2,1-c]imidazo[1,5-a][1,4] benzodiazepin-9-one as a colourless foam, Rf=0.17 (silica gel, methylene chloride/methanol 19:1).

EXAMPLE 67

4 g (11.2 mmol) of (S)-1-(3-aminomethyl-1,2,4-oxadiazol-5-yl)-8-chloro-12,12a-dihydro-9H,11H-azeto[2,1-c]imidazo[1,5-a][1,4]benzodiazepin-9-one, 50 ml of methylene chloride, 7.3 ml (42.6 mmol) of N-ethyldiisopropylamine and 3 ml (24.6 mmol) of crotyl bromide were stirred at room temperature for 7 hours. The reaction solution was washed three times with water, dried over magnesium sulfate and evaporated. The residue was chromatographed on 200 g of silica gel while eluting with methylene chloride/ethyl acetate 1/1. There were obtained 2.4 g (46%) of (S)-1-[3-bis-(but-2-enyl)-aminomethyl-1,2,4-oxadiazol-5-yl]-8-chloro-12,12a-dihydro-9H,11H-azeto [2,1-c]imidazo[1,5-a][1,4]benzodiazepin-9-one as a 4/1 E/Z mixture, which was converted into the hydrochloride of m.p. 109°–113°.

EXAMPLE 68

5 g (14 mmol) of (S)-1-(3-aminomethyl-1,2,4-oxadiazol-5-yl)-8-chloro-12,12a-dihydro-9H,11H-azeto[2,1-c]imidazo [1,5-a][1,4]benzodiazepin-9-one, 50 ml of methylene chloride, 9.1 ml (53.2mmol) of N-ethyldiisopropylamine and 3.8 ml (30.8 mmol) of 3,3-dimethylallyl bromide were stirred at room temperature for 2 hours. The reaction solution was washed three times with water, dried over magnesium sulfate and evaporated. The residue was chromatographed on 190 g of silica gel while eluting with methylene chloride/ethyl acetate 1/1. There were obtained 3.25 g (47%) of (S)-1-[3-bis-(3-methyl-but-2-enyl)aminomethyl-1,2,4-oxadiazol-5-yl]-8-chloro-12,12a-dihydro-9H,11H-azeto[2, 1-c]-imidazo[1,5-a][1,4]-benzodiazepin-9-one, which was converted into the hydrochloride of m.p. 188°–189°.

EXAMPLE 69

4 g (11.2 mmol) of (S)-1-(3-aminomethyl-1,2,4-oxadiazol-5-yl)-8-chloro-12,12a-dihydro-9H,11H-azeto[2, 1-c]-imidazo[1,5-a][1,4]benzodiazepin-9-one, 25 ml of N,N-dimethylformamide, 7.5 ml (43.7 mmol) of N-ethyldiisopropylamine and 2.9 ml (28 mmol) of 4-bromo-1-butene were stirred at 800 for 25 hours. The reaction solution was evaporated, the residue was dissolved in methylene chloride, this solution was washed three times with water, dried over magnesium sulfate and evaporated. The residue was chromatographed on 160 g of silica gel while eluting with methylene chloride/ethyl acetate 1/1. There were obtained 2.8 g (53%) of (S)-1-{3-[bis-(but-3-enyl) aminomethyl]-1,2,4-oxadiazol-5-yl}-8-chloro-12,12a-dihydro-9H,11H-azeto[2,1-c]imidazo[1,5-a][1,4] benzodiazepin-9-one, which was converted into the hydrochloride of m.p. 115°–120°.

EXAMPLE 70

4.6 g (12.9 mmol) of (S)-1-(3-aminomethyl-1,2,4-oxadiazol-5-yl)-8-chloro-12,12a-dihydro-9H,11H-azeto[2, 1-c]-imidazo[1,5-a][1,4]benzodiazepin-9-one, 25 ml of N,N-dimethylformamide, 8.6 ml (50.3 mmol) of N-ethyldiisopropylamine and 3.4 ml (32.2 mmol) of bromomethylcyclopropane were stirred at 80° for 18 hours. The reaction solution was evaporated, the residue was dissolved in methylene chloride, the solution was washed three times with water, dried over magnesium sulfate and evaporated. The residue was chromatographed on 110 g of silica gel while eluting with methylene chloride/ethyl acetate 1/1. There were obtained 2.3 g (38%) of (S)-1-[3-(bis-cyclopropylmethylaminomethyl)-1,2,4-oxadiazol-5-yl]-8-chloro-12,12a-dihydro-9H,11H-azeto[2,1-c]imidazo[1,5-a][1,4]benzodiazepin-9-one, which was converted into the hydrochloride of m.p. 155°–160°.

EXAMPLE 71

3.7 g (10 mmol) of (S)-1-(3-aminomethyl-1,2,4-oxadiazol-5-yl)-8-chloro-11,12,13,13a-tetrahydro-9H-imidazo[1,5-a]pyrrolo-[2,1-c][1,4]benzodiazepin-9-one, 30 ml of N,N-dimethylformamide, 4.27 ml (25 mmol) of N-ethyldiisopropylamine and 2.38 g (20 mmol) of propargyl bromide were stirred at room temperature for 1 hour. After evaporating the reaction solution the residue was chromatographed on 430 g of silica gel while eluting with ethyl acetate/methanol 9/1. The uniform fractions having the lower $R_f$ were evaporated. There were obtained 1.19 g (29%) of (S)-8-chloro-11,12,13,13a-tetrahydro-1-(3-propargylamino-methyl-1,2,4-oxadiazol-5-yl)-9H-imidazo[1,5-a]pyrrolo-[2,1-c][1,4]benzodiazepin-9-one of m.p. 144°–145°, which was converted into the hydrochloride of m.p. 189°–192°.

EXAMPLE 72 a) 6.35 g (20 mmol) of (S)-8-chloro-11,12,13,13a-tetrahydro-9-oxo-9H-imidazo[1,5-a]pyrrolo[2,1-c][1,4]benzodiazepine-1-carboxylic acid were dissolved in 30 ml of N,N-dimethylformamide, treated portionwise with 3.57 g (41.4 mmol) of 1,1'-carbonyldiimidazole and stirred at 50° for 20 min. After adding 9.22 g (42 mmol) of phthaloylglycine amidoxime the mixture was stirred at 90° overnight, 1 ml of trifluoroacetic acid was added and the mixture was stirred at 110° for a further 20 hours. The suspension obtained was cooled and the crystals were filtered off. There were obtained 5.74 g (57%) of (S)-8-chloro-11,12,13,13a-tetrahydro-9H-1-(3-phthalimidomethyl-1,2,4-oxadiazol-5-yl)-imidazo[1,5-a]pyrrolo[2,1-c][1,4]benzodiazepin-9-one of m.p. 275°–277°.

b) 54.25 g (108.3 mmol) of (S)-8-chloro-11,12,13,13a-tetrahydro-9H-1-(3-phthalimidomethyl-1,2,4-oxadiazol-5-yl)-imidazo[1,5-a]pyrrolo[2,1-c][1,4]benzodiazepin-9-one were stirred at 75° for 1.5 hours with 280 ml of methylamine (33%) in ethanol. The solution was concentrated, the residue was taken up in methylene chloride and 115 ml of 4N hydrochloric acid and the solution was washed three times with methylene chloride. The aqueous phase was made alkaline with 115 ml of 4N sodium hydroxide solution and extracted six times with methylene chloride. After drying the combined organic solutions and evaporating the solvent there were obtained 35.4 g (88%) of (S)-1-(3-aminomethyl-1,2,4-oxadiazol-5-yl)-8-chloro-11,12,13,13a-tetrahydro-9H-imidazo-[1,5-a]pyrrolo[2,1-c][1,4]benzodiazepin-9-one, which was used without further purification as the starting material for the Example described hereinafter.

EXAMPLE 73

3.7 g (10 mmol) of crude (S)-1-(3-aminomethyl-1,2,4-oxadiazol-5-yl)-8-chloro-11,12,13,13a-tetrahydro-9H-imidazo[1,5-a]pyrrolo[2,1-c][1,4]benzodiazepin-9-one, 30 ml of methylene chloride, 4.3 ml (25 mmol) of N-ethyldiisopropylamine and 2.3 ml (20 mmol) of 3,3-dimethylallyl bromide were stirred at room temperature for 3 hours. The reaction solution was chromatographed on 250 g of silica gel while eluting with ethyl acetate. There were obtained 2.44 g (48%) of (S)-1-[3-bis-(3-methyl-but-2-enyl)aminomethyl-1,2,4-oxadiazol-5-yl]-8-chloro-11,12,13,13a-tetrahydro-9H-imidazo[1,5-a]pyrrolo[2,1-c][1,4]benzodiazepin-9-one, which was converted into the hydrochloride of m.p. 137°–140°.

EXAMPLE 74

1 g (2.2 mmol) of (S)-1-(3-diallylaminomethyl-1,2,4-oxadiazol-5-yl)-7-fluoro-12,12a-dihydro-9H,11H-azeto[2,1-c]imidazo[1,5-a][1,4]benzodiazepin-9-one in 5 ml of methanol were hydrogenated at room temperature and normal pressure in the presence of 22 mg of 5% palladium-on-charcoal. After separating the catalyst the residue was purified by chromatography on silica gel while eluting with ethyl acetate/hexane/triethylamine 17/2/1. There was obtained 0.53 g (56%) of (S)-7-fluoro-12,12a-dihydro-1-(3-di-n-propylaminomethyl-1,2,4-oxadiazol-5-yl)-9H,11H-azeto[2,1-c]imidazo[1,5-a][1,4]benzodiazepin-9-one (oil: $R_f$ 0.36; Kieselgel 60 $F_{254}$. Eluent: ethyl acetate/hexane/triethylamine 17/2/1), which was converted into the hydrochloride.

EXAMPLE 75

328 mg (1.0 mmol) of 3-(3-aminomethyl-1,2,4-oxadiazol-5-yl)-8-fluoro-5,6-dihydro-5-methyl-4H-imidazo[1,5-a][1,4]benzodiazepin-6-one in 6 ml of methylene chloride were treated under argon with 1.2 ml (7.0 mmol) of N-ethyldiisopropylamine and 0.65 ml (6.0 mmol) of propargyl bromide (80% in toluene) and the mixture was stirred at room temperature under argon for 19 hrs. The solution was washed with 10 ml of water and evaporated, and the crude product was purified by chromatography on 15 g of silica gel (methylene chloride/acetone 9:1). The eluate was evaporated and the residue was taken up in 5 ml of methanol. The solution was acidified with 5 ml of ethereal hydrochloric acid and the white crystals were filtered off. There were obtained 200 mg (45%) of 3-[3-[bis-(prop-2-ynyl)-aminomethyl]-1,2,4-oxadiazol-5-yl]-8-fluoro-5-methyl-5,6-dihydro-4H-imidazo[1,5-a][1,4]benzodiazepin-6-one hydrochloride (4:5) of m.p. 186°–189° (dec.).

EXAMPLE 76

2.5 g of potassium carbonate and 0.48 ml (4.1 mmol) of dimethylallyl bromide were added to a solution of 660 mg (2 mmol) of (S)-1-(5-aminomethyl-1,2,4-oxadiazol-3-yl)-11,11a-dihydro-8H,10H-azeto[1,2-a]imidazo[5,1-c]thieno[3,2-e][1,4]diazepin-8-one in 20 ml of dimethylformamide and the mixture was stirred at room temperature for 12 hours. The reaction solution was subsequently filtered and the filtrate was partitioned between methylene chloride and water. The aqueous phase was back-extracted three times with methylene chloride; the combined organic phases were subsequently dried over sodium sulfate, filtered and evaporated. The residue obtained was chromatographed (silica gel, methylene chloride/methanol/aqueous ammonia 300:10:1) and there were obtained 650 mg (70%) of (S)-1-[5-[bis-(3-methyl-but-2-enyl)-aminomethyl]-1,2,4-oxadiazol-3-yl]-11,11a-dihydro-8H,10H-azeto[1,2-a]imidazo[5,1-c]thieno[3,2-e][1,4]diazepin-8-one as a colourless foam, Rf=0.16 (silica gel, methylene chloride/methanol/aqueous ammonia 300:10:1).

EXAMPLE 77

2.5 g of potassium carbonate and 0.55 g (2.1 mmol) of α,α'-dibromo-o-xylene were added to a solution of 660 mg (2 mmol) of (S)-1-(5-aminomethyl-1,2,4-oxadiazol-3-yl)-11,11a-dihydro-8H,10H-azeto[1,2-a]imidazo[5,1-c]thieno[3,2-e][1,4]diazepin-8-one in 20 ml of dimethylformamide and the mixture was stirred at room temperature for 12 hours. The reaction solution was subsequently filtered and the filtrate was partitioned between methylene chloride and water. The aqueous phase was back-extracted three times with methylene chloride; the combined organic phases were subsequently dried over sodium sulfate, filtered and evaporated. The residue obtained was chromatographed (silica gel, methylene chloride/methanol/aqueous ammonia 300:10:1) and there were obtained 535 mg (62%) of (S)-1-[5-(isoindolin-2-ylmethyl)-1,2,4-oxadiazol-3-yl]-11,11a-dihydro-8H,10H-azeto[1,2-a]imidazo[5,1-c]thieno-[3,2-a][1,4]diazepin-8-one as a colourless foam, Rf=0.12 (silica gel, methylene chloride/methanol/aqueous ammonia 300:10:1).

EXAMPLE 78 a) 6.98 g (43 mmol) of 1,1'-carbonyldiimidazole were added in one portion at room temperature to a solution of 11.88 g (41.2 mmol) of (S)-10,11,12,12a-tetrahydro-8-oxo-8H-imidazo[5,1-c]pyrrolo[1,2-a]thieno[3,2-e][1,4]diazepine-1-carboxylic acid (EP 59390 A1) in 65 ml of dimethylformamide and the mixture was stirred at 50° for 30 minutes. Subsequently, 9.2 g (41.9 mmol) of phthaloylglycine amidoxime were added in one portion and the mixture was stirred at 110° for 15 hours. The dimethylformamide was evaporated in a high vacuum and the residue obtained was treated with 150 ml of water. Extraction with methylene chloride (twice), drying over sodium sulfate, filtration and evaporation yielded a reddish residue which was subsequently chromatographed (silica gel, methylene chloride/methanol 20:1). There were obtained 7.3 g (38%) of (S)-2-[5-(8-oxo-10,11,12,12a-tetrahydro-8H-imidazo[5,1-c]pyrrolo[1,2-a]thieno[3,2-e][1,4]diazepin-1-yl)-1,2,4-oxadiazol-3-yl-methyl]-1,3-dihydro-isoindole-1,3-dione as colourless crystals of m.p. 248°–250°.

(b) 100 ml of methylamine (33% in ethanol) were added dropwise at 70° to a solution of 7.28 g (15.4 mmol) of (S)-2-[5-(8-oxo-10,11,12,12a-tetrahydro-8H-imidazo[5,1-c]pyrrolo[1,2-a]thieno[3,2-e][1,4]diazepin-1-yl)-1,2,4-oxadiazol-3-yl-methyl]-1,3-dihydro-isoindole-1,3-dione in 100 ml of ethanol and the mixture was stirred at 70° for a further two hours. The reaction mixture was evaporated and the residue was chromatographed (silica gel, methylene chloride/methanol 20:1). There were obtained 4.36 g (83%) of (S)-1-(3-aminomethyl-1,2,4-oxadiazol- 5-yl)-10,11,12,12a-tetrahydro-8H-imidazo[5,1-c]pyrrolo[1,2-a]thieno[3,2-e][1,4]diazepin-8-one as colourless crystals of m.p. 156°–158°.

EXAMPLE 79

2.4 ml (13.8 mmol) of N-ethyldiisopropylamine and 0.67 ml (8 mmol) of allyl bromide were added to a solution of 685 mg (2 mmol) of (S)-1-(3-aminomethyl-1,2,4-oxadiazol-5-yl)-10,11,12,12a-tetrahydro-8H-imidazo[5,1-c]pyrrolo[1,2-a]thieno[3,2-e][1,4]diazepin-8-one in 20 ml of methylene chloride and the mixture was stirred at room temperature for 20 hours. The reaction solution was subsequently diluted with methylene chloride and washed three times with water. The organic phases were dried over magnesium sulfate, filtered and evaporated. The residue obtained was chromatographed (silica gel, methylene chloride/methanol/aqueous ammonia 200:10:1). There were obtained 693 mg (82%) of (S)-1-(5-diallylaminomethyl-1,2,4-oxadiazol-5-yl)-10,11,12,12a-tetrahydro-8H-imidazo[5,1-c]pyrrolo[1,2-a]thieno[3,2-e][1,4]diazepin-8-one as a colourless foam, Rf=0.32 (silica gel, methylene chloride/methanol/aqueous ammonia 200:10:1).

EXAMPLE 80

328 mg (1.0 mmol) of 3-(5-aminomethyl)-1,2,4-oxadiazol-3-yl)-8-fluoro-5,6-dihydro-5-methyl-4H-imidazo[1,5-a][1,4]benzo-diazepin-6-one in 6 ml of methylene chloride were treated under argon with 0.51 ml (3.0 mmol) of N-ethyldiisopropylamine and 0.27 ml (2.5 mmol) of propargyl bromide (80% in toluene) and the mixture was stirred at room temperature under argon for 22 hrs. A further 0.09 ml of propargyl bromide (80% in toluene) and 0.05 ml of N-ethyldiisopropylamine were added and the mixture was stirred at room temperature for a further 74 hrs. The reaction mixture was washed with 10 ml of water, dried with sodium sulfate, filtered and evaporated. The crude product was purified by chromatography on 50 g of silica gel (ethyl acetate). The eluates were evaporated and the residue was taken up in 5 ml of methanol. The solution was acidified with ethereal hydrochloric acid and evaporated, and the residue was taken up in 5 ml of methanol/ether 3:2. The white crystals were filtered off and dried. There were obtained 87 mg (20%) of 3-[5-[bis-(prop-2-ynyl)-aminomethyl]-1,2,4-oxadiazol-3-yl]-8-fluoro-5-methyl-5,6-dihydro-4H-imidazo[1,5-a][1,4]benzodiazepin-6-one hydrochloride (1:1) of m.p. 175°–177° (dec.).

EXAMPLE 81 a) 2.45 g (14 mmol) of BOC-glycine were dissolved in 20 ml of N,N-dimethylformamide, whereupon the mixture was treated portionwise with 2.43 g (15 mmol) of 1,1'-carbonyldiimidazole and stirred at 50° for 20 min. After adding 3.8 g (12.4 mmol) of 7-chloro-5,6-dihydro-5-methyl-6-oxo-4H-imidazo[1,5-a][1,4]benzodiazepine-3-carboxamidoxime the mixture was stirred at 90° overnight. The reaction mixture was concentrated; the residue was dissolved in methylene chloride and washed three times with water. After drying the solution, evaporation of the solvent and crystallization of the residue from ethyl acetate and hexane there were obtained 5.33 g (96%) of 3-(5-BOC-aminomethyl-1,2,4-oxadiazol-3-yl)-7-chloro-5,6-dihydro-5-methyl-4H-imidazo[1,5-a][1,4]benzodiazepin-6-one of m.p. 144°–146°.

b) 7.03 g (16.4 mmol) of 3-(5-BOC-aminomethyl-1,2,4-oxadiazol-3-yl)-7-chloro-5,6-dihydro-5-methyl-4H-imidazo[1,5-a][1,4]benzodiazepin-6-one were stirred at room temperature in 30 ml of trifluoroacetic acid for 1 hour. The solution was concentrated, the residue was taken up in water and the solution was washed twice with methylene chloride. The aqueous phase was made alkaline with 25% ammonia and extracted seven times with methylene chloride. After drying and evaporating the combined organic phases there were obtained 4.5 g (79%) of 3-(5-aminomethyl-1,2,4-oxadiazol-3-yl)-7-chloro-5,6-dihydro-5-methyl-4H-imidazo[1,5-a][1,4]benzodiazepin-6-one, which was used without further purification as the starting material for the Example described hereinafter.

EXAMPLE 82

1.5 g (4.4 mmol) of 3-(5-aminomethyl-1,2,4-oxadiazol-3-yl)-7-chloro-5,6-dihydro-5-methyl-4H-imidazo[1,5-a][1,4]benzodiazepin-6-one, 20 ml of N,N-dimethylformamide, 210 ml (12 mmol) of N-ethyldiisopropylamine and 1.16 g (9.6 mmol) of allyl bromide were stirred at room temperature for 4 hours. The reaction solution was evaporated and the residue was chromatographed on 250 g of silica gel while eluting with ethyl acetate. The uniform fractions were evaporated. There were obtained 1.54 g (82%) of 3-(5-diallylaminomethyl-1,2,4-oxadiazol-3-yl)-7-chloro-5,6-dihydro-5-methyl-4H-imidazo[1,5-a][1,4]benzodiazepin-6-one, which was converted into the hydrochloride of m.p. 126°–130°.

EXAMPLE 83 a) 38.8 g (133 mmol) of 7-chloro-5,6-dihydro-5-methyl-6-oxo-4H-imidazo[1,5-a][1,4]-benzodiazepine-3-carboxylic acid were dissolved in 200 ml of N,N-dimethylformamide, treated portionwise with 23.7 g (146 mmol) of 1,1'-carbonyldiimidazole and stirred at 70° for 20 min. After adding 43.73 g (199.5 mmol) of phthaloylglycine amidoxime the mixture was stirred at 90° for 1 hour. 1.5 ml of trifluoroacetic acid were added and the mixture was stirred at 90° overnight and at 120° for a further 3 hours. The suspension obtained was concentrated to half of its volume and cooled, and the precipitated crystals were filtered off. There were obtained 35.3 g (56%) of 7-chloro-5,6-dihydro-5-methyl-3-(3-phthalimidomethyl-1,2,4-oxadiazol-5-yl)-4H-imidazo[1,5-a][1,4]benzodiazepin-6-one of m.p. 237°–239°.

b) 35.1 g (74 mmol) of 7-chloro-5,6-dihydro-5-methyl-3-(3-phthalimidomethyl-1,2,4-oxadiazol-5-yl)-4H-imidazo[1,5-a]-[1,4]benzodiazepin-6-one were stirred with 190 ml of methylamine in ethanol) and 100 ml of ethanol at 80° for 3 hours. The solution was concentrated, the residue was taken up in methylene chloride and 100 ml of 4N hydrochloric acid and the solution was washed three times with methylene chloride. The aqueous phase was made alkaline with 105 ml of 4N sodium hydroxide solution and extracted six times with methylene chloride. After drying the combined organic solutions and evaporating the solvent there were obtained 18.14 g (71%) of 3-(3-aminomethyl-1,2,4-oxadiazol-5-yl)-7-chloro-5,6-dihydro-5-methyl-4H-imidazo[1,5-a][1,4]benzodiazepin-6-one, which was used without further purification as the starting material for the Example described hereinafter.

EXAMPLE 84

5.17 g (15 mmol) of crude 3-(3-aminomethyl-1,2,4-oxadiazol-5-yl)-7-chloro-5,6-dihydro-5-methyl-4H-imidazo[1,5-a][1,4]benzodiazepin-6-one, 45 ml of N,N-dimethylformamide, 6.5 ml (37.5 mmol) of N-ethyldiisopropylamine and 3.63 g (30 mmol) of allyl bromide were stirred at room temperature for 1 hour. The reaction solution was evaporated and the residue was chromatographed on 250 g of silica gel while eluting with ethyl acetate. The uniform fractions having the larger Rf value were evaporated. There were obtained 4.84 g (76%) of 3-(3-diallylaminomethyl-1,2,4-oxadiazol-5-yl)-7-chloro-5,6-dihydro-5-methyl-4H-imidazo[1,5-a]-[1,4]benzodiazepin-6-one, which was converted into the hydrochloride of m.p. 125°–130°.

EXAMPLE 85

3.44 g (10 mmol) of 3-(3-aminomethyl-1,2,4-oxadiazol-5-yl)-7-chloro-5,6-dihydro-5-methyl-4H-imidazo[1,5-a][1,4]benzodiazepin-6-one, 30 ml of N,N-dimethylformamide, 3.7 ml (22 mmol) of N-ethyldiisopropylamine and 2.9 g (11 mmol) of α,α'-dibromo-o-xylene were stirred at room temperature for 6 hours. After evaporating the solvent the residue was chromatographed on 230 g of silica gel while eluting with ethyl acetate. The uniform fractions were evaporated. There were obtained 1.56 g (35%) of 7-chloro-5,6-dihydro-3-(3-isoindolin-2-yl-methyl-1,2,4-oxadiazol-5-yl)-5-methyl-4H-imidazo[1,5-a][1,4]-benzodiazepin-6-one, which was converted into the hydrochloride of m.p. 180°–184°.

EXAMPLE 86 a) 15 g (5.83 mmol) of 5,6-dihydro-5-methyl-6-oxo-4H-imidazo[1,5-a]-[1,4]benzodiazepine-3-carboxylic acid were dissolved in 100 ml of N,N-dimethylformamide, treated portionwise with 11.3 g (7 mmol) of 1,1'-carbonyldiimidazole and stirred at 70° for 20 min. After adding 19.2 g (8.75 mmol) of phthaloylglycine amidoxime the mixture was stirred at 80° for 3 hours, 5 ml of trifluoroacetic acid were added and the mixture was stirred at 110° overnight. The reaction mixture was concentrated and the residue was chromatographed on 200 g of silica gel while eluting with ethyl acetate. There were obtained 13 g (50%) of 5,6-dihydro-5-methyl-3-(3-phthalimidomethyl-1,2,4-oxadiazol-5-yl)-4H-imidazo[1,5-a][1,4]benzodiazepin-6-one of m.p. 239°–240°.

b) 13 g (29.5 mmol) of 5,6-dihydro-5-methyl-3-(3-phthalimidomethyl-1,2,4-oxadiazol-5-yl)-4H-imidazo[1,5-a][1,4]benzodiazepin-6-one were stirred with 90 ml of methylamine (33% in ethanol) and 40 ml of ethanol at 80° for 3 hours. The solution was concentrated, the residue was taken up in methylene chloride and 53 ml of 4N hydrochloric acid and the solution was washed three times with methylene chloride. The aqueous phase was made alkaline with 55 ml of 4N sodium hydroxide solution and extracted six times with methylene chloride. After drying the combined organic solutions and evaporating the solvent there were obtained 9 g (100%) of (3-(3-aminomethyl-1,2,4-oxadiazol-5-yl)-5,6-dihydro-5-methyl-4H-imidazo[1,5-a][1,4]benzodiazepin-6-one of m.p. 183°–185°, which was used without further purification as the starting material for the Example described hereinafter.

EXAMPLE 87

3.10 g (10 mmol) of crude 3-(3-aminomethyl-1,2,4-oxadiazol-5-yl)-5,6-dihydro-5-methyl-4H-imidazo[1,5-a][1,4]benzodiazepin-6-one, 20 ml of N,N-dimethylformamide, 3.7 ml (22 mmol) of N-ethyldiisopropylamine and 1.81 g (15 mmol) of allyl bromide were stirred at room temperature for 1.5 hours. After evaporating the solvent the residue was chromatographed on 220 g of silica gel while eluting with ethyl acetate. There was obtained 0.86 g (22%) of 3-(3-diallylaminomethyl-1,2,4-oxadiazol-5-yl)-5,6-dihydro-5-methyl-4H-imidazo[1,5-a][1,4]benzodiazepin-6-one, which was converted into the hydrochloride of m.p. 203°–205°.

EXAMPLE 88

1.85 g (5 mmol) of (S)-1-(3-aminomethyl-1,2,4-oxadiazol-5-yl)-8-chloro-11,12,13,13a-tetrahydro-9H-imidazo[1,5-a]pyrrolo[2,1-c][1,4]benzodiazepin-9-one, 20 ml of N,N-dimethylformamide, 2.14 ml (12.5 mmol) of N-ethyldiisopropylamine and 0.97 ml (10 mmol) of propyl iodide were stirred at 80° overnight. After evaporating the solvent the residue was chromatographed on 210 g of silica gel while eluting with ethyl acetate. There was obtained 0.81 g (36%) of (S)-8-chloro-11,12,13,13a-tetrahydro-1-(3-dipropylaminomethyl-1,2,4-oxadiazol-5-yl)-9H-imidazo[1,5-a]pyrrolo[2,1-c][1,4]benzodiazepin-9-one, which was converted into the hydrochloride of m.p. 155°–158°.

EXAMPLE 89

5.17 g (15 mmol) of 3-(3-aminomethyl-1,2,4-oxadiazol-5-yl)-7-chloro-5,6-dihydro-5-methyl-4H-imidazo[1,5-a][1,4]benzodiazepin-6-one, 45 ml of N,N-dimethylformamide, 6.5 ml (37.5 mmol) of N-ethyldiisopropylamine and 3.63 g (30 mmol) of allyl bromide were stirred at room temperature for 1 hour. The reaction solution was evaporated and the residue was chromatographed on 250 g of silica gel while eluting with ethyl acetate. The uniform fractions having the smaller $R_f$ value were evaporated. There was obtained 0.344 g (6%) of 3-(3-allylaminomethyl-1,2,4-oxadiazol-5-yl)-7-chloro-5,6-dihydro-5-methyl-4H-imidazo[1,5-a]-[1,4]benzodiazepin-6-one, which was converted into the hydrochloride of m.p. 171°–174°.

EXAMPLE 90

1.5 g (4.65 mmol) of(S)-1-(3-aminomethyl-1,2,4-oxadiazol-5-yl)-12,12a-dihydro-9H,11H-azeto[2,1-c]imidazo[1,5-a][1,4]benzodiazepin-9-one, 20 ml of N,N-dimethylformamide, 2.8 ml (16.3 mmol) of N-ethyldiisopropylamine and 1.1 ml (10.7 mmol) of bromomethylcyclopropane were stirred at 80° for 18 hours. The reaction solution was evaporated, the residue was dissolved in methylene chloride, this solution was washed three times with water, dried over magnesium sulfate and evaporated. The residue was chromatographed on 110 g of silica gel while eluting with methylene chloride/ethyl acetate 1/1. There was obtained 1 g (49%) of (S)-1-[3-(bis-cyclopropylmethyl)-aminomethyl-1,2,4-oxadiazol-5-yl]-12,12a-dihydro-9H,11H-azeto[2,1-c]imidazo[1,5-a][1,4]benzodiazepin-9-one, which was converted into the hydrochloride of m.p. 174°–176°.

EXAMPLE 91

1.28 g (4.1 mmol) of 3-(3-aminomethyl-1,2,4-oxadiazol-5-yl)-5,6-dihydro-5-methyl-4H-imidazo[1,5-a][1,4]benzodiazepin-6-one, 25 ml of N,N-dimethylformamide, 2 ml (11.7 mmol) of N-ethyldiisopropylamine and 1.19 g (4.5 mmol) of α,α'-dibromo-o-xylene were stirred at room temperature for 4 hours. After evaporating the solvent the residue was chromatographed on 180 g of silica gel while eluting with ethyl acetate. The uniform fractions were evaporated. There was obtained 0.39 g (23%) of 5,6-dihydro-3-(3-isoindolin-2-ylmethyl-1,2,4-oxadiazol-5-yl)-5-methyl-4H-imidazo[1,5-a][1,4]benzodiazepin-6-one, which was converted into the hydrochloride of m.p. 155°–160°.

EXAMPLE 92

3.44 g (10 mmol) of 3-(3-aminomethyl-1,2,4-oxadiazol-5-yl)-7-chloro-5,6-dihydro-5-methyl-4H-imidazo[1,5-a][1,4]benzodiazepin-6-one, 20 ml of N,N-dimethylformamide, 4.3 ml (25 mmol) of N-ethyldiisopropylamine and 2.98 g (20 mmol) of 3,3-dimethylallyl bromide were stirred at room temperature for 1.5 hours. The reaction solution was evaporated and the residue was chromatographed on 215 g of silica gel while eluting with ethyl acetate. There were obtained 1.8 g (37%) of 3-{3-[bis-(3-methyl-but-2-enyl)aminomethyl]-1,2,4-oxadiazol-5-yl}-7-chloro- 5,6-dihydro-5-methyl-4H-imidazo[1,5-a][1,4]benzo-diazepin-6-one, which was converted into the hydrochloride of m.p 139°–142°.

EXAMPLE 93

1.5 g (4.65 mmol) of (S)-1-(3-aminomethyl-1,2,4-oxadiazol-5-yl)-12,12a-dihydro-9H,11H-azeto[2,1-c]imidazo[1,5-a][1,4]benzodiazepin-9-one, 20 ml of N,N-dimethylformamide, 4 ml (13.9 mmol) of N-ethyldiisopropylamine and 1.3 g (4.9 mmol) of α,α'-dibromo-o-xylene were stirred at room temperature for 1 hour. The reaction solution was evaporated, the residue was dissolved in methylene chloride and chromatographed on 50 g of silica gel while eluting with methylene chloride/ethyl acetate 1/1. There were obtained 1.2 g (61%) of (S)-12,12a-dihydro-1-(3-isoindolin-2-ylmethyl-1,2,4-oxadiazol-5-yl)-9H,11H-azeto[2,1-c]imidazo[1,5-a][1,4]benzodiazepin-9-one, which was converted into the hydrochloride of m.p. 210°–213°.

EXAMPLE 94

5 g (15.5 mmol) of (S)-1-(3-aminomethyl-1,2,4-oxadiazol-5-yl)-12,12a-dihydro-9H,11H-azeto[2,1-c]imidazo[1,5-a][1,4]benzodiazepin-9-one, 50 ml of N,N-dimethylformamide, 8 ml (46.5 mmol) of N-ethyldiisopropylamine and 4 ml (32.5 mmol) of 3,3-dimethylallyl bromide were stirred at room temperature for 2 hours. The reaction solution was evaporated, the residue was dissolved in methylene chloride, the solution was washed three times with water, dried over magnesium sulfate and evaporated. The residue was chromatographed on 130 g of silica gel while eluting with methylene chloride/ethyl acetate 1/1. There were obtained 3.3 g (46%) of (S)-1-[3-bis-(3-methyl-but-2-enyl)aminomethyl-1,2,4-oxadiazol-5-yl]-12,12a-dihydro-9H,11H-azeto[2,1-c]imidazo[1,5-a][1,4]benzodiazepin-9-one, which was converted into the hydrochloride of m.p. 119°–122°.

EXAMPLE 95

1.5 g (3.7 mmol) of (S)-1-(3-diallylaminomethyl-1,2,4-oxadiazol-5-yl)-12,12a-dihydro-9H,11H-azeto[2,1-c]imidazo[1,5-a][1,4]benzodiazepin-9-one in 50 ml of ethyl acetate were hydrogenated at room temperature and normal pressure in the presence of 50 mg of 5% palladium-on-charcoal. After separating the catalyst the residue was purified by chromatography on silica gel while eluting with ethyl acetate/methylene chloride 1/1. There was obtained 0.9 g (59%) of (S)-11,12a-dihydro-1-(3-dipropylaminomethyl-1,2,4-oxadiazol-5-yl)-9H,11H-azeto[2,1-c]imidazo[1,5-a][1,4]-benzodiazepin-9-one, which was converted into the hydrochloride of m.p. 185°–187°.

EXAMPLE 96 a) 10 g (31.09 mmol) of (S)-8-chloro-7-fluoro-12,12a-dihydro-9-oxo-9H,11H-azeto[2,1-c]-imidazo[1,5-a][1,4]benzodiazepine-1-carboxylic acid were dissolved in 100 ml of N,N-dimethylformamide, treated portionwise with 6.05 g (37.3 mmol) of 1,1'-carbonyldiimidazole and stirred at room temperature for 1 hour. After adding 6.8 g (31.09 mmol) of phthaloylglycine amidoxime the mixture was stirred at room temperature overnight, 10 ml of trifluoroacetic acid were added and the mixture was stirred at 90° overnight. After evaporating the solvent the residue was crystallized from methylene chloride and methanol. There were obtained 8.55 g (54%) of (S)-8-chloro-7-fluoro-12,12a-dihydro-1-(3-phthalimidomethyl-1,2,4-oxadiazol-5-yl)-9H,11H-azeto[2,1-c]imidazo[1,5-a][1,4]benzodiazepin-9-one of m.p. 292°–294°.

b) 16 g (31.85 mmol) of (S)-8-chloro-7-fluoro-12,12a-dihydro-1-(3-phthalimidomethyl-1,2,4-oxadiazol-5-yl)-9H,11H-azeto[2,1-c]imidazo[1,5-a][1,4]benzodiazepin-9-one were treated with 100 ml of methylamine (33% in ethanol). The solution was stirred at 70° for 1 hour and subsequently cooled. The suspension obtained was filtered and the crystallizate was partially dissolved in 100 ml of methylene chloride. By filtering and evaporating the filtrate there were obtained 11.7 g (99%) of (S)-1-(3-aminomethyl-1,2,4-oxadiazol-5-yl)-8-chloro-7-fluoro-12,12a-dihydro- 9H,11H-azeto[2,1-c]imidazo[1,5-a][1,4]benzodiazepin-9-one, which was used without further purification as the starting material for the Example described hereinafter.

EXAMPLE 97

11.7 g (31.2 mmol) of crude (S)-1-(3-aminomethyl-1,2,4-oxadiazol-5-yl)-8-chloro-7-fluoro-12,12a-dihydro-9H, 11H-azeto[2,1-c]imidazo[1,5-a][1,4]benzodiazepin-9-one, 100 ml of methylene chloride, 6.04 g (50 mmol) of allyl bromide and 7.75 g (60 mmol) of N-ethyldiisopropylamine were stirred at room temperature overnight. The solution was concentrated and the residue was purified by chromatography on 500 g of silica gel while eluting with ethyl acetate. After recrystallization from methanol there were obtained 5.3 g (47%) of (S)-1-(3-diallylaminomethyl-1,2,4-oxadiazol-5-yl)-8-chloro-7-fluoro-12,12a-dihydro-9H,11H-azeto[2,1-c]imidazo[1,5-a][1,4]benzodiazepin-9-one of m.p. 139°–140°, which was converted into the hydrochloride of m.p. 127°.

EXAMPLE 98

A suspension of 328 mg (1.0 mmol) of 3-(3-aminomethyl-1,2,4-oxadiazol-5-yl)-8-fluoro-5-methyl-5,6-dihydro-4H-imidazo[1,5-a][1,4]benzodiazepin-6-one in 5 ml of methylene chloride was treated under argon with 0.38 ml (2.2 mmol) of N-ethyldiisopropylamine and 317 mg (1.2 mmol) of α,α'-dibromo-o-xylene and stirred at room temperature under argon for 5 hrs. The solution was washed once with 5 ml of water, dried with sodium sulfate, filtered and evaporated. The crude product was purified by chromatography on 30 g of silica gel (methylene chloride/acetone 4:1, then 2:1). The eluates were evaporated and the residue was taken up in 2.5 ml of methanol. The solution was acidified with ethereal hydrochloric acid and the solvent was removed in a vacuum. The residue was taken up in 6 ml of hot methanol; then cooled to about 0° and the white crystals were isolated by suction filtration. There were obtained 150 mg (32%) of 8-fluoro-3-(3-isoindolin-2-ylmethyl- 1,2,4-oxadiazol-5-yl)-5-methyl-5,6-dihydro-4H-imidazo[1,5-a][1,4]benzodiazepin-6-one hydrochloride (1:1) of m.p. 229°–233° (dec.).

EXAMPLE 99 a) A solution of 28.8 g (144.6 mmol) of 5,6-difluoro-2,4-dihydro-1H-3,1-benzoxazine-2,4-dione and 16.7 g (144.6 mmol) of L-proline in 110 ml of dimethylformamide and 20 ml of acetic acid was stirred at 120° for 16 hours. The brown solution was evaporated and the brown residue obtained was crystallized from ethanol. There were obtained 30 g (82%) of (S)-6,7-difluoro-2,3,5,10,11,11a-hexahydro-1H-pyrrolo[2,1-c][1,4]benzodiazepine-5,11-dione as colourless crystals of m.p. >250°.

b) A solution of 29.8 g (118.2 mmol) of (S)-6,7-difluoro-2,3,5,10,11,11a-hexahydro-1H-pyrrolo[2,1-c][1,4]benzodiazepine-5,11-dione in 140 ml of dimethylformamide was added dropwise at −30° to a suspension of 5.7 g (130 mmol) of NaH (55%, washed with hexane) in 10 ml of dimethylformamide and stirred at −30° for 40 minutes. After cooling to −60° a solution of 25.2 ml (118.2 mmol) of phosphoric acid diphenyl ester chloride in 50 ml of dimethylformamide was added dropwise in such a manner that the temperature did not rise above −45°. Subsequently, the mixture was stirred for a further 30 minutes.

In the meanwhile, 14.6 g (130 mmol) of potassium tert.butylate were dissolved in 50 ml of dimethylformamide and treated at −60° with 14.5 ml (126.4 mmol) of ethyl isocyanoacetate (95%). The reaction mixture obtained above was added dropwise to the solution obtained at −70° via a dropping funnel cooled to −40°. The dark brown viscous solution obtained was stirred at −60° for 1 hour and, after neutralization with 20 ml of acetic acid at −40°, poured into 400 ml of ice-water and extracted five times with methylene chloride. The combined organic phases were dried over sodium sulfate, filtered and evaporated. The pale brown residue obtained was chromatographed (silica gel, ethyl acetate). There were obtained 22 g (54%) of ethyl (S)-7,8-difluoro-9-oxo-11,12,13,13a-tetrahydro-9H-imidazo[1,5-a]pyrrolo[2,1-c][1,4]benzodiazepine-1-carboxylate as colourless crystals of m.p. 199°–200°.

c) 20.7 ml (82.7 mmol) of 4N sodium hydroxide solution were added dropwise to a suspension of 22.1 g (63.6 mmol) of ethyl (S)-7,8-difluoro-9-oxo-11,12,13,13a-tetrahydro-9H-imidazo[1,5-a]pyrrolo[2,1-c][1,4]benzodiazepine-1-carboxylate in 55 ml of ethanol and 90 ml of water and heated at reflux for 45 minutes. Subsequently, the ethanol was distilled off. The aqueous phase was washed twice with methylene chloride and adjusted to pH=3 with 4N hydrochloric acid. Extraction with methylene chloride (five times), drying with sodium sulfate, filtration and evaporation yielded 20 g (98%) of (S)-7,8-difluoro-9-oxo-11,12,13,13a-tetrahydro-9H-imidazo[1,5-a]pyrrolo[2,1-c][1,4]benzodiazepine-1-carboxylic acid as colourless crystals of m.p. 214.5°–215.5° (dec.).

d) 6.1 g (37.9 mmol) of 1,1'-carbonyldiimidazole were added portionwise to a suspension of 11 g (34.5 mmol) of (S)-7,8-difluoro-9-oxo-11,12,13,13a-tetrahydro-9H-imidazo[1,5-a]pyrrolo[2,1-c][1,4]benzodiazepine-1-carboxylic acid in 80 ml of dimethylformamide. The resulting pale brown solution was heated to 50° for 45 minutes. The solution was subsequently cooled to room temperature and 12 ml of aqueous ammonia solution were added dropwise. After stirring for a further 30 minutes the reaction mixture was poured into 150 ml of ice-water and extracted seven times with methylene chloride. Drying of the organic phases with sodium sulfate, filtration and evaporation yielded a colourless residue which was triturated with methylene chloride. After drying in a high vacuum there were obtained 9.8 g of (S)-7,8-difluoro-9-oxo-11,12,13,13a-tetrahydro-9H-imidazo[1,5-a]pyrrolo[2,1-c][1,4]benzodiazepine-1-carboxamide m.p. 221°–224°.

e) 5.2 ml (37.7 mmol) of trifluoroacetic anhydride were added dropwise at 5°–8° to a suspension of 10.9 g (34.2 mmol) of (S)-7,8-difluoro-9-oxo-11,12,13,13a-tetrahydro-9H-imidazo[1,5-a]pyrrolo[2,1-c][1,4]benzodiazepine-1-carboxamide in 50 ml of dioxan and 10 ml of pyridine. The beige solution obtained was stirred at 50° for 2.5 hours and subsequently poured into 50 ml of ice-water. Extraction with methylene chloride (seven times), drying with sodium sulfate, filtration and evaporation yielded, after recrystallization from ethanol, 8.5 g (83%) of (S)-7,8-difluoro-9-oxo-11,12,13,13a-tetrahydro-9H-imidazo[1,5-a]pyrrolo[2,1-c][1,4]benzodiazepine-1-carbonitrile as colourless crystals of m.p. >250°.

f) 2.9 g (41.9 mmol) of hydroxylamine hydrochloride were added at room temperature to a suspension of 5.4 g (93.1 mmol) of potassium carbonate in 150 ml of dimethylformamide. Subsequently, a solution of 8.9 g (28 mmol) of (S)-7,8-difluoro-9-oxo-11,12,13,13a-tetrahydro-9H-imidazo[1,5-a]pyrrolo[2,1-c][1,4]benzodiazepine-1-carbonitrile in 1 00 ml of dimethylformamide was added dropwise and the mixture was stirred at room temperature for 60 hours. The yellow suspension obtained was evaporated, the residue was partitioned between methylene chloride and water and the aqueous phase was extracted four times with methylene chloride. The organic phases were dried with sodium sulfate, filtered and evaporated. Subsequent chromatography (silica gel, methylene chloride/methanol 9:1) yielded 2.4 g (37%) of (E)- and/or (Z)-(S)-7,8,difluoro-9-oxo-11,12,13,13a-tetrahydro-9H-imidazo[1,5-a]pyrrolo[2,1-c][1,4]benzo-diazepine-1-carboxamidoxime as a colourless foam, Rf=0.1 (silica gel, methylene chloride/methanol 9:1).

g) 2.2 g (13.7 mmol) of 1,1'-carbonyldiimidazole were added to a solution of 2.2 g (12.5 mmol) of BOC-glycine in 70 ml of dimethylformamide and stirred at 50° for 30 minutes. Subsequently, 3.8 g (11.4 mmol) of (E)- and/or (Z)-(S)-7,8,difluoro-9-oxo-11,12,13,13a-tetrahydro-9H-imidazo[1,5-a]pyrrolo[2,1-c][1,4]benzodiazepin-1- carboxamidoxime were added and the mixture was stirred at 90° for 16 hours. The brown solution obtained was evaporated in a high vacuum and the brown residue obtained was chromatographed (silica gel, methylene chloride/methanol 19:1). There were obtained 4.2 g (78%) of (S)-1-(5-BOC-aminomethyl-1,2,4-oxadiazol-3-yl)-7,8-difluoro-11,12,13,13a-tetrahydro-9H-imidazo[1,5-a]pyrrolo[2,1-c][1,4]benzodiazepin-9-one as a pale yellow foam, Rf=0.22 (silica gel, methylene chloride/methanol 19:1).

h) A solution of 3.3 g (7 mmol) of (S)-1-(5-BOC-aminomethyl-1,2,4-oxadiazol-3-yl)-7,8-difluoro-11,12,13,13a-tetrahydro-9H-imidazo[1,5-a]pyrrolo[2,1-c][1,4]benzodiazepin-9-one in 20 ml of trifluoroacetic acid was stirred at room temperature for 2 hours. The yellow solution was evaporated, the residue was dissolved in water and the aqueous phase was washed three times with methylene chloride. Subsequently, the aqueous phase was made basic with 2 ml of aqueous ammonia solution and extracted six times with methylene chloride. The organic phases were dried with sodium sulfate, filtered and evaporated. The residue obtained was chromatographed (silica gel, methylene chloride/methanol/aqueous ammonia 110:10:0.1). There were obtained 2 g (77%) of (S)-1-(5-aminomethyl-1,2,4-oxadiazol-3-yl)-7,8-difluoro-11,12,13,13a tetrahydro-9H-imidazo[1,5-a]pyrrolo[2,1-c][1,4]benzodiazepin-9-one as a beige powder of m.p. 218°-220° (dec.).

EXAMPLE 100

2.1 ml (10.5 mmol) of N-ethyldiisopropylamine and 0.6 ml (7 mmol) of allyl bromide were added to a solution of 650 mg (1.76 mmol) of (S)-1-(5-aminomethyl-1,2,4-oxadiazol-3-yl)-7,8-difluoro-11,12,13,13a-tetrahydro-9H-imidazo[1,5-a]pyrrolo[2,1-c][1,4]benzodiazepin-9-one in 40 ml of methylene chloride and the mixture was stirred at room temperature for 20 hours. The reaction solution was subsequently diluted with methylene chloride and washed three times with water. The organic phases were dried with magnesium sulfate, filtered and evaporated. The residue obtained was chromatographed twice (silica gel, methylene chloride/methanol/aqueous ammonia 140:10:0.1). There were obtained 625 mg (78%) of (S)-1-[5-(diallylaminomethyl)-1,2,4-oxadiazol-3-yl]-7,8-difluoro-11,12,13,13a-tetrahydro-9H-imidazo[1,5-a]pyrrolo[2,1-c]-[1,4]benzodiazepin-9-one as a colourless foam, Rf=0.45 (silica gel, methylene chloride/methanol/aqueous ammonia 140:10:0.1).

EXAMPLE 101

2.1 ml (10.5 mmol) of N-ethyldiisopropylamine and 0.8 ml (7 mmol) of dimethylallyl bromide were added to a solution of 650 mg (1.76 mmol) of (S)-1-(5-aminomethyl-1,2,4-oxadiazol-3-yl)-7,8-difluoro-11,12,13,13a-tetrahydro-9H-imidazo[1,5-a]pyrrolo[2,1-c][1,4]benzo-diazepin-9-one in 40 ml of methylene chloride and the mixture was stirred at room temperature for 20 hours. The reaction solution was subsequently diluted with methylene chloride and washed three times with water. The organic phases were dried with magnesium sulfate, filtered and evaporated. The residue obtained was chromatographed twice (silica gel, methylene chloride/methanol/aqueous ammonia 140:10:0.1). There were obtained 589 mg (66%) of (S)-1-[5-[bis-(3-methyl-but-2-enyl)-aminomethyl]-1,2,4-oxadiazol-3-yl]-11,12,13,13a-tetrahydro-9H-imidazo[1,5-a]pyrrolo[2,1-c][1,4]benzodiazepin-9-one as a colourless foam, Rf=0.51 (silica gel, methylene chloride/methanol/aqueous ammonia 140:10:0.1).

EXAMPLE 102

2 g (5.95 mmol) of (S)-1-(3-aminomethyl-1,2,4-oxadiazol-5-yl)-8-chloro-11,12,13,13a-tetrahydro-9H-imidazo[1,5-a]pyrrolo[2,1-c][1,4]benzodiazepin-9-one, 30 ml of N,N-dimethylformamide, 3.1 ml (17.8 mmol) of N-ethyldiisopropylamine and 1.1 ml (13.1 mmol) of allyl bromide were stirred at room temperature for 1.5 hours. The reaction solution was chromatographed on 250 g of silica gel while eluting with methylene chloride/ethyl acetate 7/3. There were obtained 2 g (81%) of (S)-1-(3-diallylaminomethyl-1,2,4-oxadiazol-5-yl)-8-chloro-11,12,13,13a-tetrahydro-9H-imidazo[1,5-a]pyrrolo[2,1-c][1,4]benzodiazepin-9-one, which was converted into the hydrochloride of m.p. 175°-177°.

EXAMPLE 103

2 g (6.2 mmol) of (S)-1-(3-aminomethyl-1,2,4-oxadiazol-5-yl)-12,12a-dihydro-9H,11H-azeto[2,1-c]imidazo[1,5-a][1,4]benzodiazepin-9-one, 30 ml of N,N-dimethylformamide, 3.7 ml (21.7 mmol) of N-ethyldiisopropylamine and 1.6 ml (14.3 mmol) of 1-iodobutane were stirred at room temperature for 6 hours and at 80° for 1.5 hours. The reaction mixture was evaporated and the residue was chromatographed on 180 g of silica gel while eluting with methylene chloride/ethyl acetate 7/3. By concentrating the uniform fractions there were obtained 1.6 g (59%) of S)-1-(3-di-butylaminomethyl-1,2,4-oxadiazol-5-yl)-12,12a-dihydro- 9H,11H-azeto[2,1-c]imidazo[1,5-a][1,4]benzodiazepin-9-one, which was converted into the hydrochloride.

EXAMPLE 104

2 g (6.44 mmol) of 3-(3-aminomethyl-1,2,4-oxadiazol-5-yl)-5,6-dihydro-5-methyl-4H-imidazo[1,5-a][1,4]benzodiazepin-6-one, 20 ml of N,N-dimethylformamide, 3.3 ml (19.3 mmol) of N-ethyldiisopropylamine and 1.65 ml (13.5 mmol) of 3,3-dimethylallyl bromide were stirred at room temperature for 2 hours. After evaporating the solvent the residue was dissolved in methylene chloride and the solution was washed with water, dried and concentrated. By chromatography on 220 g of silica gel while eluting with methylene chloride/ethyl acetate 1/1 there were obtained 1.9 g (69%) of 3-[3-bis-(3-methyl-but-2-enyl)aminomethyl-1,2, 4-oxadiazol-5-yl]-5,6-dihydro-5-methyl-4H-imidazo[1,5-a][1,4]benzodiazepin-6-one, which was converted into the hydrochloride.

EXAMPLE 105

2 g (6.44 mmol) of 3-(3-aminomethyl-1,2,4-oxadiazol-5-yl)-5,6-dihydro-5-methyl-4H-imidazo[1,5-a][1,4]benzodiazepin-6-one, 20 ml of N,N-dimethylformamide, 3.8 ml (22.5 mmol) of N-ethyldiisopropylamine and 1.6 ml (14.8 mmol) of bromomethylcyclopropane were stirred at 80° for 4 hours. After evaporating the solvent the residue was dissolved in methylene chloride and the solution was washed with water, dried and concentrated. By chromatography on 220 g of silica gel while eluting with methylene chloride/ethyl acetate 1/1 there were obtained 1.3 g (48%) of 3-[3-(bis-cyclopropylmethylaminomethyl)-1,2,4-oxadiazol-5-yl ]-5,6-dihydro-5-methyl-4H-imidazo[1,5-a][1,4]benzodiazepin-6-one, which was converted into the hydrochloride of m.p. 170°–174°.

EXAMPLE 106 a) A suspension of 5.8 g (0.020 mol) of 8-fluoro-5,6-dihydro-5-methyl-6-oxo-4H-imidazo[1,5-a][1,4] benzodiazepine-3-carboxamidoxime in 60 ml of dimethylformamide was treated with 3.9 g (0.023 mol) of chloroacetic anhydride. The yellow solution obtained was stirred at 100° for 1½ hr. and then completely freed from solvents. The oily product crystallized from acetonitrile and was filtered off. The mother liquor was concentrated, the residue was chromatographed over silica gel with dichloromethane/methanol 97:3 as the eluent and the additional portion of product obtained was recrystallized from acetonitrile. There were obtained a total of 4.05 g (59%) of 3-(5-chloromethyl-1,2,4-oxadiazol-3-yl)-8-fluoro-5-methyl-5,6-dihydro-4H-imidazo[1,5-a][1,4]benzodiazepin-6-one as white crystals; m.p. 245°–247°.

b) A suspension of 1.5 g (0.0043 mol) of 3-(5-chloromethyl-1,2,4-oxadiazol-3-yl)-8-fluoro-5-methyl-5,6-dihydro-4H-imidazo[1,5-a][1,4]benzodiazepin-6-one in 15 ml of dimethylformamide was treated with 1.6 g (0.022 mol) of diethylamine. After stirring at room temperature for 16 hrs. the solution obtained was freed completely from the solvents. The residue was chromatographed over silica gel with dichloromethane/methanol 9:1 as the eluent. There were obtained 1.33 g (81%) of 3-(5-diethylaminomethyl-1,2,4-oxadiazol-3-yl)-8-fluoro-5-methyl-5,6-dihydro-4H-imidazo[1,5-a][1,4]benzodiazepin-6-one as white crystals; m.p. 172°–174°.

c) 1.30 g (0.0034 mol) of 3-(5-diethylaminomethyl-1,2,4-oxadiazol-3-yl)-8-fluoro-5-methyl-5,6-dihydro-4H-imidazo [1,5-a]-[1,4]benzodiazepin-6-one in 20 ml of ethanol were treated with 0.79 ml (0.0037 mol) of 4.78N ethanolic hydrochloric acid. Crystals separated after the addition of 100 ml of ether. There were obtained 1.28 g (90%) of 3-(5-diethylaminomethyl-1,2,4-oxadiazol-3-yl)-8-fluoro-5-methyl-5,6- dihydro-4H-imidazo[1,5-a][1,4]benzodiazepin-6-one hydrochloride as white crystals; m.p. 220°–223° (dec.).

EXAMPLE 107 a) A suspension of 1.30 g (0.0037 mol) of 3-(5-chloromethyl-1,2,4-oxadiazol-3-yl)-8-fluoro-5-methyl-5,6-dihydro-4H-imidazo[1,5-a][1,4]benzodiazepin-6-one in 15 ml of dimethylformamide was treated with 2.4 g (0.01 9 moll of dibutylamine. After stirring at room temperature for 65 hrs. the orange solution obtained was freed completely from solvent. The residue was chromatographed over silica gel with dichloromethane/methanol 19:1 as the eluent. The product was recrystallized from methanol/ether and there were obtained 1.27 g (77%) of 3-(5-dibutylaminomethyl-1, 2,4-oxadiazol-3-yl)-8-fluoro-5-methyl-5,6-dihydro-4H-imidazo[1,5-a][1,4]benzodiazepin-6-one as white crystals; m.p. 137°–140°.

b) 1.17 g (0.0027 mol) of 3-(5-dibutylaminomethyl-1,2, 4-oxadiazol-3-yl)-8-fluoro-5-methyl-5,6-dihydro-4H-imidazo[1,5-a][1,4]benzodiazepin-6-one in 30 ml of ethanol were treated with 0.65 ml (0.0031 mol) of 3.7N ethanolic hydrochloric acid. The solvent was freed completely from solvent and the residue was recrystallized from acetone. There was obtained 0.87 g (69%) of 3-(5-dibutylaminomethyl-1,2,4-oxadiazol-3-yl)-8-fluoro-5-methyl-5,6-dihydro-4H-imidazo[1,5-a][1,4] benzodiazepin-6- one hydrochloride as white crystals; m.p. 183°–185°.

EXAMPLE 108 a) A suspension of 1.50 g (0.0043 mol) of 3-(5-chloromethyl-1,2,4-oxadiazol-3-yl) -8-fluoro-5-methyl-5,6-dihydro-4H-imidazo [1,5-a][1,4]benzodiazepin-6-one in 15 ml of dimethylformamide was treated with 1.5 g (0.022 mol) of pyrrolidine. After stirring at room temperature for 65 hrs. the yellow-orange solution obtained was freed completely from solvent. The residue was chromatographed over silica gel with dichloromethane/methanol 19:1 as the eluent. The product was recrystallized from methanol/ether. There were obtained 1.35 g (82%) of 8-fluoro-5-methyl-3-(5-pyrrolidin-1-ylmethyl-1,2,4-oxadiazol-3-yl)-5,6-dihydro-4H-imidazo [1,5-a][1,4]benzodiazepin-6-one as white crystals; m.p. 158°–160°.

b) 1.32, g (0.0035 mol) of 8-fluoro-5-methyl-3-(5-pyrrolidin-1-ylmethyl-1,2,4-oxadiazol-3-yl)-5,6-dihydro-4H-imidazo [1,5-a][1,4]benzodiazepin-6-one were dissolved in 50 ml of hot ethanol. 0.8 ml (0.0038 mol) of 4.78N ethanolic hydrochloric acid was added at room temperature. The solution was concentrated to a volume of ~20 ml, whereby crystallization began. 80 ml of ether were added, the mixture was filtered and there were obtained 1.38 g (96%) of 8-fluoro-5-methyl-3-(5-pyrrolidin-1-ylmethyl-1,2, 4-oxadiazol-3-yl)-5,6-dihydro-4H-imidazo[1,5-a][1,4] benzodia-zepin-6-one hydrochloride (1:1) as white crystals; m.p. 243°–245° (dec.).

EXAMPLE 109 a) 13 ml of hydrazine hydrate were added to a suspension of 7.0 g (23 mmol) of 8-fluoro-5-methyl-6-oxo-5,6-dihydro-4H-imidazo[1,5-a][1,4]benzodiazepin-3-carboxylate in 70 ml of ethanol and the mixture was heated at reflux for 3 hours. After cooling to 0° the crystals obtained were filtered off and there were obtained 6.43 g (96%) of 8-fluoro-5-methyl-6-oxo-5,6-dihydro-4H-imidazo[1,5-a][1,4] benzodiazepine-3-carboxylic acid hydrazide as colourless needles of m.p. 288°–290°.

b) A solution of 4.46 g (21.75 mmol) of N-phthaloylglycine in 35 ml of dimethylformamide was treated at room temperature with 3.66 g (22.6 mmol) of 1,1'-carbonyldiimidazole and subsequently heated at 50°. After 30 minutes the mixture was cooled to room temperature, 6.43 g (22.15 mmol) of 8-fluoro-5-methyl-6-oxo-5,6-dihydro-4H-imidazo[1,5-a][1,4]benzodiazepine-3-carboxylic acid hydrazide were added and the mixture was stirred at room temperature for 12 hours. The suspension obtained was filtered and the colourless powder obtained was washed with ethanol and diethyl ether. There were obtained 10.2 g (98%) of 8-fluoro-5-methyl-6-oxo-5,6-dihydro-4H-imidazo[1,5-a][1,4]benzodiazepine-3- carboxylic acid N'-(2,3-dioxo-2,3-dihydro-1H-isoindol-2-ylacetyl) hydrazide of m.p. >280°.

c) A solution of 6.0 g (12.6 mmol) of 8-fluoro-5-methyl-6-oxo-5,6-dihydro-4H-imidazo[1,5-a][1,4]benzodiazepine-3-carboxylic acid N'-(2,3-dioxo-2,3-dihydro-1H-isoindol-2-ylacetyl) hydrazide in 38 g of polyphosphoric acid was stirred at 100° for 1.5 hours. After cooling to room temperature the mixture was poured into 300 ml of ice-water while stirring well, whereupon solid sodium carbonate was added to pH=8. Extraction with methylene chloride and chromatography (silica gel, methylene chloride/methanol 20:1) yielded 4.9 g (85%) of 2-[5-(8-fluoro- 5-methyl-6-oxo-5,6-dihydro-4H-imidazo[1,5-a][1,4 ]benzodiazepin-3-yl)-1,3,4-oxadiazol-2-ylmethyl]-2,3-dihydro-1H-isoindole-1,3-dione as a colourless powder of m.p. >250.

d) 60 ml of methylamine (33% in ethanol) were added dropwise at 70° to a suspension of 4.9 g (10.7 mmol) of 2-[5-(8-fluoro-5-methyl-6-oxo-5,6-dihydro-4H-imidazo[1,5-a][1,4]benzodiazepin-3-yl)-1,3,4 oxadiazol-2-ylmethyl]-2,3-dihydro-1H-isoindole-1,3-dione in 100 ml of ethanol and the mixture was stirred at 70° for one hour. The precipitate obtained was filtered while hot and the yellowish powder obtained was washed with ethanol until colourless. There were obtained 2.6 g (80%) of 3-(5-aminomethyl-1,3,4-oxadiazol-2-yl)-8-fluoro-5-methyl-5,6-dihydro-4H-imidazo[1,5-c][1,4]benzodiazepin-6-one as a colourless powder of m.p. 227°-231°.

EXAMPLE 110

3.5 ml of N-ethyldiisopropylamine and 1.1 ml (12 mmol) of 1-bromopropane were added to a solution of 0.656 g (2.0 mmol) of 3-(5-aminomethyl-1,3,4-oxadiazol-2-yl)-8-fluoro-5-methyl-5,6-dihydro-4H-imidazo[1,5-c][1,4] benzodiazepin-6-one in 15 ml of dimethylformamide, whereupon the mixture was stirred at 70° for 12 hours. The dimethylformamide was evaporated and the residue was partitioned between methylene chloride and 2N sodium (sic) carbonate solution. The aqueous phase was washed twice with methylene chloride; the organic phases were dried with sodium sulfate, filtered and evaporated. Chromatography (silica gel, ethyl acetate/methanol 20:1) yielded 0.450 g (55%) of 3-(5-dipropylaminomethyl-1,3,4-oxadiazol-2-yl)-8-fluoro-5-methyl-5,6-dihydro-4H-imidazo[1,5-c][1,4] benzodiazepin-6-one as a colourless foam, Rf=0.48 (silica gel, ethyl acetate methanol 20:1).

EXAMPLE 111

1.74 ml of N-ethyldiisopropylamine and 0.55 ml (6 mmol) of 1-bromopropane were added to a solution of 0.500 g (1.52 mmol) of (S)-1-(5-aminomethyl-1,2,4-oxadiazol-3-yl)-I 1,11a-dihydro-8H, 10H-azeto[1,2-a]imidazo[5,1-c]thieno[3,2-e][1,4]diazepin-8-one in 15 ml of dimethylformamide and the mixture was stirred at 70° for 12 hours. The dimethylformamide was evaporated and the residue was partitioned between methylene chloride and 2N sodium carbonate solution. The aqueous phase was extracted twice with methylene chloride and the organic phases were dried with sodium sulfate, filtered and evaporated. Chromatography (silica gel, ethyl acetate/methanol 20:1) yielded 0.350 g (55%) of (S)-1-(5-dipropylaminomethyl-1,2,4-oxadiazol-3-yl)-11,11a-dihydro-8H, 10H-azeto[1,2-a]imidazo[5,1-c]thieno[3,2-e][1,4]diazepin-8-one as a colourless foam, Rf=0.44 (silica gel, ethyl acetate/methanol 20:1).

EXAMPLE 112

1.04 g (3.0 mmol) of 3-(5-chloromethyl-1,2,4-oxadiazol-3-yl)-8-fluoro-5,6-dihydro-5-methyl-4H-imidazo[1,5-a][1,4]-benzodiazepin-6-one, 0.64 g (7.5 mmol) of piperidine and 10 ml of N,N-dimethylformamide were stirred at room temperature for 4 hours. The reaction mixture was concentrated, the residue was dissolved in methylene chloride and the solution was made alkaline with 4N sodium hydroxide solution. The solution was washed once with saturated sodium chloride solution, dried with magnesium sulfate and evaporated. By chromatography of the residue on silica gel while eluting with methylene chloride/methanol 9/1 there was obtained 0.89 g (75%) of 8-fluoro-5-methyl-3-[5-(piperidin-1-ylmethyl)-1,2,4-oxadiazol-3-yl]-5,6-dihydro-4H-imidazo[1,5-a][1,4]benzodiazepin-6-one of m.p. 182°-4°, which was converted into the hydrochloride of m.p. 254°-6°.

EXAMPLE 113

A suspension of 4.77 g (13.7 mmol) of 3-(5-chloromethyl-1,2,4-oxadiazol-3-yl)-8-fluoro-5-methyl-5,6-dihydro-4H-imidazo[1,5-a][1,4]benzodiazepin-6-one in 70 ml of dimethylformamide was treated with 5.6 ml (41.0 mmol) of dipropylamine. After stirring at room temperature for 18 hrs. the solution obtained was concentrated and the residue was taken up in 70 ml of water. The crystals were filtered off, washed with 10 ml of water and dried at 60° in a vacuum. The residue was chromatographed over 100 g of silica gel with dichloromethane/acetone 2:1 as the eluent. 4.19 g of white crystals were obtained. These were recrystallized twice from ethyl acetate, whereby, after drying at 60°/0.03 mbar, 2.77 g (49%) of 3-(5-dipropylaminomethyl-1,2,4-oxadiazol-3-yl)-8-fluoro-5-methyl-5,6-dihydro-4H-imidazo[1,5a][1,4]benzodiazepin-6-one were obtained as white crystals with m.p. 153°-154°.

EXAMPLE 114

2.4 ml (13.8 mmol) of N-ethyldiisopropylamine and 0.97 ml (8 mmol) of allyl bromide were added to a solution of 0.600 g (1.75 mmol) of (S)-1-(5-aminomethyl-1,3,4-oxadiazol-2-yl)-10,11,12,12a-tetrahydro-8H-imidazo [5,1-c]pyrrolo[1,2-a]thieno[3,2-e][1,4]diazepin-8-one in 30 ml of methylene chloride, whereupon the mixture was stirred at 70° for 12 hours. The reaction solution was diluted with methylene chloride and washed with 2N sodium carbonate solution. The aqueous phase was washed twice with methylene chloride and the organic phases were dried with sodium sulfate, filtered and evaporated. Chromatography (silica gel, ethyl acetate/methanol 20:1) yielded 0.580 g (78%) of (S)-1-(5-diallylaminomethyl-1,3,4-oxadiazol-2-yl)-10,11,12,12a-tetrahydro-8H-imidazo[5,1-c]pyrrolo[1,2-a]thieno[3,2-e][1,4]diazepin-8-one as a colourless foam, Rf=0.56 (silica gel, ethyl acetate/methanol 20:1).

EXAMPLE 115

2 ml (11.5 mmol) of N-ethyldiisopropylamine and 0.3 ml (2.61 mmol) of dimethylallyl bromide were added to a solution of 0.443 g (1.3 mmol) of (S)-1-(5-aminomethyl-1,3,4-oxadiazol-2-yl)-10,11,12,12a-tetrahydro-8H-imidazo[5,1-c]pyrrolo[1,2-a]thieno[3,2-e][1,4]diazepin-8-one, whereupon the mixture was stirred at 70° for 12 hours. The reaction solution was diluted with methylene chloride and washed with 2N sodium carbonate solution. The aqueous phase was washed twice with methylene chloride and the organic phases were dried with sodium sulfate, filtered and evaporated. Chromatography (silica gel, ethyl acetate/methanol 10:1) yielded 0.190 g (30%) of (S)-1-[5-[bis-(3-methyl-but-2-enyl)-aminomethyl]-1,3,4-oxadiazol-2-yl]-10,11,12,12a-tetrahydro-8H-imidazo[5,1-c]pyrrolo[1,2-a]

thieno[3,2-e][1,4]diazepin-8-one as a colourless foam, Rf=0.50 (silica gel, ethyl acetate/methanol 10:1).

EXAMPLE 116

2 ml (11.5 mmol) of N-ethyldiisopropylamine and 0.97 ml (8 mmol) of allyl bromide were added to a solution of 0.500 g (1.52 mmol) of (S)-1-(5-aminomethyl-1,3,4-oxadiazol-2-yl)-11,11a-dihydro-8H,10H-azeto[1,2-a]imidazo[5,1-c]thieno[3,2-e][1,4]diazepin-8-one in 30 ml of methylene chloride, whereupon the mixture was stirred at 70° for 12 hours. The reaction solution was diluted with methylene chloride and washed with 2N sodium carbonate solution. The aqueous phase was washed twice with methylene chloride and the organic phases were dried with sodium sulfate, filtered and evaporated. Chromatography (silica gel, ethyl acetate/methanol 10:1) yielded 0.476 g (77%) of (S)-1-[5-diallylaminomethyl-1,3,4-oxadiazol-2-yl]-11,11a-dihydro-8H,10H-azeto[1,2-a]imidazo[5,1-c]thieno[3,2-e][1,4]diazepin-8-one as a colourless foam, Rf=0.36 (silica gel, ethyl acetate/methanol 20:1).

EXAMPLE 117

2 ml (11.5 mmol) of N-ethyldiisopropylamine and 0.3 ml (2.61 mmol) of dimethylallyl bromide were added to a solution of 0.426 g (1.3 mmol) of (S)-1-(5-aminomethyl-1,3,4-oxadiazol-2-yl)-11,11a-dihydro-8H,10H-azeto[1,2-a]imidazo[5,1-c]thieno[3,2-e][1,4]diazepin-8-one in 30 ml of methylene chloride, whereupon the mixture was stirred at 70° for 12 hours. The reaction solution was diluted with methylene chloride and washed with 2N sodium carbonate solution. The aqueous phase was washed twice with methylene chloride and the organic phases were dried with sodium sulfate, filtered and evaporated. Chromatography (silica gel, ethyl acetate/methanol 40:1) yielded 0.270 g (44%) of (S)-1-[5-[bis-(3-methyl-but-2-enyl)-aminomethyl]-1,3,4-oxadiazol-2-yl]-11,11a-dihydro-8H,10H-azeto[1,2-a]imidazo[5,1-c]thieno[3,2-e][1,4]diazepin-8-one as a colourless foam, Rf=0.24 (silica gel, ethyl acetate/methanol 40:1).

EXAMPLE 118

3 ml (17.25 mmol) of N-ethyldiisopropylamine and 0.8 ml (8.8 mmol) of propyl bromide were added to a solution of 0.550 g (1.68 mmol) of (S)-1-(5-aminomethyl-1,3,4-oxadiazol-2-yl)-11,11a-dihydro-8H,10H-azeto[1,2-a]imidazo[5,1-c]thieno[3,2-e][1,4]diazepin-8-one in 30 ml of dimethylformamide, whereupon the mixture was stirred at 70° for 12 hours. The dimethylformamide was evaporated and the residue was partitioned between methylene chloride and 2N sodium carbonate solution. The aqueous phase was washed twice with methylene chloride and the organic phases were dried with sodium sulfate, filtered and evaporated. Chromatography (silica gel, ethyl acetate/methanol 20:1) yielded 0.300 g (43%) of (S)-1-(5-dipropylaminomethyl-1,3,4-oxadiazol-2-yl)-11,11a-dihydro-8H,10H-azeto[1,2-a]imidazo[5,1-c]thieno[3,2-e][1,4]diazepin-8-one as a colourless foam, Rf=0.28 (silica gel, ethyl acetate/methanol 20:1).

EXAMPLE 119

1.5 ml (8.6 mmol) of N-ethyldiisopropylamine and 0.4 ml (4.4 mmol) of propyl bromide were added to a solution of 0.300 g (0.87 mmol) (S)-1-(5-aminomethyl-1,3,4-oxadiazol-2-yl)-10,11,12,12a-tetrahydro-8H-imidazo[5,1-c]pyrrolo[1,2-a]thieno[3,2-e][1,4]diazepin-8-one in 20 ml of dimethylformamide, whereupon the mixture was stirred at 70° for 12 hours. The dimethylformamide was evaporated and the residue was partitioned between methylene chloride and 2N sodium carbonate solution. The aqueous phase was washed twice with methylene chloride and the organic phases were dried with sodium sulfate, filtered and evaporated. Chromatography (silica gel, ethyl acetate/methanol 20:1) yielded 0.140 g (38%) of (S)-1-(5-dipropylaminomethyl-1,3,4-oxadiazol-2-yl)-10,11,12,12a-tetrahydro-8H-imidazo[5,1-c]pyrrolo[1,2-a]thieno[3,2-e][1,4]diazepin-8-one as a colourless foam, Rf=0.28 (silica gel, ethyl acetate/methanol 20:1).

EXAMPLE 120

3.5 ml of N-ethyldiisopropylamine and 1.29 ml (12 mmol) of 1-bromobutane were added to a solution of 0.656 g (2.0 mmol) of 3-(5-aminomethyl-1,3,4-oxadiazol-2-yl)-8-fluoro-5-methyl-5,6-dihydro-4H-imidazo[1,5-c][1,4]benzodiazepin-6-one in 15 ml of dimethylformamide, whereupon the mixture was stirred at 70° for 12 hours. The dimethylformamide was evaporated and the residue was partitioned between methylene chloride and 2N sodium carbonate solution. The aqueous phase was washed twice with methylene chloride and the organic phases were dried with sodium sulfate, filtered and evaporated. Chromatography (silica gel, ethyl acetate/methanol 20:1) yielded 0.470 g (53%) of 3-(5-dibutylaminomethyl-1,3,4-oxadiazol-2-yl)-8-fluoro-5-methyl-5,6-dihydro-4H-imidazo[1,5-a][1,4]benzodiazepin-6-one as a colourless foam, Rf=0.66 (silica gel, ethyl acetate/methanol 20:1).

EXAMPLE 121 a) 13 ml of hydrazine hydrate were added to a suspension of 7.0 g (23.54 mmol) of ethyl (S)-12,12a-dihydro-9-oxo-9H,11H-azeto[2,1-c]imidazo[1,5-a][1,4]diazepine-1-carboxylate in 70 ml ethanol and the mixture was heated at reflux for 3 hours. After cooling to 0° the crystals obtained were filtered off and there were obtained 3.6 g (96%) of (S)-12,12a-dihydro-9-oxo-9H,11H-azeto[2,1-c]imidazo[1,5-a][1,4]diazepine-1-carboxylic acid hydrazide as colourless needles of m.p. 246°–248°.

b) A solution of 5 g (17.64 mmol) of (S)-12,12a-dihydro-9-oxo-9H,11H-azeto[2,1-c]imidazo[1,5-a][1,4]benzodiazepine-1-carboxylic acid hydrazide and 3.06 g (19.41 mmol) of ethyl chloroacetimidate in 40 ml of dimethylformamide and 10 ml of ethanol was stirred at 90° for 12 hours. The solvent was evaporated and the residue was partitioned between methylene chloride and water. The aqueous phase was back-washed once with methylene chloride. The organic phases were dried with magnesium sulfate, filtered and evaporated. Chromatography of the residue (silica gel, methylene chloride/methanol 93:3) yielded 3.26 g (55%) of (S)-1-(5-chloromethyl-1,3,4-oxadiazol-2-yl)-12,12a-dihydro-9H,11H-azeto[2,1-c]imidazo[1,5-a][1,4]benzodiazepine-9-one as a colourless foam, RF=0.5 (methylene chloride/methanol 10:1).

c) 0.94 ml (73 mmol) of dipropylamine was added to a solution of 1.17 g (3.42 mmol) of (S)-1-(5-chloromethyl-1,3,4-oxadiazol-2-yl)-12,12a-dihydro-9H,11H-azeto[2,1-c]imidazo[1,5-a][1,4]benzodiazepin-9-one in 10 ml of dimethylformamide, whereupon the mixture was stirred at room temperature for 12 hours. The dimethylformamide was evaporated and the residue was partitioned between methylene chloride and 2N sodium carbonate solution. The aqueous phase was washed twice with methylene chloride and the organic phases were dried with sodium sulfate, filtered and evaporated. Chromatography (silica gel, methylene chloride/methanol 95:5) yielded 0.900 g (65%) of (S)-1-(5-dipropylaminomethyl-1,3,4-oxadiazol-2-yl)-12,12a-dihydro-9H,11H-azeto[2,1-c]imidazo[1,5-a]-[1,4]benzodiazepin-9-one as a colourless foam, Rf=0.46 (silica gel, methylene chloride/methanol 95:5).

EXAMPLE 122

17.4 ml (1.00 mmol) of N-ethyldiisopropylamine and 7.87 ml (73 mmol) of butyl bromide were added to a solution of 4 g (12.18 mmol) of (S)-1-(5-aminomethyl-1,3,4-oxadiazol-2-yl)-11,11a-dihydro-8H,10H-azeto[1,2-a]imidazo[5,1-c]thieno[3,2-e][1,4]diazepin-8-one in 100 ml of dimethylformamide whereupon the mixture was stirred at 70° for 12 hours. The dimethylformamide was evaporated and the residue was partitioned between methylene chloride and 2N sodium carbonate solution. The aqueous phase was washed twice with methylene chloride and the organic phases were dried with sodium sulfate, filtered and evaporated. Chromatography (silica gel, ethyl acetate/methanol 10:1) yielded 2.1 g (39%) of (S)-1-(5-dibutylaminomethyl-1,3,4-oxadiazol-2-yl)-11,11a-dihydro-8H,10H-azeto-[1,2-a]imidazo[5,1-c]thieno[3,2-e][1,4]diazepin-8-one as a colourless foam, Rf=0.4 (silica gel, ethyl acetate/methanol 10:1).

EXAMPLE 123 a) A solution of 5 g (17.28 mmol) of 8-fluoro-5,6-dihydro-5-methyl-6-oxo-4H-imidazo[1,5-a][1,4]benzodiazepine-3-carboxylic acid hydrazide and 2.87 g (18.16 mmol) of ethyl chloroacetimidate in 40 ml of dimethylformamide and 10 ml of ethanol was stirred at 90° for 12 hours. The solvent was evaporated and the residue was partitioned between methylene chloride and water. The aqueous phase was backwashed once with methylene chloride. The organic phases were dried with magnesium sulfate, filtered and evaporated. Chromatography of the residue (silica gel, methylene chloride/methanol 93:3) yielded 3.66 g (55%) of (S)-1-(5-chloromethyl-1,3,4-oxadiazol-2-yl)-8-fluoro-5,6-dihydro-5-methyl-4H-imidazo[1,5-a][1,4]benzodiazepin-6-one as colourless crystals with m.p. 260°–262° (dec.).

b) 1.0 ml (12.7 mmol) of propylamine was added to a solution of 2 g (5.8 mmol) of (S)-1-(5-chloromethyl-1,3,4-oxadiazol-2-yl)-8-fluoro-5,6-dihydro-5-methyl-4H-imidazo[1,5-a][1,4]benzodiazepin-6-one in 50 ml of dimethylformamide, whereupon the mixture was stirred at 55° for 12 hours. The dimethylformamide was evaporated and the residue was partitioned between methylene chloride and 2N sodium carbonate solution. The aqueous phase was washed twice with methylene chloride and the organic phases were dried with sodium sulfate, filtered and evaporated. Chromatography (silica gel, methylene chloride/methanol/aqueous ammonia (140:10:1) yielded 1.40 g (65%) of (S)-1-(5-propylaminomethyl-1,3,4-oxadiazol-2-yl)-8-fluoro-5,6-dihydro-5-methyl-4H-imidazo[1,5-a]-[1,4]benzodiazepin-6-one as a colourless foam, Rf=0.49 (silica gel, methylene chloride/methanol/aqueous ammonia 110:10:1).

EXAMPLE 124 a) A suspension of 3.06 g (9.22 mmol) of (S)-8-chloro-9-oxo-11,12,13,13a-tetrahydro-9H-imidazo[1,5-a]pyrrolo[2,1-c][1,4]benzodiazepine-1-carboxylic acid hydrazide in 30 ml of N,N-dimethylformamide was treated with 1.97 g (0.0115 mol) of chloroacetic anhydride. The yellow solution obtained was stirred at room temperature for 1½ hr. and then completely freed from the solvents. The residue was suspended in ether and filtered off under suction. The beige crystals obtained (3.75 g, m.p. 262°–264° (dec.)) were treated with 27 ml of methanesulphonic acid and 3 g of phosphorus pentoxide, whereupon the mixture was stirred at room temperature for 65 hrs. The orange-brown solution was poured into 150 ml of ice-water, made basic with aqueous sodium hydroxide solution and extracted with methylene chloride. The crystalline product was chromatographed over silica gel with ethyl acetate as the eluent. There were obtained 2.03 g (56%) of (S)-8-chloro-1-(5-chloromethyl-1,3,4-oxadiazol-2-yl)-11,12,13,13a-tetrahydro-9H-imidazo[1,5-a]pyrrolo[2,1-c][1,4]benzodiazepin-9-one as white crystals; m.p. 230°–232° and $[a]_D^{20}=+104.5°$ (DMF, c=1%).

b) A suspension of 1.30 g (3.33 mmol) of (S)-8-chloro-1-(5-chloromethyl-1,3,4-oxadiazol-2-yl)-11,12,13,13a-tetrahydro-9H-imidazo[1,5-a]pyrrolo[2,1-c][1,4]benzodiazepin-9-one in 10 ml of N,N-dimethylformamide was treated with 1.7 g (0.017 mol) of dipropylamine. After stirring at room temperature for 20 hrs. and at 80° C. for 4 hrs. the solution obtained was completely freed from the solvents. The residue was chromatographed over silica gel with methylene chloride/methanol 39:1 as the eluent. The product was recrystallized from ether. There were obtained 1.27 g (85%) of (S)-8-chloro-1-(5-dipropylaminomethyl-1,3,4-oxadiazol-2-yl)-11,12,13,13a-tetrahydro-9H-imidazo[1,5-a]pyrrolo[2,1-c][1,4]benzodiazepin-9-one as white crystals; m.p. 158°–160° and $[a]_D^{20}=48.8°$ ($CH_2Cl_2$, c=1%).

c) 1.27 g (2.79 mmol) of (S)-8-chloro-1-(5-dipropylaminomethyl-1,3,4-oxadiazol-2-yl)-11,1 2,13,13a-tetrahydro-9H-imidazo[1,5-a]pyrrolo[2,1-c][1,4]benzodiazepin-9-one in 30 ml of ethanol were treated with 0.83 ml (3.07 mmol) of 3.7N ethanolic hydrochloric acid. After stirring at 0° for 15 minutes the solution was treated dropwise with 150 ml of ether and the white suspension obtained was filtered off under suction. There were obtained 1.27 g (93%) of (S)-8-chloro-1-(5-dipropylaminomethyl-1,3,4-oxadiazol-2-yl)-11,1 2,13,13a-tetrahydro-9H-imidazo[1,5-a]pyrrolo[2,1-c][1,4]benzodiazepin-9-one hydrochloride (1:1) as white crystals; m.p. 204°–206° and $[\alpha]_D^{20}=-43.6°$ ($H_2O$, c=1%).

EXAMPLE 125 a) 9.15 ml of hydrazine hydrate were added to a suspension of 5.47 g (0.00162 mol) of ethyl 7-chloro-8-fluoro-5-methyl-6-oxo-5,6-dihydro-4H-imidazo[1,5-a][1,4]benzodiazepine-3-carboxylate in 55 ml of ethanol and the mixture was heated at reflux for 18 hours. After cooling to 0° the crystals obtained were filtered off and there were obtained 3.28 g (63%) of 7-chloro-8-fluoro-5-methyl-6-oxo-5,6-dihydro-4H-imidazo[1,5-a][1,4]benzodiazepine-3-carboxylic acid hydrazide as white crystals; m.p. 308°–310°.

b) A suspension of 0.50 g (0.00154 mol) of 7-chloro-8-fluoro-5-methyl-6-oxo-5,6-dihydro-4H-imidazo[1,5-a ][1,4]benzodiazepine-3-carboxylic acid hydrazide in 5 ml of N,N-dimethylformamide was treated with 0.33 g (0.00193 mol) of chloroacetic anhydride. The solution obtained was stirred at room temperature for 1½ hr., whereby a suspension resulted. The suspension was cooled to 0°, treated with 40 ml of ether and suction filtered. The white crystals obtained (0.643 g, m.p. 264°–266° (dec.)) were treated with 4.5 ml of methanesulphonic acid and 0.5 g of phosphorus pentoxide, whereupon the mixture warmed up and the solution was stirred at room temperature for 1 hr. The yellow solution was poured into 75 ml of ice-water, whereupon the mixture was made basic with aqueous sodium hydroxide solution and extracted with methylene chloride. The crystalline product was chromatographed over silica gel with ethyl acetate as the eluent. There was obtained 0.193 g (33%) of 7-chloro-3-(5-chloromethyl-1,3,4-oxadiazol-2-yl)-8-fluoro-5-methyl-5,6-dihydro-4H-imidazo[1,5-a][1,4]benzodiazepin-6-one as white crystals; m.p. :234°–236°.

c) A suspension of 0.193 g (0.51 mmol) of 7-chloro-3-(5-chloromethyl-1,3,4-oxadiazol-2-yl)-8-fluoro-5-methyl-5,6-dihydro-4H-imidazo[1,5-a][1,4]benzodiazepin-6-one in 2 ml of N,N-dimethylformamide was treated with 0.26 g (2.55 mmol) of dipropylamine. After stirring at room temperature for 17 hrs. the solution obtained was completely freed from the solvents. The residue was chromatographed over silica gel with methylene chloride/methanol 39:1 as the eluent. The product was recrystallized from ether/n-hexane at 0°. There were obtained 0.094 g (41%) of 7-chloro-3-(5-dipropylaminomethyl-1,3,4-oxadiazol-2-yl)-8-fluoro-5-methyl-5,6-dihydro-4H-imidazo[1,5-a][1,4]benzodiazepin-6-one as white crystals; m.p. 128°–130°.

d) 0.094 g (0.21 mmol) of 7-chloro-3-(5-dipropylaminomethyl-1,3,4-oxadiazol-2-yl)-8-fluoro-5-methyl-5,6-dihydro-4H-imidazo[1,5-a][1,4]benzodiazepin-6-one in 10 ml of ethanol was treated with 0.06 ml (0.23 mmol) of 3.7N ethanolic hydrochloric acid. After stirring at 0° for 30 minutes the solution was completely freed from the solvents, whereupon the residue was suspended in 20 ml of ether and filtered off under suction. There were obtained 0.84 g (83%) of 7-chloro-3-(5-dipropylaminomethyl-1,3,4-oxadiazol-2-yl)-8-fluoro-5-methyl-5,6-dihydro-4H-imidazo[1,5-a][1,4]benzodiazepin-6-one hydrochloride (1:1) as white crystals; m.p. 152°–154°.

EXAMPLE 126 a) 4.4 g (13.8 mmol) of (S)-8-chloro-9-oxo-12,12a-dihydro-9H,11H-azeto[2,1-c]-imidazo[1,5-a][1,4]benzodiazepine-1-carboxylic acid hydrazide were stirred at room temperature overnight in 30 ml of N,N-dimethylformamide with 2.65 g (15.5 mmol) of chloroacetic anhydride. After evaporating the solvent the residue was stirred at room temperature for 48 hours with 20 ml of a 10% solution of phosphorus pentoxide in methanesulphonic acid. The reaction mixture was treated with ice, made alkaline with conc. sodium hydroxide solution and extracted four times with methylene chloride. By drying the organic phase over magnesium sulfate and evaporating the solvent there were obtained 3.39 g (60%) of (S)-8-chloro-1-(5-chloromethyl-1,3,4-oxadiazol-2-yl)-12,12a-dihydro-9H,11H-azeto[2,1-c]imidazo[1,5-a][1,4]benzodiazepin-9-one of m.p. 185°–189°.

b) 1.88 g (5 mmol) of (S)-8-chloro-1-(5-chloromethyl-1,3,4-oxadiazol-2-yl)-12,12a-dihydro-9H,11H-azeto[2,1-c]imidazo[1,5-a][1,4]benzodiazepin-9-one were stirred at room temperature over the weekend with 1.12 g (11 mmol) of dipropylamine and 10 ml of N,N-dimethylformamide. After evaporating the reaction mixture the residue was dissolved in methylene chloride and the solution was washed twice with water and dried over magnesium sulfate. After evaporating the solvent and crystallizing the residue from ethyl acetate and hexane there were obtained 2.15 g (98%) of (S)-8-chloro-1-(5-dipropylaminomethyl-1,3,4-oxadiazol-2-yl)-12,12a-dihydro-9H,11H-azeto[2,1-c]imidazo[1,5-a][1,4]benzodiazepin-9-one of m.p. 134°–136°, which was converted into the hydrochloride of melting point 235°–237°.

EXAMPLE 127 a) 9.4 g (34.7 mmol) of 5-methyl-6-oxo-5,6-dihydro-4H-imidazo[1,5-a][1,4]benzodiazepine-3-carboxylic acid hydrazide were stirred at room temperature for 3 hours in 75 ml of N,N-dimethyl- formamide with 27.1 g (41.5 mmol) of chloroacetic anhydride. After evaporating the solvent the residue was stirred at room temperature overnight with 75 ml of a 10% solution of phosphorus pentoxide in methanesulphonic acid. The reaction mixture was treated with ice, made alkaline with conc. sodium hydroxide solution and extracted four times with methylene chloride. By drying the organic phase over magnesium sulfate, evaporation of the solvent and chromatography of the residue on silica gel while eluting with ethyl acetate there were obtained 6.9 g (61%) of 3-(5-chloromethyl-1,3,4-oxadiazol-2-yl)-5-methyl-5,6-dihydro-4H-imidazo[1,5-a][1,4]benzodiazepin-6-one of m.p. 221°–222°.

b) 0.33 g (1 mmol) of 3-(5-chloromethyl-1,3,4-oxadiazol-2-yl)-5-methyl-5,6-dihydro-4H-imidazo[1,5-a][1,4]benzodiazepin-6-one was stirred at room temperature overnight with 2 ml (2 mmol) of diethylamine and 5 ml of N,N-dimethylformamide. After evaporation of the reaction mixture and chromatography of the residue on silica gel while eluting with ethyl acetate/ethanol 9/1 there was obtained 0.31 g (84%) of 3-(5-diethylaminomethyl- 1,3,4-oxadiazol-2-yl)-5-methyl-5,6-dihydro-4H-imidazo[1,5-a][1,4]benzodiazepin-6-one, which was converted into the hydrochloride of m.p. 235°–238°.

EXAMPLE 126 a) 50 g (156.4 mmol) of ethyl 7-chloro-5-methyl-6-oxo-5,6-dihydro-4H-imidazo[1,5-a][1,4]benzodiazepine-3-carboxylate were stirred at boiling temperature for 6 hours with 90 ml (1.85 mol) of hydrazine hydrate in 500 ml of ethanol. By cooling to −10°, filtering the suspension under suction and drying the crystallizate there were obtained 51.9 g (100%) of 7-chloro-5-methyl-6-oxo-5,6-dihydro-4H-imidazo[1,5-a][1,4]benzodiazepine-3-carboxylic acid hydrazide of m.p. 287°.

b) 15.3 g (50 mmol) of 7-chloro-5-methyl-6-oxo-5,6-dihydro-4H-imidazo[1,5-a][1,4]benzodiazepin-3-carboxylic acid hydrazide were stirred at room temperature overnight in 160 ml of N,N-dimethylformamide with 9.41 g (55 mmol) of chloroacetic anhydride. After evaporating the solvent the residue was stirred at room temperature over the weekend with 100 ml of a 10% solution of phosphorus pentoxide in methanesulphonic acid. The reaction mixture was treated with ice, made alkaline with conc. sodium hydroxide solution and extracted four times with methylene chloride. By drying the organic phase over magnesium sulfate, evaporation of the solvent and chromatography of the residue on silica gel while eluting with ethyl acetate there were obtained 9.7 g (53%) of 7-chloro-3-(5-chloromethyl-1,3,4-oxadiazol-2-yl)-5-methyl-5,6-dihydro-4H-imidazo[1,5-a][1,4]benzodiazepin-6-one of m.p. 201°–203°.

c) 1.09 g (3 mmol) of 7-chloro-3-(5-chloromethyl-1,3,4-oxadiazol-2-yl)-5-methyl-5,6-dihydro-4H-imidazo[1,5-a][1,4]benzodiazepin-6-one were stirred at room temperature overnight with 1.5 g (11.6 mmol) of dibutylamine and 15 ml of N,N-dimethylformamide. After evaporation of the reaction mixture and chromatography of the residue on silica gel while eluting with ethyl acetate there were obtained 1.09 g (79%) of 7-chloro-3-(5-dibutylaminomethyl-1,3,4-oxadiazol-2-yl)-5-methyl- 5,6-dihydro-4H-imidazo[1,5-a][1,4]benzodiazepin-6-one, which was converted into the hydrochloride of m.p. 105°–108°.

EXAMPLE 129

1.09 g (3 mmol) of 7-chloro-3-(5-chloromethyl-1,3,4-oxadiazol-2-yl)-5-methyl-5,6-dihydro-4H-imidazo[1,5-a]

[1,4]benzodiazepin-6-one were stirred at room temperature overnight with 1 g (10 mmol) of dipropylamine and 15 ml of N,N-dimethylformamide. After evaporation of the reaction mixture and chromatography of the residue on silica gel while eluting with ethyl acetate there were obtained 1.17 g (91%) of 7-chloro-3-(5-dipropylaminomethyl-1,3,4-oxadiazol-2-yl)-5-methyl-5,6-dihydro-4H-imidazo[1,5-a][1,4]benzodiazepin-6-one, which was converted into the hydrochloride of m.p. 188°–195°.

EXAMPLE 130

1.09 g (3 mmol) of 7-chloro-3-(5-chloromethyl-1,3,4-oxadiazol-2-yl)-5-methyl-5,6-dihydro-4H-imidazo[1,5-a][1,4]benzodiazepin-6-one were stirred at room temperature overnight with 1 g (13.7 mmol) of diethylamine and 15 ml of N,N-dimethylformamide. After evaporation of the reaction mixture and chromatography of the residue on silica gel while eluting with ethyl acetate/ethanol 9/1 there were obtained 1.1 8 g (98%) of 7-chloro-3-(5-diethylaminomethyl-1,3,4-oxadiazol-2-yl)-5-methyl-5,6-dihydro-4H-imidazo[1,5-a][1,4]benzodiazepin-6-one, which was converted into the hydrochloride of m.p. 188°–195°.

EXAMPLE 131

10 g (30.3 mmol) of 3-(5-chloromethyl-1,3,4-oxadiazol-2-yl)-5-methyl-5,6-dihydro-4H-imidazo[1,5-a][1,4]benzodiazepin-6-one were stirred at room temperature for 7 hours with 10.1 g (1 00 mmol) of dipropylamine and 70 ml of N,N-dimethylformamide. After evaporation of the reaction mixture and chromatography of the residue on silica gel while eluting with methylene chloride/methanol 19/1 there were obtained, after recrystallization from ethyl acetate, 7.42 g (62%) of 3-(5-dipropylaminomethyl- 1,3,4-oxadiazol-2-yl)-5-methyl-5,6-dihydro-4H-imidazo[1,5-a][1,4]benzodiazepin-6-one of m.p. 126°–127°% which was converted into the hydrochloride of m.p. 208°–210°.

EXAMPLE 132

0.66 g (2 mmol) of 3-(5-chloromethyl-1,3,4-oxadiazol-2-yl)-5-methyl-5,6-dihydro-4H-imidazo[1,5-a][1,4]benzodiazepin-6-one were stirred at 75° overnight with 1.2 g (9.3 mmol) of dibutylamine and 10 ml of N,N-dimethylformamide. After evaporation of the reaction mixture and chromatography of the residue on silica gel while eluting with ethyl acetate there was obtained 0.72 g (85%) of 3-(5-dibutylaminomethyl-1,3,4-oxadiazol-2-yl)-5-methyl-5,6-dihydro-4H-imidazo[1,5-a][1,4]benzodiazepin-6-one, which was converted into the hydrochloride of m.p. 211°–213°.

EXAMPLE 133

1.64 g (5 mmol) of 3-(5-chloromethyl-1,3,4-oxadiazol-2-yl)-5-methyl-5,6-dihydro-4H-imidazo[1,5-a][1,4]benzodiazepin-6-one were stirred at room temperature overnight with 1.62 g (12.5 mmol) of diisobutylamine and 20 ml of N,N-dimethylformamide. After evaporation of the reaction mixture and chromatography of the residue on silica gel while eluting with ethyl acetate there were obtained 1.63 g (77%) of 3-(5-diisobutylaminomethyl-1,3,4-oxadiazol-2-yl)-5-methyl-5,6-dihydro-4H-imidazo[1,5-a][1,4]benzodiazepin-6-one of m.p. 138°–140°, which was converted into the hydrochloride of m.p. 177°–180°.

EXAMPLE 134

1.09 g (3 mmol) of 7-chloro-3-(5-chloromethyl-1,3,4-oxadiazol-2-yl)-5-methyl-5,6-dihydro-4H-imidazo[1,5-a][1,4]benzodiazepin-6-one were stirred at room temperature overnight with 0.97 g (7.5 mmol) of diisobutylamine and 15 ml of N,N-dimethylformamide. After evaporation of the reaction mixture and chromatography of the residue on silica gel while eluting with ethyl acetate there were obtained 1.19 g (86%) of 7-chloro-3-( 5-diisobutylaminomethyl-1,3,4-oxadiazol-2-yl)-5-methyl-5,6-dihydro-4H-imidazo[1,5-a][1,4]benzodiazepin-6-one of m.p. 181°–182°, which was converted into the hydrochloride of m.p. 161°–163°.

EXAMPLE 135

1.64 g (5 mmol) of 3-(5-chloromethyl-1,3,4-oxadiazol-2-yl)-5-methyl-5,6-dihydro-4H-imidazo[1,5-a][1,4]benzodiazepin-6-one were stirred at room temperature overnight with 1.07 g (12.5 mmol) of piperidine and 40 ml of N,N-dimethylformamide. After evaporation of the reaction mixture and chromatography of the residue on silica gel while eluting with methylene chloride/methanol 19/1 there were obtained, after recrystallization from ethyl acetate, 1.3 g (68%) of 5-methyl-3-[5-(piperidin-1-yl)methyl-1,3,4-oxadiazol-2-yl]-5,6-dihydro-4H-imidazo[1,5-a][1,4]benzodiazepin-6-one of m.p. 160°–162°% which was converted into the hydrochloride of m.p. 255°–257°.

EXAMPLE 136

1.64 g (5 mmol) of 3-(5-chloromethyl-1,3,4-oxadiazol-2-yl)-5,6-dihydro-5-methyl-4H-imidazo[1,5-a][1,4]benzodiazepin-6-one were stirred at 70° overnight with 3 ml (21 mmol) of diisopropylamine and 30 ml of N,N-dimethylformamide. After evaporation of the reaction mixture and chromatography of the residue on silica gel while eluting with methylene chloride/methanol 19/1 there were obtained, after recrystallization from ethyl acetate, 1.32 g (67%) of 3-(5-diisopropylaminomethyl-1,3,4-oxadiazol-2-yl)-5-methyl-5,6-dihydro-4H-imidazo[1,5-a][1,4]benzodiazepin-6-one of m.p. 199°–200°% which was converted into the hydrochloride of m.p. 232°–234°.

EXAMPLE 137

1.64 g (5 mmol) of 3-(5-chloromethyl-1,3,4-oxadiazol-2-yl)-5-methyl-5,6-dihydro-4H-imidazo[1,5-a][1,4]benzodiazepin-6-one were stirred at 75° overnight overnight with 2.26 g (17.5 mmol) of di-sec.-butylamine and 25 ml of N,N-dimethylformamide. After evaporation of the reaction mixture and chromatography of the residue on silica gel while eluting with methylene chloride/methanol 19/1 there were obtained, after recrystallization from ethyl acetate, 1.35 g (64%) of 3-(5-di-sec.-butylaminomethyl-1,3,4-oxadiazol-2-yl)-5-methyl-5,6-dihydro-4H-imidazo[1,5-a][1,4]benzodiazepin-6-one of m.p. 80°–83°, which was converted into the hydrochloride (amorphous).

EXAMPLE 138

0.87 ml (5 mmol) of N-ethyldiisopropylamine and 0.17 ml (2.1 mmol) of allyl bromide were added to a solution of 340 mg (1 mmol) of (S)-1-(5-aminomethyl-1,2,4-oxadiazol-3-yl)-10,11,12,12a-tetrahydro-8H-imidazo[5,1-c]pyrrolo[1,2a]thieno[3,2-e][1,4]diazepin-8-one in 15 ml of methylenechloride and the mixture was stirred at room temperature for 12 hours. The reaction solution was subsequently diluted with methylene chloride and washed three times with water. The organic phases were dried over magnesium sulfate, filtered and evaporated. The residue obtained was chromatographed (silica gel, methylene chloride/methanol/aqueous ammonia 250:10:1). There were obtained 280 mg (66%) of (S)-1-(5-diallylaminomethyl-1,2,4-oxadiazol-3-yl)-10,11,12,12a-tetrahydro-8H-imidazo[5,1-c]pyrrolo[1,2-a]thieno[3,2-e][1,4]diazepin-8-one, Rf=0.41 (silica gel, ethyl acetate).

EXAMPLE 139

2.4 ml (13.8 mmol) of N-ethyldiisopropylamine and 0.67 ml (8 mmol) of allyl bromide were added to a solution of 756 mg (2 mmol) of (S)-1-(3-aminomethyl-1,2,4-oxadiazol-5-yl)-11,11a-dihydro-8H,10H-azeto[1,2-a]imidazo[5,1-c]thieno[3,2-e][1,4]diazepin-8-one in 20 ml of methylenechloride and the mixture was stirred at room temperature for 20 hours. The reaction solution was subsequently diluted with methylene chloride and washed three times with water. The organic phases were dried with magnesium sulfate, filtered and evaporated. The residue obtained was chromatographed (silica gel, methylene chloride/methanol/aqueous ammonia 140:10:1). There were obtained 645 mg (79%) of (S)-1-(5-diallylaminomethyl-1,2,4-oxadiazol-5-yl)-11,11a-dihydro-8H,10H-azeto[1,2-a]imidazo[5,1-c]thieno[3,2-e][1,4]diazepin-8-one as a colourless foam, Rf=0.52 (silica gel, methylene chloride/methanol/aqueous ammonia 140:10:1).

EXAMPLE 140

1.5 ml (8.6 mmol) of N-ethyldiisopropylamine and 0.28 ml (2.4 mmol) of dimethylallyl bromide were added to a solution of 453 mg (1.2 mmol) of (S)-1-(3-aminomethyl-1,2,4-oxadiazol-5-yl)-11,11a-dihydro-8H, 10H-azeto[1,2-a]imidazo[5,1-c]thieno[3,2-e][1,4]diazepin-8-one in 20 ml of methylene chloride and the mixture was stirred at room temperature for 20 hours. The reaction solution was subsequently diluted with methylene chloride and washed three times with water. The organic phases were dried with magnesium sulfate, filtered and evaporated. The is residue obtained was chromatographed (silica gel, methylene chloride/methanol/aqueous ammonia 140:10:1). There were obtained 240 mg (43%) of (S)-1-[3-bis-[3-methyl-but-2-enyl)-aminomethyl]-1,2,4-oxadiazol-5-yl]-11,11a-dihydro-8H,10H-azeto[1,2-a]imidazo[5,1-c]thieno[3,2-e][1,4]diazepin-8-one as a colourless foam, Rf=0.55 (silica gel, methylene chloride/methanol/aqueous ammonia 140:10:1).

EXAMPLE 141

4 ml (8.6 mmol) of N-ethyldiisopropylamine and 1.1 ml (12 mmol) of 1-bromopropane were added to a solution of 600 mg (1.9 mmol) of (S)-1-(3-aminomethyl-1,2,4-oxadiazol-5-yl)-11,11a-dihydro-8H, 10H-azeto[1,2-a]imidazo[5,1-c]thieno[3,2-e][1,4]diazepin-8-one in 20 ml of dimethylformamide and the mixture was stirred at 70° for 12 hours. The reaction solution was subsequently evaporated and the residue was partitioned between methylene chloride and 2N sodium carbonate solution. The aqueous phase was washed three times with methylene chloride. The organic phases were dried with magnesium sulfate, filtered and evaporated. The residue obtained was chromatographed (silica gel, methylene chloride/methanol/aqueous ammonia 140:10:1). There were obtained 410 mg (54%) of (S)-1-(dipropylaminomethyl-1,2,4-oxadiazol-5-yl)-11,11a-dihydro-8H, 10H-azeto[1,2-a]imidazo[5,1-c]thieno[3,2-e][1,4]diazepin-8-one as a colourless foam, Rf=0.55 (silica gel, methylene chloride/methanol/aqueous ammonia 140:10:1).

EXAMPLE 142

1.74 ml (10 mmol) of N-ethyldiisopropylamine and 0.55 ml (6 mmol) of 1-bromopropane were added to a solution of 340 mg (1 mmol) of (S)-1-(5-aminomethyl-1,2,4-oxadiazol-3-yl)-10,11,12,12a-tetrahydro-8H-imidazo[5,1-c]pyrrolo[1,2-a]thieno[3,2-e][1,4]diazepin-8-one in 10 ml of dimethylformamide and the mixture was stirred at 70° for 12 hours. The reaction solution was subsequently evaporated and the residue was partitioned between methylene chloride and 2N sodium carbonate solution. The aqueous phase was washed three times with methylene chloride. The organic phases were dried with magnesium sulfate, filtered and evaporated. The residue obtained was chromatographed (silica gel, methylene chloride/methanol/aqueous ammonia 240:10:1). There were obtained 162 mg (38%) of (S)-1-(5-dipropylaminomethyl-1,2,4-oxadiazol-3-yl)-10,11,12,12a-tetrahydro-8H-imidazo[5,1-c]pyrrolo[1,2-a]thieno[3,2-e][1,4]diazepin-8-one, Rf=0.26 (silica gel, ethyl acetate/methanol 40:1).

EXAMPLE 143

7 ml (23 mmol) of N-ethyldiisopropylamine and 0.9 ml (9.9 mmol) of 1-bromopropane were added to a solution of 1.5 g (4.74 mmol) of 3-(5-aminomethyl-1,2,4-oxadiazol-3-yl)-5-methyl-5,6-dihydro-4H-imidazo[1,5-a]thieno[2,3-f][1,4]diazepin-6-one in 40 ml of dimethylformamide and the mixture was stirred at 70° for 1 hour. The reaction solution was subsequently evaporated, whereupon the residue was partitioned between methylene chloride and 2N sodium carbonate solution. The aqueous phase was washed three times with methylene chloride. The organic phases were dried with magnesium sulfate, filtered and evaporated. The residue obtained was chromatographed (silica gel, methylene chloride/methanol/aqueous ammonia 250:10:1). There were obtained 930 mg (49%) of 3-(5-dipropylaminomethyl-1,2,4-oxadiazol-3-yl)-5-methyl-5,6-dihydro-4H-imidazo[1,5-a]thieno[2,3-f][1,4]diazepin-6-one of m.p. 128.5°–130.0°.

EXAMPLE 144

4 ml (23.4 mmol) of N-ethyldiisopropylamine and 1.1 ml (12 mmol) of 1-bromopropane were added to a solution of 0.6 g (1.9 mmol) of 3-(3-aminomethyl-1,2,4-oxadiazol-5-yl)-5-methyl-5,6-dihydro-4H-imidazo[1,5-a]thieno[2,3-f][1,4]diazepin-6-one in 20 ml of dimethylformamide and the mixture was stirred at 70° for 1 hour. The reaction solution was subsequently evaporated, whereupon the residue was partitioned between methylene chloride and 2N sodium carbonate solution. The aqueous phase was washed three times with methylene chloride. The organic phases were dried with magnesium sulfate, filtered and evaporated. The residue obtained was chromatographed (silica gel, ethyl acetate/methanol 25:1). There were obtained 440 mg (57%) of 3-(3-dipropylaminomethyl-1,2,4-oxadiazol-5-yl)-5-methyl-5,6-dihydro-4H-imidazo[1,5-a]thieno[2,3-f][1,4]diazepin-6-one as a colourless foam, Rf=0.34 (silica gel, ethyl acetate/methanol 25:1).

EXAMPLE 145

7.5 ml (43.6 mmol) of N-ethyldiisopropylamine and 2.3 ml (25.3 mmol) of 1-bromopropane were added to a solution 2.0 g (6.3 mmol) of 7-(5-aminomethyl-1,2,4-oxadiazol-3-yl)-5-methyl-5,6-dihydro-4H-imidazo[1,5-a]thieno[2,3-f][1,4]diazepin-4-one in 50 ml of dimethylformamide and the mixture was stirred at 70° for 1 hour. The reaction solution was subsequently evaporated, whereupon the residue was partitioned between methylene chloride and 2N sodium carbonate solution. The aqueous phase was washed three times with methylene chloride. The organic phases were dried with magnesium sulfate, filtered and evaporated. The residue obtained was chromatographed (silica gel, methylene chloride/methanol/aqueous ammonia 110:10:1). There were obtained 250 mg (10%) of 7-(5-dipropylaminomethyl-1,2,4-oxadiazol-3-yl)-5-methyl-5,6-dihydro-4H-imidazo[1,5-a]thieno[3,2-f][1,4]diazepin-4-one as a colourless foam, Rf=0.46 (silica gel, methylene chloride/methanol/aqueous ammonia 110:10:1).

EXAMPLE 146

3.75 ml (21.8 mmol) of N-ethyldiisopropylamine and 1.15 ml (12.7 mmol) of 1-bromopropane were added to a solution of 2.0 g (6.3 mmol) of 7-(5-aminomethyl-4-oxadiazol-3-yl)-5-methyl-5,6-dihydro-4H-imidazo[1,5-a]thieno[3,2-f][1,4]diazepin-4-one in 50 ml of dimethylformamide and the mixture was stirred at 70° for 1 hour. The reaction solution was subsequently evaporated, whereupon the residue was partitioned between methylene chloride and 2N sodium carbonate solution. The aqueous phase was washed three times with methylene chloride. The organic phases were dried with magnesium sulfate, filtered and evaporated. The residue obtained was chromatographed (silica gel, methylene chloride/methanol/aqueous ammonia 110:10:1). There were obtained 460 mg (20%) of 7-(5-propylaminomethyl-1,2,4-oxadiazol-3-yl)-5-methyl-5,6-dihydro-4H-imidazo[1,5-a]thieno[3,2-f][1,4]diazepin-4-one as a colourless foam, Rf=0.31 (silica gel, methylene chloride/methanol/aqueous ammonia 110:10:1).

EXAMPLE 147

3.7 ml (21.8 mmol) of N-ethyldiisopropylamine and 1.4 ml (12.6 mmol) of 1-bromobutane were added to a solution of 1.0 g (3.16 mmol) of 7-(5-aminomethyl-1,2,4-oxadiazol-3-yl)-5-methyl-5,6-dihydro-4H-imidazo[1,5-a]thieno[3,2-f][1,4]diazepin-4-one in 30 ml of dimethylformamide and the mixture was stirred at 70° for 1 hour. The reaction solution was subsequently evaporated, whereupon the residue was partitioned between methylene chloride and 2N sodium carbonate solution. The aqueous phase was washed three times with methylene chloride. The organic phases were dried with magnesium sulfate, filtered and evaporated. The residue obtained was chromatographed (silica gel, methylene chloride/methanol/aqueous ammonia 110:10:1). There were obtained 290 mg (22%) of 7-(5-dibutylaminomethyl-1,2,4-oxadiazol-3-yl)-5-methyl-5,6-dihydro-4H-imidazo[1,5-a]thieno[3,2-f][1,4]diazepin-4-one as a colourless foam, Rf=0.37 (silica gel, methylene chloride/methanol/aqueous ammonia 110:10:1).

EXAMPLE 148

1.85 ml (10.9 mmol) of N-ethyldiisopropylamine and 0.7 ml (6.3 mmol) of 1-bromobutane were added to a solution of 1.0 g (3.16 mmol) of 7-(5-aminomethyl-1,2,4-oxadiazol-3-yl)-5-methyl-5,6-dihydro-4H-imidazo[1,5-a]thieno[3,2-f][1,4]diazepin-4-one in 30 ml of dimethylformamide and the mixture was stirred at 70° for 1 hour. The reaction solution was subsequently evaporated, whereupon the residue was partitioned between methylene chloride and 2N sodium carbonate solution. The aqueous phase was washed three times with methylene chloride. The organic phases were dried with magnesium sulfate, filtered and evaporated. The residue obtained was chromatographed (silica gel, methylene chloride/methanol/aqueous ammonia 110:10:1). There were obtained 290 mg (25%) of 7-(5-butylaminomethyl-1,2,4-oxadiazol-3-yl)-5-methyl-5,6-dihydro-4H-imidazo[1,5-a]thieno[3,2-f][1,4]diazepin-4-one as a colourless foam, Rf=0.37 (silica gel, methylene chloride/methanol/aqueous ammonia 110:10:1).

EXAMPLE 149

3.75 ml (21.8 mmol) of N-ethyldiisopropylamine and 0.94 ml (12.6 mmol) of 1-bromoethane were added to a solution of 1.0 g (3.16 mmol) of 7-(5-aminomethyl-1,2,4-oxadiazol-3-yl)-5-methyl-5,6-dihydro-4H-imidazo[1,5-a]thieno[3,2-f][1,4]diazepin-4-one in 30 ml of dimethylformamide and the mixture was stirred at 70° for 1 hour. The reaction solution was subsequently evaporated, whereupon the residue was partitioned between methylene chloride and 2N sodium carbonate solution. The aqueous phase was washed three times with methylene chloride. The organic phases were dried with magnesium sulfate, filtered and evaporated. The residue obtained was chromatographed (silica gel, methylene chloride/methanol/aqueous ammonia 110:10:1). There were obtained 250 mg (21%) of 7-(5-diethylaminomethyl-1,2,4-oxadiazol-3-yl)-5-methyl-5,6-dihydro-4H-imidazo[1,5-a]thieno[3,2-f][1,4]diazepin-4-one as a colourless foam, Rf=0.56 (silica gel, methylene chloride/methanol/aqueous ammonia 110:10:1).

EXAMPLE 150

2.35 ml (13.6 mmol) of N-ethyldiisopropylamine and 1.1 ml (10.2 mmol) of butyl bromide were added to a solution of 0.54 g (1.7 mmol) of 3-(5-aminomethyl-1,2,4-oxadiazol-3-yl)-5-methyl-5,6-dihydro-4H-imidazo[1,5-a]thieno[2,3-f][1,4]diazepin-6-one in 20 ml of dimethylformamide and the mixture was stirred at 70° for 1 hour. The reaction solution was subsequently evaporated, whereupon the residue was partitioned between methylene chloride and 2N sodium carbonate solution. The aqueous phase was washed three times with methylene chloride. The organic phases were dried with magnesium sulfate, filtered and evaporated. The residue obtained was chromatographed (silica gel, methylene chloride/methanol/aqueous ammonia 110:10:1). There were obtained 265 mg (36%) of 3-(5-dibutylaminomethyl-1,2,4-oxadiazol-3-yl)-5-methyl-5,6-dihydro-4H-imidazo[1,5-a]thieno[2,3-f][1,4]diazepin-6-one as a colourless foam, Rf=0.73 (silica gel, methylene chloride/methanol/aqueous ammonia 110:10:1).

EXAMPLE 151

2.35 ml (13.6 mmol) of N-ethyldiisopropylamine and 0.76 ml (10.2 mmol) of ethyl bromide were added to a solution of 0.54 g (1.7 mmol) of 3-(5-aminomethyl-1,2,4-oxadiazol-3-yl)-5-methyl-5,6-dihydro-4H-imidazo[1,5-a]thieno[2,3-f][1,4]diazepin-6-one in 20 ml dimethylformamide and the mixture was stirred at 70° for 1 hour. The reaction solution was subsequently evaporated, whereupon the residue was partitioned between methylene chloride and 2N sodium carbonate solution. The aqueous phase was washed three times with methylene chloride. The organic phases were dried over magnesium sulfate, filtered and evaporated. The residue obtained was chromatographed (silica gel, methylene chloride/methanol/aqueous ammonia 110:10:1). There were obtained 301 mg (47%) of 3-(5-diethylaminomethyl-1,2,4-oxadiazol-3-yl)-5-methyl-5,6-dihydro-4H-imidazo[1,5-a]thieno[2,3-f][1,4]diazepin-6-one as a colourless foam, Rf=0.66 (silica gel, methylene chloride/methanol/aqueous ammonia 110:10:1).

EXAMPLE 152

0.87 ml of N-ethyldiisopropylamine and 0.28 ml (3 mmol) of 1-bromopropane were added to a solution of 0.500 g (1.52 mmol) of (S)-1-(5-aminomethyl-1,2,4-oxadiazol-3-yl)-11,11a-dihydro-8H,10H-azeto[1,2-a]imidazo[5,1-c]

thieno[3,2-e][1,4]diazepin-8-one in 15 ml of dimethylformamide, whereupon the mixture was stirred at 70° for 12 hours. The dimethylformamide was evaporated and the residue was partitioned between methylene chloride and 2N sodium carbonate solution. The aqueous phase was extracted twice with methylene chloride and the organic phases were dried with sodium sulfate, filtered and evaporated. Chromatography (silica gel, ethyl acetate/methanol 20:1) yielded 0.324 g (57%) of (S)-1-(5-propylaminomethyl-1,2,4-oxadiazol-3-yl)-11,11a-dihydro-8H, 10H-azeto[1,2-a]imidazo[5,1-c]thieno[3,2-e][1,4]diazepin-8-one as a colourless foam, Rf=0.24 (silica gel, ethyl acetate/methanol 20:1).

EXAMPLE 153

1.17 ml (6.8 mmol) of N-ethyldiisopropylamine and 0.55 ml (5.1 mmol) of butyl bromide were added to a solution of 0.54 g (1.7 mmol) of 3-(5-aminomethyl-1,2,4-oxadiazol-3-yl)-5-methyl-5,6-dihydro-4H-imidazo[1,5-a]thieno[2,3-f][1,4]diazepin-6-one in 20 ml of dimethylformamide and the mixture was stirred at 70° for 1 hour. The reaction solution was subsequently evaporated, whereupon the residue was partitioned between methylene chloride and 2N sodium carbonate solution. The aqueous phase was washed three times with methylene chloride. The organic phases were dried with magnesium sulfate, filtered and evaporated. The residue obtained was chromatographed (silica gel, methylene chloride/methanol/aqueous ammonia 110:10:1). There were obtained 310 mg (47%) of 3-(5-butylaminomethyl-1,2,4-oxadiazol-3-yl)-5-methyl-5,6-dihydro-4H-imidazo[1,5-a]thieno[2,3-f][1,4]diazepin-6-one as a colourless foam, Rf=0.73 (silica gel, methylene chloride/methanol/aqueous ammonia 110:10:1).

EXAMPLE 154 a) A freshly prepared solution of sodium methanolate in methanol (from 53.46 g (2.32 mol) of sodium in 1 l of methanol) was added dropwise within 10 min. to a suspension of 141.4 g (2.32 mol) of hydroxylamine hydrochloride in 1.2 l of methanol, whereupon the mixture was stirred at room temperature for 30 min. The separated NaCl was filtered off. The filtrate obtained was treated portionwise with 433 g (2.32 mol) of phthtalimido-acetonitrile (Ber. 55, 2961 (1921)) in such a manner that the temperature did not rise above 40°. The suspension was stirred overnight, filtered and the crystals obtained were dried at 60°/10 Torr. There were obtained 475 g of (E and/or Z)-N'-hydroxy-1,3-dioxo-2-isoindolineacetamidine as colourless crystals of m.p. 192°–195°.

b) 40 g (228 mmol) of chloroacetic anhydride were added portionwise to a suspension of 50 g (228 mmol) of (E and/or Z)-N'-hydroxy-1,3-dioxo-2-isoindolineacetamidine in 1 l of dimethylformamide, whereupon the mixture was stirred at room temperature for two hours. Subsequently, it was heated to 100° for 20 hours. The brown solution was evaporated and partitioned between methylene chloride and water. The aqueous phase was back-washed once with methylene chloride. The organic phases were dried with magnesium sulfate, filtered and evaporated. The residue was chromatographed (silica gel, methylene chloride/ethyl acetate 20:1) and subsequently crystallized from methylene chloride/diethyl ether. There were obtained 36 g (57%) of 2-(5-chloromethyl-1,2,4-oxadiazol-3-ylmethyl)-2,3-dihydro-1H-isoindole-1,3-dione of m.p. 96.5°–98°.

c) 35.6 ml (260 mmol) of dipropylamine were added dropwise at room temperature to a solution of 36 g (130 mmol) of 2-(5-chloromethyl-1,2,4-oxadiazol-3-ylmethyl)-2,3-dihydro-1H-isoindole-1,3-dione in 300 ml of methylene chloride, whereupon the mixture was stirred at room temperature for 24 hours. The yellow solution was washed with sat. sodium hydrogen carbonate solution, dried with sodium sulfate, filtered and evaporated. The residue obtained was chromatographed (silica gel, methylene chloride/aqueous ammonia 19:1). There were obtained 38 g (85%) of 2-(5-dipropylaminomethyl-1,2,4-oxadiazol-3-ylmethyl)-2,3-dihydro-1H-isoindol-1,3-dione as a beige oil, Rf=0.12 (silica gel, methylene chloride/aqueous ammonia 19:1).

d) 400 ml of methylamine (33% in ethanol) were added dropwise to a solution of 38 g (111 mmol) of 2-(5-dipropylaminomethyl-1,2,4-oxadiazol-3-ylmethyl)-2,3-dihydro-1H-isoindol-1,3-dione in 300 ml of ethanol. The mixture was stirred at 70° for 1.5 hours and subsequently evaporated. The residue was triturated in methylene chloride and filtered off. The filtrate was concentrated and chromatographed (silica gel, methylene chloride/methanol 19:1). There were obtained 15.6 g (66%) of (3-aminomethyl-1,2,4-oxadiazol-5-ylmethyl)-dipropyl-amine as a yellow oil, Rf=0.25 (silica gel, methylene chloride/methanol 9:1).

e) A solution of 15.6 g (73.5 mmol) of (3-aminomethyl-1,2,4-oxadiazol-5-ylmethyl)-dipropylamine in 100 ml of methyl formate was heated at reflux for seven hours. Subsequently, the solution was evaporated and the residue was chromatographed (silica gel, methylene chloride/methanol 19:1). There were obtained 14 g (79%) of N-(5-dipropylaminomethyl-1,2,4-oxadiazol-3-ylmethyl)-formamide, Rf=0.28 (silica gel, methylene chloride/methanol 19:1).

f) 0.92 ml (10 mmol) of phosphorus oxychloride in 5 ml of methylene chloride was added dropwise at 0° to a solution of 2.4 g (10 mmol) of N-(5-dipropylaminomethyl-1,2,4-oxadiazol-3-ylmethyl)formamide in 25 ml of methylene chloride and 4.3 ml (30 mmol) of diisopropylamine and the mixture was stirred at 0° for 45 minutes. The solution was poured into ice-water and extracted twice with methylene chloride. The organic phases were dried with magnesium sulfate, filtered and evaporated. The 5-(dipropylaminomethyl-1,2,4-oxadiazol-3-ylmethyl)isocyanide obtained was used without further purification in the reaction described hereinafter under h).

g) A solution of 7.23 g (42.75 mmol) of 6H-thieno[2,3-d]-[1,3]oxazine-4,6(7H)-dione (J. chem. Res. (M), 1986, 1459) and 1.99 g (24.75 mmol) of L-azetidine-2-carboxylic acid in 30 ml of dimethylformamide and 6 ml of acetic acid was stirred at 120° for 16 hours. The brown solution was evaporated and the brown residue obtained was crystallized from ethanol. There were obtained 3.74 g (42%) of (S)-7,7a-dihydroazeto[1,2-a]thieno[2,3-e][1,4]diazepine-4,8(6H,9H)-dione as colourless needles of m.p. 272°–274°.

h) A solution of 1.94 g (9.3 mmol) of (S)-7,7a-dihydroazeto[1,2-a]thieno[2,3-e][1,4]diazepine-4,8(6H,9H)-dione 20 ml of dimethylformamide was added dropwise at −30° to a suspension of 0.45 g (10.3 mmol) of NaH (55%, washed with hexane) in 10 ml of dimethylformamide, whereupon the mixture was stirred at −30° for 40 minutes. After cooling to −60° a solution of 2 ml (9.3 mmol) of diphenyl chlorophosphate in 5 ml of dimethylformamide was added dropwise in such a manner that the temperature did not rise above −45°. Subsequently, the mixture was stirred for a further 30 minutes.

In the meanwhile, 1.2 g (10.3 mmol) of potassium tert-.butylate were dissolved in 20 ml of dimethylformamide and treated at −60° with 2.2 g (10 mmol) of 5-(dipropylaminomethyl-1,2,4-oxadiazol-3-ylmethyl) isocyanide in 20 ml of dimethylformamide. The reaction mixture obtained above was added dropwise to the thus-obtained solution at −70° via a dropping funnel cooled to −40°. The dark brown viscous solution obtained was stirred at −60° for 1 hour and, after neutralization with 10 ml of acetic acid at −40°, poured into ice-water, whereupon the mixture was extracted three times with methylene chloride. The combined organic phases were dried with sodium sulfate, filtered and evaporated. Chromatography (silica gel, ethyl acetate/methanol 20:1) yielded 0.370 g (10 %) of (S)-1-(5-dipropylaminomethyl-1,2,4-oxadiazol-3-yl)-11,11a-dihydro-8H, 10H-azeto[1,2-a]imidazo[5,1-c]thieno[3,2-e][1,4]diazepin-8-one as a colourless foam, Rf=0.21 (silica gel, ethyl acetate/methanol 20:1).

EXAMPLE 155

A solution of 1.94 g (9.3 mmol) of 6-fluoro-3,4-dihydro-4-methyl-2H-1,4-benzodiazepine-2,5-(1H)-dione (EPA 27 214) in 20 ml of N,N-dimethylformamide was added dropwise at −30° to a suspension of 0.45 g (10.3 mmol) of NaH (55%, washed with hexane) in 10 ml of N,N-dimethylformamide, whereupon the mixture was stirred at −30° for 40 minutes. After cooling to −60° a solution of 2 ml (9.3 mmol) of diphenyl chlorophosphate in 5 ml of N,N-dimethylformamide was added dropwise in such a manner that the temperature did not rise above −45°. Subsequently, the mixture was stirred for a further 30 minutes.

In the meanwhile, 1.2 g (10.3 mmol) of potassium tert-.butylate were dissolved in 20 ml of N,N-dimethylformamide and treated at −60° with 2.2 g (10mmol) of 5-(dipropylaminomethyl-1,2,4-oxadiazol-3-ylmethyl) isocyanide in 20 ml of N,N-dimethylformamide. The reaction mixture obtained above was added dropwise to the thus-obtained solution at −70° via a dropping funnel cooled to −40°. The dark brown viscous solution obtained was stirred at −60° for 1 hour and, after neutralization with 10 ml of acetic acid at −40°, poured into ice-water, whereupon the mixture was extracted three times with methylene chloride. The combined organic phases were dried with sodium sulfate, filtered and evaporated. Chromatography (silica gel, ethyl acetate/methanol, 20:1) yielded 0.480 g (12%) of 7-fluoro-5-methyl-3-(5-dipropylaminomethyl-1,2,4-oxadiazol-3-yl)-5,6-dihydro-4H-imidazo[1,5-a][1,4]benzodiazepin-6-one as a colourless foam, Rf=0.26 (silica gel, methylene chloride/methanol/aqueous ammonia 140:10:1).

EXAMPLE 156 a) A solution of 10 g (55.2 mmol) of 5-fluoro-2H-3,1-benzoxazine-2,4(1H)-dione and 5.66 g (55.2 mmol) of L-azetidine-2-carboxylic acid in 75 ml of dimethylformamide and 15 ml of acetic acid was stirred at 120° for 16 hours. The brown solution was evaporated and the brown residue obtained was crystallized from ethanol. There were obtained 6 g (42%) of (S)-5-fluoro-1,2,4,9,10,10a-hexahydroazeto[2,1-c][1,4]benzodiazepine-4,10-dione as beige needles of m.p. 232°-233.5°.

b) A solution of 2.05 g (9.3 mmol) of (S)-5-fluoro-1,2,4,9,10,10a-hexahydroazeto[2,1-c][1,4]benzodiazepine-4,10-dione in 20 ml of dimethylformamide was added dropwise at −30° to a suspension of 0.45 g (10.3 mmol) of NaH (55%, washed with hexane) in 10 ml of dimethylformamide and the mixture was stirred at −30° for 40 minutes. After cooling to −60° a solution of 2 ml (9.3 mmol) of diphenyl chlorophosphate in 5 ml of dimethylformamide was added dropwise in such a manner that the temperature did not rise above −45°. Subsequently, the mixture was stirred for a further 30 minutes. In the meanwhile, 1.2 g (10.3 mmol) of potassium tert.butylate were dissolved in 20 ml of dimethylformamide and treated at −60° with 2.2 g (10 mmol) of 5-(dipropylaminomethyl-1,2,4-oxadiazol-3-ylmethyl) isocyanide in 20 ml of dimethylformamide. The reaction mixture obtained above was added dropwise to the thus-obtained solution at −70° via a dropping funnel cooled to −40°. The dark brown viscous solution obtained was stirred at 60° for 1 hour and, after neutralization with 10 ml of acetic acid at −40°, poured into ice-water, whereupon the mixture was extracted three times with methylene chloride. The combined organic phases were dried over sodium sulfate, filtered and evaporated. Chromatography (silica gel, ethyl acetate/methanol 20:1) yielded 0.360 g (9%) of (S)-8-fluoro-1-(5-dipropylaminomethyl-1,2,4-oxadiazol-3-yl)-12,12a-dihydro-9H,11H-azeto[2,1-c]imidazo[1,5-a][1,4]benzodiazepin-9-one as a colourless foam, Rf=0.28 (silica gel, methylene chloride/methanol/aqueous ammonia 140:10:1).

EXAMPLE 157

A solution of 2.2 g (9.3 mmol) of (S)-5,6-difluoro-1,2,4,9,10,10a-hexahydroazeto[2,1-c][1,4]benzodiazepine-4,10-dione in 20 ml of N,N-dimethylformamide was added dropwise at −30° to a suspension of 0.45 g (10.3 mmol) of NaH (55%, washed with hexane) in 10 ml of dimethylformamide and the mixture was stirred at −30° for 40 minutes. After cooling to −60° a solution of 2 ml (9.3 mmol) of diphenyl chlorophosphate in 5 ml of N,N-dimethylformamide was added dropwise in such a manner that the temperature did not rise above −45°. Subsequently, the mixture was stirred for a further 30 minutes.

In the meanwhile, 1.2 g (10.3 mmol) of potassium tert-.butylate were dissolved in 20 ml of N,N-dimethylformamide and treated at −60° with 2.2 g (10 mmol) of 5-dipropylaminomethyl-1,2,4-oxadiazol-3-ylmethyl isocyanide in 20 ml of N,N-dimethylformamide. The reaction mixture obtained above was added dropwise to the thus-obtained solution at −70° via a dropping funnel cooled to −40°. The dark brown viscous solution obtained was stirred at −60° for 1 hour and, after neutralization with 10 ml of acetic acid at −40°, poured into ice-water, whereupon the mixture was extracted three times with methylene chloride. The combined organic phases were dried over sodium sulfate, filtered and evaporated. Chromatography (silica gel, ethyl acetate/methanol 20:1) yielded 0.380 g (9%) of (S)-7,8-difluoro-1-(5-dipropylaminomethyl-1,2,4-oxadiazol-3-yl)-12,12a-dihydro-9H,11H-azeto[2,1-c]imidazo[1,5-a][1,4]benzodiazepin-9-one as a colourless foam, Rf=0.25 (silica gel, methylene chloride/methanol/aqueous ammonia 140:10:1).

EXAMPLE 158 a) 1.9 g (11.1 mmol) of chloroacetic anhydride were added to a solution of 2.8 g (9.68 mmol) of (E)-and/or (Z)-(S)-1-(aminohydroxyimino-methyl)-11,11a-dihydro-8H,10H-azeto[1,2-a]imidazo[5,1-c]thieno[3,2-e][1,4]diazepin-8-one in 25 ml N,N-dimethylformamide and the mixture was stirred at room temperature for 1.5 hours. Subsequently, it was heated to 105° for 2 hours. The solution was evaporated and the residue was partitioned between 2N sodium hydroxide solution and methylene chloride. The aqueous phase was back-washed with methylene chloride and the organic phases were dried with magnesium sulfate, filtered and evaporated. The residue obtained was crystallized from methylene chloride/ethanol. There were obtained 2.4 g (71%) of (S)-1-(5-chloromethyl-1,2,4-oxadiazol-3-yl)-11,11a-dihydro-8H,10H-azeto[1,2-a]imidazo[5,1-c]thieno[3,2-e][1,4]diazepin-8-one as a beige powder of m.p. 210°–213°.

b) 0.36 ml (3.45 mmol) of diethylamine was added to a suspension of 400 mg (1.1 5 mmol) of (S)-1-(5-chloromethyl-1,2,4-oxadiazol-3-yl)-11,11a-dihydro-8H,10H-azeto[1,2-a]imidazo[5,1-c]thieno-[3,2-e][1,4]diazepin-8-one in 10 ml N,N-dimethylformamide and the mixture was stirred at room temperature for 12 hours. The solution was evaporated and the residue was partitioned between methylene chloride and 2N sodium carbonate solution. The aqueous solution was extracted with methylene chloride and the organic phases were dried with magnesium sulfate, filtered and evaporated. The residue was chromatographed (silica gel, ethyl acetate/methanol 10:1). There were obtained 410 mg (92%) of (S)-1-(5-diethylaminomethyl-1,2,4-oxadiazol-3-yl)-11,11 a-dihydro-8H, 10H-azeto[1,2-a]imidazo[5,1-c]thieno[3,2-e][1,4]diazepin-8-one as a colourless foam. Rf=0.31 (silica gel, ethyl acetate/methanol 10:1).

EXAMPLE 159

0.6 ml (3.45 mmol) of dibutylamine was added to a suspension of 400 mg (1.15 mmol) of (S)-1-(5-chloromethyl-1,2,4-oxadiazol-3-yl)-11,11a-dihydro-8H,10H-azeto[1,2-a]imidazo[5,1-c]thieno[3,2-e]-[1,4]diazepin-8-one in 10 ml of N,N-dimethylformamide and the mixture was stirred at room temperature for 12 hours. The solution was evaporated and the residue was partitioned between methylene chloride and 2N sodium carbonate solution. The aqueous solution was extracted with methylene chloride and the organic phases were dried with magnesium sulfate, filtered and evaporated. The residue was chromatographed (silica gel, methyl acetate/methanol 10:1). There were obtained 425 mg (84%) of (S)-1-(5-dibutylaminomethyl-1,2,4-oxadiazol-3-yl)-11,11a-dihydro-8H,10H-azeto[1,2-a]imidazo[5,1-c]thieno[3,2-e][1,4]diazepin-8-one as a colourless foam. Rf=0.31 (silica gel, methyl acetate/methanol 10:1).

EXAMPLE 160

0.34 ml (3.45 mmol) of piperidine was added to a suspension of 400 mg (1.15 mmol) of (S)-1-(5-chloromethyl-1,2,4-oxadiazol-3-yl)-11,11a-dihydro-8H, 10H-azeto[1,2-a]-imidazo[5,1-c]thieno[3,2-e][1,4]diazepin-8-one in 10 ml of N,N-dimethylformamide and the mixture was stirred at room temperature for 12 hours. The solution was evaporated and the residue was partitioned between methylene chloride and 2N sodium carbonate solution. The aqueous solution was extracted with methylene chloride and the organic phases were dried, filtered and evaporated. The residue was chromatographed (silica gel, methyl acetate/methanol 15:1). There were obtained 375 mg (82%) of (S)-1-(5-piperidin-1-ylmethyl-1,2,4-oxadiazol-3-yl)-11,11a-dihydro-8H, 10H-azeto[1,2-a]imidazo[5,1-c]thieno[3,2-e]-[1,4]diazepin-8-one as a colourless foam, Rf=0.22 (silica gel, methyl acetate/methanol 15:1).

EXAMPLE 161 a) 13.44 g (78.5 mmol) of chloroacetic anhydride were added to a solution of 18.92 g (68.48 mmol) of (E)-and/or (Z)-3-(amino-hydroxyimino-methyl)-5-methyl-5,6-dihydro-4H-imidazo[1,5-a]thieno[2,3-f]-[1,4]diazepin-6-one in 250 ml of N,N-dimethylformamide and the mixture was stirred at room temperature for 1.5 hours. Subsequently, it was heated to 105° for 2 hours. The solution was evaporated and the residue was partitioned between 2N sodium hydroxide solution and methylene chloride. The aqueous phase was back-washed with methylene chloride and the organic phases were dried with magnesium sulfate, filtered and evaporated. The residue obtained was crystallized from methylene chloride/ethanol. There were obtained 18 g (78%) of 3-(5-chloromethyl-1,2,4-oxadiazol-3-yl)-5-methyl-5,6-dihydro-4H-imidazo[1,5-a]thieno[2,3-f][1,4]diazepin-6-one as a beige powder of m.p. 221°–223°.

b) 0.73 ml (9 mmol) of propylamine was added to a suspension of 1 g (3 mmol) of 3-(5-chloromethyl-1,2,4-oxadiazol-3-yl)-5-methyl-5,6-dihydro-4H-imidazo[1,5-a]thieno[2,3-f][1,4]diazepin-6-one in 30 ml of N,N-dimethylformamide and the mixture was stirred at room temperature for 12 hours. The solution was evaporated and the residue was partitioned between methylene chloride and 2N sodium carbonate solution. The aqueous solution was extracted with methylene chloride and the organic phases were dried, filtered and evaporated. The residue was chromatographed (silica gel, methylene chloride/methanol/aqueous ammonia 140:10:1). There was obtained 0.86 g (80%) of (S)-1-(5-propylaminomethyl-1,2,4-oxadiazol-3-yl)-11,11a-dihydro-8H, 10H-azeto[1,2-a]imidazo[5,1-c]thieno[3,2-e][1,4]diazepin-8-one as a colourless foam, Rf=0.38 (silica gel, methylene chloride/methanol/aqueous ammonia 140:10:1).

EXAMPLE 162

0.93 g (3 mmol) of 3-(3-aminomethyl-1,2,4-oxadiazol-5-yl)-5-methyl-5,6-dihydro-4H-imidazo[1,5-a][1,4]benzodiazepin-6-one was stirred at room temperature overnight with 0.51 g (3 mmol) of benzyl bromide and 0.52 g (4 mmol) of N-ethyldiisopropylamine in 10 ml of methylene chloride. By evaporation of the solvent and chromatography of the residue on silica gel while eluting with ethyl acetate/methanol 6/1 there was obtained 3-(3-benzylaminomethyl-1,2,4-oxadiazol-5-yl)-5-methyl-5,6-dihydro-4H-imidazo[1,5-a][1,4]benzodiazepin-6-one, which was converted into the hydrochloride (0.25 g; 17%) of m.p. 195°–198°.

EXAMPLE 163

0.93 g (3 mmol) of 3-(3-aminomethyl-1,2,4-oxadiazol-5-yl)-5-methyl-5,6-dihydro-4H-imidazo[1,5-a][1,4]benzodiazepin-6-one was stirred at 100° overnight with 0.99 g (6.6 mmol) of 5-bromo-1-pentene and 1.04 g (8 mmol) of N-ethyldiisopropylamine in 20 ml of N,N-dimethylformamide. By evaporation of the solvent and chromatography of the residue on silica gel while eluting with ethyl acetate there was obtained 3-{3-[bis-(pent-4-enyl)aminomethyl]-1,2,4-oxadiazol-5-yl)-5-methyl-5,6-dihydro-4H-imidazo[1,5-a][1,4]benzodiazepin-6-one, which was converted into the hydrochloride (0.55 g; 38%) of m.p. 167°–169°.

EXAMPLE 164

3.4 g (10 mmol) of 3-(3-aminomethyl-1,2,4-oxadiazol-5-yl)-7-chlor-5-methyl-5,6-dihydro-4H-imidazo[1,5-a][1,4]benzodiazepin-6-one were stirred at 70° over the weekend with 2.7 g (20 mmol) of 4-bromo-1-butene and 2.7 g (23 mmol) of N-ethyldiisopropylamine in 30 ml of N,N-dimethylformamide. By evaporation of the solvent and chromatography of the residue on silica gel while eluting with methylene chloride/methanol 19/1 there was obtained, after recrystallization from ethyl acetate, 0.61 g (13.5%) of 3-{3-[bis-(but-3-enyl)aminomethyl]-1,2,4-oxadiazol-5-yl}-7-chlor-5-methyl-5,6-dihydro-4H-imidazo[1,5-a][1,4]benzodiazepin-6-one of melting point 143°–5°, which was converted into the hydrochloride of m.p. 145°–150°.

EXAMPLE 165 a) 11.5 g (71 mmol) of 1,1'-carbonyldiimidazole were added portionwise to a suspension of 17 g (64.6 mmol) of 5-methyl-4-oxo-5,6-dihydro-4H-imidazo[1,5-a]thieno[3,2-f][1,4]diazepin-7-carboxylic acid (EP 285 837 A1)in 100 ml of N,N-dimethylformamide. The resulting pale brown solution was heated to 50° during 45 minutes. Subsequently, the solution was cooled to room temperature and 20 ml of aqueous ammonia solution were added dropwise thereto. After stirring for a further 30 minutes the reaction mixture was poured into 100 ml of ice-water and the resulting precipitate was filtered off and rinsed with water, ethanol and subsequently with ether. After drying at 70°/10 Torr there were obtained 15 g (89%) of 5-methyl-4-oxo-5,6-dihydro-4H-imidazo[1,5-a]thieno[3,2-f][1,4]diazepine-7-carboxamide as colourless crystals of m.p. >250°.

b) 8.7 ml (62.9 mmol) of trifluoroacetic anhydride were added dropwise at 5°–8° to a suspension of 15 g (57.2 mmol) of 5-methyl-4-oxo-5,6-dihydro-4H-imidazo[1,5-a]thieno[3,2-f][1,4]diazepine-7-carboxamide in 80 ml of dioxan and 20 ml of pyridine. The beige solution obtained was stirred at 50° for 2.5 hours and subsequently poured into 220 ml of ice-water. The resulting precipitate was filtered off. After drying at 70°/10 Torr there were obtained 12.70 g (91%) of 5-methyl-4-oxo-5,6-dihydro-4H-imidazo[1,5-a]thieno[3,2-f][1,4]diazepine-7-carbonitrile as a white powder of m.p. 197°–200°.

c) 8.7 g (35.6 mmol) of 5-methyl-4-oxo-5,6-dihydro-4H-imidazo[1,5-a]thieno[3,2-f][1,4]diazepine-7-carbonitrile and 3.7 g (53.4 mmol) of hydroxylamine hydrochloride were added to a freshly prepared solution of sodium methylate in methanol (from 1.1 g (49.9 mmol) of sodium in 200 ml of methanol), whereupon the mixture was stirred at room temperature for 16 hours. Subsequently, the suspension was evaporated and the residue was treated with 100 ml of water. The precipitate obtained was filtered off and dried in a high vacuum. There were obtained 7.70 g (78%) of (E)- and/or (Z)-7-(amino-hydroxyiminomethyl)-5-methyl-5,6-dihydro-4H-imidazo[1,5-a]thieno[3,2-f][1,4]diazepin-4-one as a colourless powder of m.p. 216°–217°.

d) 5.40 g (33.3 mmol) of 1,1'-carbonyldiimidazole were added to a solution of 5.40 g (30.5 mmol) of BOC-glycine in 150 ml of N,N-dimethylformamide and the mixture was stirred at 50° for 30 minutes. Subsequently, 7.70 g (7.58 mmol) of (E)- and/or (Z)-7-(amino-hydroxyiminomethyl)-5-methyl-5,6-dihydro-4H-imidazo[1,5-a]thieno[3,2-f][1,4]diazepin-4-one were added and the mixture was stirred at 90° for 15 hours. The brown solution obtained was evaporated in a high vacuum and the brown residue obtained was chromatographed (silica gel, methylene chloride/methanol 19:1). There were obtained 8.40 g (73%) of 7-(5-BOC-aminomethyl-1,2,4-oxadiazol-3-yl)-5-methyl-5,6-dihydro-4H-imidazo[1,5-a]thieno[3,2-f][1,4]diazepin-4-one as a colourless foam, Rf=0.35 (silica gel, methylene chloride/methanol 19:1).

e) A solution of 8.40 g (20.2 mmol) of 7-(5-BOC-aminomethyl-1,2,4-oxadiazol-3-yl)-5-methyl-6-oxo-5,6-dihydro-4H-imidazo-[1,5-a]thieno[3,2-f][1,4]diazepin-4-one in 50 ml of trifluoroacetic acid was stirred at room temperature for 2 hours. The yellow solution was evaporated, the residue was dissolved in water and the aqueous phase was washed three times with methylene chloride. Subsequently, the aqueous phase was made basic with 10 ml of aqueous ammonia solution and extracted six times with methylene chloride. The organic phases were dried with sodium sulfate, filtered and evaporated. The residue obtained was crystallized from methylene chloride/ethanol. There were obtained 5 g (78%) of 7-(5-aminomethyl-1,2,4-oxadiazol-3-yl)-5-methyl-5,6-dihydro-4H-imidazo[1,5-a]thieno[3,2-f][1,4]diazepin-4-one as a beige powder of m.p. 181°–183°.

EXAMPLE 166

2.98 g (9.25 mmol) of (S)-1-(3-aminomethyl-1,2,4-oxadiazol-5-yl)-12,12a-dihydro-9H,11H-azeto[2,1-c]imidazo[1,5-a][1,4]benzodiazepin-9-one were stirred at 75° for 60 hours with 3.2 g (25 mmol) of N-ethyldiisopropylamine and 2.5 g (18.5 mmol) of 4-bromo-1-butene in 20 ml of N,N-dimethylformamide. By evaporation of the solvent and chromatography of the residue on silica gel while eluting with ethyl acetate there was obtained 0.62 g (15%) of (S)-1-{3-[bis-(but-3-enyl)aminomethyl]-1,2,4-oxadiazol-5-yl}-12,12a-dihydro-9H,11H-azeto[2,1-c]-imidazo[1,5-a][1,4]benzodiazepin-9-one which was converted into the hydrochloride of m.p. 80°–87°.

EXAMPLE 167

1.5 g (4.5 mmol) of 3-(5-chloromethyl-1,2,4-oxadiazol-3-yl)-5-methyl-5,6-dihydro-4H-imidazo[1,5-a][1,4]benzodiazepin-6-one were stirred at room temperature in 10 ml of benzylamine for 24 hours. By evaporation of the reaction mixture, chromatography of the residue on silica gel while eluting with methylene chloride/methanol 19/1 and crystallization from ethyl acetate and hexane there were obtained 1.3 g (71%) of 3-(5-benzylaminomethyl-1,2,4-oxadiazol-3-yl)-5-methyl-5,6-dihydro-4H-imidazo[1,5-a][1,4]benzodiazepin-6-one of melting point 88°–92°, which was converted into the hydrochloride of m.p. 178°–182°.

EXAMPLE 168

1.8 g (4 mmol) of (S)-1-(3-diallylaminomethyl-1,2,4-oxadiazol-5-yl)-11,12,13,13a-tetrahydro-9H-imidazo[1,5-a]pyrrolo[2,1-c][1,4]benzodiazepin-9-one were dissolved in 50 ml of methanol and hydrogenated at normal pressure and room temperature in the presence of 60 mg of 5% palladium-charcoal. The catalyst was separated and the solution was evaporated. By chromatography of the residue on silica gel while eluting with methylene chloride/methanol 19.5/0.5 there was obtained 1 g (60%) of (S)-1-(3-dipropylaminomethyl-1,2,4-oxadiazol-5-yl)-11,12,13,13a-tetrahydro-9H-imidazo[1,5-a]pyrrolo[2,1-c][1,4]benzodiazepin-9-one, which was converted into the hydrochloride of m.p. 198°–201°.

EXAMPLE 169

1.5 g (4.5 mmol) of 3-(5-chloromethyl-1,2,4-oxadiazol-3-yl)-5-methyl-5,6-dihydro-4H-imidazo[1,5-a][1,4]benzodiazepin-6-one were stirred at 80° for 2 hours in 1.1 ml (14 mmol) of pyrrolidine and 30 ml of N,N-dimethylformamide. By evaporation of the reaction mixture and chromatography of the residue on silica gel while eluting with methylene chloride/methanol 19/1 there were obtained 1.4 g (84%) of 5-methyl-3-[5-(pyrrolidin-1-yl)methyl-1,2,4-oxadiazol-3-yl]-5,6-dihydro-4H-imidazo[1,5-a][1,4]benzodiazepin-6-one, which was converted into the hydrochloride of m.p 251°–254°.

EXAMPLE 170

1.5 g (4.2 mmol) of (S)-1-(3-aminomethyl-1,2,4-oxadiazol-5-yl)-8-chloro-12,12a-dihydro-9H,11H-azeto[2,1-c]imidazo[1,5-a][1,4]benzodiazepin-9-one were stirred at 80° for 2.5 hours with 0.8 ml (9.7 mmol) of ethyl iodide and 2.5 ml (14.7 mmol) of N-ethyldiisopropylamine in 30 ml of N,N-dimethylformamide. By evaporation of the reaction mixture and chromatography of the residue on silica gel while eluting with methylene chloride/methanol 19.5/0.5 there was obtained 0.8 g (46%) of (S)-8-chloro-1-(3-diäthylaminomethyl-1,2,4-oxadiazol-5-yl)-12,12a-dihydro-9H,11H-azeto[2,1-c]imidazo[1,5-a][1,4]benzodiazepin-9-one, which was converted into the hydrochloride of m.p. 169°–171°.

EXAMPLE 171

1.5 g (4.5 mmol) of 3-(5-chloromethyl-1,2,4-oxadiazol-3-yl)-5-methyl-5,6-dihydro-4H-imidazo[1,5-a][1,4]benzodiazepin-6-one were stirred at 80° for 20 hours in 1 ml (14 mmol) 3-pyrroline and 30 ml of N,N-dimethylformamide. By evaporation of the reaction mixture and chromatography of the residue on silica gel while eluting with methylene chloride/methanol 19/1 there was obtained 0.2 g (12%) of 5-methyl-3-[5-(3-pyrrolin-1-yl)methyl-1,2,4-oxadiazol-3-yl]-5,6-dihydro-4H-imidazo[1,5-a][1,4]benzodiazepin-6-one, which was converted into the hydrochloride of m.p. 215°–220°.

EXAMPLE 172

1.7 g (5 mmol) of 3-(5-chloromethyl-1,2,4-oxadiazol-3-yl)-8-fluoro-5-methyl-5,6-dihydro-4H-imidazo[1,5-a][1,4]benzodiazepin-6-one were stirred at room temperature for 2 hours with 5 ml (7.2 mmol) of cyclopropylamine and 15 ml of N,N-dimethylformamide. After evaporation of the reaction mixture the residue was taken up in methylene chloride and washed with aqueous ammonia. After drying the organic phase over magnesium sulfate, evaporation of the solvent and recrystallization of the residue from ethyl acetate and hexane there were obtained 1.17 g (65%) of 3-(5-cyclopropylaminomethyl-1,2,4-oxadiazol-3-yl)-8-fluoro-5-methyl-5,6-dihydro-4H-imidazo[1,5-a][1,4]benzodiazepin-6-one of m.p. 176°–178°, which was converted into the hydrochloride.

EXAMPLE 173

2.2 g (6.3 mmol) of 3-(5-chloromethyl-1,2,4-oxadiazol-3-yl)-8-fluoro-5-methyl-5,6-dihydro-4H-imidazo[1,5-a ][1,4]benzodiazepin-6-one were stirred with 20 ml (183 mmol) of benzylmethylamine at room temperature overnight and at 70° for 1 hour. After evaporating the reaction mixture the residue was chromatographed on silica gel while eluting with ethyl acetate. After crystallization from ethyl acetate there were obtained 1.80 g (66%) of 3-[5-(N-benzyl-N-methylamino)methyl-1,2,4-oxadiazol-3-yl]-8-fluoro-5-methyl-5,6-dihydro-4H-imidazo[1,5-a]-[1,4]benzodiazepin-6-one of m.p. 161°–162°, which was converted into the hydrochloride.

EXAMPLE 174 a) 4.1 g (10 mmol) of 3-(5-BOC-aminomethyl-1,2,4-oxadiazol-3-yl)-5-methyl-5,6-dihydro-4H-imidazo[1,5-a][1,4]benzodiazepin-6-one were dissolved in 15 ml of N,N-dimethylformamide and deprotonized with 0.44 g (10 mmol) of sodium hydride dispersion (55% in oil). After adding 1.7 g (10 mmol) of propyl iodide the mixture was stirred at room temperature overnight. By evaporation of the solvent and chromatography of the residue on silica gel while eluting with ethyl acetate there were obtained, after crystallization from ethyl acetate, 2.46 g (54%) of 3-(5-N-BOC-N-propylaminomethyl-1,2,4-oxadiazol-3-yl)-5-methyl-5,6-dihydro-4H-imidazo[1,5-a][1,4]benzodiazepin-6-one of m.p. 148°–150°.

b) 2.53 g (6.6 mmol) of 3-(5-N-BOC-N-propylaminomethyl-1,2,4-oxadiazol-3-yl)-5-methyl-5,6-dihydro-4H-imidazo[1,5-a][1,4]benzodiazepin-6-one were stirred at room temperature overnight with 30 ml of 3N methanolic hydrochloric acid. The suspension obtained was diluted with ether, cooled to 0° and suction filtered. There were obtained 1.99 g (77%) of 5-methyl-3-(5-propylaminomethyl-1,2,4-oxadiazol-3-yl)-5,6-dihydro-4H-imidazo[1,5-a][1,4]benzodiazepin-6-one as the hydrochloride of m.p. 248°–250°.

EXAMPLE 175 a) 10.5 g (60 mmol) of BOC-glycine were dissolved in 50 ml of N,N-dimethylformamide, treated portionwise with 9.73 g (60 mmol) of 1,1'-carbonyldiimidazole and stirred at 55° for 20 minutes. After adding 15.5 g (57.1 mmol) of 5-methyl-6-oxo-5,6-dihydro-4H-imidazo[1,5-a][1,4]benzodiazepine-3-carboxamidoxime the mixture was stirred at 90° overnight. The reaction mixture was concentrated, the residue was dissolved in methylene chloride and the solution was washed three times with water. After drying the solution, evaporating the solvent and crystallizing the residue from ethanol there were obtained 20.4 g (87%) of 3-(5-BOC-aminomethyl-1,2,4-oxadiazol-3-yl)-5-methyl-5,6-dihydro-4H-imidazo[1,5-a][1,4]benzodiazepin-6-one of m.p. 108°–113°.

b) 15.9 g (38.7 mmol) of 3-(5-BOC-aminomethyl-1,2,4-oxadiazol-3-yl)-5-methyl-5,6-dihydro-4H-imidazo[1,5-a][1,4]benzodiazepin-6-one were stirred in 40 ml of trifluoroacetic acid at room temperature for 3 hours. The solution was concentrated, the residue was taken up in methylene chloride and the solution was washed with saturated sodium bicarbonate solution. The aqueous phase was extracted three times with methylene chloride and six times with ethyl acetate. After drying and evaporation of the combined organic phases and chromatography of the residue on silica gel while eluting with methylene chloride/methanol 19/1 there were obtained 2.03 g (17%) of 3-(5-aminomethyl-1,2,4-oxadiazol-3-yl)-5-methyl-5,6-dihydro-4H-imidazo[1,5-a][1,4]benzodiazepin-6-one of m.p. 192°–195°.

EXAMPLE 176 a) 192.4 g (714.6 mmol) of (S)-9-oxo-12,12a-dihydro-9H,11H-azeto[2,1-c]imidazo[1,5-a][1,4]benzodiazepine-1-carboxylic acid were suspended in 900 ml of N,N-dimethylformamide, treated at room temperature with 116 g (715 mmol) of 1,1'-carbonyldiimidazole and stirred at 50° for 30 minutes. 173 ml of 25% ammonia were added dropwise at 25°–30° within 30 minutes. After stirring for 30 minutes the reaction mixture was concentrated and the residue was dissolved in 500 ml of alcohol. After adding 250 ml of ether the mixture was cooled to 0° and the crystallizate was filtered off under suction and dried. There were obtained 133.6 g (69%) of (S)-9-oxo-12,12a-dihydro-9H,11H-azeto[2,1-c]imidazo[1,5-a][1,4]benzodiazepine-1-carboxamide of m.p. 228°–230°.

b) 78 g (290 mmol) of (S)-9-oxo-12,12a-dihydro-9H,11H-azeto[2,1-c]imidazo[1,5-a][1,4]benzodiazepine-1-carboxamide were suspended in 380 ml of dioxan and 68 ml of pyridine and treated dropwise at 0° with 59 ml (424 mmol) of trifluoroacetic anhydride. After stirring at 50° for two hours the reaction mixture was poured into 2 l of ice-water and the crystals were filtered off under suction, rinsed with water and dried. There were obtained 60 g (82%) of (S)-9-oxo-12,12a-dihydro-9H,11H-azeto[2,1-c]imidazo [1,5-a][1,4]benzodiazepine-1-carbonitrile of m.p. 232°–234°.

c) 64.7 g (258 mmol) of (S)-9-oxo-12,12a-dihydro-9H, 11H-azeto[2,1-c]imidazo[1,5-a][1,4]benzodiazepine-1-carbonitrile were heated to reflux for 2.5 hours with 52.8 g (497 mmol) of sodium carbonate and 42.36 g (608 mmol) of hydroxylamine hydrochloride in 1.5 l of alcohol and 300 ml of water. The alcohol was evaporated and the suspension obtained was cooled to 0°. The crystals were filtered off under suction, washed with water and dried. There were obtained 68.5 g (93%) of (S)-9-oxo-12,12a-dihydro-9H, 11H-azeto[2,1-c]imidazo[1,5-a][1,4]benzodiazepine-1-carboxamidoxime of decomposition point 216°.

d) 34.5 g (122 mmol) of (S)-9-oxo-12,12a-dihydro-9H, 11H-azeto[2,1-c]imidazo[1,5-a][1,4]benzodiazepine-1-carboxamidoxime were stirred with 23 g (140 mmol) of chloroacetic anhydride in 200 ml of N,N-dimethylformamide at room temperature overnight and at 110° for 2 hours. After evaporating the reaction mixture the residue was dissolved in methylene chloride and the solution was washed with saturated sodium bicarbonate solution. The organic phase was dried over magnesium sulfate and concentrated. The residue was chromatographed on silica gel while eluting with methylene chloride/methanol 19/1. There were obtained 24 g (58%) of (S)-1-(5-chloromethyl-1,2,4-oxadiazol-3-yl)-12,12a-dihydro-9H,11H-azeto[2,1-c] imidazo[1,5-a][1,4]benzodiazepine-9-one of m.p. 205°–207°.

e) 1.4 g (4 mmol) of (S)-1-(5-chloromethyl-1,2,4-oxadiazol-3-yl)-12,12a-dihydro-9H,11H-azeto[2,1-c] imidazo[1,5-a][1,4]benzodiazepin-9-one were stirred at room temperature for 1 hour with 5.2 g (90 mmol) of propylamine and 15 ml of N,N-dimethylformamide. By evaporation of the reaction mixture and chromatography of the residue on silica gel while eluting with methylene chloride/methanol 19/1 there were obtained 1.07 g (73%) of (S)-1-(5-propylaminomethyl-1,2,4-oxadiazol-3-yl)-12,12a-dihydro-9H,11H-azeto[2,1-c]imidazo[1,5-a]-[1,4] benzodiazepin-9-one, which was converted into the hydrochloride (amorphous).

EXAMPLE 177 a) 36.4 g (205 mmol) of BOC-glycine were dissolved in 300 ml of N,N-dimethylformamide and treated portionwise with 35.8 g (220 mmol) of 1,1'-carbonyldiimidazole. The solution was stirred at 50° for 30 minutes, 54.7 g (194 mmol) of (S)-9-oxo-12,12a-dihydro-9H,11H-azeto[2,1- c]imidazo [1,5-a][1,4]benzodiazepine-1-carboxamidoxime were added thereto and the mixture was stirred at 90° overnight. After evaporating the solvent the residue was dissolved in methylene chloride and the solution was washed with water, dried over magnesium sulfate and concentrated. By chromatography of the residue on silica gel while eluting with ethyl acetate there were obtained 73 g (89%) of (S)-1-(5-BOC-aminomethyl-1,2,4-oxadiazol-3-yl)-12,12a-dihydro-9H, 11H-azeto[2,1-c]imidazo[1,5-a][1,4]benzodiazepin-9-one as a white foam, which was used in the next step without further purification.

b) 25 g (59.3 mmol) of (S)-1-(5-BOC-aminomethyl-1,2, 4-oxadiazol-3-yl)-12,12a-dihydro-9H,11H-azeto[2,1-c] imidazo[1,5-a]-[1,4]benzodiazepin-9-one were stirred at room temperature overnight with 60 ml of 3N methanolic hydrochloric acid. After evaporating the solvent the residue was dissolved in water and the solution was extracted three times with methylene chloride. The aqueous phase was made alkaline with conc. ammonia and extracted seven times with methylene chloride. By drying the organic phase over magnesium sulfate and evaporating the solvent there were obtained 16.9 g (88%) of (S)-1-(5-aminomethyl-1,2, 4-oxadiazol-3-yl)-12,12a-dihydro-9H,11H-azeto[2,1-c]-imidazo[1,5-a][1,4]-benzodiazepin-9-one of m.p. 211°–214°.

EXAMPLE 178

6.9 g (21.4 mmol) of (S)-1-(5-aminomethyl-1,2,4-oxadiazol-3-yl)-12,12a-dihydro-9H,11H-azeto[2,1-c] imidazo[1,5-a][1,4]benzodiazepin-9-one were stirred at 80° overnight and at 100° for 2 hours with 7.65 g (45 mmol) of propyl iodide in 80 ml of 1,3-dimethyl-3,4,5,6-tetrahydro-2(1H)-pyrimidinone and 6.5 g ([50 mmol) of N-ethyldiisopropylamine. By evaporation of the reaction mixture and chromatography of the residue on silica gel while eluting with ethyl acetate there were obtained 3.32 g (38%) of (S)-1-(5-dipropylaminomethyl-1,2,4-oxadiazol-3-yl)-12,12a-dihydro-9H,11H-azeto[2,1-c]imidazo[1,5-a][1, 4]benzodiazepin-9-one, which was converted into the hydrochloride of m.p. 208°–210°.

EXAMPLE 179

1.96 g (4.1 mmol) of (S)-1-(5-diallylaminomethyl-1,2,4-oxadiazol-3-yl)-7-fluoro-11,1 2,13,13a-tetrahydro-9H-imidazo[1,5-a]pyrrolo[2,1-c][1,4]-benzodiazepin-9-one were dissolved in 25 ml of ethyl acetate and hydrogenated at normal pressure and room temperature in the presence of 37 mg of 5% palladium-charcoal. The catalyst was separated and the solution was evaporated. By chromatography of the residue on silica gel while eluting with ethyl acetate there were obtained 1.49 g (83%) of (S)-1-(5-dipropylaminomethyl-1,2,4-oxadiazol-3-yl)-7-fluoro-11, 12,13, 13a-tetrahydro-9H-imidazo[1,5-a]pyrrolo[2,1-c][1,4] benzodiazepin-9-one, which was converted into the hydrochloride of m.p. 222°–225°.

EXAMPLE 180 a) A suspension of 11.9 g (0.0394 mol) of (S)-8-chloro-9-oxo-12,12a-dihydro-9H,11H-azeto[2, 1-c]imidazo[1,5-a] [1,4]benzodiazepine-1-carboxamide in a mixture of 85 ml of dioxan and 6.8 ml of pyridine was treated at 0° with 7.1 ml (0.051 mol) of trifluoroacetic anhydride. The suspension was stirred at 50° for 3 hrs., cooled and poured into ice-cold water. After stirring for 1½ hr. the suspension was suction filtered. There were obtained 11.2 g (100%) of (S)-8-chloro-9-oxo-12,12a-dihydro-9H,11H-azeto[2,1-c]imidazo[1,5-a] [1,4]-benzodiazepine-1-carbonitrile as white crystals; m.p. 130° (dec.).

b) 178.7 g (628 mmol) of (S)-8-chloro-9-oxo-12,12a-dihydro-9H,11H-azeto[2,1-c]imidazo[1,5-a][1,4]-benzodiazepine-1-carbonitrile and 65.5 g (941 mmol) of hydroxylamine hydrochloride were added to a solution prepared from 17.3 g (753 mmol) of sodium and 1.5 l of methanol. The reaction mixture was stirred at room temperature overnight and subsequently diluted with 1 l of water. The suspension obtained was suction filtered and the crystals were dried. There were obtained 169.7 g (85%) of (S)-8-chloro-9-oxo-12,12a-dihydro-9H,11H-azeto[2,1-c] imidazo[1,5-a][1,4]-benzodiazepine-1-carboxamidoxime of decomposition point 269°.

c) 31.7 g (100 mmol) of (S)-8-chloro-9-oxo-12,12a-dihydro-9H, 11H-azeto[2,1-c]imidazo[1,5-a][1,4]-benzodiazepine-1-carboxamidoxime were suspended in 200 ml of N,N-dimethylformamide and treated with 18.8 g (110 mmol) of chloroacetic anhydride. The reaction mixture was heated to 105° for 2 hours and evaporated. By chromatography of the residue on silica gel while eluting with chloroform/methanol 9/1 there were obtained 27.9 g (74%) of (S)-8-chloro-1-(5-chloromethyl-1,2,4-oxadiazol-3-yl)-12,12a-dihydro-9H,11H-azeto[2,1-c]-imidazo[1,5-a][1,4]benzodiazepin-9-one of m.p. 211°–212°.

d) 3.76 g (10 mmol) of (S)-8-chloro-1-(5-chloromethyl-1,2,4-oxadiazol-3-yl)-12,12a-dihydro-9H, 11H-azeto[2,1-c]imidazo[1,5-a][1,4]benzodiazepin-9-one were stirred at room temperature for 2 hours with 10 g (82 mmol) of benzylmethylamine and 15 ml of N,N-dimethylformamide. By evaporation of the reaction mixture and chromatography of the residue on silica gel while eluting with ethyl acetate there were obtained 4.4 g (95%) of (S)-1-(5-N-benzyl-N-methylaminomethyl-1,2,4-oxadiazol-3-yl)-8-chloro-12,12a-dihydro-9H,11H-azeto[2,1-c]imidazo[1,5-a][1,4]benzodiazepin-9-one, which was converted into the hydrochloride of m.p. 213°–215°.

EXAMPLE 181

3.76 g (10 mmol) of (S)-8-chloro-1-(5-chloromethyl-1,2,4-oxadiazol-3-yl)-12,12a-dihydro-9H,11H-azeto[2,1-c]imidazo[1,5-a][1,4]benzodiazepin-9-one were stirred at room temperature overnight with 2 g (20 mmol) of isopropylmethylamine and 20 ml of N,N-dimethylformamide. By evaporation of the reaction mixture and chromatography of the residue on silica gel while eluting with ethyl acetate/ethanol 9/1 there were obtained 3.4 g (90%) of (S)-8-chloro-1-(5-N-isopropyl-N-methylaminomethyl-1,2,4-oxadiazol-3-yl)-12,12a-dihydro-9H,11H-azeto[2,1-c]-imidazo[1,5-a][1,4]benzodiazepin-9-one, which was converted into the hydrochloride of m.p. 198°–203°.

EXAMPLE 182

3.76 g (10 mmol) of (S)-8-chloro-1-(5-chloromethyl-1,2,4-oxadiazol-3-yl)-12,12a-dihydro-9H,11H-azeto[2,1-c]imidazo[1,5-a][1,4]benzodiazepin-9-one were stirred at room temperature overnight with 2.19 g (30 mmol) of diethylamine and 30 ml of N,N-dimethylformamide. By evaporation of the reaction mixture and chromatography of the residue on silica gel while eluting with methylene chloride/methanol 19/1 there were obtained 4.5 g (96%) of (S)-8-chloro-1-(5-diethylamino-methyl-1,2,4-oxadiazol-3-yl)-12,12a-dihydro-9H,11H-azeto[2,1-c]-imidazo[1,5-a][1,4]benzodiazepin-9-one, which was converted into the hydrochloride of m.p. 218°–220°.

EXAMPLE 183 a) 9.8 g (32 mmol) of 7-chloro-5-methyl-6-oxo-5,6-dihydro-4H-imidazo[1,5-a][1,4]benzodiazepine-3-carboxamidoxime were stirred in 60 ml of N,N-dimethylformamide with 7 g (41 mmol) of chloroacetic anhydride at room temperature for 1 hour and at 105° for 4 hours. After evaporating the solvent the residue was dissolved in methylene chloride and the solution was washed with saturated sodium bicarbonate solution and dried over magnesium sulfate. By evaporation of the solvent and chromatography of the residue on silica gel while eluting with ethyl acetate there were obtained 6.63 g (65%) of 7-chloro-3-(5-chloromethyl-1,2,4-oxadiazol-3-yl)-5-methyl-5,6-dihydro-4H-imidazo[1,5-a][1,4]benzodiazepine-6-one.

b) 1.09 g (3 mmol) of 7-chloro-3-(5-chloromethyl-1,2,4-oxadiazol-3-yl)-5-methyl-5,6-dihydro-4H-imidazo[1,5-a][1,4]benzodiazepin-6-one were stirred at room temperature for 4.5 hours with 1.02 g (10 mmol) of dipropylamine and 15 ml of N,N-dimethylformamide. By evaporation of the reaction mixture and chromatography of the residue on silica gel while eluting with ethyl acetate there were obtained 1.16 g (90%) of 7-chloro-3-(5-dipropylaminomethyl-1,2,4-oxadiazol-3-yl)-5-methyl- 5,6-dihydro-4H-imidazo[1,5-a][1,4]benzodiazepin-6-one, which was converted into the hydrochloride of m.p. 212°–215°.

EXAMPLE 184 a) 4.4 g (10 mmol) of 3-(5-BOC-aminomethyl-1,2,4-oxadiazol-3-yl)-7-chloro-5-methyl-5,6-dihydro-4H-imidazo[1,5-a][1,4]benzodiazepin-6-one were deprotonized in 15 ml of N,N-dimethylformamide at 0° to room temperature with 0.44 g of sodium hydride dispersion (55% in oil). 1.7 g (10 mmol) of propyl iodide were added at 10° and the reaction mixture was stirred at room temperature for 5 hours. By evaporation of the reaction mixture and chromatography of the residue on silica gel while eluting with ethyl acetate there were obtained 2.50 g (51%) of 7-chloro-5-methyl-3-(5-N-BOC-N-propylamino-methyl-1,2,4-oxadiazol-3-yl)-5,6-dihydro-4H-imidazo[1,5-a][1,4]benzodiazepin-6-one as a white foam, which was without further purification.

b) 2.5 g (5.1 mmol) of 7-chloro-5-methyl-3-(5-N-BOC-N-propylamino-methyl-1,2,4-oxadiazol-3-yl)-5,6-dihydro-4H-imidazo [1,5-a][1,4]benzodiazepin-6-one were stirred at room temperature for 3 hours with 10 ml 3N methanolic hydrochloric acid. The suspension obtained was cooled to 0° and suction filtered. After recrystallization from methanol there was obtained 0.94 g (41%) of 7-chloro-5-methyl-3-(5-propylamino-methyl-1,2,4-oxadiazol-3-yl)-5,6-dihydro-4H-imidazo [1,5-a]-[1,4]benzodiazepin-6-one hydrochloride of decomposition point 235°.

EXAMPLE 185

1.5 g (4.1 mmol) of 7-chloro-3-(5-chloromethyl-1,2,4-oxadiazol-3-yl)-5-methyl-5,6-dihydro-4H-imidazo[1,5-a][1,4]benzodiazepin-6-one were stirred at room temperature for 2 hours with 5 g (41.3 mmol) of benzylmethylamine and 10 ml of N,N-dimethylformamide. By evaporation of the reaction mixture and chromatography of the residue on silica gel while eluting with methylene chloride/methanol 19/1 there were obtained 1.29 g (72%) of 3-(5-N-benzyl-N-methylaminomethyl-1,2,4-oxadiazol-3-yl)-7-chloro-5-methyl-5,6-dihydro-4H-imidazo[1,5-a][1,4]benzodiazepin-6-one, which was converted into the hydrochloride of m.p. 214°–216°.

EXAMPLE 186

3.76 g (10 mmol) of (S)-8-chloro-1-(5-chloromethyl-1,2,4-oxadiazol-3-yl)-12,12a-dihydro-9H,11H-azeto[2,1-c]imidazo[1,5-a]-[1,4]benzodiazepin-9-one were stirred at room temperature overnight with 5 g (39 mmol) of dibutylamine and 25 ml of N,N-dimethylformamide. By evaporation of the reaction mixture and chromatography of the residue on silica gel while eluting with ethyl acetate there were obtained 4.3 g (92%) of (S)-8-chloro-1-(5-dibutylaminomethyl-1,2,4-oxadiazol-3-yl)-12,12a-dihydro-9H,11H-azeto[2,1-c]imidazo[1,5-a][1,4]-benzodiazepin-9-one, which was converted into the hydrochloride of m.p. 120°–125°.

EXAMPLE 187

3.76 g (10 mmol) of (S)-8-chloro-1-(5-chloromethyl-1,2,4-oxadiazol-3-yl)-12,12a-dihydro-9H,11H-azeto[2,1-c]

imidazo[1,5-a][1,4]benzodiazepin-9-one were stirred at room temperature overnight with 5 g (58 mmol) of piperidine and 25 ml of N,N-dimethylformamide. By evaporation of the reaction mixture and chromatography of the residue on silica gel while eluting with ethyl acetate/methanol 9/1 there were obtained 4.1 g (96%) of (S)-8-chloro-1-[5-(piperidin-1-yl)methyl-1,2,4-oxadiazol-3-yl]-12,12a-dihydro-9H,11H-azeto[2,1-c]imidazo[1,5-a][1,4]benzodiazepin-9-one of m.p. 177°–179°, which was converted into the hydrochloride.

EXAMPLE 188

0.94 g (2.5 mmol) of (S)-8-chloro-1-(5-chloromethyl-1,2,4-oxadiazol-3-yl)-12,12a-dihydro-9H,11H-azeto[2,1-c]imidazo[1,5-a][1,4]benzodiazepin-9-one was stirred at room temperature for 4 hours with 2 g (20 mmol) of hexamethyleneimine and 15 ml of N,N-dimethylformamide. By evaporation of the reaction mixture and chromatography of the residue on silica gel while eluting with ethyl acetate there were obtained 1.01 g (92%) of (S)-8-chloro-1-[5-(hexamethylenemin-1-yl)methyl-1,2,4-oxadiazol-3yl)-12,12a-dihydro-9H,11H-azeto[2,1-c]imidazo[1,5-a][1,4]benzodiazepin-9-one, which was converted into the hydrochloride (amorphous).

EXAMPLE 189

1.13 g (3 mmol) of (S)-8-chloro-1-(5-chloromethyl-1,2,4-oxadiazol-3-yl)-12,12a-dihydro-9H,11H-azeto[2,1-c]imidazo[1,5-a][1,4]benzodiazepin-9-one were stirred at room temperature overnight with 1.5 g (13.3 mmol) of heptamethyleneimine and 15 ml of N,N-dimethylformamide. By evaporation of the reaction mixture and chromatography of the residue on silica gel while eluting with ethyl acetate there were obtained 1.2 g (88%) of (S)-8-chloro-1-[5-(heptamethyleneimine-1-yl)methyl-1,2,4-oxadiazol-3-yl]-12,12a-dihydro-9H,11H-azeto[2,1-c]imidazo[1,5-a][1,4]benzodiazepin-9-one, which was converted into the hydrochloride (amorphous).

EXAMPLE 190

0.94 g (2.5 mmol) of (S)-8-chloro-1-(5-chloromethyl-1,2,4-oxadiazol-3-yl)-12,12a-dihydro-9H,11H-azeto[2,1-c]imidazo[1,5-a][1,4]benzodiazepin-9-one was stirred at room temperature overnight with 3 g (26.5 mmol) of methylcyclohexylamine and 15 ml of N,N-dimethylformamide. By evaporation of the reaction mixture and chromatography of the residue on silica gel while eluting with ethyl acetate/methanol 19/1 there was obtained 0.79 g (69%) of (S)-8-chloro-1-(5-N-cyclohexyl-N-methylaminomethyl-1,2,4-oxadiazol-3-yl)-12,12a-dihydro-9H,11H-azeto[2,1-c]imidazo[1,5-a][1,4]benzodiazepin-9-one, which was converted into the hydrochloride (amorphous).

EXAMPLE 191

0.94 g (2.5 mmol) of (S)-8-chloro-1-(5-chloromethyl-1,2,4-oxadiazol-3-yl)-12,12a-dihydro-9H,11H-azeto[2,1-c]imidazo[1,5-a][1,4]benzodiazepin-9-one was stirred at room temperature overnight with 2 g (23 mmol) of tert.-butylmethylamine and 15 ml of N,N-dimethylformamide. By evaporation of the reaction mixture and chromatography of the residue on silica gel while eluting with ethyl acetate/methanol 9/1 there was obtained 0.81 g (75%) of (S)-1-(5-N-tert.-butyl-N-methylaminomethyl-1,2,4-oxadiazol-3-yl)-8-chloro-12,12a-dihydro-9H,11H-azeto[2,1-c]imidazo[1,5-a][1,4]benzodiazepin-9-one, which was converted into the hydrochloride (amorphous).

EXAMPLE 192

0.94 g (2.5 mmol) of (S)-8-chloro-1-(5-chloromethyl-1,2,4-oxadiazol-3-yl)-12,12a-dihydro-9H,11H-azeto[2,1-c]imidazo[1,5-a][1,4]benzodiazepin-9-one was stirred at room temperature overnight with 2 g (27 mmol) of tert.-butylamine and 15 ml of N,N-dimethylformamide. By evaporation of the reaction mixture and chromatography of the residue on silica gel while eluting with ethyl acetate/methanol 9/1 there was obtained 0.91 g (88%) of (S)-1-(5-tert.-butylamino-methyl-1,2,4-oxadiazol-3-yl)-8-chloro-12,12a-dihydro-9H,11H-azeto[2,1-c]-imidazo[1,5-a][1,4]benzodiazepin-9-one, which was converted into the hydrochloride (amorphous).

EXAMPLE 193

0.94 g (2.5 mmol) of (S)-8-chloro-1-(5-chloromethyl-1,2,4-oxadiazol-3-yl)-12,12a-dihydro-9H,11H-azeto[2,1-c]imidazo[1,5-a][1,4]benzodiazepin-9-one was stirred at 80° for 5 hours with 2 g (19.8 mmol) of diisopropylamine and 15 ml of N,N-dimethylformamide. By evaporation of the reaction mixture and chromatography of the residue on silica gel while eluting with ethyl acetate there was obtained 0.81 g (73%) of (S)-8-chloro-1-(5-diisopropyl-aminomethyl-1,2,4-oxadiazol-3-yl)-12,12a-dihydro-9H,11H-azeto[2,1-c]imidazo[1,5-a][1,4]benzodiazepin-9-one, which was converted into the hydrochloride (amorphous).

EXAMPLE 194

1.88 g (5 mmol) of (S)-8-chloro-1-(5-chloromethyl-1,2,4-oxadiazol-3-yl)-12,12a-dihydro-9H,11H-azeto[2,1-c]imidazo[1,5-a][1,4]benzodiazepin-9-one were stirred at room temperature for 2 hours with 1.5 g (15 mmol) of diethanolamine and 15 ml of N,N-dimethyl-formamide. By evaporation of the reaction mixture and chromatography of the residue on silica gel while eluting with methylene chloride/methanol 9/1 there were obtained 1.89 g (85%) of (S)-8-chloro-1-(5-diethanol-aminomethyl-1,2,4-oxadiazol-3-yl)-12,12a-dihydro-9H,11H-azeto[2,1-c]-imidazo[1,5-a][1,4]benzodiazepin-9-one of m.p. 173°–175°, which was converted into the hydrochloride.

EXAMPLE 195 a) 10.1 g (231 mmol) of sodium hydride dispersion (55% in oil) were washed with hexane and suspended in 180 ml of N,N-dimethylformamide. 45.8 g (208 mmol) of (S)-6-fluoro-1,2,4, 9,10,10a-hexahydro-azeto[2,1-c][1,4]benzodiazepine-4,10-dione were added portionwise at −40° to −20° and the deprotonization was carried out for 1 hour at −40° to −20°. The mixture was cooled to −60°, a solution of 59 g (219 mmol) of diphenyl chlorophosphate in 10 ml of N,N-dimethylformamide and 24.9 g (220 mmol) of ethyl isocyanate were added in succession and subsequently a solution of 24.5 g (218 mmol) of potassium tert.-butylate in 50 ml of N,N-dimethylformamide was added dropwise at −60° to −55°. The reaction mixture was left to warm to room temperature, neutralized with 7 ml of acetic acid and poured into 600 ml of ice-water. The mixture was extracted ten times with methylene chloride, the combined organic phases were washed four times with water and dried over magnesium sulfate. By evaporating the solvent and crystallizing the residue from methylene chloride there were obtained 13.6 g of white crystals. By chromatography of the mother liquor on silica gel while eluting with ethyl acetate there was obtained a further amount of 10.9 g (total yield 62%) of ethyl (S)-7-fluoro-12,12a-dihydro-9-oxo-9H,11H-azeto-[2,1-c]imidazo[1,5-a][1,4]benzodiazepine-1-carboxylate of m.p. 226°–227°.

b) 40.58 g (128.7 mmol) of ethyl (S)-7-fluoro-12,12a-dihydro-9-oxo-9H,11H-azeto-[2,1-c]imidazo[1,5-a][1,4]benzodiazepine-1-carboxylate, 300 ml of ethanol and 32.5 ml (130 mmol) of 4N-sodium hydroxide solution were heated to reflux on a steam bath for 1.5 hours. The alcohol was evaporated on a rotary evaporator. The aqueous phase was washed twice with methylene chloride and acidified to pH 3–4 with 32.5 ml (130 mmol) of 4N hydrochloric acid. The suspension obtained was cooled and suction filtered. The filter residue was washed with a small amount of ice-water and dried. There were obtained 36.67 g (99%) of (S)-7-fluoro-9-oxo-12,12a-dihydro-9H,11H-azeto[2,1-c]-imidazo[1,5-a][1,4]benzodiazepine-1-carboxylic acid of m.p. 159°–160°.

c) 100 g (348 mmol) of (S)-7-fluoro-9-oxo-12,12a-dihydro-9H,11H-azeto[2,1-c]imidazo[1,5-a][1,4]benzodiazepine-1-carboxylic acid were suspended in 600 ml of N,N-dimethylformamide and treated with 64.1 g (395 mmol) of 1,1'-carbonyldiimidazole. After stirring at 50° for 30 minutes 80 ml of 25% ammonia were added dropwise at 13° to 20° and the mixture was stirred for 30 minutes and poured into 2 l of water. By suction filtration of the resulting suspension and drying the crystals there were obtained 52.7 g (76%) of (S)-7-fluoro-9-oxo-12,12a-dihydro-9H,11H-azeto[2,1-c]imidazo[1,5-a][1,4]benzodiazepine-1-carboxamide of m.p. 223°–224°.

d) 75.6 g (264 mmol) of (S)-7-fluoro-9-oxo-12,12a-dihydro-9H,11H-azeto[2,1-c]imidazo[1,5-a][1,4]-benzodiazepine-1-carboxamide were suspended in 340 ml of dioxan and 45 ml of pyridine and treated dropwise at about 7° with (323 mmol) of trifluoroacetic anhydride. The reaction mixture was stirred at room temperature overnight and poured into 2 l of water. By suction filtration of the resulting suspension and drying the crystals there were obtained 45.65 g (64%) of (S)-7-fluoro-9-oxo-12,12a-dihydro-9H,11H-azeto[2,1-c]imidazo[1,5-a][1,4]-benzodiazepine-1-carbonitrile, which was used in the next step without further purification.

e) 4.2 g (180 mmol) of sodium were dissolved in 225 ml of methanol. 13.55 g (195 mmol) of hydroxylamine hydrochloride and 40 g (149 mmol) of (S)-7-fluoro-9-oxo-12,12a-dihydro-9H,11H-azeto[2,1-c]imidazo[1,5-a][1,4]benzodiazepine-1-carbonitrile were added and the reaction mixture was stirred at boiling temperature overnight. The suspension was cooled to 5° and suction filtered. The crystals were rinsed with water and dried. There were obtained 38.9 g (87%) of (S)-7-fluoro-9-oxo-12,12a-dihydro-9H,11H-azeto[2,1-c]imidazo[1,5-a][1,4]benzodiazepine-1-carboxamidoxime, which was used in the next step without further purification.

f) 15.9 g (52.8 mmol) of (S)-7-fluoro-9-oxo-12,12a-dihydro-9H,11H-azeto[2,1-c]imidazo[1,5-a][1,4]benzodiazepine-1-carboxamidoxime were stirred with 9.93 g (58 mmol) of chloroacetic anhydride and 50 ml of N,N-dimethylformamide at room temperature for 0.5 hour and at 105° for 2 hours. After evaporating the reaction mixture the residue was dissolved in methylene chloride and the solution was washed with saturated sodium bicarbonate solution. By drying the organic phase over magnesium sulfate, evaporation of the solvent and chromatography of the residue on silica gel while eluting with ethyl acetate there were obtained 11 g (58%) of (S) 1-(5-chloromethyl-1,2,4-oxadiazol-3-yl)-7-fluoro-12,12a-dihydro-9H,11H-azeto[2,1-c]imidazo[1,5-a][1,4]benzodiazepin-9-one.

g) 1.8 g (5 mmol) of (S) 1-(5-chloromethyl-1,2,4-oxadiazol-3-yl)-7-fluoro-12,12a-dihydro-9H,11H-azeto[2,1-c]imidazo[1,5-a][1,4]benzodiazepin-9-one were stirred at room temperature overnight with mmol) of dipropylamine and 20 ml of N,N-dimethylformamide. By evaporation of the solvent and chromatography of the residue on silica gel while eluting with ethyl acetate there were obtained 1.8 g (85%) of (S)-1-(5-dipropylaminomethyl-1,2,4-oxadiazol-3-yl)-7-fluoro-12,12a-dihydro-9H,11H-azeto[2,1-c]imidazo[1,5-a][1,4]benzodiazepin-9-one, which was converted into the hydrochloride (amorphous).

EXAMPLE 196

1.8 g (5 mmol) of (S)-1-(5-chloromethyl-1,2,4-oxadiazol-3-yl)-7-fluoro-12,12a-dihydro-9H,11H-azeto[2,1-c]imidazo[1,5-a][1,4]benzodiazepin-9-one were stirred at room temperature for 2 hours with 2 g (34 mmol) of propylamine and 20 ml of N,N-dimethylformamide. By evaporation of the solvent and chromatography of the residue on silica gel while eluting with ethyl acetate/methanol 9/1 there were obtained 1.4 g (73%) of (S)-7-fluoro-1-(5-propylaminomethyl-1,2,4-oxadiazol-3-yl)-12,12a-dihydro-9H,11H-azeto[2,1-c]imidazo[1,5-a][1,4]benzodiazepin-9-one, which was converted into the hydrochloride (amorphous).

EXAMPLE 197

0.99 g (3 mmol) of 3-(5-chloromethyl-1,2,4-oxadiazol-3-yl)-5-methyl-5,6-dihydro-4H-imidazo[1,5-a][1,4]benzodiazepin-6-one were stirred at room temperature overnight in 1.2 g (16 mmol) of diethylamine and 15 ml of N,N-dimethylformamide. By evaporation of the reaction mixture and chromatography of the residue on silica gel while eluting with ethyl acetate/methanol 9/1 there was obtained 0.9 g (81%) of 3-(5-diethylaminomethyl-1,2,4-oxadiazol-3-yl)-5-methyl-5,6-dihydro-4H-imidazo[1,5-a][1,4]benzodiazepin-6-one of m.p. 153°–154°, which was converted into the hydrochloride.

EXAMPLE 198

0.99 g (3 mmol) of 3-(5-chloromethyl-1,2,4-oxadiazol-3-yl)-5-methyl-5,6-dihydro-4H-imidazo[1,5-a][1,4]benzodiazepin-6-one was stirred at room temperature overnight in 2 g (16 mmol) of dibutylamine and 15 ml of N,N-dimethylformamide. By evaporation of the reaction mixture and chromatography of the residue on silica gel while eluting with ethyl acetate there was obtained 0.82 g (65%) of 3-(5-dibutylaminomethyl-1,2,4-oxadiazol-3-yl)-5-methyl-5,6-dihydro-4H-imidazo[1,5-a][1,4]benzodiazepin-6-one, which was converted into the hydrochloride of m.p. 105°–110°.

EXAMPLE 199

1.15 g (3.5 mmol) of (S)-1-(5-chloromethyl-1,2,4-oxadiazol-3-yl)-12,12a-dihydro-9H,11H-azeto[2,1-c]imidazo[1,5-a][1,4]benzodiazepin-9-one were stirred at room temperature overnight with 0.73 g (10 mmol) of diethylamine and 10 ml of N,N-dimethylformamide. By evaporation of the reaction mixture and chromatography of the residue on silica gel while eluting with methylene chloride/methanol 19/1 there were obtained 1.23 g (93%) of (S)-1-(5-diethylaminomethyl-1,2,4-oxadiazol-3-yl)-12,12a-dihydro-9H,11H-azeto[2,1-c]imidazo[1,5-a][1,4]benzodiazepin-9-one, which was converted into the hydrochloride of m.p. 209°–211°.

EXAMPLE 200

1.15 g (3.5 mmol) of (S)-1-(5-chloromethyl-1,2,4-oxadiazol-3-yl)-12,12a-dihydro-9H,11H-azeto[2,1-c]

imidazo[1,5-a][1,4]benzodiazepin-9-one were stirred at room temperature overnight with 1.29 g (10 mmol) of dibutylamine and 10 ml of N,N-dimethylformamide. By evaporation of the reaction mixture and chromatography of the residue on silica gel while eluting with ethyl acetate there were obtained 1.04 g (68%) of (S)-1-(5-dibutylaminomethyl-1,2,4-oxadiazol-3-yl)-12,12a-dihydro-9H,11H-azeto[2,1-c]imidazo[1,5-a][1,4]benzodiazepin-9-one, which was converted into the hydrochloride (amorphous).

EXAMPLE 201 a) 30 g (106.7 mmol) of (S)-5-bromo-1,10a-dihydro-2H-azeto[2,1-c][1,4]benzodiazepine-4,10(9H)-dione were dissolved in 50 ml of N,N-dimethylformamide, treated at −20° with 5.6 g (128 mmol) of sodium hydride dispersion (55% in oil) (washed with hexane) and deprotonized at −30° to −20° for 30 minutes. A solution of 43 g (160 mmol) of diphenyl chlorophosphate in 25 ml of N,N-dimethylformamide was added thereto at −60° and the mixture was stirred at max. −45° for 35 minutes. In the meanwhile and separately, 12 g (107 mmol) of potassium tert.-butylate were dissolved in 20 ml of N,N-dimethylformamide and treated at −60° with 12.1 g (107 mmol) of ethyl isocyanoacetate. The reaction mixture is added dropwise to the deprotonized ethyl isocyanoacetate at max. −65° within 1¼ hours. The mixture was stirred for 1 hour in an acetone/dry-ice bath, neutralized with 10 ml of acetic acid and poured into 500 ml of ice-water. The mixture was extracted five times with methylene chloride (a total of 1.21), dried over magnesium sulfate and evaporated to dryness. By recrystallization of the residue from ethanol and ether there were obtained 23.7 g (49%) of ethyl (S)-8-bromo-9-oxo-12,12a-dihydro-9H,11H-azeto[2,1-c]imidazo[1,5-a]-[1,4]-benzodiazepine-1-carboxylate of m.p. 184°–185°.

b) 21.8 g (57.9 mmol) of ethyl (S)-8-bromo-9-oxo-12,12a-dihydro-9H,11H-azeto [2,1-c]imidazo [1,5-a][1,4]benzodiazepine-1-carboxylate were heated to reflux for 15 minutes with 17 ml of 4N sodium hydroxide solution and 200 ml of ethanol. 17 ml of 4N hydrochloric acid and 250 ml of water were added at room temperature. The alcohol was evaporated and the suspension was cooled to 0°. By suction filtration and drying the crystals there were obtained 19.8 g (98%) of (S)-8-bromo-9-oxo-12,12a-dihydro-9H,11H-azeto[2,1-c]imidazo[1,5-a][1,4]-benzodiazepine-1-carboxylic acid of m.p. 178°–180°.

c) 19.8 g (56.9 mmol) of (S)-8-bromo-9-oxo-12,12a-dihydro-9H,11H-azeto[2,1-c]imidazo[1,5-a][1,4]benzodiazepine-1-carboxylic acid were suspended in 100 ml of N,N-dimethylformamide, treated at room temperature with 10.1 g (62.6 mmol) of 1,1'-carbonyldiimidazole and stirred at 70° for 30 minutes. 50 ml of 25% ammonia were added dropwise at 25°–30°. The reaction mixture was diluted with 50 ml of water and cooled to 0°, and the crystallizate was filtered off under suction and dried. There were obtained 133.6 g (69%) of (S)-8-bromo-9-oxo-12,12a-dihydro-9H,11H-azeto[2,1-c]imidazo[1,5-a][1,4]benzodiazepine-1-carboxamide of m.p. 314°–317°.

d) A suspension of 19 g (54.7 mmol) of (S)-8-bromo-9-oxo-12,12a-dihydro-9H,11H-azeto[2,1-c]imidazo[1,5-a][1,4]benzodiazepine-1-carboxamide in a mixture of 100 ml of dioxan and 15 ml of pyridine was treated with 15 ml of trifluoroacetic anhydride at 7° to 10°. The suspension was stirred at room temperature for 1 hour and poured into 600 ml of water. After 1 hour the suspension was suction filtered. There were obtained 13.1 g (72%) of (S)-8-bromo-9-oxo-12,12a-dihydro-9H,11H-azeto[2,1-c]imidazo[1,5-a][1,4]benzodiazepine-1-carbonitrile of m.p. 133°–136°.

e) 13 g (39.5 mmol) of (S)-8-bromo-9-oxo-12,12a-dihydro-9H,11H-azeto[2,1-c]imidazo[1,5-a][1,4]benzodiazepine-1-carbonitrile were stirred with 7.5 g (71 mmol) of sodium carbonate and 5.7 g (82 mmol) of hydroxylamine hydrochloride in 200 ml of ethanol and 40 ml of water at 50° for 1 hour and at 75° for 10 minutes. After dilution with 50 ml of water the suspension was suction filtered, whereupon the crystals were dried. There were obtained 7.33 g (51%) of (S)-8-bromo-9-oxo-12,12a-dihydro-9H,11H-azeto[2,1-c]imidazo[1,5-a][1,4]benzodiazepine-1-carboxamidoxime of m.p. 265°–266°.

f) 7 g (19.3 mmol) of (S)-8-bromo-9-oxo-12,12a-dihydro-9H,11H-azeto[2,1-c]imidazo[1,5-a][1,4]-benzodiazepine-1-carboxamidoxime were stirred with 3.8 g (22.2 mmol) of chloroacetic anhydride in 50 ml of N,N-dimethylformamide at room temperature for 1 hour and at 105° for 2 hours. After evaporating the reaction mixture the residue was dissolved in methylene chloride and the solution was washed with saturated sodium bicarbonate solution. The organic phase was dried over magnesium sulfate and concentrated. After recrystallizing the residue from methanol there were obtained 5.3 g (65%) of (S)-8-bromo-1-(5-chloromethyl-1,2,4-oxadiazol-3-yl)-12,12a-dihydro-9H,11H-azeto[2,1-c]imidazo[1,5-a][1,4]benzodiazepin-9-one of m.p. 210°–211°.

g) 1.26 g (3 mmol) of (S)-8-bromo-1-(5-chloromethyl-1,2,4-oxadiazol-3-yl)-12,12a-dihydro-9H,11H-azeto[2,1-c]imidazo[1,5-a][1,4]benzodiazepin-9-one were stirred at room temperature for 5 hours with 0.44 g (6 mmol) of diethylamine and 10 ml of N,N-dimethylformamide. By evaporation of the reaction mixture and chromatography of the residue on silica gel while eluting with methylene chloride/methanol 19/1 there were obtained 1.14 g (82%) of (S)-8-bromo-1-(5-diethylaminomethyl-1,2,4-oxadiazol-3-yl)-12,12a-dihydro-9H,11H-azeto[2,1-c]imidazo[1,5-a][1,4]benzodiazepin-9-one, which was converted into the hydrochloride of m.p. 206°–209°.

EXAMPLE 202 a) A suspension of 12.8 g (35.4 mmol) of (S)-8-bromo-9-oxo-11,12,13,13a-tetrahydro-9H-imidazo[1,5-a]pyrrolo[2,1-c][1,4]-benzodiazepine-1-carboxamide in a mixture of 50 ml of dioxan and 7 ml of pyridine was treated at 7 to 10° with 6.5 ml of trifluoroacetic anhydride. The suspension was stirred at room temperature for 2.5 hours and poured into 200 ml of water. After 1 hour the suspension was suction filtered. There were obtained 12.1 g (100%) of (S)-8-bromo-9-oxo-11,12,13,13a-tetrahydro-9H-imidazo[1,5-a]pyrrolo[2,1-c][1,4]benzodiazepine-1-carbonitrile of m.p. 253°–254°.

b) 12 g (35 mmol) of (S)-8-bromo-9-oxo-11,12,13,13a-tetrahydro-9H-imidazo[1,5-a]pyrrolo[2,1-c][1,4]benzodiazepine-1-carbonitrile were stirred at boiling temperature for 2 hours with 9.6 g (94 mmol) of sodium bicarbonate and 7.3 g (105 mmol) of hydroxylamine hydrochloride in 170 ml of ethanol and 40 ml of water. After evaporating the alcohol the suspension obtained was cooled and the crystallizate was filtered off under suction and dried. There were obtained 11.4 g (86%) of (S)-8-bromo-9-oxo-11,12,13,13a-tetrahydro-9H-imidazo[1,5-a]pyrrolo[2,1-c][1,4]benzodiazepine-1-carboxamidoxime of m.p. 235°–237°.

c) 11.5 g (30.6 mmol) of (S)-8-bromo-9-oxo-11,12,13,13a-tetrahydro-9H-imidazo[1,5-a]pyrrolo[2,1-c][1,4]

benzodiazepine-1-carboxamidoxime were treated with 6.02 g (35.2 mmol) of chloroacetic anhydride in 60 ml of N,N-dimethylformamide at room temperature for 1 hour and at 105° for 3 hours. After evaporating the solvent the residue was dissolved in methylene chloride and the solution was washed with saturated sodium bicarbonate solution. By drying the organic phase over magnesium sulfate, evaporation of the solvent and chromatography of the residue on silica gel while eluting with ethyl acetate there were obtained 10.2 g (76%) of (S)-8-bromo-1-(5-chloromethyl-1,2,4-oxadiazol-3-yl)- 11,12,13,13a-tetrahydro-9H-imidazo[1,5-a]pyrrolo[2,1-c][1,4]benzodiazepin-9-one of m.p. 242°–244°.

d) 1.3 g (3 mmol) of (S)-8-bromo-1-(5-chloromethyl-1,2,4-oxadiazol-3-yl)-11,12,13,13a-tetrahydro-9H-imidazo[1,5-a]pyrrolo[2,1-c][1,4]benzodiazepine-9-one were stirred at room temperature for 5 hours with 1.02 g (10 mmol) of dipropylamine and 15 ml of N,N-dimethylformamide. By evaporation of the solvent and chromatography of the residue on silica gel while eluting with methylene chloride/methanol 19/1 there were obtained 1.41 g (94%) of (S)-8-bromo-1-(5-dipropylaminomethyl-1,2,4-oxadiazol-3-yl)-11,12,13,13a-tetrahydro-9H-imidazo[1,5-a]pyrrolo[2,1-c][1,4]benzodiazepin-9-one, which was converted into the hydrochloride (amorphous).

EXAMPLE 203 a) 6.24 g (18.2 mmol) of (S)-8-chloro-7-fluoro-9-oxo-12,12a-dihydro-9H,11H-azeto[2,1-c]imidazo[1,5-a][1,4]benzodiazepine-1-carboxamidoxime were stirred with 3.43 g (20 mmol) of chloroacetic anhydride and 40 ml of N,N-dimethylformamide at room temperature for 60 hours and at 105° for 2.5 hours. By evaporation of the reaction mixture and chromatography of the residue on silica gel while eluting with methylene chloride/methanol 19/1 there were obtained 1.88 g (26%) of (S)-8-chloro-1-(5-chloromethyl-1,2,4-oxadiazol-3-yl)-7-fluoro-12,12a-dihydro-9H,11H-azeto[2,1-c]imidazo[1,5-a][1,4]benzodiazepin-9-one of m.p. 214°–217°.

b) 1 g (2.5 mmol) of (S)-8-chloro-1-(5-chloromethyl-1,2,4-oxadiazol-3-yl)-7-fluoro-12,12a-dihydro-9H,11H-azeto[2,1-c]imidazo[1,5-a][1,4]benzodiazepin-9-one was stirred at room temperature overnight with 0.98 g (7.5 mmol) of dibutylamine and 10 ml of N,N-dimethylformamide. By evaporation of the reaction mixture and chromatography of the residue on silica gel while eluting with ethyl acetate there was obtained 0.44 g (36%) of (S)-8-chloro-1-(5-dibutylaminomethyl-1,2,4-oxadiazol-3-yl)-7-fluoro-12,12a-dihydro-9H,11H-azeto[2,1-c]imidazo[1,5-a][1,4]benzodiazepin-9-one, which was converted into the hydrochloride (amorphous).

EXAMPLE 204

0.88 g (2.5 mmol) of (S)-8-chloro-1-(5-chloromethyl-1,2,4-oxadiazol-3-yl)-7-fluoro-12,12a-dihydro-9H,11H-azeto[2,1-c]imidazo[1,5-a][1,4]benzodiazepin-9-one was stirred at room temperature overnight with 0.5 g (6.8 mmol) of diethylamine and 10 ml of N,N-dimethylformamide. After evaporating the reaction mixture the residue was dissolved in methylene chloride and the solution was washed with water. By drying the organic phase over magnesium sulfate and evaporating the solvent there was obtained 0.9 g (95%) of (S)-8-chloro-1-(5-diethylaminomethyl-1,2,4-oxadiazol-3-yl)-7-fluoro-12,12a-dihydro-9H,11H-azeto[2,1-c]imidazo[1,5-a][1,4]benzodiazepin-9-one, which was converted into the hydrochloride (amorphous).

EXAMPLE 205

1.19 g (3 mmol) of 3-(5-chloromethyl-1,2,4-oxadiazol-3-yl)-5-methyl-7-trifluoromethyl-5,6-dihydro-4H-imidazo[1,5-a][1,4]benzodiazepin-6-one were stirred at room temperature for 5 hours with 1.02 g (10 mmol) of dipropylamine and 15 ml of N,N-dimethylformamide. After evaporating the reaction mixture the residue was dissolved in methylene chloride and the solution was washed with water. By drying the organic phase over magnesium sulfate and evaporating the solvent there were obtained 1.33 g (96%) of 3-(5-dipropylaminomethyl-1,2,4-oxadiazol-3-yl)-5-methyl-7-trifluoromethyl-5,6-dihydro-4H-imidazo[1,5-a][1,4]benzodiazepin-6-one, which was converted into the hydrochloride of m.p. 216°–218°.

EXAMPLE 206 a) 7 g (20.6 mmol) of 5-methyl-6-oxo-7-trifluoromethyl-5,6-dihydro-4H-imidazo[1,5-a][1,4]benzodiazepine-3-carboxamidoxime were stirred in 50 ml of N,N-dimethylformamide with 4.05 g (23.7 mmol) of chloroacetic anhydride at room temperature for 2 hours and at 105° for 2 hours. By evaporation of the reaction mixture and chromatography of the residue on silica gel while eluting with ethyl acetate there were obtained 7.12 g (87%) of 3-(5-chloromethyl-1,2,4-oxadiazol-3-yl)-5-methyl-7-trifluoromethyl-5,6-dihydro-4H-imidazo[1,5-a][1,4]benzodiazepin-6-one of m.p. 180°–184°.

b) 1.19 g (3 mmol) of 3-(5-chloromethyl-1,2,4-oxadiazol-3-yl)-5-methyl-7-trifluoromethyl-5,6-dihydro-4H-imidazo [1,5-a ][1,4]benzodiazepine-6-one were stirred at room temperature overnight with 5.3 g (90 mmol) of propylamine and 10 ml of N,N-dimethylformamide. After evaporating the reaction mixture the residue was dissolved in methylene chloride and the solution was washed with water. By drying the organic phase over magnesium sulfate and evaporating the solvent there was obtained 0.84 g (67%) of 5-methyl-3-(5-propylaminomethyl-1,2,4-oxadiazol-3-yl)-7-trifluoromethyl-5,6-dihydro-4H-imidazo[1,5-a][1,4]benzodiazepin-6-one, which was converted into the hydrochloride of m.p. 234°–237°.

EXAMPLE 207 a) 24.9 g (74.1 mmol) of 7-bromo-5-methyl-6-oxo-5,6-dihydro-4H-imidazo[1,5-a][1,4]benzodiazepine-3-carboxylic acid were suspended in 100 ml of N,N-dimethylformamide, treated at room temperature with 14.3 g (89 mmol) of 1,1'-carbonyldiimidazole and stirred at 70° for 30 minutes. 50 ml of 25% ammonia were added dropwise at 25°–30°. The reaction mixture was diluted with 200 ml of water and cooled to 0°, and the crystallizate was filtered off under suction and dried. There were obtained 21.6 g (86%) of 7-bromo-5-methyl-6-oxo-5,6-dihydro-4H-imidazo[1,5-a][1,4]benzodiazepine-3-carboxamide of m.p. 278°–279°.

b) A suspension of 21.5 g (64.1 mmol) of 7-bromo-5-methyl-6-oxo-5,6-dihydro-4H-imidazo[1,5-a][1,4]benzodiazepine-3-carboxamide in a mixture of 100 ml of dioxan and 15 ml of pyridine was treated at 7° to 10° with 15 ml of trifluoroacetic anhydride. The suspension was stirred at room temperature for 1 hour and poured into 600 ml of water. After 1 hour the suspension was suction filtered. There were obtained 17.8 g (88%) of 7-bromo-5-methyl-6-oxo-5,6-dihydro-4H-imidazo[1,5-a][1,4]benzodiazepine-3-carbonitrile of m.p. 226°–228°.

c) 17.85 g (56.3 mmol) of 7-bromo-5-methyl-6-oxo-5,6-dihydro-4H-imidazo[1,5-a][1,4]benzodiazepine-3- carbonitrile were stirred with 10.3 g (97.7 mmol) of sodium carbonate and 8 g (115.1 mmol) of hydroxylamine hydrochloride in 300 ml of ethanol and 60 ml of water at 50° for 1 hour and at 75° for 20 minutes. After dilution with 50 ml of water the suspension was suction filtered and the crystals were dried. There were obtained 16.95 g (86%) of 7-bromo-5-methyl-6-oxo-5,6-dihydro-4H-imidazo[1,5-a][1,4]benzodiazepine-3-carboxamidoxime of m.p. 265°–266°.

d) 16.9 g (48.3 mmol) of 7-bromo-5-methyl-6-oxo-5,6-dihydro-4H-imidazo[1,5-a][1,4]benzodiazepine-3-carboxamidoxime were stirred with 9.5 g (55.5 mmol) of chloroacetic anhydride in 100 ml of N,N-dimethylformamide at room temperature for 1 hour and at 105° for 3 hours. After evaporating the solvent the residue was dissolved in methylene chloride and the solution was washed with saturated sodium bicarbonate solution. By drying the organic phase over magnesium sulfate, evaporation of the solvent and chromatography of the residue on silica gel while eluting with methylene chloride/methanol 9/1 there were obtained 16.3 g (84%) of 7-bromo-3-(5-chloromethyl-1,2,4-oxadiazol-3-yl)-5-methyl-5, 6-dihydro-4H-imidazo[1,5-a][1,4]benzodiazepin-6-one of m.p. 242°–244°.

e) 2.04 g (5 mmol) of 7-bromo-3-(5-chloromethyl-1,2,4-oxadiazol-3-yl)-5-methyl-5,6-dihydro-4H-imidazo[1,5-a][1,4]-benzodiazepin-6-one were stirred at room temperature for 4 hours with 1.5 g (15 mmol) of dipropylamine and 15 ml of N,N-dimethylformamide. By evaporation of the reaction mixture and chromatography of the residue on silica gel while eluting with ethyl acetate there were obtained 1.61 g (68%) of 7-bromo-3-(5-dipropylaminomethyl-1,2,4-oxadiazol-3-yl)-5-methyl-5,6-dihydro-4H-imidazo[1,5-a][1,4]benzodiazepin-6-one, which was converted into the hydrochloride of m.p. 135°–145°.

EXAMPLE 208

2.1 g (5 mmol) of (S)-8-bromo-1-(5-chloromethyl-1,2,4-oxadiazol-3-yl)-12,12a-dihydro-9H,11H-azeto[2,1-c]imidazo[1,5-a][1,4]benzodiazepin-9-one were stirred at room temperature for 2 hours with 1.52 g (15 mmol) of dipropylamine and 15 ml of N,N-dimethylformamide. By evaporation of the reaction mixture and chromatography of the residue on silica gel while eluting with ethyl acetate there were obtained, after recrystallization from ethyl acetate, 1.2 g (50%) of (S)-8-bromo-1-(5-dipropylaminomethyl-1,2,4-oxadiazol-3-yl)-12,12a-dihydro-9H,11H-azeto[2,1-c]imidazo[1,5-a][1,4]benzodiazepin-9-one of m.p. 1222°–124°, which was converted into the hydrochloride of m.p. 196°–198°.

EXAMPLE 209

1.88 g (5 mmol) of (S)-8-chloro-1-(5-chloromethyl-1,2,4-oxadiazol-3-yl)-12,12a-dihydro-9H,11H-azeto[2,1-c]imidazo[1,5-a][1,4]benzodiazepin-9-one were stirred at room temperature for 4 hours with 2 g (2.2 mmol) of bis(2-methoxyethyl)-amine and 15 ml of N,N-dimethylformamide. After evaporating the solvent the reaction mixture was taken up in 4N sodium hydroxide solution, whereupon the mixture was extracted three times with methylene chloride. By drying the organic phase over magnesium sulfate and evaporating the solvent there were obtained 2.2 g (93%) of (S)-8-chloro-1-[5-di(2-methoxyethyl)aminomethyl-1,2,4-oxadiazol-3-yl]-12,12a-dihydro-9H,11H-azeto[2,1-c]imidazo[1,5-a][1,4]benzodiazepin-9-one, which was converted into the hydrochloride of m.p. 188°–190°.

EXAMPLE 210

0.94 g (2.5 mmol) of (S)-8-chloro-1-(5-chloromethyl-1,2,4-oxadiazol-3-yl)-12,12a-dihydro-9H,11H-azeto[2,1-c]imidazo[1,5-a][1,4]benzodiazepin-9-one was stirred at room temperature overnight with 1 g (17 mmol) of propylamine and 15 ml of N,N-dimethylformamide. By evaporation of the reaction mixture and chromatography of the residue on silica gel while eluting with ethyl acetate/methanol 9/1 there was obtained 0.92 g (92%) of (S)-8-chloro-1-(5-propylaminomethyl-1,2,4-oxadiazol-3-yl)-12,12a-dihydro-9H,11H-azeto[2,1-c]imidazo[1,5-a][1,4]benzodiazepin-9-one of m.p. 237°–239°, which was converted into the hydrochloride.

EXAMPLE 211

1.5 g (4.5 mmol) of 3-(5-chloromethyl-1,2,4-oxadiazol-3-yl)-5-methyl-5,6-dihydro-4H-imidazo[1,5-a][1,4]benzodiazepin-6-one were stirred at room temperature overnight with 0.5 g (4.4 mmol) of heptamethyleneimine and 10 ml of N,N-dimethylformamide. By evaporation of the reaction mixture and chromatography of the residue on silica gel while eluting with ethyl acetate there was obtained 0.2 g (12%) of 3-[5-(heptamethylenimin-1-yl)methyl-1,2,4-oxadiazol-3-yl]-5-methyl-5,6-dihydro-4H-imidazo[1,5-a][1,4]benzodiazepin-6-one, which was converted into the hydrochloride of m.p. 246°–248°.

EXAMPLE 212

0.7 g (2.1 mmol) of 3-(5-chloromethyl-1,2,4-oxadiazol-3-yl)-5-methyl-5,6-dihydro-4H-imidazo[1,5-a][1,4]benzodiazepin-6-one was stirred at room temperature overnight with 0.5 g (5 mmol) of hexamethylenimine and 10 ml of N,N-dimethylformamide. By evaporation of the reaction mixture and chromatography of the residue on silica gel while eluting with ethyl acetate there was obtained 0.76 g (90%) of 3-[5-(hexamethylenimin-1-yl) methyl-1,2,4-oxadiazol-3-yl]-5-methyl-5,6-dihydro-4H-imidazo[1,5-a][1,4]benzodiazepin-6-one of m.p. 158°–159°, which was converted into the hydrochloride.

EXAMPLE 213

1.13 g (3 mmol) of (S)-8-chloro-1-(5-chloromethyl-1,2,4-oxadiazol-3-yl)-12,12a-dihydro-9H,11H-azeto[2,1-c]imidazo[1,5-a][1,4]benzodiazepine-9-one were stirred at 65° overnight with 5 ml (25 mmol) of dicyclohexylamine and 7 ml of N,N-dimethylformamide. By evaporation of the reaction mixture and chromatography of the residue on silica gel while eluting with ethyl acetate there was obtained 0.8 g (51%) of (S)-8-chloro-1-(5-dicyclohexylaminomethyl-1,2,4-oxadiazol-3-yl)-12,12a-dihydro-9H,11H-azeto[2,1-c]imidazo[1,5-a][1,4]benzodiazepin-9-one, which was converted into the hydrochloride of m.p. 155°–185°.

EXAMPLE 214

1.13 g (3 mmol) of (S)-8-chloro-1-(5-chloromethyl-1,2,4-oxadiazol-3-yl)-12,12a-dihydro-9H,11H-azeto[2,1-c]imidazo[1,5-a][1,4]benzodiazepin-9-one were stirred at 70° for 4 hours with 2 g (17 mmol) of 2,6-dimethylpiperidine and 15 ml of N,N-dimethylformamide. By evaporation of the reaction mixture and chromatography of the residue on silica gel while eluting with ethyl acetate/methanol 9/1 there was obtained 0.83 g (61%) of (S)-8-chloro-1-[5-(2,6-dimethylpiperidin-1-yl)methyl-1,2,4-oxadiazol-3-yl]-12,12a-dihydro-9H,11H-azeto[2,1-c]imidazo[1,5-a][1,4] benzodiazepin-9-one, which was converted into the hydrochloride of m.p. 233°–236°.

EXAMPLE 215

1.13 g (3 mmol) of (S)-8-chloro-1-(5-chloromethyl-1,2,4-oxadiazol-3-yl)-12,12a-dihydro-9H,11H-azeto[2,1-c]imidazo[1,5-a][1,4]benzodiazepin-9-one were stirred at room temperature overnight with 2 g (12.7 mmol) of dipentylamine and 15 ml of N,N-dimethylformamide. By evaporation of the reaction mixture and chromatography of the residue on silica gel while eluting with ethyl acetate there were obtained 1.01 g (68%) of (S)-8-chloro-1-(5-dipentylaminomethyl-1,2,4-oxadiazol-3-yl)-12,12a-dihydro-9H,11H-azeto[2,1-c]imidazo[1,5-a][1,4]benzodiazepin-9-one, which was converted into the hydrochloride (amorphous).

EXAMPLE 216

1.13 g (3 mmol) of (S)-8-chloro-1-(5-chloromethyl-1,2,4-oxadiazol-3-yl)-12,12a-dihydro-9H,11H-azeto[2,1-c]imidazo[1,5-a][1,4]benzodiazepin-9-one were stirred at room temperature overnight with 2 g (17.7 mmol) of 3,3-dimethylpiperidine and 15 ml of N,N-dimethylformamide. By evaporation of the reaction mixture and chromatography of the residue on silica gel while eluting with ethyl acetate there were obtained 1.34 g (98%) of (S)-8-chloro-1-[5-(3,3-dimethyl-piperidin-1-yl)methyl-1,2,4-oxadiazol-3-yl]-12,12a-dihydro-9H,11H-azeto[2,1-c]imidazo[1,5-a][1,4]benzodiazepin-9-one, which was converted into the hydrochloride (amorphous).

EXAMPLE 217 a) 9.8 g (32.1 mmol) of 7-chloro-5-methyl-6-oxo-5,6-dihydro-4H-imidazo[1,5-a][1,4]-benzodiazepine-3-carboxamidoxime were stirred with 7 g (41 mmol) of chloroacetic anhydride in 60 ml of N,N-dimethylformamide at room temperature for 1 hour and at 105° for 4 hours. After evaporating the reaction mixture the residue was dissolved in methylene chloride and the solution was washed with saturated sodium bicarbonate solution. The organic phase was dried over magnesium sulfate and concentrated, and the residue was chromatographed on silica gel while eluting with ethyl acetate. There were obtained 6.63 g (57%) of 7-chloro-3-(5-chloromethyl-1,2,4-oxadiazol-3-yl)-5-methyl-5,6-dihydro-4H-imidazo[1,5-a][1,4]benzodiazepin-6-one of m.p. 208°–210°.

b) 1.6 g (4.4 mmol) of 7-chloro-3-(5-chloromethyl-1,2,4-oxadiazol-3-yl)-5-methyl-5,6-dihydro-4H-imidazo[1,5-a][1,4]benzodiazepin-6-one were stirred at room temperature for 4.5 hours with 1.1 g (15 mmol) of diethylamine and 10 ml of N,N-dimethylformamide. By evaporation of the reaction mixture and chromatography of the residue on silica gel while eluting with methylene chloride/methanol 9/1 there were obtained 1.50 g (85%) of 7-chloro-3-(5-diethylaminomethyl-1,2,4-oxadiazol-3-yl)-5-methyl-5,6-dihydro-4H-imidazo[1,5-a][1,4]benzodiazepin-6-one, which was converted into the hydrochloride of m.p. 250°–252°.

EXAMPLE 218

1.6 g (4.4 mmol) of 7-chloro-3-(5-chloromethyl-1,2,4-oxadiazol-3-yl)-5-methyl-5,6-dihydro-4H-imidazo[1,5-a][1,4]benzodiazepin-6-one were stirred at room temperature for 48 hours with 3.6 ml (21 mmol) of dibutylamine and 10 ml of N,N-dimethylformamide. By evaporation of the reaction mixture and chromatography of the residue on silica gel while eluting with ethyl acetate there was obtained 1.23 g (61%) of 7-chloro-3-(5-dibutylaminomethyl-1,2,4-oxadiazol-3-yl)-5-methyl-5,6-dihydro-4H-imidazo[1,5-a][1,4]benzodiazepin-6-one of m.p. 140°–142°, which was converted into the hydrochloride of m.p. 184°–187°.

EXAMPLE 219

1.13 g (3 mmol) of (S)-8-chloro-1-(5-chloromethyl-1,2,4-oxadiazol-3-yl)-12,12a-dihydro-9H,11H-azeto[2,1-c]imidazo[1,5-a][1,4]benzodiazepin-9-one were stirred at room temperature overnight with 1.7 g (9 mmol) of dihexylamine and 15 ml of N,N-dimethylformamide. By evaporation of the reaction mixture and chromatography of the residue on silica gel while eluting with ethyl acetate there was obtained 0.89 g (56%) of (S)-8-chloro-1-(5-dihexylaminomethyl-1,2,4-oxadiazol-3-yl)-12,12a-dihydro-9H,11H-azeto[2,1-c]imidazo[1,5-a][1,4]benzodiazepin-9-one, which was converted into the hydrochloride (amorphous).

EXAMPLE 220

1.15 g (3.5 mmol) of 3-(5-chloromethyl-1,2,4-oxadiazol-3-yl)-5-methyl-5,6-dihydro-4H-imidazo[1,5-a][1,4]benzodiazepin-6-one were stirred at room temperature for 1 hour with 1 g (8.8 mmol) of 3,3-dimethylpiperidine and 10 ml of N,N-dimethylformamide. By evaporation of the reaction mixture and chromatography of the residue on silica gel while eluting with ethyl acetate/ethanol 9/1 there were obtained 1.32 g (92%) of 3-[5-(3,3-dimethylpiperidin-1-yl)methyl-1,2,4-oxadiazol-3-yl]-5-methyl-5,6-dihydro-4H-imidazo[1,5-a][1,4]benzodiazepin-6-one of m.p. 167°–168°, which was converted into the hydrochloride.

EXAMPLE 221

1.15 g (3.5 mmol) of 3-(5-chloromethyl-1,2,4-oxadiazol-3-yl)-5-methyl-5,6-dihydro-4H-imidazo[1,5-a][1,4]benzodiazepin-6-one were stirred at room temperature for 1 hour with 1 g (11.7 mmol) of piperidine and 10 ml of N,N-dimethylformamide. By evaporation of the reaction mixture and chromatography of the residue on silica gel while eluting with ethyl acetate/ethanol 9/1 there was obtained 0.98 g (74%) of 5-methyl-3-[5-(piperidin-1-yl)methyl-1,2,4-oxadiazol-3-yl]-5,6-dihydro-4H-imidazo[1,5-a][1,4]benzodiazepin-6-one of m.p. 167°–168°, which was converted into the hydrochloride.

EXAMPLE 222

1.3 g (3.6 mmol) of 7-chloro-3-(5-chloromethyl-1,2,4-oxadiazol-3-yl)-5-methyl-5,6-dihydro-4H-imidazo[1,5-a][1,4]benzodiazepin-6-one were stirred at room temperature overnight with 1.6 ml (8.9 mmol) of diisobutylamine and 15 ml of N,N-dimethylformamide. By evaporation of the reaction mixture and chromatography of the residue on silica gel while eluting with ethyl acetate there was obtained 0.69 g (42%) of 7-chloro-3-(5-diisobutylaminomethyl-1,2,4-oxadiazol-3-yl)-5-methyl-5,6-dihydro-4H-imidazo[1,5-a][1,4]benzodiazepin-6-one of m.p. 158°–160°, which was converted into the hydrochloride of m.p. 125°–128°.

EXAMPLE 223

1.13 g (3 mmol) of (S)-8-chloro-1-(5-chloromethyl-1,2,4-oxadiazol-3-yl)-12,12a-dihydro-9H,11H-azeto[2,1-c]imidazo[1,5-a][1,4]benzodiazepin-9-one were stirred at room temperature overnight with 0.97 g (7.5 mmol) of diisobutylamine and 15 ml of N,N-dimethylformamide. By evaporation of the reaction mixture and chromatography of the residue on silica gel while eluting with ethyl acetate there was obtained 1.07 g (76%) of (S)-8-chloro-1-(5-diisobutylaminomethyl-1,2,4-oxadiazol-3-yl)-12,12a-dihydro-9H,11H-azeto[2,1-c]imidazo[1,5-a][1,4]benzodiazepin-9-one, which was converted into the hydrochloride of m.p. 125°–140°.

EXAMPLE 224

72 g (212 mmol) of 3-(5-chloromethyl-1,2,4-oxadiazol-3-yl)-5-methyl-5,6-dihydro-4H-imidazo[1,5-a][1,4]benzodiazepin-6-one were stirred at 80° for 16 hours in 150 ml (1.06 mol) of diisopropylamine and 300 ml of N,N-dimethylformamide. After evaporating the solvent the residue was dissolved in methylene chloride and the solution was extracted twice with 100 ml of 2N hydrochloric acid. The acidic phase was made alkaline with conc. sodium hydroxide solution and extracted with methylene chloride. The organic phase was dried over magnesium sulfate and evaporated. By chromatography of the residue on silica gel while eluting with ethyl acetate/methanol/acetic acid 95/3/2 and recrystallization from ethanol there were obtained 51.6 g (61%) of 3-(5-diisopropylaminomethyl-1,2,4-oxadiazol-3-yl)-5-methyl-5,6-dihydro-4H-imidazo[1,5-a][1,4]benzodiazepin-6-one of m.p. 117°–119°.

EXAMPLE 225

1 g (3 mmol) of (5-chloromethyl-1,2,4-oxadiazol-3-yl)-5-methyl-5,6-dihydro-4H-imidazo[1,5-a][1,4]benzodiazepine-6-one was stirred at room temperature overnight in 3 ml (17 mmol) of diisobutylamine and 15 ml of N,N-dimethylformamide. By evaporation of the reaction mixture and chromatography of the residue on silica gel while eluting with ethyl acetate there were obtained 1.2 g (94%) of 3-(5-diisobutylaminomethyl-1,2,4-oxadiazol-3-yl)-5-methyl-5,6-dihydro-4H-imidazo[1,5-a][1,4]benzodiazepin-6-one of m.p. 170°–172°, which was converted into the hydrochloride of m.p. 200°–202°.

EXAMPLE 226

1.65 g (5 mmol) of 3-(5-chloromethyl-1,2,4-oxadiazol-3-yl)-5-methyl-5,6-dihydro-4H-imidazo[1,5-a][1,4]benzodiazepin-6-one were stirred at 75° for 24 hours in 3 ml (17.5 mmol) of di-sec.-butylamine and 25 ml of N,N-dimethylformamide. By evaporation of the reaction mixture and chromatography of the residue on silica gel while eluting with methylene chloride/methanol 19/1 and crystallization from ethyl acetate there were obtained 1.23 g (58%) of 3-(5-di-sec.-butylaminomethyl-1,2,4-oxadiazol-3-yl)-5-methyl-5,6-dihydro-4H-imidazo[1,5-a][1,4]-benzodiazepin-6-one of m.p. 155°–157°, which was converted into the hydrochloride of m.p. 133°–140°.

EXAMPLE 227

1.82 g (5 mmol) of 7-chloro-3-(5-chloromethyl-1,2,4-oxadiazol-3-yl)-5-methyl-5,6-dihydro-4H-imidazo[1,5-a][1,4]benzodiazepin-6-one were stirred at 80° overnight with 3 ml (21.3 mmol) of diisopropylamine and 20 ml of N,N-dimethylformamide. By evaporation of the reaction mixture and chromatography of the residue on silica gel while eluting with cyclohexane/ether/isopropanol/ammonia 15/15/5/0.5 there were obtained 1.41 g (66%) of 7-chloro-3-(5-diisopropylaminomethyl-1,2,4-oxadiazol-3-yl)-5-methyl-5,6-dihydro-4H-imidazo[1,5-a][1,4]benzodiazepin-6-one of m.p. 58°–63°, which was converted into the hydrochloride of m.p. 230°–231°.

EXAMPLE 228

3.30 g (10 mmol) of 3-(5-chloromethyl-1,2,4-oxadiazol-3-yl)-5-methyl-5,6-dihydro-4H-imidazo[1,5-a][1,4]benzodiazepin-6-one were stirred at room temperature for 2.5 hours with 3 g (50 mmol) of isopropylamine and 20 ml of N,N-dimethylformamide. After evaporating the solvent the residue was dissolved in methylene chloride and the solution was washed twice with water. The organic solution was dried over magnesium sulfate and concentrated. By recrystallizing the residue from ethyl acetate there were obtained 2.37 g (67%) of 3-(5-isopropylaminomethyl-1,2,4-oxadiazol-3-yl)-5-methyl-5,6-dihydro-4H-imidazo[1,5-a][1,4]benzodiazepin-6-one of m.p. 142°–144°, which was converted into the hydrochloride of m.p. 252°–254°.

EXAMPLE 229 a) A suspension of 7.07 g (21.3 mmol) of (S)-8-chloro-9-oxo-11,12,13,13a-tetrahydro-9H-imidazo[1,5-a]pyrrolo[2,1-c][1,4]benzodiazepine-1-carboxamidoxime in 50 ml of N,N-dimethylformamide was treated with 4.0 g (23.4 mmol) of chloroacetic anhydride. The yellow solution obtained was stirred at 105° for 2 hrs. and then completely freed from the solvents. The oily product was chromatographed over silica gel with methylene chloride/methanol 9:1 as the eluent and the oily product obtained was recrystallized from ethyl acetate/ether. The mother liquor was concentrated, the residue was again chromatographed over silica gel with acetonitrile as the eluent and the additional portion of product obtained was recrystallized from ethyl acetate/ether. There were obtained a total of 6.27 g (75%) of (S)-8-chloro-1-(5-chloromethyl-1,2,4-oxadiazol-3-yl)-11,12,13,13a-tetrahydro-9H-imidazo[1,5-a]pyrrolo[2,1-c][1,4]benzodiazepin-9-one as white crystals; m.p. 184°–186° and $[\alpha]_D^{20}=+36.1°$ (MeOH, c=1%).

b) A suspension of 1.85 g (4.74 mmol) of (S)-8-chloro-1-(5-chloromethyl-1,2,4-oxadiazol-3-yl)-11,12,13,13a-tetrahydro-9H-imidazo[1,5-a]pyrrolo[2,1-c][1,4]benzodiazepin-9-one in 30 ml of N,N-dimethylformamide was treated with 1.73 g (23.7 mmol) of diethylamine. After stirring at room temperature for 16 hrs. the solution obtained was completely freed from the solvents. The residue was chromatographed over silica gel with methylene chloride/methanol 19:1 as the eluent. There were obtained 1.54 g (76%) of (S)-8-chloro-1-(5-diethylaminomethyl-1,2,4-oxadiazol-3-yl)-11,12,13,13a-tetrahydro-9H-imidazo-[1,5-a]pyrrolo[2,1-c][1,4]benzodiazepin-9-one as a pale yellow oil. A sample was recrystallized from ether and gave white crystals; m.p. 151°–153° and $[\alpha]_D^{20}=+35.5°$ (MeOH, c=1%).

c) 0.84 g (1.96 mmol) of (S)-8-chloro-1-(5-diethylaminomethyl-1,2,4-oxadiazol-3-yl)-11,12,13,13a-tetrahydro-9H-imidazo[1,5-a]pyrrolo[2,1-c][1,4]benzodiazepin-9-one in 10 ml of ethanol was treated with 0.41 ml (1.96 mmol) of 4.78N ethanolic hydrochloric acid. After stirring at room temperature for 10 minutes the solution obtained was completely freed from the solvents. The residue was recrystallized from ethanol/ether. There was obtained 0.70 g (77%) of (S)-8-chloro-1-(5-diethylaminomethyl-1,2,4-oxadiazol-3-yl)-11,12,13,13a-tetrahydro-9H-imidazo[1,5-a]pyrrolo[2,1-c][1,4]benzodiazepin-9-one hydrochloride (1:1) as white crystals; m.p. 205°–207° and $[\alpha]_D^{20}=+25.2°$ (MeOH, c=1%).

EXAMPLE 230 a) A suspension of 1.85 g (4.74 mmol) of (S)-8-chloro-1-(5-chloromethyl-1,2,4-oxadiazol-3-yl)-11,12,13,13a-tetrahydro-9H-imidazo[1,5-a]pyrrolo[2,1-c][1,4]benzodiazepin-9-one in 30 ml of N,N-dimethylformamide was treated with 2.40 g (23.7 mmol) of dipropylamine. After stirring at room temperature for 16 hrs. the solution obtained was completely freed from the solvents. The residue was chromatographed over silica gel with methylene chloride/methanol 19:1 as the eluent. There were obtained 2.03 g (94%) of (S)-8-chloro-1-(5-dipropylaminomethyl-1,2,4-oxadiazol-3-yl)-11,12,13,13a-tetrahydro-9H-imidazo[1,5-a]pyrrolo[2,1-c][1,4]benzodiazepin-9-one as a pale yellow oil; $[\alpha]_D^{20}=+29.3°$ (MeOH, c=1%).

b) 1.93 g (4.24 mmol) of (S)-8-chloro-1-(5-dipropylaminomethyl-1,2,4-oxadiazol-3-yl)-11,12,13,13a-tetrahydro-9H-imidazo[1,5-a]pyrrolo[2,1-c][1,4]benzodiazepin-9-one in 20 ml of ethanol were treated with 0.88 ml (4.2 mmol) 4.78N ethanolic hydrochloric acid. After stirring at room temperature for 10 minutes the solution obtained was completely freed from the solvents. The residue was recrystallized from ethanol/ether. There were obtained 1.42 g (68%) of (S)-8-chloro-1-(5-dipropylaminomethyl-1,2,4-oxadiazol-3-yl)-11,12,13,13a-tetrahydro-9H-imidazo[1,5-a]pyrrolo[2,1-c][1,4]benzodiazepin-9-one hydrochloride (1:1) as white crystals; m.p. 183°–185° and $[\alpha]_D^{20}=+24.4°$ (MeOH, c=1%).

EXAMPLE 231 a) A suspension of 1.85 g (4.74 mmol) of (S)-8-chloro-1-(5-chloromethyl-1,2,4-oxadiazol-3-yl)-11,12,13,13a-tetrahydro-9H-imidazo[1,5-a]pyrrolo[2,1-c][1,4]benzodiazepin-9-one in 30 ml of N,N-dimethylformamide was treated with 3.06 g (23.7 mmol) of dibutylamine. After stirring at room temperature for 16 hrs. the solution obtained was completely freed from the solvents. The residue was chromatographed over silica gel with methylene chloride/methanol 19:1 as the eluent. There were obtained 2.15 g (94%) of (S)-8-chloro-1-(5-dibutylaminomethyl-1,2,4-oxadiazol-3-yl)-11,12,13,13a-tetrahydro-9H-imidazo[1,5-a]-pyrrolo[2,1-c][1,4]benzodiazepin-9-one as a pale yellow oil; $[\alpha]_D^{20}=+28.7°$ (MeOH, c=1%).

b) 2.01 g (4.16 mmol) of (S)-8-chloro-1-(5-dibutylaminomethyl-1,2,4-oxadiazol-3-yl)-11,12,13,13a-tetrahydro-9H-imidazo[1,5-a]pyrrolo[2,1-c][1,4]benzodiazepin-9-one in 20 ml of ethanol were treated with 1.12 ml (4.14 mmol) of 3.70N ethanolic hydrochoric acid. After stirring at room temperature for 10 minutes the solution obtained was completely freed from the solvents. The residue was recrystallized from ethanol/ether. There were obtained 1.99 g (92%) of (S)-8-chloro-1-(5-dibutylaminomethyl-1,2,4-oxadiazol-3-yl)-11,12,13,13a-tetrahydro-9H-imidazo[1,5-a]pyrrolo[2,1-c][1,4]benzodiazepin-9-one hydrochloride (1:1) as white crystals; m.p. 163°–165° and $[\alpha]_D^{20}=+23.2°$ (MeOH, c=1%).

EXAMPLE 232 a) 0.66 g (1.9 mmol) of 3-(5-chloromethyl-1,2,4-oxadiazol-3-yl)-8-fluoro-5-methyl-5,6-dihydro-4H-imidazo[1,5-a][1,4]benzodiazepin-6-one was dissolved in 20 ml of N,N-dimethylformamide. A weak stream of ethylamine gas was introduced at room temperature, the reaction temperature rising to 36°. After stirring at room temperature for 16 hrs. the solution obtained was completely freed from the solvents. The residue was chromatographed over silica gel with methylene chloride/methanol 19:1 as the eluent. After concentration there was obtained a beige foam which was taken up in ether. There was obtained 0.40 g (59%) of 3-(5-ethylaminomethyl-1,2,4-oxadiazol-3-yl)-8-fluoro-5-methyl-5,6-dihydro-4H-imidazo[1,5-a][1,4]benzodiazepin-6-one as beige crystals; m.p. 166°–168°.

b) 0.37 g (1.04 mmol) of 3-(5-ethylaminomethyl-1,2,4-oxadiazol-3-yl)-8-fluoro-5-methyl-5,6-dihydro-4H-imidazo[1,5-a][1,4]benzodiazepin-6-one in 6 ml ethanol was treated with 0.31 ml (1.14 mmol) of 3.70N ethanolic hydrochloric acid. Crystals separated after adding 20 ml of acetic acid at 0°. There was obtained 0.30 g (73%) of 3-(5-ethylaminomethyl-1,2,4-oxadiazol-3-yl)-8-fluoro-5-methyl-5,6-dihydro-4H-imidazo[1,5-a][1,4]benzodiazepin-6-one hydrochloride (1:1) as whitish crystals; m.p. 250°–252° (dec.).

EXAMPLE 233 a) 19.8 g (0.0639 mol) of 7-chloro-8-fluoro-5-methyl-6-oxo-5,6-dihydro-4H-imidazo[1,5-a][1,4]benzodiazepine-3-carboxylic acid were suspended in 100 ml of N,N-dimethylformamide while gassing with argon and treated portionwise at room temperature with 10.9 g (0.0671 mol) of 1,1'-carbonyldiimidazole. After the $CO_2$ evolution had finished the beige suspension was stirred at 50° for 30 min., cooled and treated dropwise at a temperature below 25° within about 10 min. with 20 ml of 25% ammonia. After stirring for 15 minutes the brownish solution obtained was poured into 600 ml of ice-water. The mixture was stirred at room temperature for 30 min. and filtered, whereupon the crystals were rinsed with a total of 200 ml of water. After drying there were obtained 14.4 g (73%) of 7-chloro-8-fluoro-5-methyl-6-oxo-5,6-dihydro-4H-imidazo[1,5-a][1,4]benzodiazepine-3-carboxamide as beige crystals; m.p. 292°–294°.

b) 14.4 g (0.0466 mol) of 7-chloro-8-fluoro-5-methyl-6-oxo-5,6-dihydro-4H-imidazo[1,5-a][1,4]benzodiazepine-3-carboxamide was suspended in 60 ml of dioxan and 8 ml of pyridine and treated dropwise at a temperature of −8° within 10 min. with 10.3 g (0.049 mol) of trifluoroacetic anhydride. The mixture was stirred at 50° for 3 hours and poured into 400 ml of water. The mixture was extracted with ethyl acetate, dried over magnesium sulfate, filtered and the filtrate was concentrated. The residue was dissolved in 300 ml of hot ethyl acetate, the solution was suction filtered over 100 g of silica gel, the silica gel was rinsed with 200 ml of ethyl acetate and the filtrate was evaporated. There were obtained 12 g (89%) of 7-chloro-8-fluoro-5-methyl-6-oxo-5,6-dihydro-4H-imidazo[1,5-a][1,4]benzodiazepine-3-carbonitrile as light yellowish crystals; m.p. 221°–223°.

c) 1.0 g (0.0432 mol) of sodium was dissolved in 60 ml of methanol. 8.85 g (0.0304 mol) of 7-chloro-8-fluoro-5-methyl-6-oxo-5,6-dihydro-4H-imidazo[1,5-a][1,4]benzodiazepine-3-carbonitrile and 3.25 g (0.0469 mol) of hydroxylamine hydrochloride were added thereto in succession at room temperature. The white suspension was stirred at room temperature for 67 hrs. and evaporated, whereupon the residue was suspended in 100 ml of water and the crystals were filtered off. By drying the crystallizate there were obtained 8.2 g (83%) of 7-chloro-8-fluoro-5-methyl-6-oxo-5,6-dihydro-4H-imidazo[1,5-a][1,4]benzodiazepine-3-carboxamidoxime as white crystals; m.p. 228°–231°.

The aqueous phase was extracted with ethyl acetate, dried over magnesium sulfate, filtered and concentrated, there being obtained 0.95 g (10%) of additional material (m.p. 225°–228°).

d) A suspension of 7.0 g (0.0216 mol) of 7-chloro-8-fluoro-5-methyl-6-oxo-5,6-dihydro-4H-imidazo[1,5-a][1,4]benzodiazepine-3-carboxamidoxime in 70 ml of N,N-dimethylformamide was treated with 4.38 g (0.0256 mol) of chloroacetic anhydride. The yellow solution obtained was stirred at 100° for 2 hrs. and then completely freed from the solvents. The oily product was taken up in 300 ml of acetonitrile, whereupon the solution was treated with active charcoal, boiled at reflux and filtered while hot over 100 g of silica gel; the silica gel was rinsed with 200 ml of acetone and the filtrate was evaporated. The crystalline foam was suspended in 100 ml of ether and suction filtered. Additional material could be obtained from the mother liquor. There was obtained a total of 5.65 g (68%) of 7-chloro-3-(5-chloromethyl-1,2,4-oxadiazol-3-yl)-8-fluoro-5-methyl-5,6-dihydro-4H-imidazo[1,5-a ][1,4]benzodiazepin-6-one as white-yellowish crystals; m.p. 215°–218°.

e) A suspension of 1.30 g (3.4 mmol) of 7-chloro-3-(5-chloromethyl-1,2,4-oxadiazol-3-yl)-8-fluoro-5-methyl-5,6-dihydro-4H-imidazo[1,5-a][1,4]benzodiazepin-6-one in 13 ml of N,N-dimethylformamide was treated with 1.24 g (0.017 mol) of diethylamine. After stirring at room temperature for 16 hrs. the solution obtained was completely freed from the solvents. The residue was chromatographed over silica gel with methylene chloride/methanol 39:1 as the eluent. The product was recrystallized from ether/n-hexane. There was obtained 1.3 g (91%) of 7-chloro-3-(5-diethylaminomethyl-1,2,4-oxadiazol-3-yl)-8-fluoro-5-methyl-5,6-dihydro-4H-imidazo[1,5-a][1,4]benzodiazepin-6-one as white crystals; m.p. 140°–144° (dec.).

f) 1.28 g (3.06 mmol) of 7-chloro-3-(5-diethylaminomethyl-1,2,4-oxadiazol-3-yl)-8-fluoro-5-methyl-5,6-dihydro-4H-imidazo[1,5-a][1,4]benzodiazepin-6-one in 20 ml of ethanol were treated with 0.91 ml (3.36 mmol) of 3.7N ethanolic hydrochloric acid. After stirring at room temperature for 10 minutes the white suspension obtained was treated with 100 ml of ether and suction filtered. There were obtained 1.31 g (94%) of 7-chloro-3-(5-diethylaminomethyl-1,2,4-oxadiazol-3-yl)-8-fluoro-5-methyl-5,6-dihydro-4H-imidazo[1,5-a][1,4]benzodiazepine-6-one hydrochloride (1:1) as white crystals; m.p. 206°–209° (dec.).

EXAMPLE 234 a) A suspension of 1.30 g (3.4 mmol) of 7-chloro-3-(5-chloromethyl-1,2,4-oxadiazol-3-yl)-8-fluoro-5-methyl-5,6-dihydro-4H-imidazo[1,5-a][1,4]benzodiazepin-6-one in 13 ml of N,N-dimethylformamide was treated with 1.72 g (0.017 mol) of dipropylamine. After stirring at room temperature for 16 hrs. the solution obtained was completely freed from the solvents. The residue was chromatographed over silica gel with methylene chloride/methanol as the eluent. The product was recrystallized from ether/n-hexane. There were obtained 1.32 g (87%) of 7-chloro-3-(5-dipropylaminomethyl-1,2,4-oxadiazol-3-yl) -8-fluoro-5-methyl-5,6-dihydro-4H-imidazo[1,5-a][1,4]benzodiazepin-6-one as white crystals; m.p. 143°–146° (dec.).

b) 1.25 g (2.8 mmol) of 7-chloro-3-(5-dipropylaminomethyl-1,2,4-oxadiazol-3-yl) -8-fluoro-5-methyl-5,6-dihydro-4H-imidazo [1,5-a][1,4]benzodiazepin-6-one in 20 ml ethanol were treated with 0.84 ml (3.07 mmol) of 3.7N ethanolic hydrochloric acid. After stirring at 0° for 30 minutes the solution was treated with 100 ml of ether and the white suspension obtained was suction filtered. There were obtained 1.13 g (84%) of 7-chloro-3-(5-dipropylaminomethyl-1,2,4-oxadiazol-3-yl)-8-fluoro-5-methyl-5,6-dihydro-4H-imidazo[1,5-a][1,4]benzodiazepin-6-one hydrochloride (1:1) as white crystals; m.p. 209°–211° (dec.).

EXAMPLE 235 a) A suspension of 1.30 g (3.4 mmol) of 7-chloro-3-(5-chloromethyl-1,2,4-oxadiazol-3-yl)-8-fluoro-5-methyl-5,6-dihydro-4H-imidazo[1,5-a][1,4]benzodiazepin-6-one in 13 ml of N,N-dimethylformamide was treated with 1.44 g (0.017 mol) of dipropylamine. After stirring at room temperature for 16 hrs. the solution obtained was completely freed from the solvents. The residue was chromatographed over silica gel with methylene chloride/methanol 39:1 as the eluent. The product was recrystallized from ether/n-hexane. There were obtained 1.39 g (95%) of 7-chloro-8-fluoro-5-methyl-3-(5-piperidin-1-ylmethyl-1,2,4-oxadiazol-3-yl)-5,6-dihydro-4H-imidazo[1,5-a][1,4]benzodiazepin-6-one as white crystals; m.p. 210°–212° (dec.).

b) 1.37 g (3.18 mmol) of 7-chloro-8-fluoro-5-methyl-3-(5-piperidin-1-ylmethyl-1,2,4-oxadiazol-3-yl)-5,6-dihydro-4H-imidazo[1,5-a][1,4]benzodiazepin-6-one were dissolved in 50 ml of hot ethanol and treated at 40° with 0.95 ml (3.5 mol) of 3.7N ethanolic hydrochloric acid. After stirring at 0° for 30 minutes the solution was concentrated to a volume of ~20 ml and treated with 100 ml of ether. The white suspension obtained was suction filtered. There were obtained 1.30 g (88%) of 7-chloro-8-fluoro-5-methyl-3-(5-piperidin-1-ylmethyl-1,2,4-oxadiazol-3-yl)-5,6-dihydro-4H-imidazo[1,5-a][1,4]benzodiazepin-6-one hydrochloride (1:1) as white crystals; m.p. 240°–243° (dec.).

EXAMPLE 236 a) A suspension of 1.20 g (3.14 mmol) of 7-chloro-3-(5-chloromethyl-1,2,4-oxadiazol-3-yl)-8-fluoro-5-methyl-5,6-dihydro-4H-imidazo[1,5-a][1,4]benzodiazepin-6-one in 20 ml of N,N-dimethylformamide was treated with 1.59 g (0.0166 mol) of diisopropylamine. After stirring at 80° for 20 hrs. the solution obtained was completely freed from the solvents. The residue was chromatographed over silica gel with methylene chloride/methanol 39:1 as the eluent. The product was recrystallized from ether/n-hexane. There was obtained 0.84 g (60%) of 7-chloro-3-(5-diisopropylaminomethyl-1,2,4-oxadiazol-3-yl)-8-fluoro-5-methyl-5,6-dihydro-4H-imidazo[1,5-a][1,4]benzodiazepin-6-one as whitish crystals; m.p. 153°–156°.

b) 0.82 g (1.84 mmol) of 7-chloro-3-(5-diisopropylaminomethyl-1,2,4-oxadiazol-3-yl)-8-fluoro-5-methyl-5,6-dihydro-4H-imidazo[1,5-a][1,4]benzodiazepin-6-one was dissolved in 20 ml of hot ethanol and treated at 0° with 0.55 ml (2.02 mmol) of 3.7N ethanolic hydrochloric acid. After stirring at 0° for 30 minutes the solution was totally concentrated. The product was recrystallized from hot acetonitrile/ethyl acetate. There was obtained 0.74 g (83%) of 7-chloro-3-(5-diisopropylaminomethyl-1,2,4-oxadiazol-3-yl)-8-fluoro-5-methyl-5,6-dihydro-4H-imidazo [1,5-a][1,4]benzodiazepin-6-one hydrochloride (1:1) as white crystals; m.p. 206°–210° (dec.).

EXAMPLE 237 a) 7.7 ml (55.3 mmol) of trifluoroacetic anhydride were added dropwise at 5°–8° to a suspension of 13.8 g (50.3 mmol) of 7-fluoro-5-methyl-6-oxo-5,6-dihydro-4H-imidazo-[1,5-a][1,4]benzodiazepine-3-carboxamide (EPA 150 040) in 80 ml of dioxan and 20 ml of pyridine. The beige solution obtained was stirred at 5° for 2.5 hours and subsequently poured into 220 ml of ice-water. The resulting precipitate was filtered off. After drying at 70°/10 Torr there were obtained 11 g (85%) of 7-fluoro-5-methyl-6-oxo-5,6-dihydro-4H-imidazo[1,5-a][1,4]benzodiazepine-3-carbonitrile as a white powder of m.p. >250°.

b) 2 g (7.8 mmol) of 7-fluoro-5-methyl-6-oxo-5,6-dihydro-4H-imidazo[1,5-a][1,4]benzodiazepine-3-carbonitrile and 1.1 g (15.6 mmol) of hydroxylamine hydrochloride were added to a freshly prepared solution of sodium methylate in methanol (from 0.27 g (11.7 mmol) of sodium in 50 ml of methanol), whereupon the mixture was stirred at room temperature for 16 hours. Subsequently, the suspension was evaporated and treated with 100 ml of water. The precipitate obtained was filtered off and dried in a high vacuum. There were obtained 2 g (89%) of (E)-and/or (Z)-3-(amino-hydroxyimino-methyl)-7-fluoro-5-methyl-5, 6-dihydro-4H-imidazo[1,5-a][1,4]benzodiazepin-6-one as a colourless foam. Rf=0.25 (silica gel, methylene chloride/ methanol 9:1).

c) 1.3 g (7.5 mmol) of chloroacetic anhydride, were added to a solution of 1.8 g (6.2 mmol) of (E)- and/or (Z)-3-(amino-hydroxyimino-methyl)-7-fluoro-5-methyl-5,6-dihydro-4H-imidazo[1,5-a][1,4]benzodiazepin-6-one in 50 ml of N,N-dimethylformamide and the mixture was stirred at room temperature for 1.5 hours. Subsequently, it was heated to 105° for 2 hours. The solution was evaporated and the residue was partitioned between 2N sodium hydroxide solution and methylene chloride. The aqueous phase was back-washed with methylene chloride and the organic phases were dried with magnesium sulfate, filtered and evaporated. The residue obtained was crystallized from methylene chloride/ethanol. There were obtained 1.75 g (81%) of 3-(5-chloromethyl-1,2,4-oxadiazol-3-yl)-7-fluoro-5-methyl-5,6-dihydro-4H-imidazo[1,5-a][1,4] benzodiazepin-6-one as a beige powder of m.p. 205.5°–206.5°.

d) 1 ml (12.2 mmol) of propylamine was added to a suspension of 1.7 g (4.9 mmol) of 3-(5-chloromethyl-1,2,4-oxadiazol-3-yl)-7-fluoro-5-methyl-5,6-dihydro-4H-imidazo-[1,5-a][1,4]benzodiazepin-6-one in 40 ml of N,N-dimethylformamide and the mixture was stirred at room temperature for 12 hours. The solution was evaporated and the residue was partitioned between methylene chloride and 2N sodium carbonate solution. The aqueous solution was extracted with methylene chloride and the organic phases were dried with magnesium sulfate, filtered and evaporated. The residue was chromatographed (silica gel, ethyl acetate/ methanol 9:1). There were obtained 1.21 g (67%) of 3-(5-propylaminomethyl-1,2,4-oxadiazol-3-yl)-7-fluoro-5-methyl-5,6-dihydro-4H-imidazo[1,5-a][1,4]benzodiazepin-6-one, Rf=0.22 (silica gel, ethyl acetate/methanol 4:1).

EXAMPLE 238

490 mg (1.2 mmol) of 3-(3-diallylaminomethyl-1,2,4-oxadiazol-5-yl)-8-fluoro-5-methyl-5,6-dihydro-4H-imidazo [1,5-a][1,4]benzodiazepin-6-one were hydrogenated at room temperature and normal pressure in 10 ml of ethyl acetate in the presence of 24 mg of 5% palladium-charcoal. After separating the catalyst the solution was concentrated. The 3-(3-dipropylaminomethyl-1,2,4-oxadiazol-5-yl)-8-fluoro-5-methyl-5,6-dihydro-4H-imidazo[1,5-a][1,4] benzodiazepin-6-one, which was still contaminated with a small amount of educt, was chromatographed on 40 g of silica gel with ethyl acetate, the eluate was evaporated, the residue was dissolved in 4 ml of isopropanol and the solution was acidified with ethereal hydrochloric acid. The separated crystals were filtered off and dried. There was obtained 0.37 g (69%) of 3-(3-dipropylaminomethyl-1,2,4-oxadiazol-5-yl) -8-fluoro-5-methyl-5,6-dihydro-4H-imidazo[1,5-a][1,4] benzodiazepin-6-one hydrochloride (1:1) as white crystals of m.p. 167°–169°.

EXAMPLE 239

A suspension of 0.49 g (1.5 mmol) of 3-(5-aminomethyl-1,2,4-oxadiazol-3-yl)-8-fluoro-5-methyl-5,6-dihydro-4H-imidazo[1,5-a][1,4]benzodiazepin-6-one in 8 ml of N,N,-dimethylformamide was treated under argon with 0.41 ml (4.5 mmol) of n-propyl bromide and 1.04 g (7.5 mmol) of potassium carbonate and stirred at room temperature under argon for 73 hrs. The solution was filtered and the filtrate was evaporated, a yellowish oil being obtained. The crude product was purified by chromatography on 50 g of silica silica gel (methylene chloride/acetone 9:1, 4:1, 2:1, finally methylene chloride/methanol 19:1) The eluate was evaporated, the residue was taken up in 5 ml of methanol and the solution was acidified with ethereal hydrochloric acid, whereby the product crystallized out. The solvent was again evaporated and the residue was heated in 30 ml of ethyl acetate. The mixture was cooled in an ice bath and the separated crystals were filtered off under suction. After drying in a vacuum there were obtained 315 mg (51%) of 3-(5-propylaminomethyl- 1,2,4-oxadiazol-3-yl)-8-fluoro-5-methyl-5,6-dihydro-4H-imidazo[1,5-a][1,4]benzodiazepin-6-one hydrochloride (1:1) of m.p. 144°–148° (dec.).

EXAMPLE 240 a) 0.79 g (11.4 mmol) of hydroxylamine hydrochloride and 2.0 g (7.6 mmol) of (S)-9-oxo-11,12,13,13a-tetrahydro-9H-imidazo[1,5-a]pyrrolo[2,1-c][1,4]benzodiazepine-1-carbonitrile were added under argon to a freshly prepared solution of sodium methylate in methanol (from 230 mg (10.0 mmol) of sodium in 10 ml of methanol) and the mixture was stirred at room temperature for 90 hrs. Subsequently, the suspension was evaporated and the residue was taken up in 30 ml of water. The insoluble constituent was filtered off under suction. The aqueous phase was saturated with sodium chloride, whereby further product crystallized out. This was filtered off under suction and dried in a vacuum with the previously obtained material. There were obtained 2.15 g (95%) of (E)- and/or (Z)-(S)-1-(amino-hydroximino-methyl)-11,12,13,13a-tetrahydro-9H-imidazo [1,5-a]pyrrolo[2,1-c][1,4]benzodiazepin-9-one of m.p. 253°–254° (dec., methanol/diethyl ether).

b) 1.1 g (6.5 mmol) of chloroacetic anhydride were added under argon to a suspension of 1.68 g (5.65 mmol) of (E)-and/or (Z)-(S)-1-(amino-hydroximino-methyl)-11,12,13, 13a-tetrahydro-9H-imidazo[1,5-a]pyrrolo[2,1-c][1,4] benzodiazepin-9-one in 11 ml of dimethylformamide and the mixture was stirred at about 25° for 30 min. and thereupon heated to 110° for 1 hr. The solution was evaporated in a high vacuum and the brown residue was taken up in 20 ml of methylene chloride. The solution was washed three times with 10 ml of saturated sodium hydrogen carbonate solution and the solvent was removed in a vacuum. The crude material was chromatographed on 100 g of silica gel (methylene chloride/acetone 9:1, then 4:1). There were obtained 1.45 g (72%) of (S)-1-(5-chloromethyl-1,2,4-oxadiazol-3-yl)-11,12,13,13a-tetrahydro-9H-imidazo[1,5-a] pyrrolo[2,1-c][1,4]benzodiazepin-9-one as colourless crystals of m.p. 205°–206° (acetonitrile).

c) A solution of 711 mg (2.0 mmol) of (S)-1-(5-chloromethyl-1,2,4-oxadiazol-3-yl)-11,12,13,13a-tetrahydro-9H-imidazo[1,5-a]pyrrolo[2,1-c][1,4] benzodiazepin-9-one in 10 ml of N,N-dimethylformamide was treated with 0.82 ml (6.0 mmol) of dipropylamine and stirred at room temperature under argon for 2 hrs. The solution was evaporated, the residue was triturated in 10 ml of water and the crystals were filtered off. The crude product was chromatographed on 30 g of silica gel (methylene chloride/acetone 9:1, then 4:1). There were obtained 840 mg of (S)-1-(5-dipropylaminomethyl-1,2,4-oxadiazol-3-yl)-11, 12,13,13a-tetrahydro-9H-imidazo[1,5-a]pyrrolo[2,1-c][1,4]

benzodiazepin-9-one, which was converted with ethereal hydrochloric acid into the hydrochloride. By recrystallization from acetonitrile there were obtained 685 mg (73%) of (S)-1-(5-dipropylaminomethyl-1,2,4-oxadiazol-3-yl)-11,12, 13,13a-tetrahydro-9H-imidazo[1,5-a]pyrrolo[2,1-c][1,4] benzodiazepin-9-one hydrochloride (1:1.3) of m.p. 137°–140° (dec.).

EXAMPLE 241

A solution of 710 mg (2.0 mmol) of (S)-1-(5-chloromethyl-1,2,4-oxadiazol-3-yl)-11,12,13,13a-tetrahydro-9H-imidazo[1,5-a]pyrrolo[2,1-c][1,4] benzodiazepin-9-one in 10 ml of N,N-dimethylformamide was treated with 0.5 ml (6.0 mmol) of propylamine and stirred at room temperature under argon for 2 hrs. The solution was evaporated, the residue was triturated in 5 ml of water and the crystals were filtered off. Additional crude product was obtained by extracting the aqueous phase with methylene chloride. The combined crude products (0.65 g) were chromatographed on 25 g of silica gel (methylene chloride/methanol 2%, 5%, 10%). There were obtained 540 mg of (S)-1-(5-propylaminomethyl-1,2,4-oxadiazol-3-yl)-11,12,13,13a-tetrahydro-9H-imidazo[1,5-a]pyrrolo[2,1-c][1,4]benzodiazepin-9-one, which was dissolved in 5 ml of acetonitrile and thereupon converted with ethereal hydrochloric acid into the hydrochloride. By recrystallization from acetonitrile there were obtained 560 mg (62%) of (S)-1-(5-propylaminomethyl-1,2,4-oxadiazol-3-yl)-11,12,13,13a-tetrahydro-9H-imidazo[1,5-a]pyrrolo[2,1-c][1,4]benzodiazepin-9-one hydrochloride (1:2) of m.p. 169°–173° (dec.).

EXAMPLE 242

A solution of 710 mg (20 mmol) of (S)-1-(5-chloromethyl-1,2,4-oxadiazol-3-yl)-11,12,13,13a-tetrahydro-9H-imidazo[1,5-a]pyrrolo[2,1-c][1,4] benzodiazepin-9-one in 10 ml of N,N-dimethylformamide was treated with 0.78 ml (6.0 mmol) of N,N,N'-trimethylethylenediamine and stirred at room temperature under argon for 2 hrs. The solution was evaporated and the residue was dissolved in 10 ml of water. The solution was saturated with sodium chloride and extracted several times with methylene chloroide. The combined extracts were dried with sodium sulfate, filtered and evaporated, there being obtained 0.85 g of a yellowish foam. The crude product was chromatographed on 30 g of silica gel (methylene chloride/acetone 9:1, methylene chloride/methanol 9:1, 4:1 and finally methylene chloride/methanol/triethylamine 80:19:1). There was obtained 0.64 g (76%) of (S)-1-[5-[methyl-(2-dimethylamino-ethyl)-aminomethyl]-1,2,4-oxadiazol-3-yl]-11,12,13,13a-tetrahydro-9H-imidazo[1,5-a]pyrrolo[2,1-c][1,4]benzodiazepin-9-one. The crude product was dissolved in 10 ml of acetonitrile and filtered over Celite. Thereupon, it was acidified with ethereal hydrochloric acid and evaporated. The residue was crystallized from 15 ml of hot acetonitrile. There were obtained 690 mg (65%) of (S)-1-[5-[methyl-(2-dimethylamino-ethyl)-aminomethyl]-1,2,4-oxadiazol-3-yl]-11,12,13,13a-tetrahydro-9H-imidazo[1,5-a]pyrrolo[2, 1-c][1,4]benzodiazepin-9-one hydrochloride (1:3) of m.p. 198°–200° (dec.).

EXAMPLE 243

A solution of 711 mg (2.0 mmol) of (S)-1-(5-chloromethyl-1,2,4-oxadiazol-3-yl)-11,12,13,13a-tetrahydro-9H-imidazo[1,5-a]pyrrolo[2,1-c][1,4] benzodiazepin-9-one in 10 ml of N,N-dimethylformamide was treated with 1.0 ml (6.0 mmol) of dibutylamine and stirred at room temperature under argon for 3 hrs. The solution was evaporated, the residue was triturated in 10 ml of water and the crystals were filtered off under suction. The crude product was dissolved in methylene chloride, the solution was dried with sodium sulfate, whereupon it was chromatographed on 30 g of silica gel (methylene chloride/acetone 9:1, then 4:1). There was obtained 0.73 g of (S)-1-(5-dibutylaminomethyl-1,2,4-oxadiazol-3-yl)- 11,12,13, 13a-tetrahydro-9H-imidazo[1,5-a]pyrrolo[2,1-c][1,4] benzodiazepin-9-one, which was converted in 10 ml of acetonitrile with ethereal hydrochloric acid into the hydrochloride. By crystallization from hot ethyl acetate there was obtained 0.75 g (77%) of (S)-1-(5-dibutylaminomethyl-1,2, 4-oxadiazol-3-yl)-11,12,13,13a-tetrahydro-9H-imidazo[1,5-a]pyrrolo[2,1-c][1,4]benzodiazepin-9-one hydrochloride (1:1) of m.p. 115°–123° (dec.).

EXAMPLE 244 a) 5.4 ml of 5N sodium hydroxide solution were added dropwise to a suspension of 6.9 g (21.6 mmol) of ethyl 8-chloro-5-methyl-6-oxo-5,6-dihydro-4H-imidazo[1,5-a][1, 4]benzodiazepine-3-carboxylate in 5 ml of ethanol and 7 ml of water and the mixture was heated to reflux for 30 minutes. The solution was filtered while hot, concentrated to about 6 ml and acidified with 5.5 ml 5N hydrochloric acid. The product was filtered off under suction. There were obtained 4.7 g (75%) of 8-chloro-5-methyl-6-oxo-5,6-dihydro-4H-imidazo [1,5-a][1,4]benzodiazepine-3-carboxylic acid as colourless crystals of m.p. 263°–267° (dec.).

b) 2.7 g (16.8 mmol) of 1,1'-carbonyldiimidazole were added portionwise to a suspension of 4.7 g (16.0 mmol) of 8-chloro-5-methyl-6-oxo-5,6-dihydro-4H-imidazo[1,5-a][1, 4]benzodiazepine-3-carboxylic acid in 25 ml of N,N-dimethylformamide. After the $CO_2$ evolution had finished the mixture was heated to 60° for 45 min. Subsequently, the solution was cooled to room temperature and 3.9 ml of conc. aqueous ammonia solution were added dropwise thereto. After stirring for a further 90 minutes the reaction mixture was poured into 90 ml of ice-water and stirred for 1 hr. The white crystals were filtered off under suction and washed with a small amount of water. After drying in a high vacuum there were obtained 3.84 g (83%) of 8-chloro-5-methyl-6-oxo-5,6-dihydro-4H-imidazo[1,5-a][1,4]benzodiazepine-3-carboxamide of m.p. 275°–277°.

c) 1.85 ml (13.4 mmol) of trifluoroacetic anhydride were added dropwise at <8° to a suspension of 3.72 g (12.8 mmol) of 8-chloro-5-methyl-6-oxo-5,6-dihydro-4H-imidazo[1,5-a] [1,4]benzodiazepine-3-carboxamide in 17 ml of dioxan and 2 ml of pyridine. The beige solution obtained was stirred at 50°–60° for 4 hrs., cooled and treated with 80 ml of water. The white crystals were filtered off under suction and dried in a high vacuum. There were obtained 3.08 g (88%) of 8-chloro-5-methyl-6-oxo-5,6-dihydro-4H-imidazo[1,5-a][1, 4]benzodiazepine-3-carbonitrile as colourless crystals of m.p. 272°–275°.

d) 1.1 g (15.8 mmol) of hydroxylamine hydrochloride and 2.90 g (10.6 mmol) of 8-chloro-5-methyl-6-oxo-5,6-dihydro-4H-imidazo[1,5-a][1,4]benzodiazepine-3-carbonitrile were added portionwise to a sodium methylene solution (prepared from 342 mg (14.8 mmol) of sodium and 14 ml of methanol) and the mixture was stirred at room temperature for 18 hrs. The yellow suspension obtained was cooled in an ice bath and suction filtered. Subsequently, the crude material was suspended in 10 ml of water, again filtered off under suction and dried in a high vacuum. There were obtained 2.9 g (89%) of (E)- and/or (Z)-3-(aminohydroximino-methyl)-8-chloro-5-methyl-5,6-dihydro-4H-imidazo[1,5-a][1,4]benzodiazepin-6-one of m.p. 266°–270° (acetonitrile/DMF).

e) 0.55 g (3.2 mmol) of chloroacetic anhydride was added under argon to a suspension of 0.90 g (2.9 mmol) of (E)- and/or (Z)-3-(aminohydroximino-methyl)-8-chloro-5-methyl-5,6-dihydro-4H-imidazo[1,5-a][1,4]benzodiazepin-6-one in 9 ml of dimethylformamide and the mixture was stirred at about 25° for 1 hr. and thereupon heated to 110° for 1 hr. The solution was evaporated in a high vacuum and the brown residue was taken up in 50 ml of methylene chloride. The solution was washed three times with 10 ml of saturated sodium hydrogen carbonate solution and the solvent was removed in a vacuum. The crude material was chromatographed on 30 g of silica gel (methylene chloride/acetone 9:1). There was obtained 0.76 g (71%) of 8-chloro-3-(5-chloromethyl-1,2,4-oxadiazol-3-yl)-5-methyl-5,6-dihydro-4H-imidazo[1,5-a][1,4]benzodiazepin-6-one as almost colourless crystals of m.p. 229° (acetonitrile).

f) A solution of 370 mg (1.01 mmol) of 8-chloro-3-(5-chloromethyl-1,2,4-oxadiazol-3-yl)-5-methyl-5,6-dihydro-4H-imidazo[1,5-a][1,4]benzodiazepin-6-one in 5 ml of N,N-dimethylformamide was treated with 0.42 ml (3.03 mmol) of dipropylamine and stirred at room temperature under argon for 2 hrs. The solution was evaporated and the residue was triturated in 10 ml of water. The white crystals were filtered off. The product was chromatographed on 20 g of silica gel (ethyl acetate/hexane 1:1, then ethyl acetate). There were obtained 259 mg of 8-chloro-3-(5-dipropylaminomethyl-1,2,4-oxadiazol-3-yl)-5-methyl-5,6-dihydro-4H-imidazo[1,5-a][1,4]benzodiazepin-6-one, which was converted with ethereal hydrochloric acid into the hydrochloride. By recrystallization from acetonitrile there were obtained 268 mg (54%) of 8-chloro-1-(5-dipropylaminomethyl-1,2,4-oxadiazol-3-yl)-5-methyl-5,6-dihydro-4H-imidazo[1,5-a][1,4]benzodiazepin-6-one hydrochloride (1:1.6) of m.p. 180°–192° (dec.).

EXAMPLE 245

A solution of 278 mg (0.76 mmol) of 8-chloro-3-(5-chloromethyl-1,2,4-oxadiazol-3-yl)-5-methyl-5,6-dihydro-4H-imidazo[1,5-a][1,4]benzodiazepin-6-one in 5 ml of N,N-dimethylformamide was treated with 0.39 ml (2.3 mmol) of dibutylamine and stirred at room temperature under argon for 1.5 hrs. The solution was evaporated, the residue was dissolved in 20 ml of methylene chloride and the solution was washed three times with water. The organic phase was dried with sodium sulfate, filtered and evaporated. The crude product was chromatographed on 20 g of silica gel (methylene chloride/acetone 4:1). There were obtained 250 mg of 8-chloro-3-(5-dibutylaminomethyl-1,2,4-oxadiazol-3-yl)-5-methyl-5,6-dihydro-4H-imidazo[1,5-a][1,4]benzodiazepin-6-one, which was converted with ethereal hydrochloric acid into the hydrochloride. By crystallization from acetonitrile there were obtained 151 mg (39%) of 8-chloro-1-(5-dibutylaminomethyl-1,2,4-oxadiazol-3-yl)-5-methyl-5,6-dihydro-4H-imidazo[1,5-a][1,4]benzodiazepin-6-one hydrochloride (1:1.3) of m.p. 165°–175° (dec.).

EXAMPLE 246

A solution of 200 mg (0.54 mmol) of 8-chloro-3-(5-chloromethyl-1,2,4-oxadiazol-3-yl)-5-methyl-5,6-dihydro-4H-imidazo[1,5-a][1,4]benzodiazepin-6-one in 4 ml of N,N-dimethylformamide was treated with 0.17 ml (1.65 mmol) of diethylamine and stirred at room temperature under argon for 1.5 hrs. The solution was evaporated and the residue was triturated in 10 ml of water. The crystals were filtered off under suction, the filtrate was extracted once with ethyl acetate and the extract was evaporated. The combined crude products were chromatographed on 20 g of silica gel (methylene chloride/acetone 4:1, 2:1). There were obtained 124 mg of 8-chloro-3-(5-diethylaminomethyl-1,2,4-oxadiazol-3-yl)-5-methyl-5,6-dihydro-4H-imidazo[1,5-a][1,4]benzodiazepin-6-one, which was converted in acetone with ethereal hydrochloric acid into the hydrochloride. By crystallization from acetonitrile there were obtained 108 mg (42%) of 8-chloro-1-(5-diethylaminomethyl-1,2,4-oxadiazol-3-yl)-5-methyl-5,6-dihydro-4H-imidazo[1,5-a][1,4]benzodiazepin-6-one hydrochloride (1:1.9) of m.p. 191°–205° (dec.).

EXAMPLE 247

A solution of 200 mg (0.54 mmol) of 8-chloro-3-(5-chloromethyl-1,2,4-oxadiazol-3-yl)-5-methyl-5,6-dihydro-4H-imidazo[1,5-a][1,4]benzodiazepin-6-one in 4 ml of N,N-dimethylformamide was treated with 0.136 ml (1.65 mmol) of propylamine and stirred at room temperature under argon for 1.5 hrs. The solution was evaporated and the residue was triturated in 10 ml of water. The aqueous phase was extracted with methylene chloride and the combined extracts were washed twice with water, dried with sodium sulfate, filtered and evaporated. The combined crude products were chromatographed on 30 g of silica gel (ethyl acetate methylene chloride/methanol 9:1). There were obtained 126 mg of 8-chloro-3-(5-propylaminomethyl-1,2,4-oxadiazol-3-yl)-5-methyl-5,6-dihydro-4H-imidazo[1,5-a][1,4]benzodiazepin-6-one as a foam which was converted in acetonitrile with ethereal hydrochloric acid into the hydrochloride. By crystallization from hot acetonitrile there were obtained 102 mg (42%) of 8-chloro-1-(5-propylaminomethyl-1,2,4-oxadiazol-3-yl)-5-methyl-5,6-dihydro-4H-imidazo[1,5-a][1,4]benzodiazepin-6-one hydrochloride (1:1.8) of m.p. 230°–240° (dec.).

EXAMPLE 248

A suspension of 695 mg (2.0 mmol) of 3-(5-chloromethyl-1,2,4-oxadiazol-3-yl)-8-fluoro-5-methyl-5,6-dihydro-4H-imidazo[1,5-a][1,4]benzodiazepin-6-one in 7 ml of N,N-dimethylformamide was treated with 0.78 ml (6.0 mmol) of N,N,N'-trimethylethylenediamine. After stirring at room temperature for 2 hrs. the solution was concentrated and the residue was taken up in 70 ml of water. The crystals were filtered off and taken up with 20 ml of saturated sodium chloride solution, whereupon extraction was carried out four times with ethyl acetate and three times with methylene chloride. The extracts were dried with sodium sulfate, filtered and evaporated. The residue was recrystallized from acetonitrile. There were obtained 460 mg (56%) of 3-[5-[methyl-(2-dimethylaminoethyl)-aminomethyl]-1,2,4-oxadiazol-3-yl]-8-fluoro-5-methyl-5,6-dihydro-4H-imidazo[1,5a][1,4]benzodiazepin-6-one as white crystals. These were dissolved in acetonitrile and the solution was acidified with ethereal hydrochloric acid. After crystallization from hot acetonitrile there were obtained 408 mg (40%) of 3-[5-[methyl-(2-dimethylaminoethyl)-aminomethyl]-1,2,4-oxadiazol-3-yl]-8-fluoro-5-methyl-5,6-dihydro-4H-imidazo[1,5a][1,4]benzodiazepin-6-one hydrochloride (1:2.5) as white crystals of m.p. 217°–222° (dec.).

EXAMPLE 249 a) 59.3 g (0.3 mol) of 5-chloro-isatoic anhydride and 30.3 g (0.3 mol) of (S)-azetidine-2-carboxylic acid were suspended in 400 ml of N,N-dimethylformamide/acetic acid 5:1 and heated to 87°–90° in an oil bath under argon for 64 hrs. The solvent was removed in a vacuum and the residue was taken up in 500 ml of methanol, whereupon the mixture was stirred at room temperature for 30 min. The white, pure crystals were filtered off under suction. The solvent was removed in a vacuum and the semi-crystalline residue was recrystallized from 60 ml of methanol (hot filtration). The products were combined and dried in a vacuum. There were obtained 61.3 g (86%) of (S)-6-chloro-1,2,4,9,10,10a-hexahydro-azeto[2,1-c][1,4]benzodiazepine-4,10-dione of m.p. 229°–231° (dec.).

b) 23.6 g (0.1 mol) of (S)-6-chloro-1,2,4,9,10,10a-hexahydro-azeto[2,1-c][1,4]benzodiazepine-4,10-dione in 300 ml of THF/DMPU 5:1 were added dropwise under argon at about −75° to a LDA solution (prepared in the usual manner from 16 ml (0.11 mol) of diisopropylamine in 200 ml of THF and 69 ml of 1.6M n-butyllithium solution in hexane). The mixture was stirred for a further 40 min. 23 ml (0.11 mol) of diphenyl chlorophosphate were added dropwise thereto at about −75° and the mixture was stirred at −75° for 35 min. In the meanwhile and separately, a further LDA solution was prepared as described above (100 ml of THF). Thereto there was now added dropwise at about −75° a solution of 12.0 ml (0.11 mol) of ethyl isocyano-acetate in 20 ml of THF/DMPU 1:1. The deprotonized ethyl isocyanoacetate was added dropwise at about −70° via a dropping funnel cooled with dry ice within 30 min. to the initially described reaction mixture. The mixture was stirred in an acetone/dry-ice bath for 2 hrs, 100 ml of 20% ammonium chloride solution were added at <−60° and the mixture was poured into 800 ml of ice-water. The mixture was extracted three times with 200 ml of methylene chloride, dried with sodium sulfate and evaporated. The brown oil was dissolved in 300 ml of ethyl acetate, whereupon 300 ml of n-hexane were added slowly. The crystals were filtered off. Further product was obtained by chromatography of the mother liquor on 300 g of silica gel (methylene chloride/acetone 9:1). After drying in a vacuum there were obtained 17.8 g (54%) of ethyl (S)-7-chloro-12,12a-dihydro-9-oxo-9H,11H-azeto[2,1-c]imidazo[1,5-a][1,4]benzodiazepine-1-carboxylate of m.p. 190°–194° (ethyl acetate).

c) 20.8 g (62.8 mmol) of ethyl (S)-7-chloro-12,12a-dihydro-9-oxo-9H,11H-azeto[2,1-c]imidazo[1,5-a][1,4]benzodiazepine-1-carboxylate in 250 ml of ethanol and 75 ml (75 mmol) of 1N sodium hydroxide solution were heated to reflux for 30 min. The alcohol was evaporated on a rotary evaporator. The residue was dissolved in 250 ml of water and acidified with 1N hydrochloric acid. The crystals were filtered off under suction, washed with water and dried in a vacuum. There were obtained 18.2 g (96%) of (S)-7-chloro-12,12a-dihydro-9-oxo-9H,11H-azeto[2,1-c]imidazo[1,5-a][1,4]benzodiazepine-1-carboxylic acid of m.p. 249°–250° (dec.).

d) 3.04 g (10.0 mmol) of (S)-7-chloro-12,12a-dihydro-9-oxo-9H,11H-azeto[2,1-c]imidazo[1,5-a][1,4]benzodiazepine-1-carboxylic acid were suspended in 15 ml of N,N-dimethylformamide and treated portionwise at room temperature with 1.78 g (11.0 mmol) of 1,1'-carbonyldiimidazole. After the $CO_2$ evolution had finished the clear brown solution was stirred at 50° for 30 min., cooled and treated dropwise at a temperature below 25° within about 10 min. with 2.5 ml of conc. ammonia. After stirring for 30 minutes the suspension obtained was evaporated and the residue was triturated with 30 ml of water. The white crystals were filtered off under suction and dried in a vacuum. There were obtained 2.8 g (92%) of (S)-7-chloro-12,12a-dihydro-9-oxo-9H,11H-azeto[2,1-c]imidazo[1,5-a][1,4]benzodiazepine-1-carboxamide of m.p. 251°–253°.

e) 2.38 g (7.85 mmol) of (S)-7-chloro-12,12a-dihydro-9-oxo-9H,11H-azeto[2,1-c]imidazo[1,5-a][1,4]benzodiazepine-1-carboxamide were suspended in 15 ml of dioxan and 1.4 ml of pyridine and treated dropwise at a temperature of about 10° with 1.2 ml (8.25 mmol) of trifluoroacetic anhydride. The mixture was stirred at room temperature for 45 min. and a further 0.26 ml of pyridine and 0.11 ml of trifluoroacetic anhydride were added. The reaction mixture was stirred for 30 min. Thereupon, the solvent was removed in a vacuum and the residue was triturated with 30 ml of water. The crude material was chromatographed on 50 g of silica gel (methylene chloride/acetone 9:1). The product was recrystallized from acetonitrile. There were obtained 1.75 g (80%) of (S)-7-chloro-12,12a-dihydro-9-oxo-9H,11H-azeto[2,1-c]imidazo[1,5-a][1,4]benzodiazepine-1-carbonitrile of m.p. 258°–261°.

f) 4.5 g (65.1 mmol) of hydroxylamine hydrochloride and 12.35 g (43.3 mmol) of (S)-7-chloro-12,12a-dihydro-9-oxo-9H,11H-azeto[2,1-c]imidazo[1,5-a][1,4]benzodiazepine-1-carbonitrile were added portionwise to a sodium methylate solution (prepared from 1.49 g (64.7 mmol) of sodium and 67 ml of methanol) and the mixture was stirred at room temperature for 108 hrs. The crystals were filtered off under suction, stirred in 40 ml of water for 30 min., again filtered off under suction and dried in a high vacuum. There were obtained 13.3 g (96%) of (E)- and/or (Z)-1-(amino-hydroximino-methyl)-7-chloro-12,12a-dihydro-9H,11H-azeto[2,1-c]imidazo[1,5-a][1,4]benzodiazepin-9-one of m.p. 282°–283° (dec.).

g) 1.0 ml (5.75 mmol) of chloroacetic anhydride was added to a suspension of 1.59 g (5.0 mmol) of (E)- and/or (Z)-1-(amino-hydroximino-methyl)-7-chloro-12,12a-dihydro-9H,11H-azeto[2,1-c]imidazo[1,5-a][1,4]benzodiazepin-9-one in 10 ml of N,N-dimethylformamide under argon and the mixture was stirred at about 25° for 1 hr. and thereupon heated to 110° for 1 hr. The solution was evaporated in a high vacuum and the brown residue obtained was dissolved in 120 ml of methylene chloride. The solution was washed three times with 20 ml of saturated sodium hydrogen carbonate solution and the solvent was removed in a vacuum. The crude material was chromatographed on 80 g of silica gel (methylene chloride/acetone 9:1, then 4:1). After drying in a high vacuum there were obtained 1.47 g (78%) of (S)-7-chloro-1-(5-chloromethyl-1,2,4-oxadiazol-3-yl)-12,12a-dihydro-9H,11H-azeto[2,1-c]imidazo[1,5-a][1,4]benzodiazepin-9-one as colourless crystals of m.p. 238°–241° (acetonitrile).

h) A suspension of 1.13 g (3.0 mmol) of (S)-7-chloro-1-(5-chloromethyl-1,2,4-oxadiazol-3-yl)-12,12a-dihydro-9H,11H-azeto[2,1-c]imidazo[1,5-a][1,4]benzodiazepin-9-one in 15 ml of N,N-dimethylformamide was treated with 0.74 ml (9.0 mmol) of propylamine and stirred at room temperature under argon for 3 hrs. The solution was evaporated, the residue was taken up in 20 ml of water and the aqueous phase was extracted with methylene chloride. The combined extracts were washed twice with water, dried with sodium sulfate, filtered and evaporated. The crude product was chromatographed on 30 g of silica gel (methylene chloride/acetone 4:1, then 2:1 and finally methylene chloride/methanol 9:1). There were obtained 840 mg of (S)-7-chloro-1-(5-propylaminomethyl-1,2,4-oxadiazol-3-yl)-12,12a-dihydro-9H,11H-azeto[2,1-c]imidazo[1,5-a][1,4]benzodiazepin-9-one, which was converted in acetonitrile in the presence of fumaric acid into the fumarate. By recrystallization from acetonitrile there were obtained 588 mg (35%) of (S)-7-chloro-1-(5-propylaminomethyl-1,2,4-oxadiazol-3-yl)-12,12a-dihydro-9H,11H-azeto[2,1-c]imidazo[1,5-a][1,4]benzodiazepin-9-one fumarate (1:1.4) of m.p. 135°-140° (dec.).

EXAMPLE 250

A suspension of 1.04 g (3.0 mmol) of 3-(5-chloromethyl-1,2,4-oxadiazol-3-yl)-8-fluoro-5-methyl-5,6-dihydro-4H-imidazo[1,5-a]-[1,4]benzodiazepin-6-one in 10 ml of N,N-dimethylformamide was treated with 1.27 ml (9.0 mmol) of diisopropylamine. After stirring at room temperature for 18 hrs. the solution obtained was concentrated and the residue was taken up in 10 ml of water and stirred in an ultrasound bath for 2 hrs. The crystals were filtered off under suction and dissolved in methylene chloride, and the solution was dried with sodium sulfate, is filtered and evaporated. The crude material was chromatographed on silica gel (ethyl acetate), dissolved in acetonitrile and acidified with ethereal hydrochloric acid. The solution was again evaporated and the residue was recrystallized from acetonitrile. After drying in a vacuum there were obtained 542 mg (38%) of 3-(5-diisopropylaminomethyl-1,2,4-oxadiazol-3-yl)-8-fluoro-5-methyl-5,6-dihydro-4H-imidazo[1,5-a][1,4]benzodiazepin-6-one as white crystals of m.p. 173°-178° (dec.).

EXAMPLE 251 a) 12.33 g (76 mmol) of 1,1'-carbonyldiimidazole were added portionwise to a suspension of 22 g (76 mmol) of (S)-10,11,12,12a-tetrahydro-8-oxo-8H-imidazo[5,1-c]pyrrolo[1,2-a]thieno[3,2-e][1,4]diazepine-1-carboxylic acid (EP 59 390 A1) in 100 ml of dimethylformamide. The resulting pale brown solution was heated to 50° for 45 minutes. Subsequently, the solution was cooled to room temperature and 14 ml of aqueous ammonia solution were added dropwise thereto. After a further 30 minutes the reaction mixture was poured into 100 ml of ice-water and the resulting precipitate was filtered off and rinsed with water, ethanol and subsequently with ether. After drying at 70°/10 Torr there were obtained 20 g (91%) of (S)-10,11,12,12a-tetrahydro-8-oxo-8H-imidazo[5,1-c]pyrrolo[1,2-a]thieno[3,2-e][1,4]diazepine-1-carboxamide as colourless crystals of m.p. 222°-223°.

b) 4.44 ml (31.9 mmol) of trifluoroacetic anhydride were added dropwise at 5°-8° to a suspension of 8.98 g (31.1 mmol) of (S)-10,11,12,12a-tetrahydro-8-oxo-8H-imidazo[5,1-c]pyrrolo[1,2-a]thieno[3,2-e][1,4]diazepine-1-carboxamide in 50 ml of dioxan and 5.4 ml of pyridine. The beige solution obtained was stirred at 50° for 2.5 hours and subsequently poured into 220 ml of ice-water. The resulting precipitate was filtered off. After drying at 70°/10 Torr there were obtained 6.78 g (80%) of (S)-10,11,12,12a-tetrahydro-8-oxo-8H-imidazo[5,1-c]pyrrolo[1,2-a]thieno[3,2-e][1,4]diazepine-1-carbonitrile as a white powder of m.p. 249°-251°.

c) 12.7 g (47 mmol) of (S)-10,11,12,12a-tetrahydro-8-oxo-8H-imidazo[5,1-c]pyrrolo[1,2-a]thieno[3,2-e][1,4]diazepine-1-carbonitrile and 5 g (72.2 mmol) of hydroxylamine hydrochloride were added to a freshly prepared solution of sodium methylate in methanol (from 1.55 g (67 mmol) of sodium in 70 ml of methanol), whereupon the mixture was stirred at room temperature for 48 hours. Subsequently, the suspension was evaporated and treated with 100 ml of water. The precipitate obtained was filtered off and dried in a high vacuum. There were obtained 9.46 g (66%) of (E)- and/or (Z)- (S)-1-(amino-hydroxyimino-methyl)-10,11,12,12a-tetrahydro-8H-imidazo[5,1-c]pyrrolo[1,2-a]thieno[3,2-e][1,4]diazepin-8-one as a colourless powder of m.p. 106°-108°.

d) 1.40 g (8.04 mmol) of 1,1'-carbonyldiimidazole were added to a solution of 1.42 g (8.07 mmol) of BOC-glycine in 13 ml of dimethylformamide and the mixture was stirred at 50° for 30 minutes. Subsequently, 2.30 g (7.58 mmol) of (E)- and/or (Z)- (S)-1-(aminohydroxyimino-methyl)-10,11,12,12a-tetrahydro-8H-imidazo[5,1-c]pyrrolo-[1,2-a]thieno[3,2-e][1,4]diazepin-8-one were added thereto and the mixture was stirred at 90° for 15 hours. The brown solution obtained was evaporated in a high vacuum and the brown residue obtained was chromatographed (silica gel, methylene chloride/methanol 10:1). There were obtained 1.50 g (44%) of (S)-1-(5-BOC-aminomethyl-1,2,4-oxadiazol- 3-yl) -10,11,12,12a-tetrahydro-8H-imidazo[5,1-c]pyrrolo[1,2-a]thieno[3,2-e][1,4]diazepin-8-one as a colourless foam, Rf=0.62 (silica gel, methylene chloride/methanol 10:1).

e) A solution of 1.50 g (3.4 mmol) of (S)-1-(5-BOC-aminomethyl-1,2,4-oxadiazol-3-yl)-10,11,12,12a-tetrahydro-8H-imidazo[5,1-c]pyrrolo[1,2-a]thieno[3,2-e][1,4]diazepin-8-one in 6 ml of trifluoroacetic acid was stirred at room temperature for 2 hours. The yellow solution was evaporated, the residue was dissolved in water and the aqueous phase was washed three times with methylene chloride. Subsequently, the aqueous phase was made basic with 10 ml of aqueous ammonia solution and extracted six times with methylene chloride. The organic phases were dried with sodium sulfate, filtered and evaporated. The residue obtained was chromatographed (silica gel, methylene chloride/methanol 9:1). There is was obtained 850 mg (73%) of (S)-1-(5-aminomethyl-1,2,4-oxadiazol-3-yl)-10,11,12,12a-tetrahydro-8H-imidazo[5,1-c]pyrrolo[1,2-a]thieno[3,2-e][1,4]diazepin-8-one as a colourless foam, Rf=0.25 (silica gel, methylene chloroide/methanol 9:1).

EXAMPLE 252 a) 3.15 g (19.4 mmol) of 1,1'-carbonyldiimidazole were added in one portion at room temperature to a solution of 5.13 g (18.6 mmol) of (S)-11,11 a-dihydro-9-oxo-9H,10H-azeto[1,2-a]imidazo[5,1-c]thieno[3,2-e][1,4]diazepine-1-carboxylic acid in 30 ml of dimethylformamide and the mixture was stirred at 50° for 30 minutes. Subsequently, 4.16 g (18.9 mmol) of phthaloylglycine amidoxime were added in one portion and the mixture was stirred at 110° for 15 hours. The dimethylformamide was evaporated in a high vacuum and the residue obtained was treated with 150 ml of water. Extraction with methylene chloride (twice), drying with sodium sulfate, filtration and evaporation yielded a reddish residue, which was subsequently chromatographed (silica gel, methylene chloride/methanol 20:1). There were obtained 3.92 g (46%) of (S)-2-[5-(8-oxo-11,11a-dihydro-8H,10H-azeto[1,2-a]imidazo[5,1-c]thieno[3,2-e][1,4]diazepin-1-yl]-1,2,4-oxadiazol-3-ylmethyl]-2,3-dihydro-1H-isoindole-1,3-dione as pale brown crystals of m.p. 155°-157°.

b) 30 ml of methylamine (33% in ethanol) were added dropwise at 70° to a solution of 2.4 g (5.23 mmol) of (S)-2-[5-(8-oxo-11,11 a-dihydro-8H,10H-azeto[1,2-a]imidazo[5,1-c]thieno[3,2-e][1,4]diazepin-1-yl)-1,2,4-oxadiazol-3-yl-methyl]-2,3-dihydro-1H-isoindole-1,3-dione in 40 ml ethanol and the mixture was stirred at 70° for a further 2 hours. The reaction mixture was evaporated and the residue was chromatographed (silica gel, methylene chloride/methanol 20:1). There were obtained 1.60 g (93%) of (S)-1-(3-aminomethyl-1,2,4-oxadiazol-5-yl)-11,11a-dihydro-8H,10H-azeto[1,2-a]imidazo[5,1-c]thieno[3,2-e][1,4]diazepin-8-one as colourless crystals of m.p. 227° (dec.).

EXAMPLE 253 a) 5.66 g (34.9 mmol) of 1,1'-carbonyldiimidazole were added portionwise to a suspension of 8.8 g (33.4 mmol) of 5-methyl-6-oxo-5,6-dihydro-4H-imidazo[1,5-a]thieno[2,3-f][1,4]diazepin-3-carboxylic acid (EP 150 040 A2) in 80 ml of dimethylformamide. The resulting pale brown solution was heated to 50° for 45 minutes. Subsequently, the solution was cooled to room temperature and 8.1 ml of aqueous ammonia solution were added dropwise thereto. After a further 30 minutes the reaction mixture was poured into 100 ml of ice-water and the resulting precipitate was filtered off and rinsed with water, ethanol and subsequently with ether. After drying at 70°/10 Torr there were obtained 7.6 g (86%) of 5-methyl-6-oxo-5,6-dihydro-4H-imidazo[1,5-a]thieno[2,3-f][1,4]diazepin-3-carboxamide as colourless crystals of m.p. 294°–296°.

b) 4.05 ml (29 mmol) of trifluoroacetic anhydride were added dropwise at 5°–8° to a suspension of 7.43 g (28.3 mmol) of 5-methyl-6-oxo-5,6-dihydro-4H-imidazo[1,5-a]thieno[2,3f][1,4]diazepine-3-carboxamide in 40 ml of dioxan and 5 ml of pyridine. The beige solution obtained was stirred at 5° for 2.5 hours and subsequently poured into 220 ml of ice-water. The resulting precipitate was filtered off. After drying at 70°/10 Torr there were obtained 5.6 g (81%) of 5-methyl-6-oxo-5,6-dihydro-4H-imidazo[1,5-a]thieno[2,3-f][1,4]diazepine-3-carbonitrile as a white powder of m.p. 206°–208°.

c) 5.54 g (22.7 mmol) of 5-methyl-6-oxo-5,6-dihydro-4H-imidazo[1,5-a]thieno[2,3-f][1,4]diazepine-3-carbonitrile and 2.5 g (36.1 mmol) of hydroxylamine hydrochloride were added to a freshly prepared solution of sodium methylate in methanol (from 0.74 g (32.3 mmol) of sodium in 40 ml of methanol), whereupon the mixture was stirred at room temperature for 48 hours. Subsequently, the suspension was evaporated and treated with 100 ml of water. The precipitate obtained was filtered off and dried in a high vacuum. There were obtained 5.7 g (90%) of (E)- and/or (Z)-3-(amino-hydroxyimino-methyl)-5-methyl-5,6-dihydro-4H-imidazo[1,5-a]thieno[2,3-f][1,4]diazepin-6-one as a colourless powder of m.p. 248°–250°.

d) 3.82 g (23.5 mmol) of 1,1'-carbonyldiimidazole were added to a solution of 3.85 g (21.9 mmol) of BOC-glycine in 45 ml of dimethylformamide and the mixture was stirred at 50° for 30 minutes. Subsequently, 5.7 g (20.56 mmol) of (E)- and/or (Z)-3-(aminohydroxyimino-methyl)-5-methyl-5,6-dihydro-4H-imidazo[1,5-a]thieno[2,3-f][1,4]diazepin-6-one were added thereto and the mixture was stirred at 90° for 15 hours. The brown solution obtained was evaporated in a high vacuum and the brown residue obtained was chromatographed (silica gel, methylene chloride/methanol 10:1). There were obtained 7.2 g (84%) of not quite pure 3-(5-BOC-aminomethyl-1,2,4-oxadiazol-3-yl)-5-methyl-5,6-dihydro-4H-imidazo[1,5-a]thieno[2,3-f][1,4]diazepin-6-one as a colourless foam, Rf=0.28 (silica gel, methylene chloride/methanol 10:1).

e) A solution of 7.2 g (17.2 mmol) of 3-(5-BOC-aminomethyl-1,2,4-oxadiazol-3-yl)-5-methyl-5,6-dihydro-4H-imidazo[1,5-a]thieno[2,3-f][1,4]diazepin-6-one in 15 ml of trifluoroacetic acid was stirred at room temperature for 2 hours. The yellow solution was evaporated, the residue was dissolved in water and the aqueous phase was washed three times with methylene chloride. Subsequently, the aqueous phase was made basic with 10 ml of aqueous ammonia solution and extracted six times with methylene chloride. The organic phases were dried with sodium sulfate, filtered and evaporated. The residue obtained was chromatographed (silica gel, methylene chloride/methanol 10:1). There were obtained 3.2 g (58%) of 3-(5-aminomethyl-1,2,4-oxadiazol-3-yl)-5-methyl-5,6-dihydro-4H-imidazo[1,5-a]thieno[2,3-f][1,4]diazepin-6-one as colourless crystals of m.p.202°–204°.

EXAMPLE 254 a) 3.39 g (20 mmol) of 1,1'-carbonyldiimidazole were added in one portion at room temperature to a solution of 5.27 g (20 mmol) of 5-methyl-6-oxo-5,6-dihydro-4H-imidazo[1,5-a]thieno[2,3-f][1,4]diazepine-3-carboxylic acid in 50 ml of dimethylformamide and the mixture was stirred at 50° for 30 minutes. Subsequently, 4.47 g (20 mmol) of phthaloylglycinamide oxime were added in one portion and the mixture was stirred at 110° for 15 hours. The dimethylformamide was evaporated in a high vacuum and the residue obtained was treated with 150 ml of water. Extraction with methylene chloride (twice), drying with sodium sulfate, filtration and evaporation yielded a reddish residue, which was subsequently chromatographed (silica gel, methylene chloride/methanol 20:1). After recrystallization from acetonitrile there were obtained 4.21 g (47%) of 5-(5-methyl-6-oxo-5,6-dihydro-4H-imidazo[1,5-a]thieno[2,3-f][1,4]diazepin-3-ylmethyl)-2,3-dihydro-1H-isoindole-1,3-dione as pale brown crystals of m.p. 245°–246°.

b) 50 ml of methylamine (33% in ethanol) were added dropwise at 70° to a solution of 4.2 g (9.41 mmol) of 5-(5-methyl-6-oxo-5,6-dihydro-4H-imidazo[1,5-a]thieno[2,3-f][1,4]diazepin-3-ylmethyl)-2,3-dihydro-1H-isoindole-1,3-dione in 50 ml of ethanol and the mixture was stirred at 70° for a further two hours. The reaction mixture was cooled and the crystals obtained were filtered off. There was obtained 1.2 g (40%) of 3-(3-aminomethyl-1,2,4-oxadiazol-5-yl)-5-methyl-5,6-dihydro-4H-imidazo[1,5-a]thieno[2,3-f][1,4]diazepin-6-one as colourless crystals of m.p. 203° (dec.).

EXAMPLE 255 a) 8 ml of hydrazine hydrate were added to a suspension of 4.0 g (12.6 mmol) of ethyl (S)-10,11,12,12a-tetrahydro-8-oxo-8H-imidazo[5,1-c]pyrrolo[1,2-a]thieno[3,2-e][1,4]diazepine-1-carboxylate in 40 ml of ethanol and the mixture was heated at reflux for 3 hours. After cooling to 0° the crystals obtained were filtered off and there were obtained 3.6 g (94%) of (S)-10,11,12,12a-tetrahydro-8-oxo-8H-imidazo[5,1-c]pyrrolo[1,2-a]thieno[3,2-e][1,4]diazepine-1-carboxylic acid hydrazide as colourless needles of m.p. >260°.

b) A solution of 1.0 g (4.9 mmol) of N-phthaloylglycine in 8 ml of dimethylformamide was treated at room temperature with 0.83 g is (5.11 mmol) of 1,1'-carbonyldiimidazole and the mixture was subsequently heated to 50°. After 30 minutes the mixture was cooled to room temperature, 1.5 g (5 mmol) of (S)-10,11,12,12a-tetrahydro-8-oxo-8H-imidazo[5,1-c]pyrrolo[1,2-a]thieno[3,2-e][1,4]diazepine-1-carboxylic acid hydrazide were added thereto and the mixture was stirred at room temperature for 12 hours. The suspension obtained was filtered and the colourless powder obtained was washed with ethanol and diethyl ether. There were obtained 2.2 g (100%) of (S)-N'-(1,3-dioxo-2,3-dihydro-1H-isoindol-2-ylacetyl)-8-oxo-10,11,12,12a-tetrahydro-8H-imidazo[5,1-c]pyrrolo[1,2-a]thieno[3,2-e][1,4]diazepine-1-carboxylic acid hydrazide of m.p. >260°.

c) A solution of 10 g (20.4 mmol) of (S)-N'-(1,3-dioxo-2,3-dihydro-1H-isoindol-2-ylacetyl)-8-oxo-10, 11,12,12a-tetrahydro-8H-imidazo[5,1-c]pyrrolo[1,2-a]thieno[3,2-e][1, 4]diazepine-1-carboxylic acid hydrazide in 90 g of polyphosphoric acid was stirred at 100° for 1.5 hours. After cooling to room temperature the mixture was poured into 300 ml of ice-water while stirring well, whereupon solid sodium carbonate was added to pH=8. Extraction with methylene chloride and chromatography (silica gel, methylene chloride/methanol 20:1) yielded 7.5 g (78%) of (S)-2-[5-(8-oxo-10,11,12,12a-tetrahydro-8H-imidazo[5,1-c]pyrrolo[1,2-a]thieno[3,2-e][1,4]diazepin-1-yl)-1,3,4-oxadiazol-2-ylmethyl ]-2,3-dihydro-1H-isoindole-1,3-dione as a colourless powder of m.p. >250.

d) 30 ml of methylamine (33% in ethanol) were added dropwise at 70° to a suspension of 2.5 g (5.3 mmol) of (S)-2-[5-(8-oxo-10,11,12,12a-tetrahydro-8H-imidazo[5,1-c]pyrrolo[1,2-a]thieno[3,2-e][1,4]diazepin-1-yl)-1,3,4-oxadiazol-2-ylmethyl]-2,3-dihydro-1H-isoindole-1,3-dione in 30 ml of ethanol and the mixture was stirred at 70° for one hour. The precipitate obtained was filtered off while hot and the yellowish powder obtained was washed colourless with ethanol. There were obtained 1.23 g (68%) of (S)-1-(5-aminomethyl-1,3,4-oxadiazol-2-yl)-10,11,12,12a-tetrahydro-8H-imidazo[5,1-c]pyrrolo[1,2-a]thieno[3,2-e]-[1,4]diazepin-8-one as a colourless powder of m.p. 214°–216°.

EXAMPLE 256 a) 10 ml of hydrazine hydrate were added to a suspension of 6.0 g (19.8 mmol) of ethyl (S)-8-oxo-11,11a-dihydro-8H,10H-azeto[1,2-a]imidazo[5,1-c]thieno[3,2-e][1,4]diazepine-1-carboxylate in 50 ml of ethanol and the mixture was heated at reflux for 3 hours. After cooling to 0° the crystals obtained were filtered off and there were obtained 5.6 g (98%) of S)-8-oxo-11,11a-dihydro-8H,10H-azeto[1,2-a]imidazo[5,1-c]thieno-[3,2-e][1,4]diazepine-1-carboxylic acid hydrazide as colourless needles of m.p. 260°–263°.

b) A solution of 5.8 g (19 mmol) of N-phthaloylglycine in 30 ml of dimethylformamide was treated at room temperature with 3.2 g (19.75 mmol) of 1,1'-carbonyldiimidazole and the mixture was subsequently heated to 50°. After 30 minutes the mixture was cooled to room temperature, 5.6 g (19.63 mmol) of (S)-8-oxo-11,11 a-dihydro-8H,10H-azeto[1,2-a]imidazo[5,1-c]thieno-[3,2-e][1,4]diazepine-1-carboxylic acid hydrazide were added thereto and the mixture was stirred at room temperature for 12 hours. The suspension obtained was filtered and the colour-less powder obtained was washed with ethanol and diethyl ether. There were obtained 8.7 g (96%) of (S)-N'-(1,3-dioxo-2,3-dihydro-1H-isoindol-2-ylacetyl)-8-oxo-11,11a-dihydro-8H,10H-azeto [1,2-a]imidazo[5,1-c]thieno[3,2-e][1,4] diazepine-1-carboxylic acid hydrazide of m.p. >260°.

c) A solution of 8.5 g (16.8 mmol) of (S)-N'-(1,3-dioxo-2,3-ihydro-1H-isoindol-2-ylacetyl)-8-oxo-11,11a-dihydro-8H,10H-azeto[1,2-a]imidazo[5,1-c]thieno[3,2-e][1,4] diazepine-1-carboxylic acid hydrazide in 70 g of polyphosphoric acid was stirred at 100° for 1.5 hours. After cooling to room temperature the mixture was poured into 300 ml of icewater while stirring well, whereupon solid sodium carbonate was added to pH=8. Extraction with methylene chloride and chromatography (silica gel, methylene chloride/methanol 20:1) yielded 6.8 g (88%) of (S)-2-[5-(8-oxo-11,11a-dihydro-8H,10H-azeto[1,2-a]imidazo [5,1-c]thieno[3,2-e][1,4]diazepin-1-yl)-1,3,4-oxadiazol-2-ylmethyl]-2,3-dihydro-1H-isoindole-1,3-dione as a colourless powder of m.p. >250.

d) 30 ml of methylamine (33% in ethanol) were added dropwise at 70° to a suspension of 2.5 g (5.4 mmol) of (S)-2-[5-(8-oxo-11,11a-dihydro-8H,10H-azeto[1,2-a] imidazo[5,1-c]thieno[3,2-e][1,4]diazepin-1-yl)-1,3,4-oxadiazol-2-ylmethyl]-2,3-dihydro-1H-isoindole-1,3-dione in 30 ml of ethanol and the mixture was stirred at 70° for one hour. The precipitate obtained was filtered off while hot and the yellowish powder obtained was washed colourless with ethanol. There were obtained 1.18 g (66%) of (S)-1-(5-aminomethyl-1,3,4-oxadiazol-2-yl)-11,11a-dihydro-8H,10H-azeto[1,2-a]imidazo[5,1-c]thieno[3,2-e][1,4]-diazepin-8-one as a colourless powder of m.p. 233°–235°.

EXAMPLE 257 a) 13 ml of hydrazine hydrate were added to a suspension of 7.0 g (24 mmol) of ethyl 5-methyl-6-oxo-5,6-dihydro-4H-imidazo[1,5-a]thieno[2,3-f][1,4]diazepine-3-carboxylate in 70 ml of ethanol and the mixture was heated at reflux for 3 hours. After cooling to 0° the crystals obtained were filtered off and there were obtained 6.5 g (97%) of 5-methyl-6-oxo-5,6-dihydro-4H-imidazo[1,5-a]thieno[2,3-f][1,4]diazepine-3-carboxylic acid hydrazide as colourless needles of m.p. >260°.

b) A solution of 4.74 g (23.12 mmol) of N-phthaloylglycine in 35 ml of dimethylformamide was treated at room temperature with 3.9 g (24.07 mmol) of 1,1'-carbonyldiimidazole and the mixture was subsequently heated to 50°. After 30 minutes the mixture was cooled to room temperature, 6.53 g of 5-methyl-6-oxo-5,6-dihydro-4H-imidazo[1,5-a]thieno[2,3-f][1,4]diazepine-3-carboxylic acid hydrazide were added thereto and the mixture was stirred at room temperature for 12 hours. The suspension obtained was filtered and the colourless powder obtained was washed with ethanol and diethyl ether. There were obtained 10.4 g (97%) of (S)-N'-(1,3-dioxo-2,3-dihydro-1H-isoindol-2-ylacetyl)-5-methyl-6-oxo-5,6-dihydro-4H-imidazo[1,5-a]thieno[2,3-f][1,4]diazepine-3-carboxylic acid hydrazide of m.p. >260°.

c) A solution of 5 g (10.8 mmol) of (S)-N'-(1,3-dioxo-2,3-dihydro-1H-isoindol-2-ylacetyl)-5-methyl-6-oxo-5,6-dihydro-4H-imidazo[1,5-a]thieno[2,3-f][1,4]diazepine-3-carboxylic acid hydrazide in 35 g of polyphosphoric acid was stirred at 100° for 1.5 hours. After cooling to room temperature the mixture was poured into 300 ml of ice-water while stirring well, whereupon solid sodium carbonate was added to pH=8. Extraction with methylene chloride and chromatography (silica gel, methylene chloride/methanol 20:1) yielded 4.3 g (89%) of (S)-2-[5-(5-methyl-6-oxo-5,6-dihydro-4H-imidazo[1,5-a]thieno[2,3-f][1,4]-diazepin-3-yl)-1,3,4-oxadiazol-2-ylmethyl]-2,3-dihydro-1H-isoindole-1,3-dione as a colourless powder of m.p. 262°–264°.

d) 60 ml of methylamine (33% in ethanol) were added dropwise at 70° to a suspension of 4.3 g (5.3 mmol) of (S)-2-[5-(5-methyl-6-oxo-5,6-dihydro-4H-imidazo[1,5-a] thieno[2,3-f][1,4]diazepin-3-yl)-1,3,4-oxadiazol-2-ylmethyl]-2,3-dihydro-1H-isoindole-1,3-dione in 100 ml of ethanol and the mixture was stirred at 70° for one hour. The precipitate obtained was filtered off while hot and the yellowish powder obtained was washed colourless with ethanol. There were obtained 2.7 g (88%) of 3-(5-aminomethyl-1,3,4-oxadiazol-2-yl)-5-methyl-5,6-dihydro-4H-imidazo[1,5-a]thieno[2,3-f][1,4]diazepin-6-one as a colour-less powder of m.p. 217°–219°.

EXAMPLE 258

3.48 ml (20 mmol) of N-ethyldiisopropylamine and 1.1 ml (12 mmol) of propyl bromide were added to a solution of 0.632 g (2 mmol) of 3-(5-aminomethyl-1,3,4-oxadiazol-2- yl)-5-methyl-5,6-dihydro-4H-imidazo[1,5-a]thieno[2,3-f][1,4]diazepin-6-one in 20 ml of dimethylformamide, whereupon the mixture was stirred at 70° for 12 hours. The dimethylformamide was evaporated and the residue was partitioned between methylene chloride and 2N sodium carbonate solution. The aqueous phase was washed twice with methylene chloride and the organic phases were dried with sodium sulfate, filtered and evaporated. Chromatography (silica gel, ethyl acetate/methanol 20:1) yielded 0.395 g (49%) of 3-(5-dipropylaminomethyl-1,3,4-oxadiazol-2-yl)-5-methyl-5,6-dihydro-4H-imidazo[1,5-a]thieno[2,3-f][1,4]diazepin-6-one as a colourless foam. Rf=0.33 (silica gel, ethyl acetate/methanol 20:1).

EXAMPLE 259

2 ml (11.5 mmol)of N-ethyldiisopropylamine and 0.97 ml (8 mmol) of allyl bromide were added to a solution of 0.500 g (1.58 mmol) of 3-(5-aminomethyl-1,3,4-oxadiazol-2-yl)-5-methyl-5,6-dihydro-4H-imidazo[1,5-a]thieno[2,3-f][1,4]diazepin-6-one in 40 ml of methylene chloride, whereupon the mixture was stirred at 70° for 12 hours. The reaction solution was diluted with methylene chloride and washed with 2N sodium carbonate solution. The aqueous phase was washed twice with methylene chloride and the organic phases were dried with sodium sulfate, filtered and evaporated. Chromatography (silica gel, ethyl acetate/methanol 10:1) yielded 0.510 g (81%) of 3-(5-diallyl-aminomethyl-1,3,4-oxadiazol-2-yl)-5-methyl-5,6-dihydro-4H-imidazo[1,5-a]thieno[2,3-f][1,4]diazepin-6-one as a colourless foam, Rf=0.54 (silica gel, ethyl acetate/methanol 10:1).

EXAMPLE A (S)-8-chloro-1-(5-dipropylaminomethyl-1,2,4-oxadiazol-3-yl)-12,12a-dihydro-9H,11H-azeto[2,1-c]imidazo[1,5-a][1,4]benzodiazepin-9-one, 3-(5-dipropylaminomethyl-1,2,4-oxadiazol-3-yl)-8-fluoro-5-methyl-5,6-dihydro-4H-imidazo[1,5-a][1,4]benzodiazepin-6-one or another compound selected from those which hereinabove have been stated to be particularly preferred can be used as the active substance for the production of an injection solution of the following composition:

| Active substance | 1 mg |
|---|---|
| 1N HCl | 20 µl |
| Acetic acid | 0,5 mg |
| NaCl | 8 mg |
| Benzene alcohol | 10 mg |
| 1N NaOH q.s. ad pH 5 | |
| H₂O q.s. ad 1 ml | |

We claim:

1. A compound of the formula

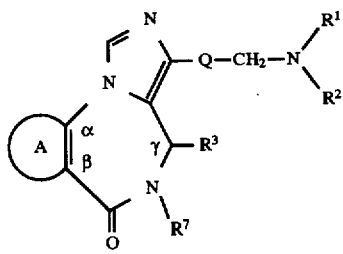

wherein

A together with the two carbon atoms denoted by α and β is one of the residues

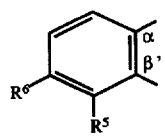 (A¹)

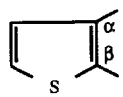 (A²)

and

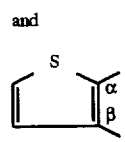 (A³)

Q is one of the residues

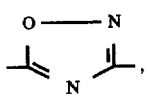 (Q¹)

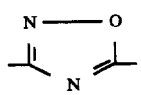 (Q²)

and

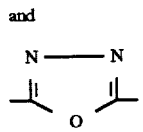 (Q³)

$R^1$ and $R^2$ each independently are hydrogen, lower alkyl, lower alkenyl, lower alkynyl, lower hydroxyalkyl, lower alkoxy-lower alkyl, ($C_3$–$C_6$)-cycloalkyl, ($C_3$–$C_6$)-cycloalkyl-lower alkyl, amino-lower alkyl, lower alkylamino-lower alkyl, di-lower alkylamino-lower alkyl or aryl-lower alkyl or together with the nitrogen atom are 1-pyrrolidinyl, 1-pyrrolinyl, piperidino, 2,6-dimethylpiperidino, 3,3-dimethylpiperidino, hexamethyleneimin-1-yl, heptamethyleneimin-1-yl, morpholino, 4-methyl-1-piperazinyl, or isoindolin-2-yl, $R^3$ is hydrogen and $R^4$ is lower alkyl or $R^3$ and $R^4$ together are dimethylene or trimethylene and $R^5$ and $R^6$ each independently are hydrogen, halogen, trifluoromethyl, lower alkoxy or nitro, the compounds of formula I having the (S) configuration with reference to the carbon atom denoted by γ when $R^3$ and $R^4$ together are dimethylene or trimethylene, or a pharmaceutically acceptable acid addition salt thereof.

2. A compound according to claim 1, wherein Q is the residue $Q^2$.

3. A compound according to claim 1, wherein Q is the residue $Q^3$.

4. A compound according to claim 1, wherein $R^1$ and $R^2$ each independently are lower alkyl, lower hydroxyalkyl or ($C_3$–$C_6$)-cycloalkyl-lower alkyl or together with the nitrogen atom are piperidino or isoindolin-2-yl.

5. A compound according to claim 1, wherein A together with the two carbon atoms denoted by α and β is the residue $A^1$ or $A^2$, $R^5$ is hydrogen, chlorine, fluorine, trifluoromethyl or lower alkoxy and $R^6$ is hydrogen or fluorine.

6. A compound according to claim 1, wherein $R^3$ is hydrogen and $R^4$ is methyl or $R^3$ and $R^4$ together are dimethylene.

7. A compound according to claim 1, 3-(5-dipropylaminomethyl-1,2,4-oxadiazol-3-yl)-8-fluoro-5-methyl-5,6-dihydro-4H-imidazo[1,5-a][1,4]benzodiazepin-6-one.

8. A compound according to claim 1, (S)-8-chloro-1-(5-dipropylaminomethyl-1,2,4-oxadiazol-3-yl)-12,12a-dihydro-9H,11H-azeto[2,1-c]imidazo[1,5-a][1,4]benzodiazepin-9-one.

9. A compound according to claim 1, (S)-1-(5-dipropylaminomethyl-1,2,4-oxadiazol-3-yl)-11,11a-dihydro-8H,10H-azeto[1,2-a]imidazo[5,1-c]thieno[3,2-e][1,4]diazepin-8-one.

10. A compound according to claim 1, 8-fluoro-5-methyl-3-[5-(piperidin-1-ylmethyl)-1,2,4-oxadiazol-3-yl]-5,6-dihydro-4H-imidazo[1,5-a][1,4]benzodiazepin-6-one.

11. A compound according to claim 1, (S)-1-(5-diallylaminomethyl-1,2,4-oxadiazol-3-yl)-8-chloro-7-fluoro-12,12a-dihydro-9H,11H-azeto[2,1-c]imidazo[1,5-a][1,4]benzodiazepin-9-one.

12. A compound according to claim 1, 3-(5-dipropylaminomethyl-1,2,4-oxadiazol-3-yl)-5-methyl-5,6-dihydro-4H-imidazo[1,5-a][1,4]benzodiazepin-6-one.

13. A compound according to claim 1, 3-(5-dipropylaminomethyl-1,3,4-oxadiazol-2-yl)-8-fluoro-5-methyl-5,6-dihydro-4H-imidazo[1,5-c][1,4]benzodiazepin-6-one.

14. A compound according to claim 1, 3-(5-diethylaminomethyl-1,2,4-oxadiazol-3-yl)-8-fluoro-5-methyl-5,6-dihydro-4H-imidazo[1,5-a][1,4]benzodiazepin-6-one.

15. A compound according to claim 1, (S)-8-chloro-1-[5-(piperidin-1-yl)methyl-1,2,4-oxadiazol-3-yl]-12,12a-dihydro-9H,11H-azeto[2,1-c]imidazo[1,5-a][1,4]benzodiazepin-9-one.

16. A compound according to claim 1, 7-fluoro-5-methyl-3-(5-dipropylaminomethyl-1,2,4-oxadiazol-3-yl)-5,6-dihydro-4H-imidazo[1,5-a][1,4]benzodiazepin-6-one.

17. A compound according to claim 1, 7-chloro-3-(5-diethylaminomethyl-1,2,4-oxadiazol-3-yl)-5-methyl-5,6-dihydro-4H-imidazo[1,5-a][1,4]benzodiazepin-6-one.

18. A compound according to claim 1, 7-chloro-3-(5-dipropylaminomethyl-1,3,4-oxadiazo-2-yl)-5-methyl-5,6-dihydro-4H-imidazo[1,5-a][1,4]benzodiazepin-6-one.

19. A compound according to claim 1, (S)-1-(5-diethylaminomethyl-1,2,4-oxadiazol-3-yl)-11,11a-dihydro-8H,10H-azeto[1,2-a]imidazo [5,1-c]thieno[3,2-e][1,4]diazepin-8-one.

20. A compound according to claim 1, (S)-1-(5-dibutylaminomethyl-1,3,4-oxadiazol-2-yl)-11,11a-dihydro-8H,10H-azeto[1,2-a]imidazo[5,1-c]thieno[3,2-e][1,4]diazepin-8-one.

21. A compound according to claim 1, 3-(5-diisopropylaminomethyl-1,2,4-oxadiazol-3-yl)-5-methyl-5,6-dihydro-4H-imidazo[1,5-a][1,4]benzodiazepin-6-one.

22. A compound according to claim 1, 3-(5-diisopropylaminomethyl-1,2,4-oxadiazol-3-yl)-8-fluor-5-methyl-5,6-dihydro-4H-imidazo[1,5-a][1,4]benzodiazepin-6-one.

23. A compound according to claim 1 selected from the group consisting of (S)-1-(5-diallylaminomethyl-1,2,4-oxadiazol-3-yl)-8-chlor-12,12a-dihydro-9H,11H-azeto[2,1-c]imidazo[1,5-a][1,4]benzodiazepin-9-one;

(S)-1-(5-diallylaminomethyl-1,2,4-oxadiazol-3-yl)-8-trifluoromethyl-12,12a-dihydro-9H,11H-azeto[2,1-c]imidazo[1,5-a][1,4]benzodiazepin-9-one;

3-(5-diallylaminomethyl-1,2,4-oxadiazol-3-yl)-8-fluoro-5-methyl-5,6-dihydro-4H-imidazo[1,5-a][1,4]benzodiazepin-6-one;

8-fluoro-3-(5-isoindolin-2-ylmethyl-1,2,4-oxadiazol-3-yl)-5-methyl-5,6-dihydro-4H-imidazo[1,5-a][1,4]benzodiazepin-6-one; and (S)-1-(5-diallylaminomethyl-1,2,4-oxadiazol-3-yl)-11,11a-dihydro-8H,10H-azeto[1,2-a]imidazo[5,1-c]thieno[3,2-e][1,4]diazepin-8-one.

24. A compound according to claim 1 selected from the group consisting of 3-(5-dipropylaminomethyl-1,2,4-oxadiazol-3-yl)-5-methyl-5,6-dihydro-4H-imidazo[1,5-a]thieno[2,3-f][1,4]diazepin-6-one;

3-(5-dipropylaminomethyl-1,2,4-oxadiazol-3-yl)-5-methyl-7-trifluoromethyl-5,6-dihydro-4H-imidazo[1,5-a][1,4]benzodiazepin-6-one; and (S)-8-chloro-1-(5-dipropylaminomethyl-1,3,4-oxadiazol-2-yl)-12,12a-dihydro-9H,11H-azeto[2,1-c]imidazo[1,5-a][1,4]benzodiazepin-9-one.

25. A pharmaceutical composition comprising an effective amount of a compound of the formula

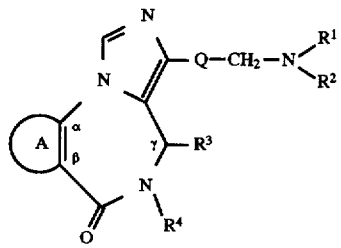

wherein

A together with the two carbon atoms denoted by α and β is one of the residues

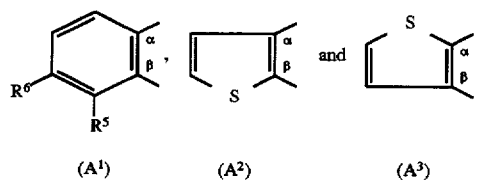

(A¹)    (A²)    (A³)

Q is one of the residues

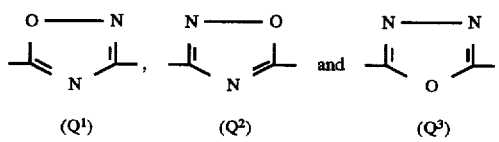

(Q¹)    (Q²)    (Q³)

$R^1$ and $R^2$ each independently are hydrogen, lower alkyl, lower alkenyl, lower alkynyl, lower hydroxyalkyl, lower alkoxy-lower alkyl, ($C_3$–$C_6$)-cycloalkyl, ($C_3$–$C_6$)-cycloalkyl-lower alkyl, amino-lower alkyl, lower alkylamino-lower alkyl, di-lower alkylamino-lower alkyl or aryl-lower alkyl or together with the nitrogen atom are 1-pyrrolidinyl, 1-pyrrolinyl, piperidino, 2,6-dimethylpiperidino, 3,3-dimethylpiperidino, hexamethyleneimin-1-yl, heptamethyleneimin-1-yl, morpholino, 4-methyl-1-piperazinyl, or isoindolin-2-yl, $R^3$ is hydrogen and $R^4$ is lower alkyl or $R^3$ and $R^4$ together are dimethylene or trimethylene and $R^5$ and $R^6$ each independently are hydrogen, halogen, trifluoromethyl, lower alkoxy or nitro, the compounds of formula I having the (S) configuration with reference to the carbon atom denoted by γ when $R^3$ and $R^4$ together are dimethylene or trimethylene, or a pharmaceutically acceptable acid addition salt thereof.

26. A method of treating convulsion, anxiety states, muscle tensions, tension states and insomnia which comprises administering to a patient in need of such treatment an effective amount of a compound of the formula

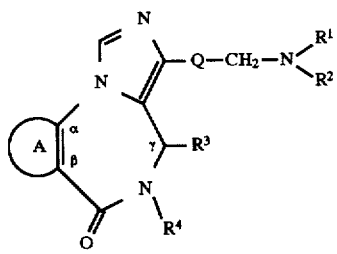

wherein

A together with the two carbon atoms denoted by α and β is one of the residues

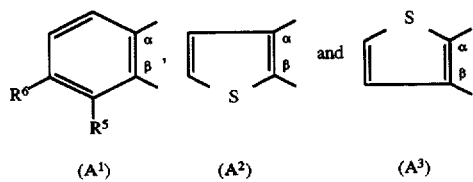

Q is one of the residues

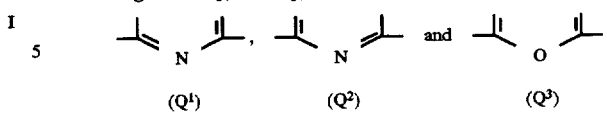

$R^1$ and $R^2$ each independently are hydrogen, lower alkyl, lower alkenyl, lower alkynyl, lower hydroxyalkyl, lower alkoxy-lower alkyl, ($C_3$–$C_6$)-cycloalkyl, ($C_3$–$C_6$)-cycloalkyl-lower alkyl, amino-lower alkyl, lower alkylamino-lower alkyl, di-lower alkylamino-lower alkyl or aryl-lower alkyl or together with the nitrogen atom are a 5- to 8-membered heterocycle optionally containing a further hetero atom or a fused benzene ring, $R^3$ is hydrogen and $R^4$ is lower alkyl or $R^3$ and $R^4$ together are dimethylene or trimethylene and $R^5$ and $R^6$ each independently are hydrogen, halogen, trifluoromethyl, lower alkoxy or nitro, the compounds of formula I having the (S) configuration with reference to the carbon atom denoted by γ when $R^3$ and $R^4$ together are dimethylene or trimethylene, or a pharmaceutically acceptable acid addition salt thereof.

\* \* \* \* \*

UNITED STATES PATENT AND TRADEMARK OFFICE
CERTIFICATE OF CORRECTION

PATENT NO. : 5,665,718
DATED : September 9, 1997
INVENTOR(S) : Godel, et al.

It is certified that error appears in the above-identified patent and that said Letters Patent is hereby corrected as shown below:

Claim 1, Column 123, lines 55-64 formula I reads

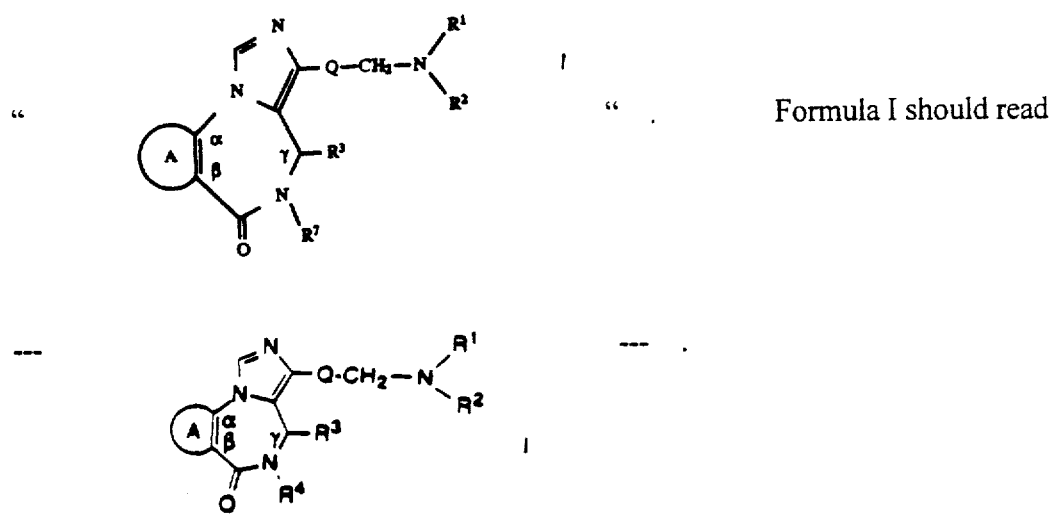

Signed and Sealed this

Ninth Day of December, 1997

Attest:

BRUCE LEHMAN

Attesting Officer

Commissioner of Patents and Trademarks